United States Patent
Yu et al.

(10) Patent No.: US 9,555,038 B2
(45) Date of Patent: Jan. 31, 2017

(54) HETEROCYCLE-SUBSTITUTED TETRACYCLIC COMPOUNDS AND METHODS OF USE THEREOF FOR THE TREATMENT OF VIRAL DISEASES

(71) Applicant: Merck Sharp & Dohme Corp., Rahway, NJ (US)

(72) Inventors: Wensheng Yu, Edison, NJ (US); Ling Tong, Warren, NJ (US); Joseph A. Kozlowski, Princeton, NJ (US); Oleg Selyutin, West Windsor, NJ (US); Lei Chen, Roselle Park, NJ (US); Jae-Hun Kim, Scotch Plains, NJ (US); Deyou Sha, Yardley, PA (US); Razia Rizvi, Bloomfield, NJ (US); Bandarpalle Shankar, Branchburg, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/761,256

(22) PCT Filed: Dec. 31, 2013

(86) PCT No.: PCT/CN2013/001676
§ 371 (c)(1),
(2) Date: Jul. 15, 2015

(87) PCT Pub. No.: WO2014/110705
PCT Pub. Date: Jul. 24, 2014

(65) Prior Publication Data
US 2015/0335648 A1 Nov. 26, 2015

(30) Foreign Application Priority Data
Jan. 16, 2013 (WO) ................ PCT/CN2013/000038

(51) Int. Cl.
| | |
|---|---|
| *C07D 498/04* | (2006.01) |
| *C07D 513/04* | (2006.01) |
| *A61K 31/5365* | (2006.01) |
| *A61K 45/06* | (2006.01) |
| *A61K 31/4985* | (2006.01) |
| *A61K 31/7056* | (2006.01) |
| *A61K 31/7072* | (2006.01) |

(52) U.S. Cl.
CPC ....... *A61K 31/5365* (2013.01); *A61K 31/4985* (2013.01); *A61K 31/7056* (2013.01); *A61K 31/7072* (2013.01); *A61K 45/06* (2013.01); *C07D 498/04* (2013.01); *C07D 513/04* (2013.01)

(58) Field of Classification Search
CPC .. C07D 498/04; C07D 513/04; A61K 31/5365
USPC ........................................ 544/89; 514/229.5
See application file for complete search history.

(56) References Cited

U.S. PATENT DOCUMENTS

| | | | |
|---|---|---|---|
| 7,153,848 | B2 | 12/2006 | Hudyma et al. |
| 7,662,809 | B2 | 2/2010 | Ercolani et al. |
| 7,973,040 | B2 | 7/2011 | Harper et al. |
| 8,080,654 | B2 | 12/2011 | Harper et al. |
| 8,377,980 | B2 | 2/2013 | Belema et al. |
| 8,871,759 | B2 | 10/2014 | Coburn et al. |
| 2006/0019974 | A1 | 1/2006 | Mederski et al. |
| 2006/0258682 | A1 | 11/2006 | Liao et al. |
| 2007/0049593 | A1 | 3/2007 | Oka et al. |
| 2007/0110708 | A1 | 5/2007 | Miller et al. |
| 2007/0185175 | A1 | 8/2007 | Liu et al. |

(Continued)

FOREIGN PATENT DOCUMENTS

| | | |
|---|---|---|
| CN | 101336248 | 12/2008 |
| EP | 1719773 A1 | 11/2006 |

(Continued)

OTHER PUBLICATIONS

Alper, P.B., "Discovery Evaluation of Benzo[x]Carbazole-based Small Molecular Agonists of the Thrombopoietin (Tpo) Receptor", Biorganic and Medicinal Chem. Lett., 2008, pp. 5255-5258, vol. 18, US.

(Continued)

*Primary Examiner* — Kahsay Habte
(74) *Attorney, Agent, or Firm* — Jeffrey P. Bergman; Catherine D. Fitch

(57) ABSTRACT

The present invention relates to novel Heterocycle-Substituted Tetracyclic Compounds of Formula (I): (I) and pharmaceutically acceptable salts thereof, wherein A, A', R² R³, R⁴ and R are as defined herein. The present invention also relates to compositions comprising at least one Heterocycle-Substituted Tetracyclic Compound, and methods of using the Heterocycle-Substituted Tetracyclic Compounds for treating or preventing HCV infection in a patient.

(I)

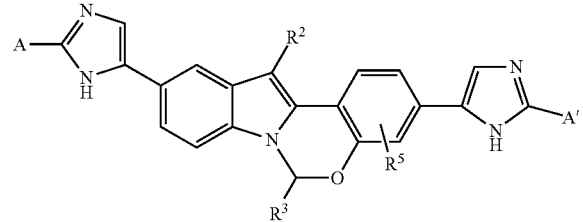

24 Claims, No Drawings

(56) References Cited

U.S. PATENT DOCUMENTS

| | | |
|---|---|---|
| 2008/0299075 A1 | 12/2008 | Bachand et al. |
| 2009/0004111 A1 | 1/2009 | Rice et al. |
| 2009/0042860 A1 | 2/2009 | Bergstrom et al. |
| 2010/0316607 A1 | 12/2010 | Or et al. |
| 2011/0104109 A1 | 5/2011 | Bennett et al. |
| 2011/0130361 A1 | 6/2011 | Grimm et al. |
| 2011/0223134 A1 | 9/2011 | Nair et al. |
| 2011/0224211 A1 | 9/2011 | Schmitz et al. |
| 2012/0040962 A1 | 2/2012 | Li et al. |
| 2012/0083448 A1 | 4/2012 | Xu et al. |
| 2013/0156731 A1 | 6/2013 | Chen et al. |
| 2013/0164258 A1 | 6/2013 | Chen et al. |

FOREIGN PATENT DOCUMENTS

| | | | |
|---|---|---|---|
| JP | 10101591 | 4/1984 | |
| WO | 2007009120 A2 | 1/2007 | |
| WO | 2007084413 A2 | 7/2007 | |
| WO | 2009023179 A2 | 2/2009 | |
| WO | 2009102325 A1 | 8/2009 | |
| WO | 2009102568 A1 | 8/2009 | |
| WO | 2010041687 A1 | 4/2010 | |
| WO | 2010065674 A1 | 6/2010 | |
| WO | 2010011483 A1 | 9/2010 | |
| WO | 2012040923 A1 | 4/2012 | |
| WO | 2012050850 A1 | 4/2012 | |
| WO | WO 2012041014 A1 * | 4/2012 | ........... C07D 471/04 |
| WO | 2014110705 A1 | 7/2014 | |

OTHER PUBLICATIONS

CAPLUS Accession No. 1980:471599, (1980).
CAPLUS Accession No. 2009:295362 (JP2009-054809), (2009).
Marsilje, T.H., et al, "Optimization of Small Molecule Agonists of the Thrombopoietin (Tpo) Receptor Derived From a Benzo[a]Carbazole Hit Scaffold", Bioorganic and Medicinal Chem. Lett., 2008, pp. 5259-5262, vol. 18, US.
Wilson, et al., "Tunable DNA Photocleavage by an Acridine-Imidazole Conjugate", Inorganic Chemistry, 2005, pp. 6159-6173, vol. 44, No. 18, US.

* cited by examiner

US 9,555,038 B2

HETEROCYCLE-SUBSTITUTED TETRACYCLIC COMPOUNDS AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/CN2013/001676, filed Dec. 31, 2013 which claims priority to PCT International Application No. PCT/CN2013/000038, filed Jan. 16, 2013. Each of the aforementioned PCT and priority applications is incorporated by reference in its entirety.

FIELD OF THE INVENTION

The present invention relates to novel Heterocycle-Substituted Tetracyclic Compounds, compositions comprising at least one Heterocycle-Substituted Tetracyclic Compound, and methods of using the Heterocycle-Substituted Tetracyclic Compounds for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal.

Recent attention has been focused toward the identification of inhibitors of HCV NS5A. HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y. et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula

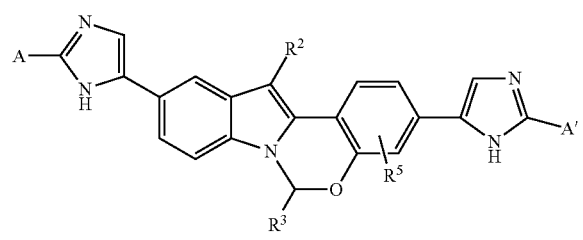

(I)

or a pharmaceutically acceptable salt thereof, wherein:
A is:

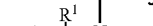

A' is:

each occurrence of $R^1$ is independently selected from H, $C_1$-$C_6$ alkyl, $C_1$-$C_6$ haloalkyl and halo;
each occurrence of $R^{1A}$ is independently selected from H, $C_1$-$C_6$ alkyl, $C_1$-$C_6$ haloalkyl and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;
each occurrence of $R^{1B}$ is independently H, $C_1$-$C_6$ alkyl, $C_1$-$C_6$ haloalkyl or halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group having the formula —$CH_2$— or —$CH_2CH_2$—;
$R^2$ is H, $C_1$-$C_6$ alkyl, $C_3$-$C_7$ cycloalkyl, phenyl or halo;
$R^3$ is thiazolyl or thiadiazolyl wherein said thiazolyl group and said thiadiazolyl group can be optionally substituted on one or more ring carbon atoms with $R^6$, and wherein said thiazole group or thiadiazole group can optionally be fused to a $C_3$-$C_7$ cycloalkyl group;
each occurrence of $R^4$ is independently selected from —C(O)—C($R^7$)$_2$NHC(O)O—$R^8$;
$R^5$ represents up to 3 substituents, each independently selected from halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, $C_6$-$C_{10}$ aryl, benzyl and —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said $C_6$-$C_{10}$ aryl group, or the phenyl moiety of said benzyl group can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);
$R^6$ represents up to 2 substituents, each independently selected from halo, —CN, $C_1$-$C_6$ alkyl, $C_1$-$C_6$ haloalkyl, —O—($C_1$-$C_6$ haloalkyl), $C_2$-$C_6$ alkynyl, $C_1$-$C_6$ hydroxyalkyl, —($C_1$-$C_6$ alkylene)$_m$-O—$C_1$-$C_6$ alkyl, —N($R^6$)$_2$, $C_6$-$C_{10}$ aryl, —($C_1$-$C_6$ alkylene)$_m$-($C_3$-$C_7$ cycloalkyl), —O—($C_6$-$C_{10}$ aryl), 4 to 7-membered monocyclic heterocycloalkyl, 5 or 6-membered monocyclic heteroaryl, —O-(5 or 6-membered monocyclic heteroaryl), 8 to 10-membered bicyclic heteroaryl and —O-(8 to 10-membered bicyclic heteroaryl), wherein said $C_6$-$C_{10}$ aryl group, said $C_3$-$C_7$ cycloalkyl group, said 4 to 7-membered monocyclic heterocycloalkyl group, said 5 or 6-membered monocyclic heteroaryl group and said 8 to 10-membered bicyclic heteroaryl group, can be optionally substituted with up to 3 groups, each independently selected from halo, hydroxy, $C_1$-$C_6$ alkyl, $C_1$-$C_6$ haloalkyl and —O—$C_1$-$C_6$ alkyl, and wherein said $C_6$-$C_{10}$ aryl group, said 5 or 6-membered monocyclic heteroaryl group and said 8 to 10-membered bicyclic heteroaryl group, can be optionally fused with a 3 to 6 membered cycloalkyl group;

each occurrence of $R^7$ is independently selected from H, $C_1$-$C_6$ alkyl, $C_1$-$C_6$ haloalkyl, phenyl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N($R^6$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^7$ groups, that are attached to a common carbon atom, together with the common carbon atom to which they are attached, join to form a $C_3$-$C_7$ cycloalkyl group;

each occurrence of $R^8$ is independently $C_1$-$C_6$ alkyl, $C_3$-$C_7$ cycloalkyl and $C_6$-$C_{10}$ aryl; and each occurrence of m is independently 0 or 1.

The Compounds of Formula (I) (also referred to herein as the "Heterocycle-Substituted Tetracyclic Compounds") and pharmaceutically acceptable salts thereof can be useful, for example, for inhibiting HCV viral replication or replicon activity, and for treating or preventing HCV infection in a patient. Without being bound by any specific theory, it is believed that the Heterocycle-Substituted Tetracyclic Compounds inhibit HCV viral replication by inhibiting HCV NS5A.

Accordingly, the present invention provides methods for treating or preventing HCV infection in a patient, comprising administering to the patient an effective amount of at least one Heterocycle-Substituted Tetracyclic Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Heterocycle-Substituted Tetracyclic Compounds, compositions comprising at least one Heterocycle-Substituted Tetracyclic Compound, and methods of using the Heterocycle-Substituted Tetracyclic Compounds for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Heterocycle-Substituted Tetracyclic Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —$N(alkyl)_2$, —NH(cycloalkyl), —O—C(O)-alkyl, —O—C(O)-aryl, —O—C(O)— cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —$N(alkyl)_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

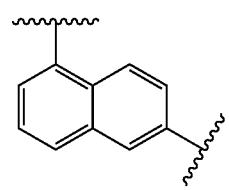

is understood to represent both:

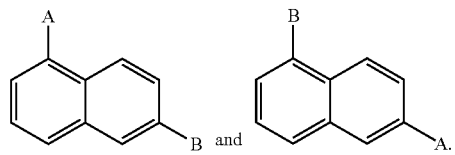

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

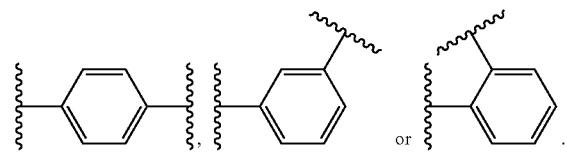

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms.

Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

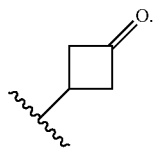 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms. Unless otherwise indicated, a cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and had 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

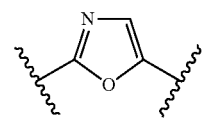 [SMILES: *c1cnc(*)o1]

is understood to represent both:

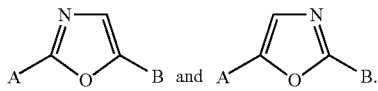

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

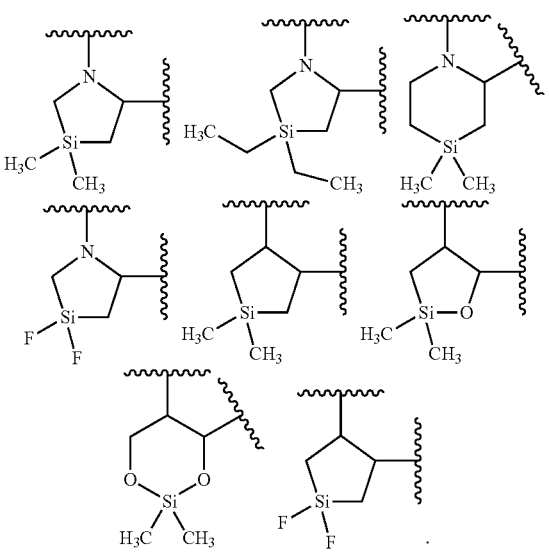

A ring carbon atom of a heterocycloalkyl group may be functionalized as a carbonyl group. An illustrative example of such a heterocycloalkyl group is:

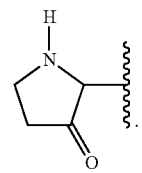

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having from 4 to 6 ring atoms. Unless otherwise indicated, a heterocycloalkenyl group is unsubstituted.

Examples of "ring system substituents" include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O— alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

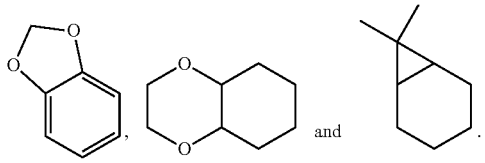

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently C$_1$-C$_6$ alkyl, phenyl or a 3 to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include —CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., R$^1$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Heterocycle-Substituted Tetracyclic Compound or a pharmaceutically acceptable salt or solvate of the compound. The transformation may occur by various mechanisms (e.g., by metabolic or chemical processes), such as, for example, through hydrolysis in blood.

For example, if a Heterocycle-Substituted Tetracyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 6 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)alkylcarbamoyl-(C$_1$-C$_2$)alkyl and piperidino-, pyrrolidino- or morpholino(C$_2$-C$_3$)alkyl, and the like.

Similarly, if a Heterocycle-Substituted Tetracyclic Compound contains an alcohol functional group, a prodrug can be formed by the replacement of the hydrogen atom of the alcohol group with a group such as, for example, $(C_1\text{-}C_6)$alkanoyloxymethyl, 1-$((C_1\text{-}C_6)$alkanoyloxy)ethyl, 1-methyl-1-$((C_1\text{-}C_6)$alkanoyloxy)ethyl, $(C_1\text{-}C_6)$alkoxycarbonyloxymethyl, N—$(C_1\text{-}C_6)$alkoxycarbonylaminomethyl, succinoyl, $(C_1\text{-}C_6)$alkanoyl, α-amino$(C_1\text{-}C_4)$alkyl, α-amino$(C_1\text{-}C_4)$alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O$(C_1\text{-}C_6)$alkyl)$_2$ or glycosyl (the radical resulting from the removal of a hydroxyl group of the hemiacetal form of a carbohydrate), and the like.

If a Heterocycle-Substituted Tetracyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1\text{-}C_{10})$alkyl, $(C_3\text{-}C_7)$cycloalkyl, benzyl, a natural α-aminoacyl, —C(OH)C(O)OY$^1$ wherein Y$^1$ is H, $(C_1\text{-}C_6)$alkyl or benzyl, —C(OY$^2$)Y$^3$ wherein Y$^2$ is $(C_1\text{-}C_4)$alkyl and Y$^3$ is $(C_1\text{-}C_6)$alkyl; carboxy$(C_1\text{-}C_6)$alkyl; amino$(C_1\text{-}C_4)$alkyl or mono-N- or di-N,N—$(C_1\text{-}C_6)$alkylaminoalkyl; —C(Y$^4$)Y$^5$ wherein Y$^4$ is H or methyl and Y$^5$ is mono-N- or di-N,N—$(C_1\text{-}C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1\text{-}4}$alkyl, —O—$(C_{1\text{-}4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1\text{-}20}$ alcohol or reactive derivative thereof, or by a 2,3-di($C_{6\text{-}24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Heterocycle-Substituted Tetracyclic Compounds can form salts which are also within the scope of this invention. Reference to a Heterocycle-Substituted Tetracyclic Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Heterocycle-Substituted Tetracyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Heterocycle-Substituted Tetracyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Heterocycle-Substituted Tetracyclic Compounds may be atropisomers (e.g., substituted biaryls) and are considered as part of this invention. Enantiomers can also be directly separated using chiral chromatographic techniques.

It is also possible that the Heterocycle-Substituted Tetracyclic Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Heterocycle-Substituted Tetracyclic Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Heterocycle-Substituted Tetracyclic Compounds, and of the salts, solvates, hydrates, esters and prodrugs of the Heterocycle-Substituted Tetracyclic Compounds, are intended to be included in the present invention.

The following abbreviations are used below and have the following meanings: Ac is acyl; AcCl is acetyl chloride; AcOH or HOAc is acetic acid; Amphos is (4-(N,N)-dimethylaminophenyl)-di-tertbutylphosphine; Aq is aqueous; $BF_3.OEt_2$ is boron trifluoride etherate; BOC or Boc is tert-butyloxycarbonyl; $Boc_2O$ is Boc anhydride; Boc-Pro-OH is Boc protected proline; L-Boc-Val-OH is Boc protected L-valine; BOP is Benzotriazole-1-yl-oxy-tris-(dimethylamino)-phosphonium hexafluorophosphate; n-BuLi is n-butyllithium; CBZ or Cbz is carbobenzoxy; DCM is dichloromethane; DDQ is 2,3-dichloro-5,6-dicyano-1,4-benzoquinone; Dess-Martin reagent is, 1,1-Triacetoxy-1,1-dihydro-1,2-benziodoxol-3(1H)-one; DIPEA is diisopropylethylamine; DME is dimethoxyethane; DMF is N,N-dimethylformamide; dppf is diphenylphosphinoferrocene; DMSO is dimethylsulfoxide; EtMgBr is ethylmagnesium bromide; EtOAc is ethyl acetate; $Et_2O$ is diethyl ether; $Et_3N$ or $NEt_3$ is triethylamine; HATU is O-(7-azabenzotriazol-1-yl)-N,N,N',N'-tetramethyluronium hexafluorophosphate; HPLC is high performance liquid chromatography; HRMS is high resolution mass spectrometry; KOAc is potassium acetate; LCMS is liquid chromatography/mass spectrometry; LiHMDS is lithium hexamethyldisilazide; LRMS is low resolution mass spectrometry; MeI is iodomethane; MeOH is methanol; NBS is N-bromosuccinimide; $NH_4OAc$ is ammonium acetate; NMM is N-methylmorpholine; Pd/C is palladium on carbon; $Pd(PPh_3)_4$ is tetrakis(triphenylphosphine)palladium(0); $PdCl_2(dppf)_2$ is [1,1'-Bis(diphenylphosphino) ferrocene]dichloro palladium(II); $PdCl_2(dppf)_2.CH_2Cl_2$ is [1,1'-Bis(diphenylphosphino)ferrocene] dichloro palladium(II) complex with dichloromethane; $pinacol_2B_2$ is bis(pinacolato)diboron; PPTS is pyridinium p-toluene sulfonate; RPLC is reverse-phase liquid chromatography; Select-F is 1-Chloromethyl-4-Fluoro-1,4-Diazoniabicyclo[2.2.2]Octane Bis-(Tetrafluoroborate); SEM-Cl is 2-(trimethylsilyl)ethoxymethyl chloride; TBAF is tetrabutylammonium fluoride; TBDMSCl is tert-butyldimethylsilyl chloride; TFA is trifluoroacetic acid; $Tf_2O$ is triflic anhydride; THF is tetrahydrofuran; TLC is thin-layer chromatography; and TosCl is p-toluenesulfonyl chloride.

The Compounds of Formula (I)

The present invention provides Heterocycle-Substituted Tetracyclic Compounds of Formula (I):

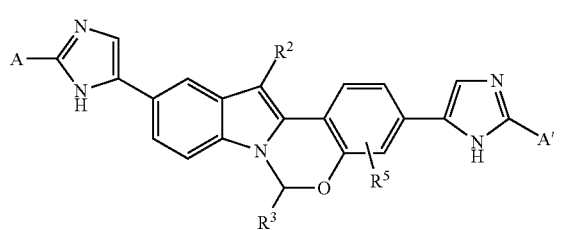

and pharmaceutically acceptable salts thereof, wherein A, A', $R^2$, $R^3$, $R^4$ and $R^5$ are defined above for the Compounds of Formula (I).

In one embodiment, $R^2$ is H

In another embodiment, $R^2$ is halo.

In another embodiment, $R^2$ is $C_1$-$C_6$ alkyl.

In one embodiment, $R^5$ is H.

In another embodiment, $R^5$ is F.

In one embodiment, A and A' are each a 5-membered heterocycloalkyl group.

In another embodiment, A and A' are each a 6-membered heterocycloalkyl group.

In another embodiment, A and A' are each independently selected from:

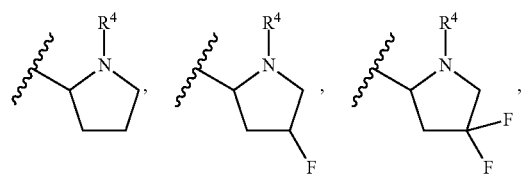

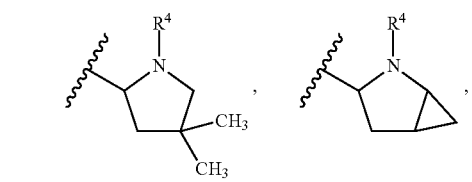

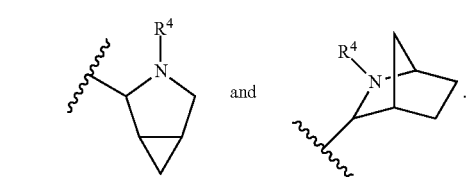

In still another embodiment, A and A' are each independently selected from:

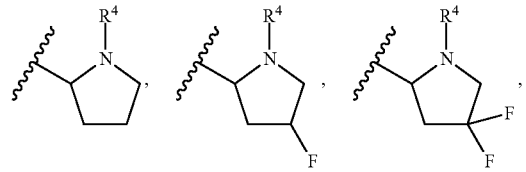

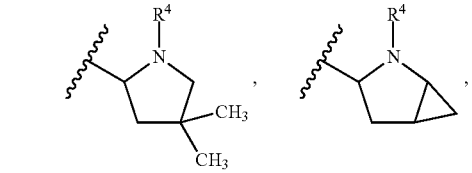

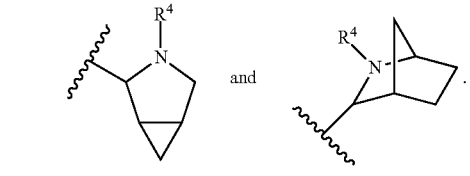

In another embodiment, A and A' are each independently selected from:

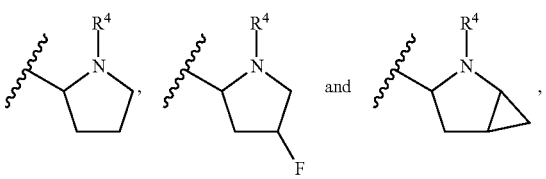

In another embodiment, A and A' are each independently:

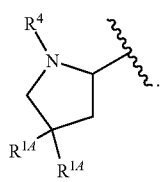

In another embodiment, A and A' are each independently:

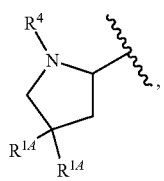

wherein each occurrence of $R^{13}$ is independently H, $CH_3$, or F.

In one embodiment, each occurrence of $R^4$ is independently:

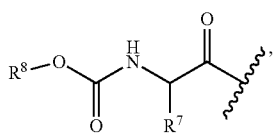

wherein $R^7$ is selected from $C_1$-$C_6$ alkyl, $C_1$-$C_6$ haloalkyl and 4 to 6-membered monocyclic heterocycloalkyl, wherein said 4 to 6-membered monocyclic heterocycloalkyl group can be optionally substituted with up to five groups, each independently selected from halo, $C_1$-$C_6$ alkyl and $C_3$-$C_7$ cycloalkyl, and wherein said 4 to 6-membered monocyclic heterocycloalkyl group can be optionally substituted on a ring carbon atom with a spirocyclic $C_3$-$C_6$ cycloalkyl group; and $R^8$ is $C_1$-$C_6$ alkyl.

In one embodiment, each occurrence of $R^4$ is independently:

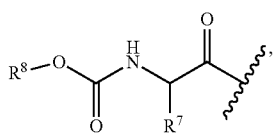

wherein $R^7$ is isopropyl, —CF(CH$_3$)$_2$,
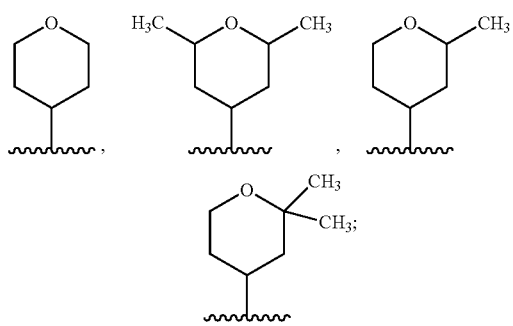
and $R^8$ is $C_1$-$C_6$ alkyl.
In another embodiment, each occurrence of $R^4$ is independently:
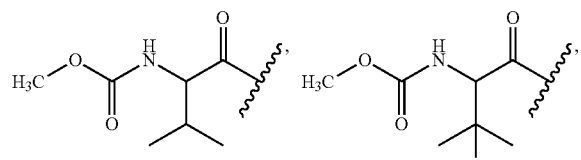
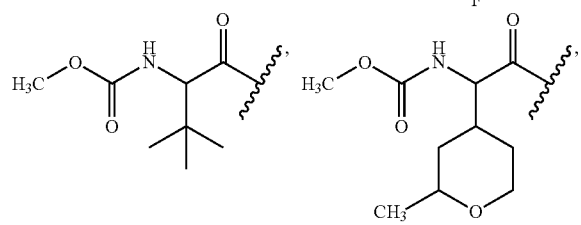
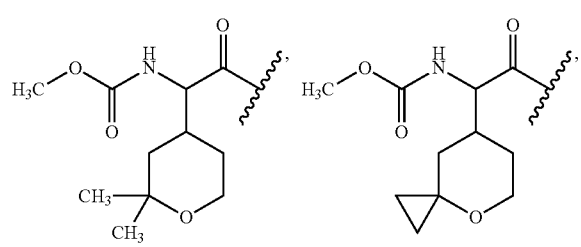
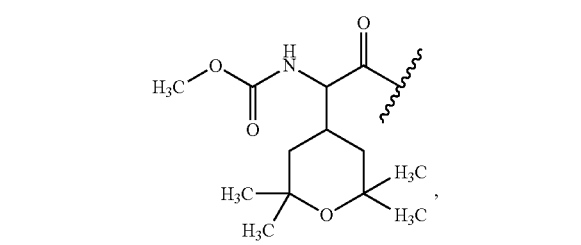
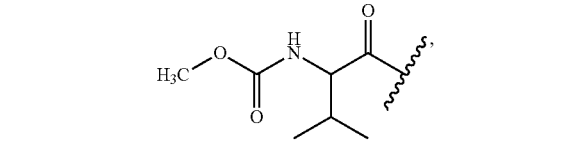 [SMILES: *C(=O)C(NC(=O)OC)C(C)C]
In one embodiment, A and A' are each independently selected from:
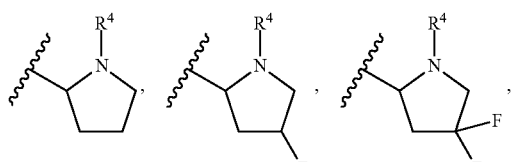
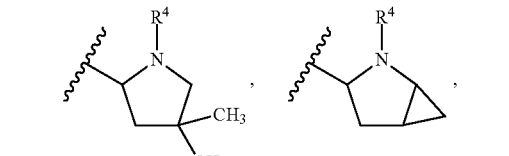
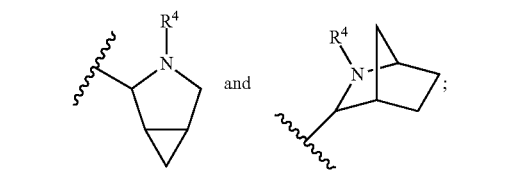
and each occurrence of $R^4$ is independently:
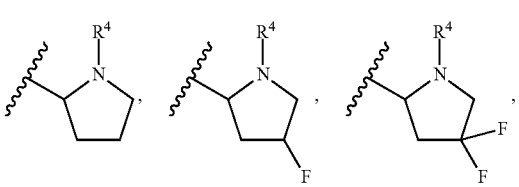
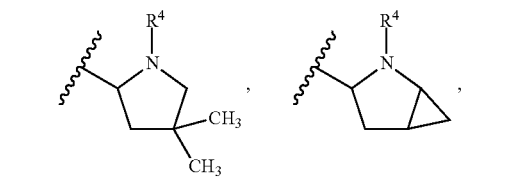
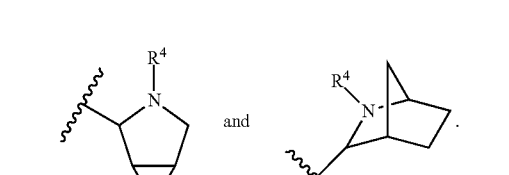
wherein $R^7$ is isopropyl, —CF(CH$_3$)$_2$,
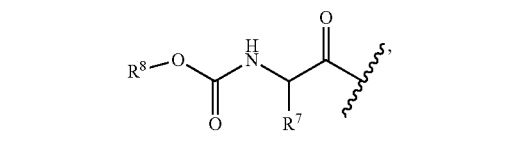
and $R^8$ is $C_1$-$C_6$ alkyl.

In another embodiment, A and A' are each independently selected from:

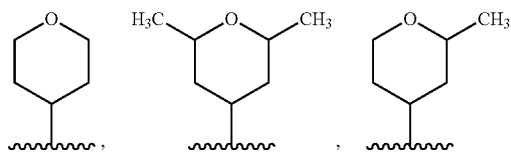

and $R^4$ is:

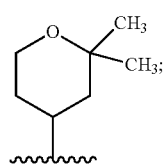

In yet another embodiment, A and A' are each:

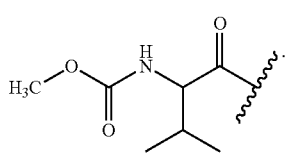

wherein each occurrence of $R^{13}$ is independently H, $CH_3$, or F; each occurrence of $R^4$ is independently:

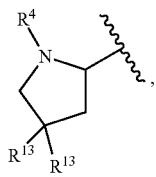

wherein $R^7$ is isopropyl, $-CF(CH_3)_2$,

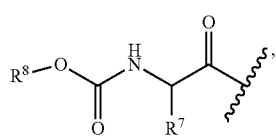

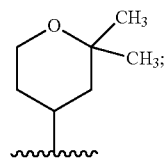

and $R^8$ is $C_1$-$C_6$ alkyl.

In another embodiment, A and A' are each independently selected from:

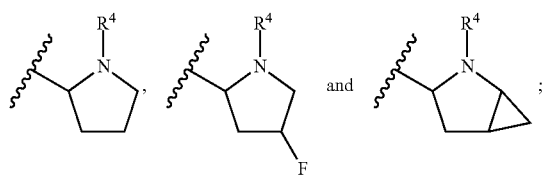

each occurrence of $R^4$ is independently:

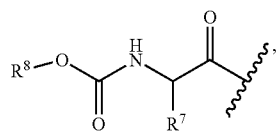

wherein $R^7$ is isopropyl, $-CF(CH_3)_2$,

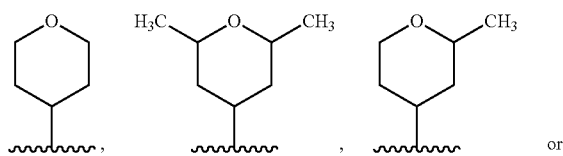

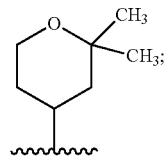

and $R^8$ is methyl.

In one embodiment, variables A, A', $R^2$, $R^3$, $R^4$ and $R^5$ for the Compounds of Formula (I) are selected independently of each other.

In another embodiment, the Compounds of Formula (I) are in substantially purified form.

In one embodiment, the Compounds of Formula (I) have the formula (Ia):

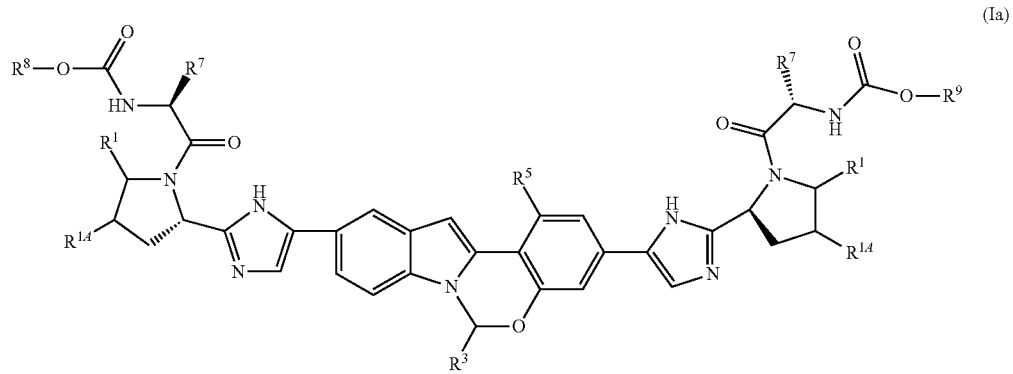

(Ia)

or a pharmaceutically acceptable salt thereof,
wherein:
$R^1$ is H;
$R^{1A}$ is H, or an $R^{1A}$ groups and an $R^1$ group that are attached to same ring, together with the ring carbon atoms to which they are attached, can combine to form a fused cyclopropyl group;
$R^3$ is:

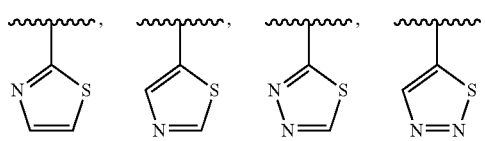

wherein $R^3$ can be optionally substituted on one or more ring carbon atoms with a group selected from methyl, ethyl, n-propyl, isopropyl, t-butyl, —$CF_3$, cyclopropyl, —$CH_2$-cyclopropyl, cyclobutyl, cyclopentyl, methoxy, —O-(halo-substituted phenyl), —$OCF_3$, —$C(CH_3)_2OH$, —$CH_2CH_2OCH_3$, halo-substituted phenyl and —CN;

each occurrence of $R^5$ is independently selected from H, methyl and F;

each occurrence of $R^7$ is independently selected from $C_1$-$C_6$ alkyl, $C_1$-$C_6$ haloalkyl and 4 to 6-membered monocyclic heterocycloalkyl, wherein said 4 to 6-membered monocyclic heterocycloalkyl group can be optionally substituted with up to 5 groups, each independently selected from halo, $C_1$-$C_6$ alkyl and $C_3$-$C_7$ cycloalkyl, and wherein said 4 to 6-membered monocyclic heterocycloalkyl group can be optionally substituted on a ring carbon atom with a spirocyclic $C_3$-$C_6$ cycloalkyl group;

each occurrence of $R^8$ is independently $C_1$-$C_6$ alkyl.

In one embodiment, variables $R^1$, $R^{1A}$, $R^3$, $R^5$, $R^7$ and $R^8$ for the Compounds of Formula (Ia) are selected independently of each other.

In another embodiment, the Compounds of Formula (Ia) are in substantially purified form.

In another embodiment, the Compounds of Formula (I) have the formula (Ib) or (Ic):

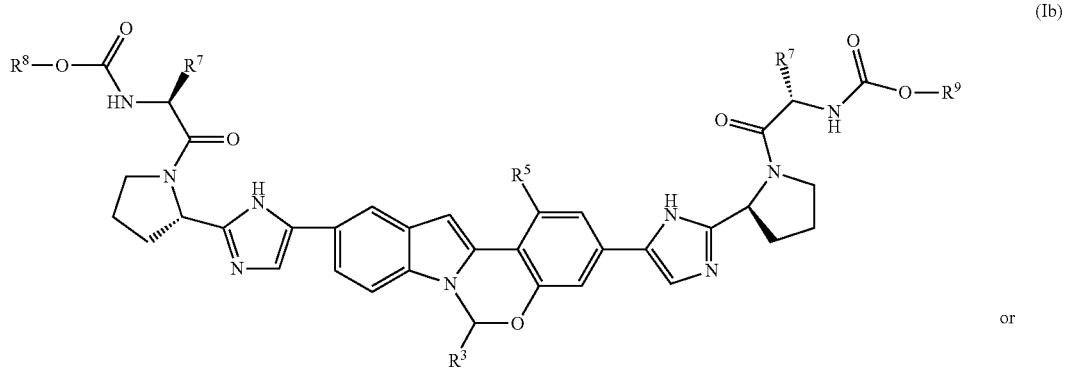

(Ib)

or

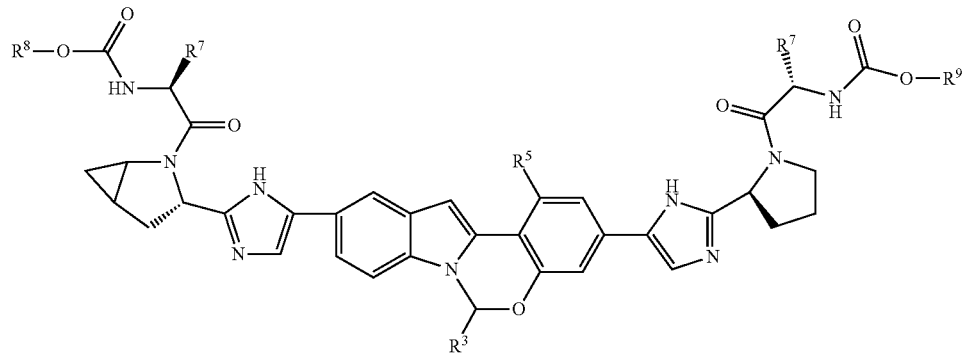
(Ic)
or a pharmaceutically acceptable salt thereof,
wherein:
$R^3$ is:
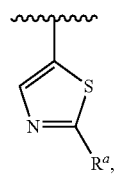
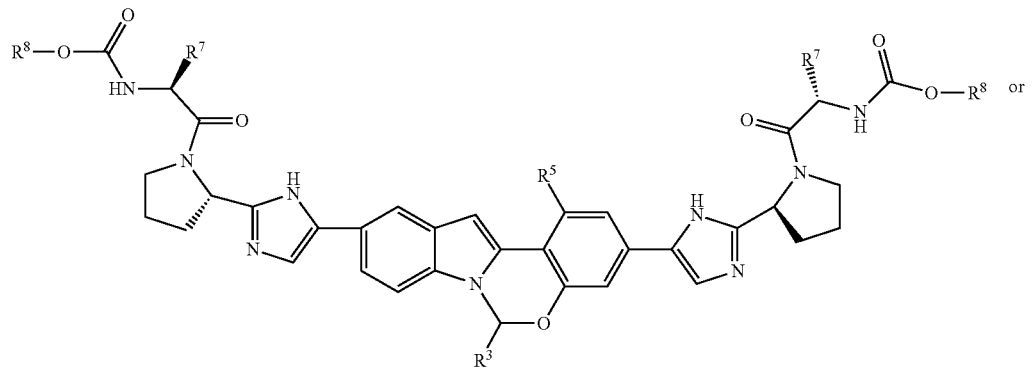
(Ib)
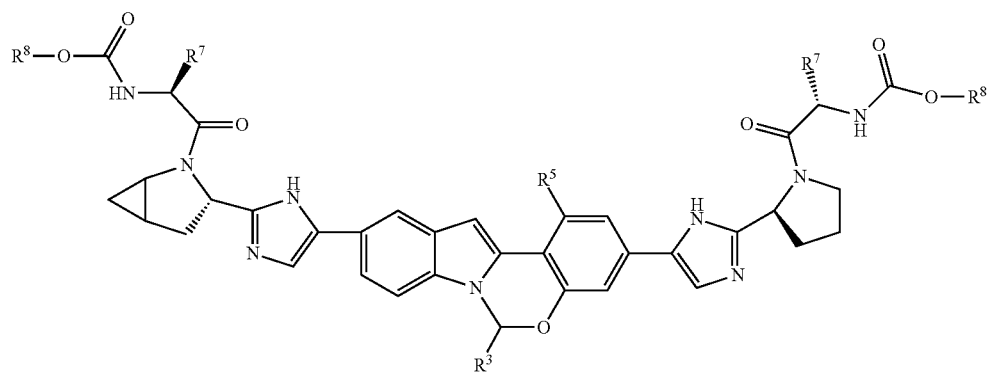
(Ic)

R$^a$ is
or a pharmaceutically acceptable salt thereof,
wherein:
R$^3$ is:

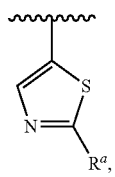

R$^a$ is C$_1$-C$_6$ alkyl or C$_3$-C$_7$ cycloalkyl;
R$^5$ is H or F;
each occurrence of R$^7$ is independently selected from C$_1$-C$_6$ alkyl, C$_1$-C$_6$ haloalkyl or tetrahydropyranyl, wherein said tetrahydropyranyl group can be can be optionally substituted with up to 5 groups, each independently selected from halo, C$_1$-C$_6$ alkyl and C$_3$-C$_7$ cycloalkyl, and wherein said tetrahydropyranyl group can be optionally substituted on a ring carbon atom with a spirocyclic cyclopropyl group; and
each occurrence of R$^8$ is methyl.

In one embodiment, for the compounds of formula (I), (Ia), (Ib) or (Ic), each occurrence of R$^7$ is isopropyl, —CF(CH$_3$)$_2$,

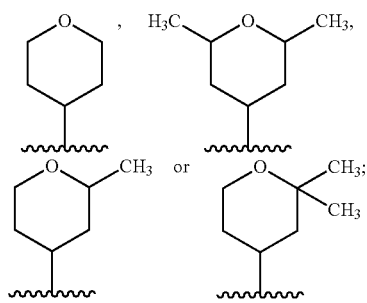

and each occurrence of R$^8$ is C$_1$-C$_6$ alkyl.

In another embodiment, for the compounds of formula (I), (Ia), (Ib) or (Ic), each occurrence of R$^7$ is isopropyl, —CF(CH$_3$)$_2$,

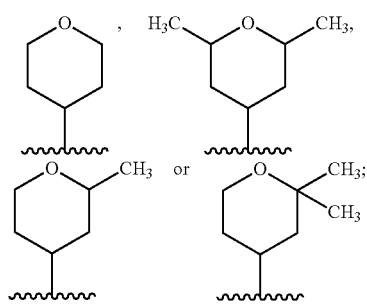

and each occurrence of R$^8$ is methyl.

In one embodiment, for the compounds of formula (Ib) or (Ic), R$^a$ is cyclopropyl, cyclobutyl, cyclopentyl, n-propyl, isopropyl, isobutyl or t-butyl; R$^5$ is F and each occurrence of R$^7$ is independently selected from isopropyl, —CF(CH$_3$)$_2$ or:

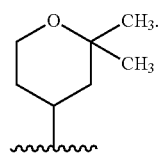

In another embodiment, for the compounds of formula (Ib) or (Ic), R$^a$ is cyclopropyl or cyclobutyl; R$^5$ is F and each occurrence of R$^7$ is independently isopropyl or —CF(CH$_3$)$_2$.

In one embodiment, for the compounds of formula (I), (Ia), (Ib) or (Ic), R$^3$ is:

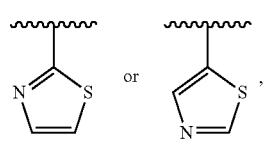 [SMILES: *c1nccs1 ; *c1cncs1]

each of which can be optionally substituted with up to two R$^6$ groups.

In another embodiment, for the compounds of formula (I), (Ia), (Ib) or (Ic), R$^3$ is:

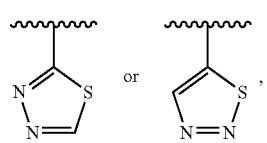

each of which can be optionally substituted with up to two R$^6$ groups.

In one embodiment, variables R$^3$, R$^5$, R$^7$ and R$^8$ for the Compounds of Formula (Ib) are selected independently of each other.

In another embodiment, the Compounds of Formula (Ib) are in substantially purified form.

In one embodiment, variables R$^3$, R$^5$, R$^7$ and R$^8$ for the Compounds of Formula (Ic) are selected independently of each other.

In another embodiment, the Compounds of Formula (Ic) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine; (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 1-547, as set forth in the Examples below, and pharmaceutically acceptable salts thereof.

In one embodiment, the invention provides Compounds of Formula (I) having the following structures:

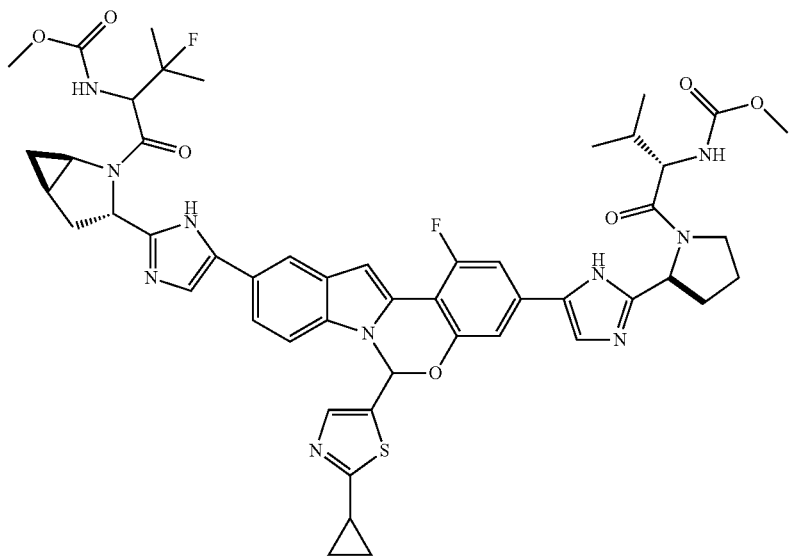

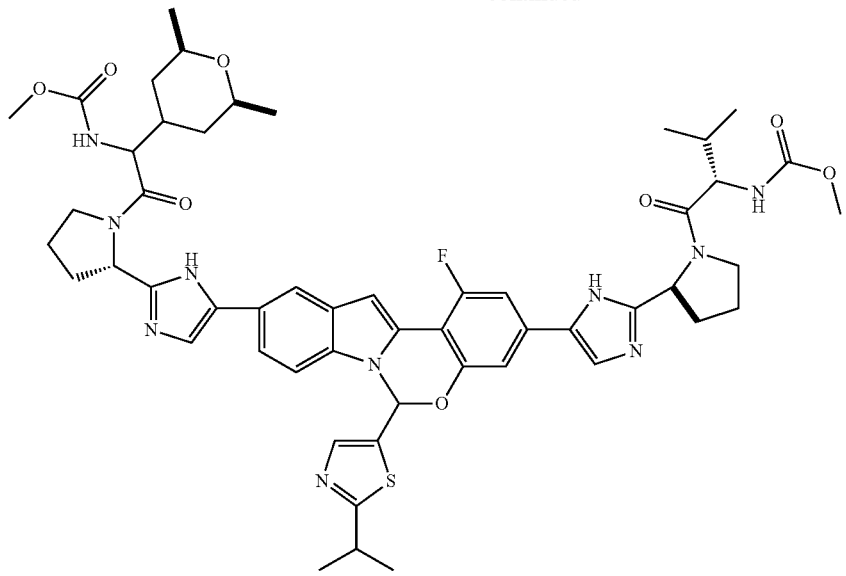
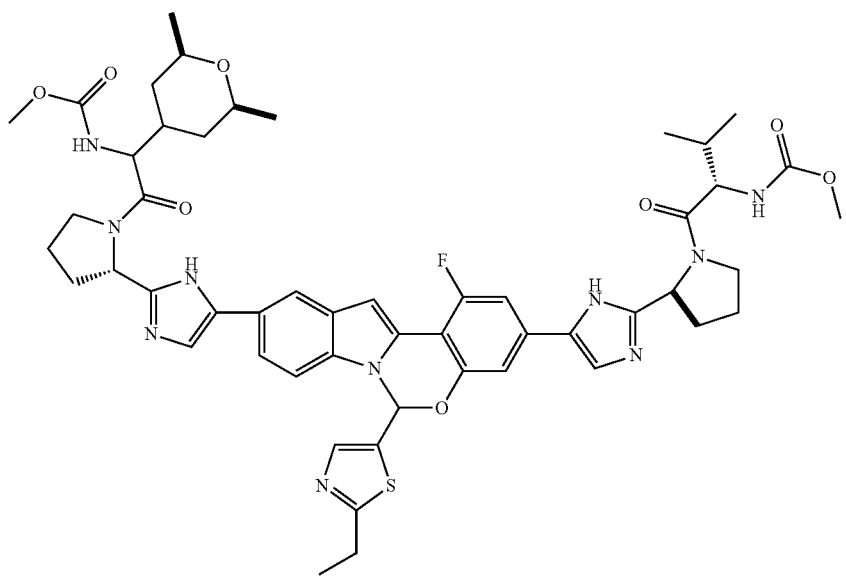
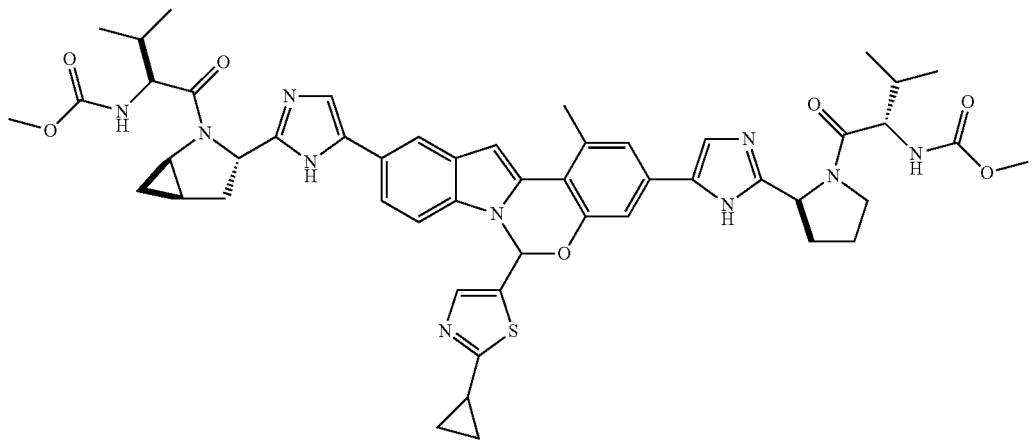

-continued
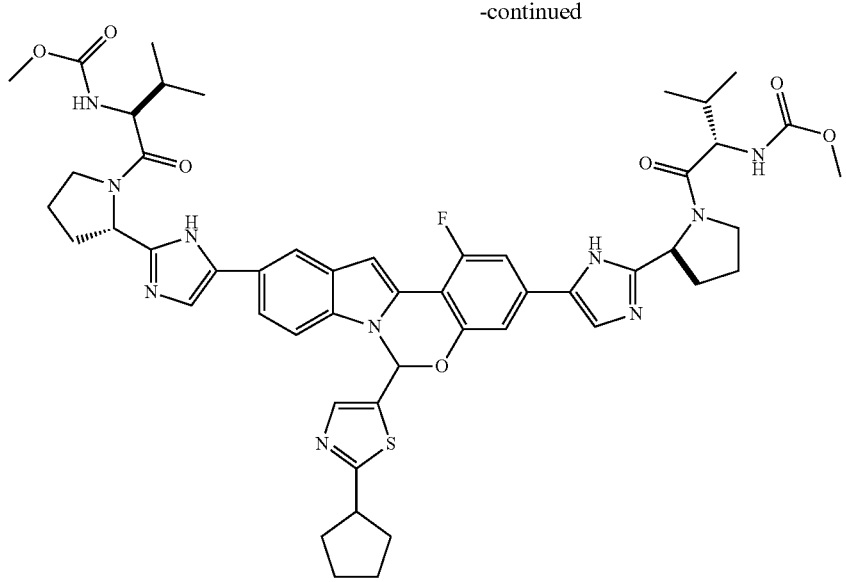
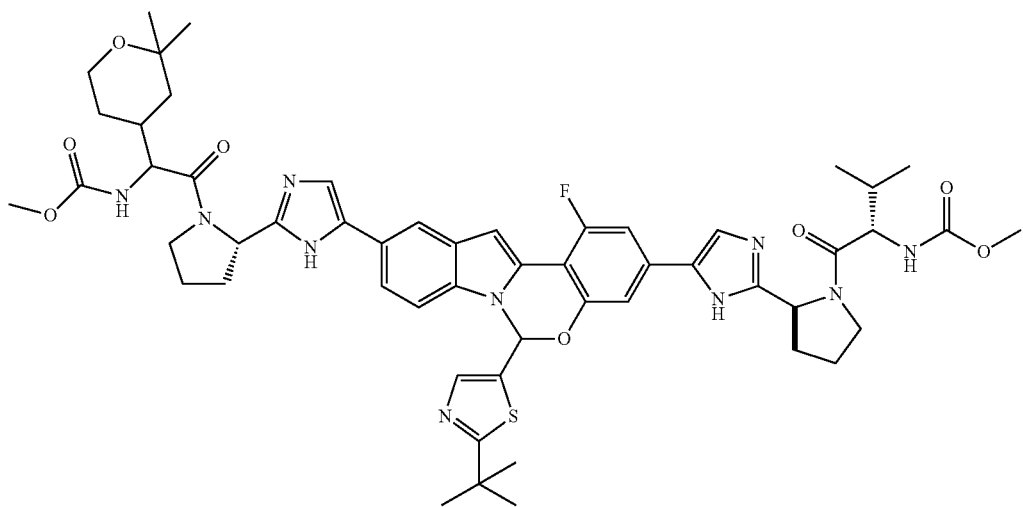
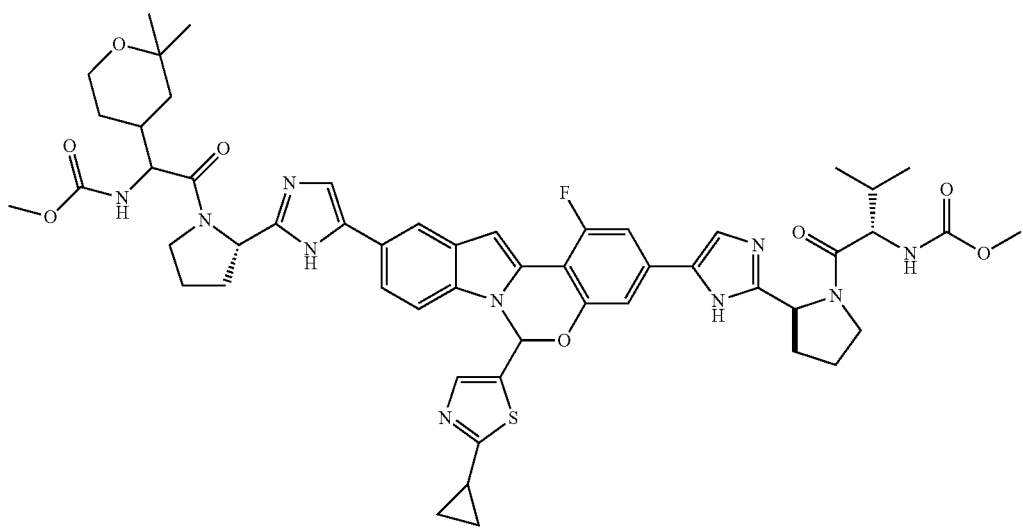

-continued
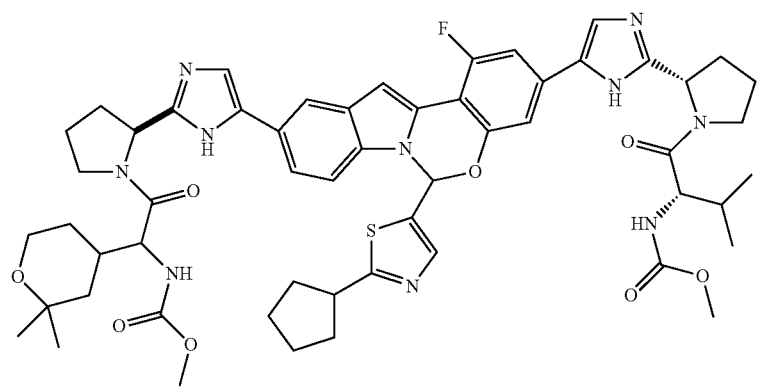
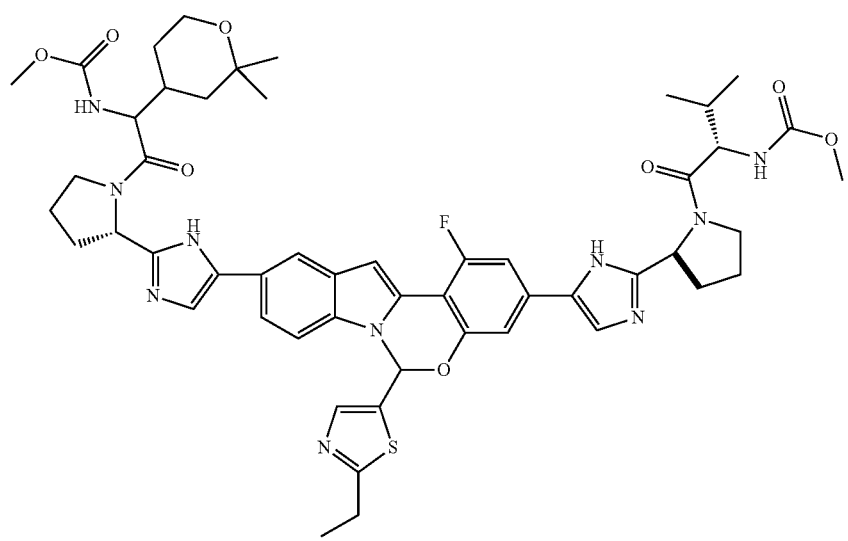
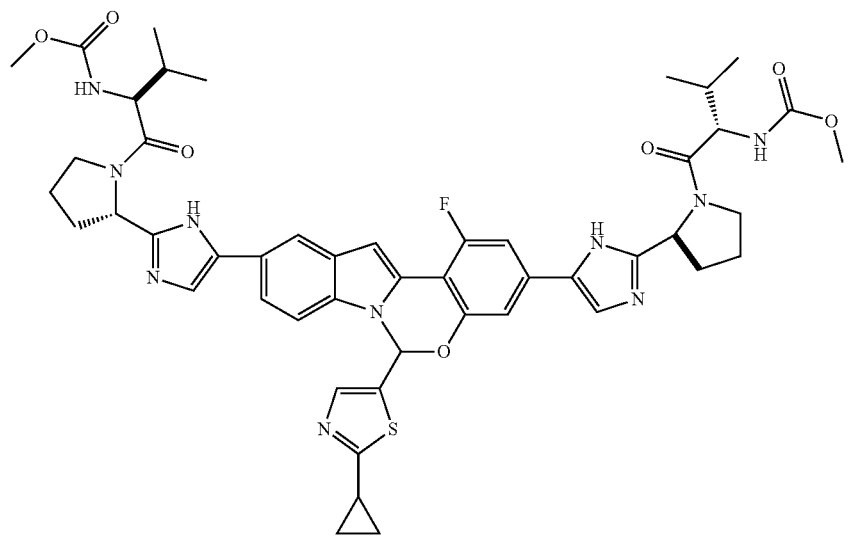

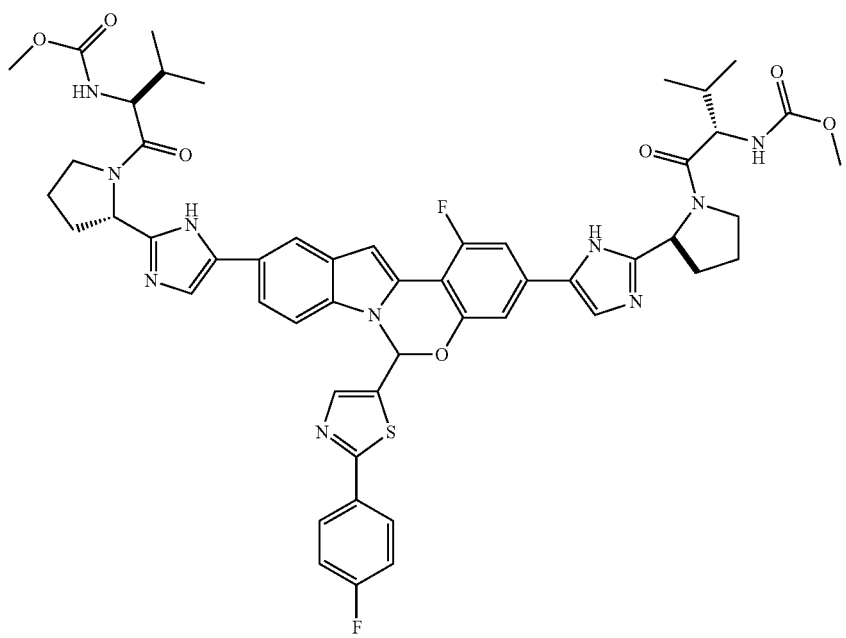
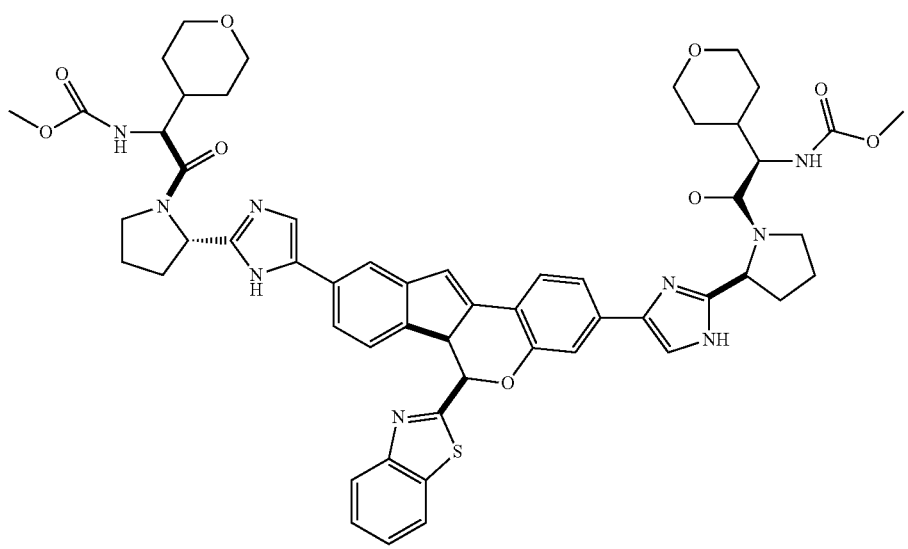
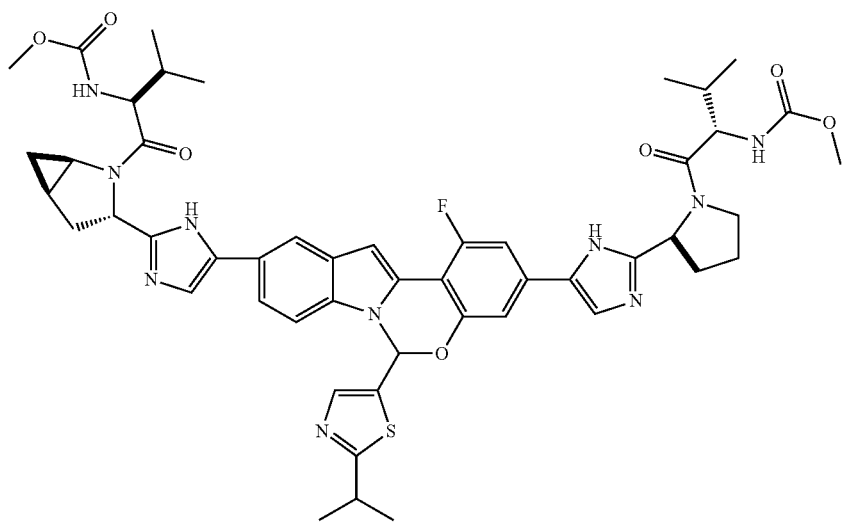

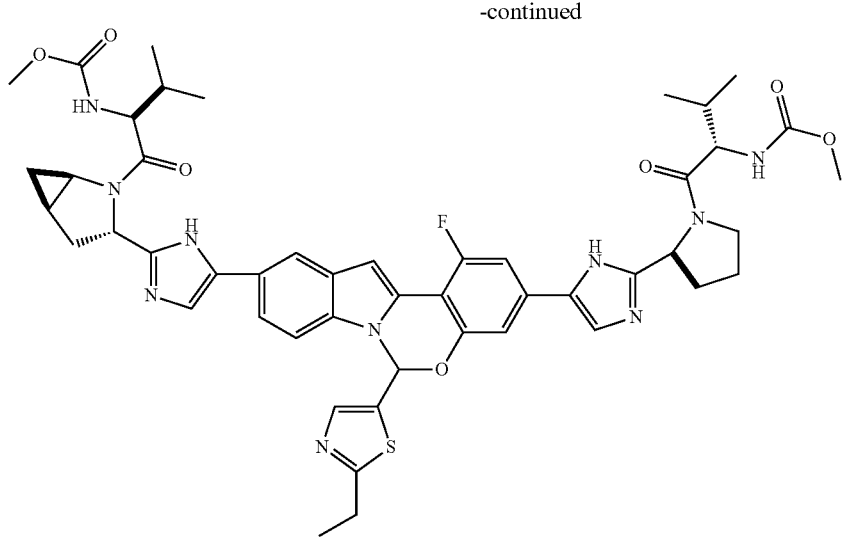
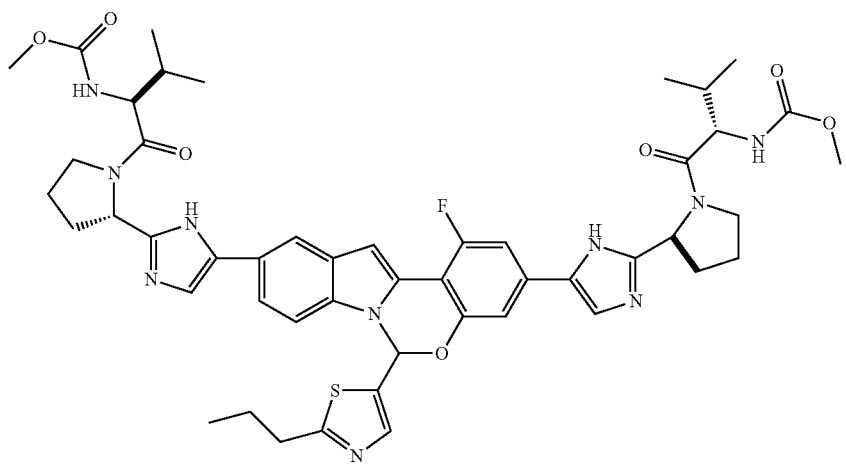
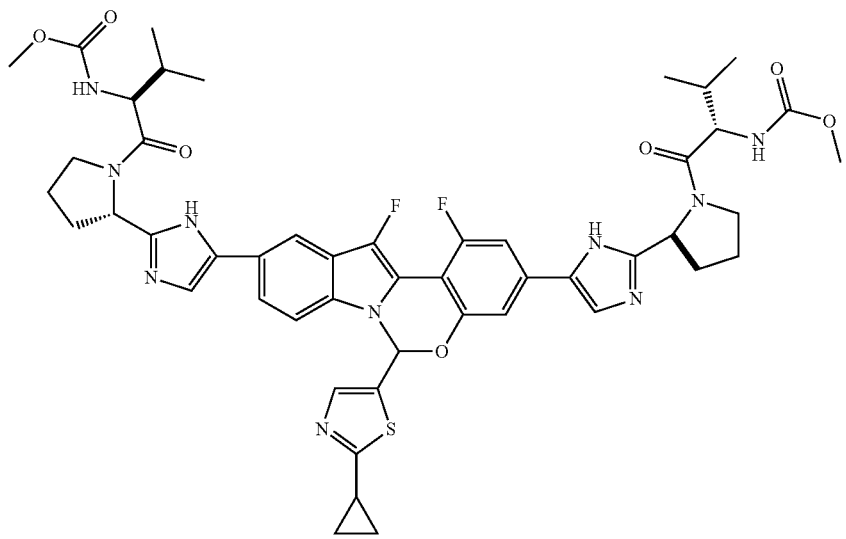

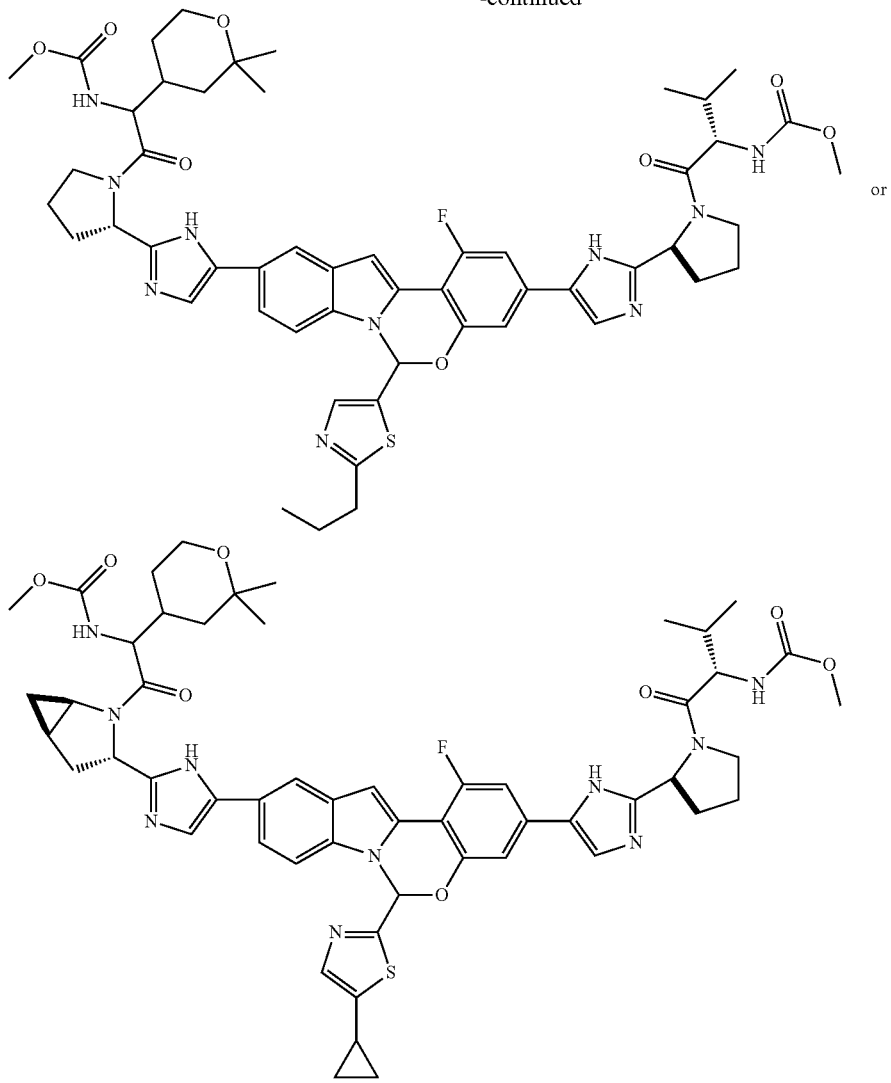

and pharmaceutically acceptable salts thereof

Uses of the Heterocycle-Substituted Tetracyclic Compounds

The Heterocycle-Substituted Tetracyclic Compounds are useful in human and veterinary medicine for treating or preventing a viral infection in a patient. In one embodiment, the Heterocycle-Substituted Tetracyclic Compounds can be inhibitors of viral replication. In another embodiment, the Heterocycle-Substituted Tetracyclic Compounds can be inhibitors of HCV replication. Accordingly, the Heterocycle-Substituted Tetracyclic Compounds are useful for treating viral infections, such as HCV. In accordance with the invention, the Heterocycle-Substituted Tetracyclic Compounds can be administered to a patient in need of treatment or prevention of a viral infection.

Accordingly, in one embodiment, the invention provides methods for treating a viral infection in a patient comprising administering to the patient an effective amount of at least one Heterocycle-Substituted Tetracyclic Compound or a pharmaceutically acceptable salt thereof.

Treatment or Prevention of a Flaviviridae Virus

The Heterocycle-Substituted Tetracyclic Compounds can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Heterocycle-Substituted Tetracyclic Compounds are useful in the inhibition of HCV replication, the treatment of HCV infection and/or reduction of the likelihood or severity of symptoms of HCV infection and the inhibition of HCV viral replication and/or HCV viral production in a cell-based system. For example, the Heterocycle-Substituted Tetracyclic Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Heterocycle-Substituted Tetracyclic Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Heterocycle-Substituted Tetracyclic Compounds are also useful in the preparation and execution of screening assays for antiviral compounds. For example the Heterocycle-Substituted Tetracyclic Compounds are useful for identifying resistant HCV replicon cell lines harboring mutations within NS5A, which are excellent screening tools for more powerful antiviral compounds. Furthermore, the Heterocycle-Substituted Tetracyclic Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Heterocycle-Substituted Tetracyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Heterocycle-Substituted Tetracyclic Compound, or a pharmaceutically acceptable salt thereof, and (ii) at least one additional therapeutic agent that is other than a Heterocycle-Substituted Tetracyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Heterocycle-Substituted Tetracyclic Compound and an additional therapeutic agent may be present in fixed amounts (dosage amounts) in a single dosage unit (e.g., a capsule, a tablet and the like).

In one embodiment, the at least one Heterocycle-Substituted Tetracyclic Compound is administered during a time when the additional therapeutic agent(s) exert their prophylactic or therapeutic effect, or vice versa.

In another embodiment, the at least one Heterocycle-Substituted Tetracyclic Compound and the additional therapeutic agent(s) are administered in doses commonly employed when such agents are used as monotherapy for treating a viral infection.

In another embodiment, the at least one Heterocycle-Substituted Tetracyclic Compound and the additional therapeutic agent(s) are administered in doses lower than the doses commonly employed when such agents are used as monotherapy for treating a viral infection.

In still another embodiment, the at least one Heterocycle-Substituted Tetracyclic Compound and the additional therapeutic agent(s) act synergistically and are administered in doses lower than the doses commonly employed when such agents are used as monotherapy for treating a viral infection.

In one embodiment, the at least one Heterocycle-Substituted Tetracyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Heterocycle-Substituted Tetracyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Heterocycle-Substituted Tetracyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), GS-7977 (sofosbuvir, Gilead), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J. in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, SCH503034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5): 607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, MK-5172 (Merck) and the following compounds:

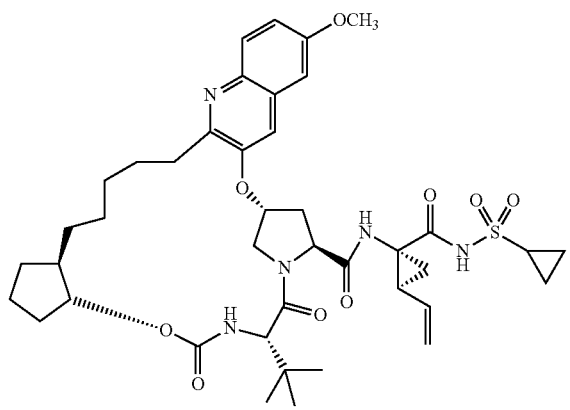

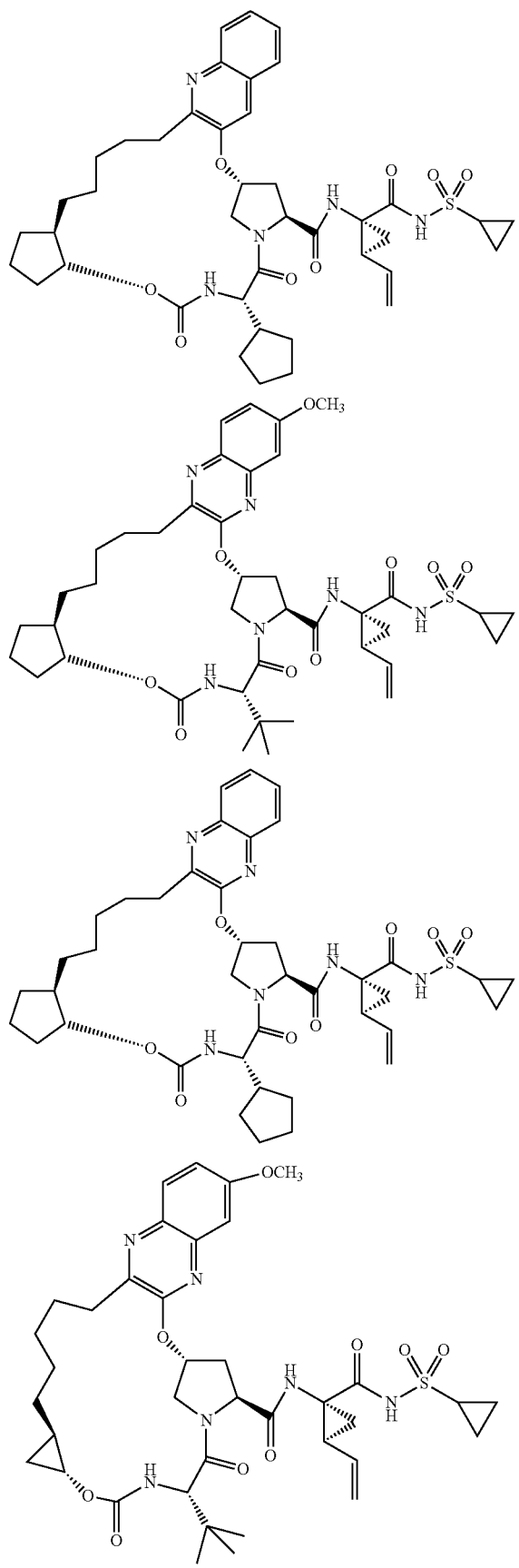

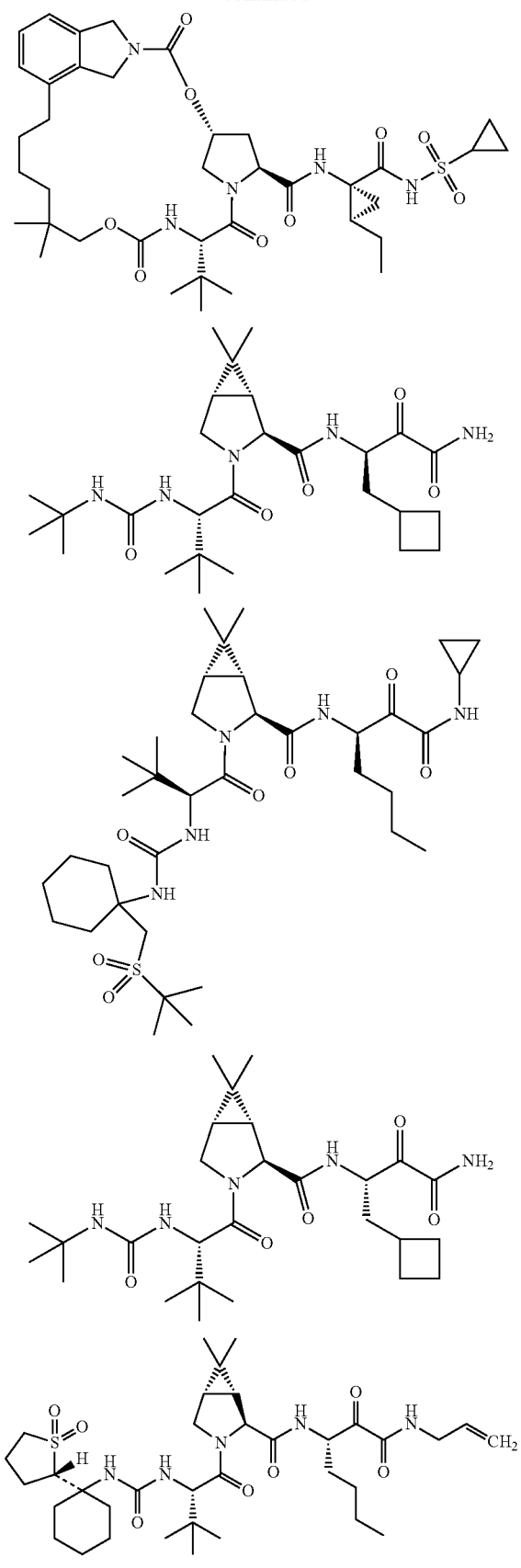

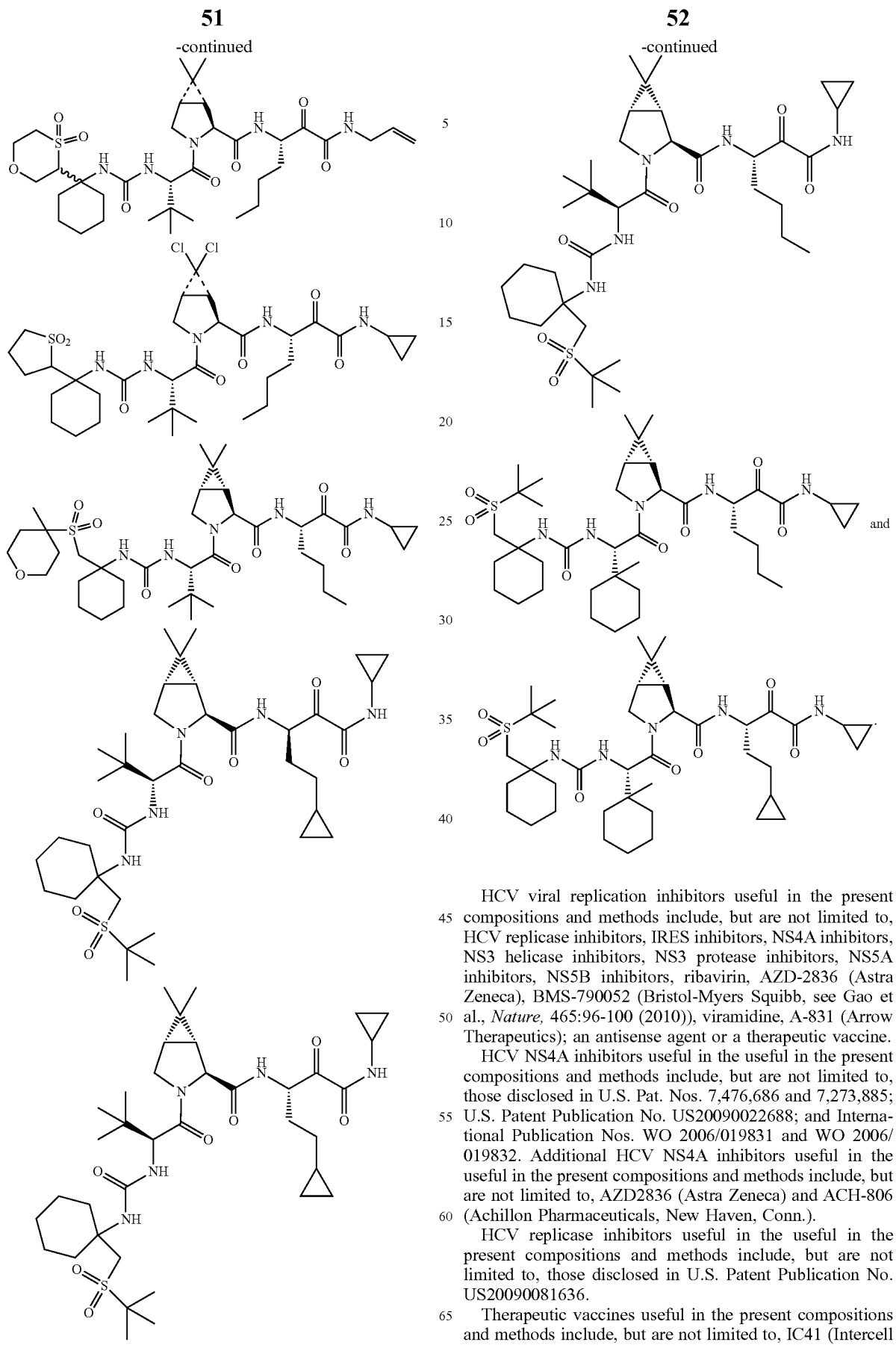

HCV viral replication inhibitors useful in the present compositions and methods include, but are not limited to, HCV replicase inhibitors, IRES inhibitors, NS4A inhibitors, NS3 helicase inhibitors, NS3 protease inhibitors, NS5A inhibitors, NS5B inhibitors, ribavirin, AZD-2836 (Astra Zeneca), BMS-790052 (Bristol-Myers Squibb, see Gao et al., Nature, 465:96-100 (2010)), viramidine, A-831 (Arrow Therapeutics); an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Heterocycle-Substituted Tetracyclic Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside and ribavirin. The combination therapies can include any combination of these additional therapeutic agents.

In another embodiment, one or more compounds of the present invention are administered with one additional therapeutic agent selected from an HCV protease inhibitor and ribavirin.

In still another embodiment, one or more compounds of the present invention are administered with two additional therapeutic agents selected from an HCV protease inhibitor, an HCV replication inhibitor, a nucleoside and ribavirin.

In another embodiment, one or more compounds of the present invention are administered with an HCV protease inhibitor and ribavirin. In another specific embodiment, one or more compounds of the present invention are administered with ribavirin.

In another embodiment, one or more compounds of the present invention are administered with three additional therapeutic agents selected from an HCV protease inhibitor, an HCV replication inhibitor, a nucleoside, a pegylated interferon and ribavirin.

In one embodiment, one or more compounds of the present invention are administered with one or more additional therapeutic agents selected from an HCV polymerase inhibitor, a viral protease inhibitor, and a viral replication inhibitor. In another embodiment, one or more compounds of the present invention are administered with one or more additional therapeutic agents selected from an HCV polymerase inhibitor, a viral protease inhibitor, and a viral replication inhibitor. In another embodiment, one or more compounds of the present invention are administered with one or more additional therapeutic agents selected from an HCV polymerase inhibitor, a viral protease inhibitor, and ribavirin.

In one embodiment, one or more compounds of the present invention are administered with one additional therapeutic agent selected from an HCV polymerase inhibitor, a viral protease inhibitor, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, and a viral replication inhibitor.

In another embodiment, one or more compounds of the present invention are administered with ribavirin and another therapeutic agent.

In another embodiment, one or more compounds of the present invention are administered with ribavirin and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin and a viral protease inhibitor.

In another embodiment, one or more compounds of the present invention are administered with ribavirin and an HCV protease inhibitor.

In another embodiment, one or more compounds of the present invention are administered with ribavirin and either boceprevir or telaprevir.

In a further embodiment, one or more compounds of the present invention are administered with ribavirin and an HCV polymerase inhibitor.

In another embodiment, one or more compounds of the present invention are administered with ribavirin.

In one embodiment, one or more compounds of the present invention are administered with MK-5172.

In one embodiment, one or more compounds of the present invention are administered with sofosbuvir.

Compositions and Administration

Due to their activity, the Heterocycle-Substituted Tetracyclic Compounds are useful in veterinary and human medicine. As described above, the Heterocycle-Substituted Tetracyclic Compounds are useful for treating or preventing HCV infection in a patient in need thereof.

When administered to a patient, the Heterocycle-Substituted Tetracyclic Compounds can be administered as a component of a composition that comprises a pharmaceutically acceptable carrier or vehicle. The present invention provides pharmaceutical compositions comprising an effective amount of at least one Heterocycle-Substituted Tetracyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Heterocycle-Substituted Tetracyclic Compounds are administered orally.

In another embodiment, the one or more Heterocycle-Substituted Tetracyclic Compounds are administered intravenously.

In still another embodiment, the one or more Heterocycle-Substituted Tetracyclic Compounds are administered sublingually.

In one embodiment, a pharmaceutical preparation comprising at least one Heterocycle-Substituted Tetracyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Heterocycle-Substituted Tetracyclic Compound(s) by weight or volume. In various embodiments, the present compositions can contain, in one embodiment, from about 1% to about 70% or from about 5% to about 60% of the Heterocycle-Substituted Tetracyclic Compound(s) by weight or volume.

The amount and frequency of administration of the Heterocycle-Substituted Tetracyclic Compounds will be regulated according to the judgment of the attending clinician considering such factors as age, condition and size of the patient as well as severity of the symptoms being treated. Generally, a total daily dosage of the at least one Heterocycle-Substituted Tetracyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Heterocycle-Substituted Tetracyclic Compound or a pharmaceutically acceptable salt thereof; (ii) one or more additional therapeutic agents that are not a Heterocycle-Substituted Tetracyclic Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and two additional therapeutic agents, each of which are independently selected from the group consisting of HCV antiviral agents, immunomodulators, and anti-infective agents.

Kits

In one aspect, the present invention provides a kit comprising a therapeutically effective amount of at least one Heterocycle-Substituted Tetracyclic Compound, or a pharmaceutically acceptable salt, solvate, ester or prodrug of said compound and a pharmaceutically acceptable carrier, vehicle or diluent.

In another aspect the present invention provides a kit comprising an amount of at least one Heterocycle-Substituted Tetracyclic Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Heterocycle-Substituted Tetracyclic Compounds and the one or more additional therapeutic agents are provided in the same container. In one embodiment, the one or more Heterocycle-Substituted Tetracyclic Compounds and the one or more additional therapeutic agents are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4 below. Alternative synthetic pathways and analogous structures will be apparent to those skilled in the art of organic synthesis.

Scheme 1 shows methods useful for making the compounds of formula G3, which are useful intermediates for making the Compounds of Formula (I).

Scheme 1

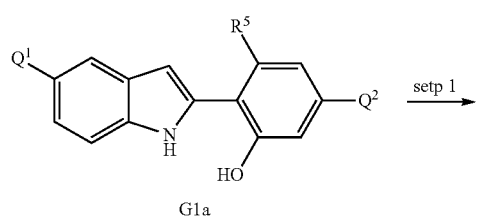

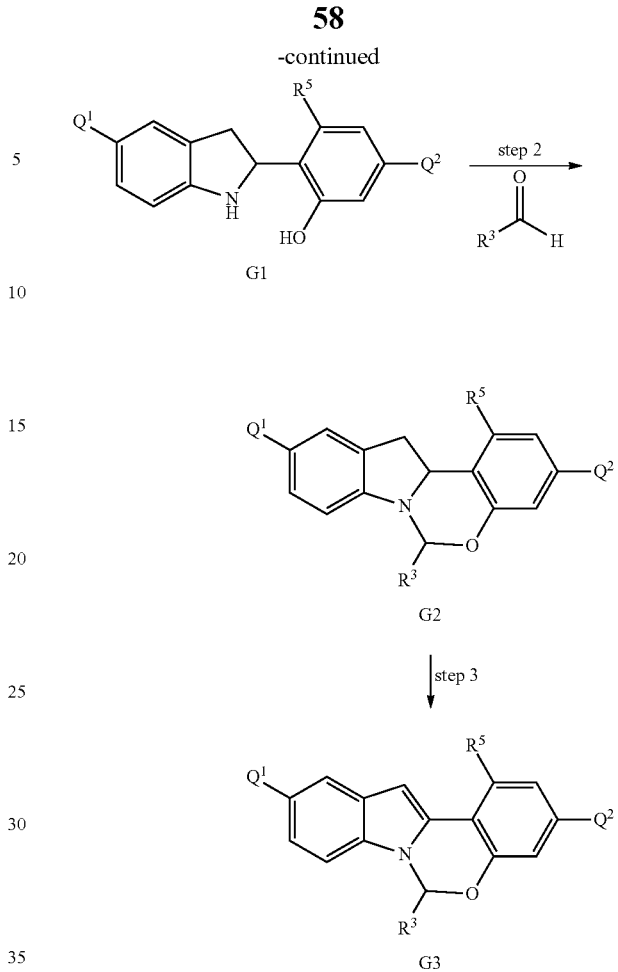

Wherein $R^3$ and $R^5$ are defined above for the Compounds of Formula (I) and $Q^1$ and $Q^2$ are each independently halo, hydroxyl, or a protected hydroxyl group, such as a methoxy or benzyloxy group.

An indole compound of formula G1a (which can be prepared as described in International Publication No. WO 2012/040923) can be treated with tin in conc.HCl/EtOH solution to provide compounds of formula G1. A compound of formula G1 can be reacted with an aldehyde of formula $R^3$CHO in the presence of an acid to provide tetracyclic compounds of formula G2. Compounds of formula G2 can then be oxidized to provide the tetracyclic compounds of formula G3.

Scheme 2 shows methods useful for making the compounds of formula G5, which are useful intermediates for making the Compounds of Formula (I).

Scheme 2

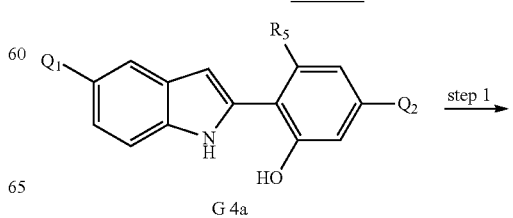

-continued

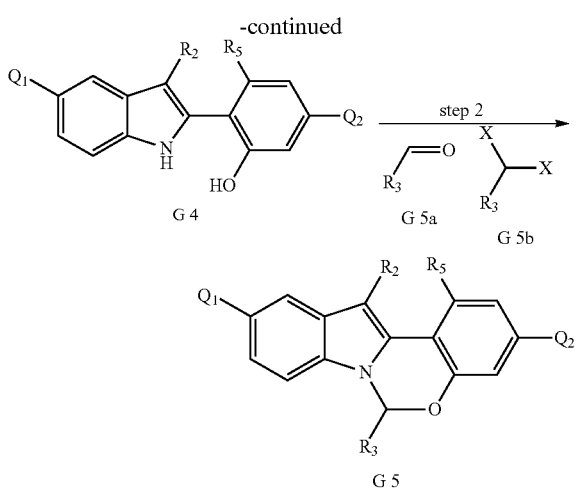

Wherein $R^2$, $R^3$ and $R^5$ are defined above for the Compounds of Formula (I), X is halo, and $Q^1$ and $Q^2$ are each independently halo, hydroxyl, or a protected hydroxyl group, such as a methoxy or benzyloxy group.

A compound of formula G4a (which can be prepared as described in International Publication No. WO 2012/040923) can be halogenated to provide the compounds of formula G4. A compounds of formula G4 can then be converted to the compounds of formula G5 via reaction with an aldehyde of formula G5a in the presence of an acid, or alternatively, by reaction with a dihalo compound of formula G5b in the presence of a base.

Scheme 3 shows methods useful for making the compounds of formula G12, which are useful intermediates for making the Compounds of Formula (I).

Scheme 3

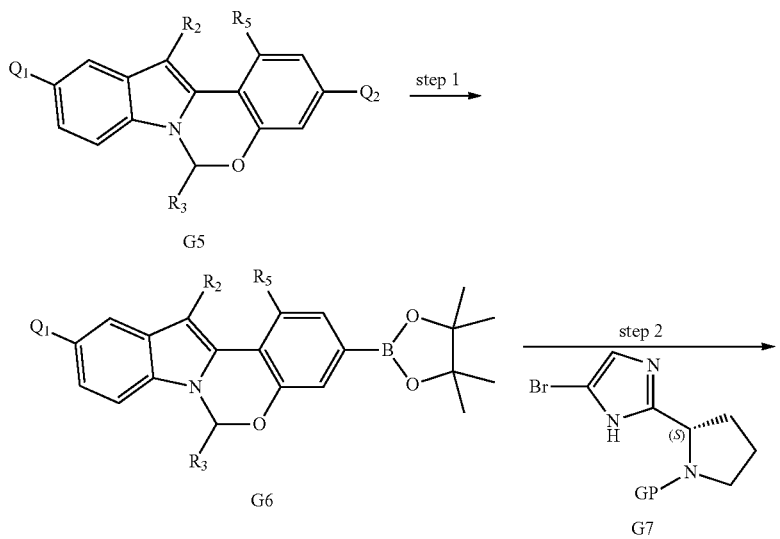

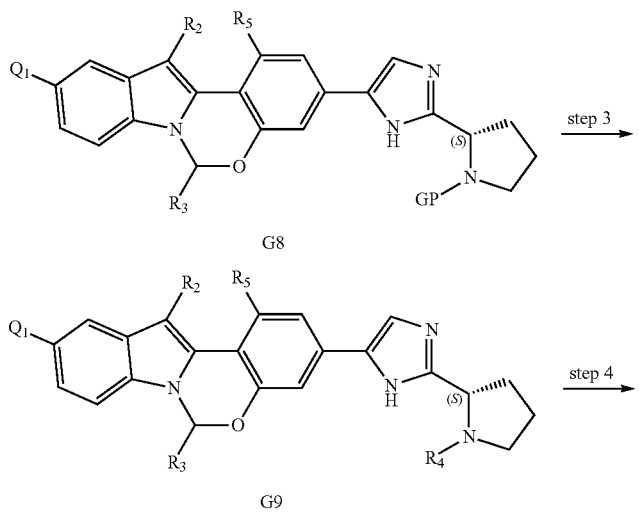

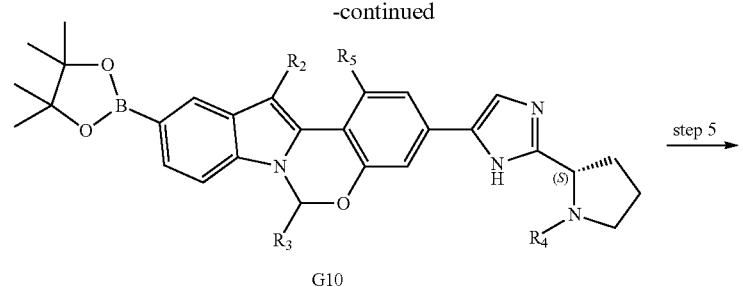

G10

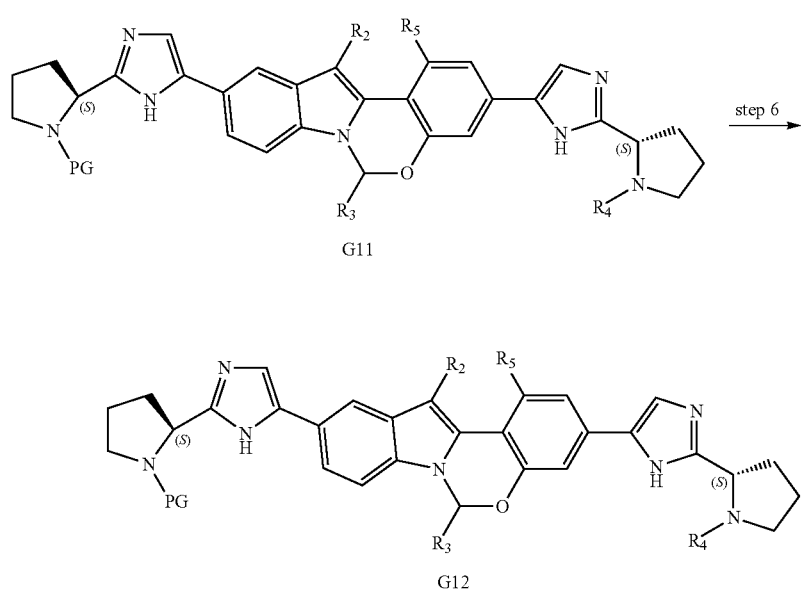

G11

G12

Wherein $R^2$, $R^3$, $R^4$ and $R^5$ are defined above for the Compounds of Formula (I), PG is a secondary amino protecting group, and $Q^1$ and $Q^2$ are each independently halo, hydroxyl, or a protected hydroxyl group, such as a methoxy or benzyloxy group.

A compound of formula G5 can be reacted with bis(pinacolato)diboron to provide the compounds of formula G6. A compound of formula G6 can then undergo a Pd-mediated coupling with a bromo compound of formula G7 (prepared as described in International Publication No. WO 2012/040923) to provide the compounds of formula G8. Compounds of formula G8 can then be deprotected and subjected to an amide coupling with a desired cap compound to provide a compound of formula G9. A compound of formula G9 is then subjected to a Pd-mediated coupling with bis(pinacolato)diboron to provide the boronic ester compounds of formula G10. A compound of formula G10 can then undergo a Pd-mediated coupling with a bromo compound of formula G7 (prepared as described in International Publication No. WO 2012/040923) to provide the compounds of formula G11. Compounds of formula G11 can then be deprotected and subjected to an amide coupling with a desired cap compound to provide a compound of formula G12. Diastereoisomers of the synthetic intermediates and final products can be separated using SFC or HPLC with chiral columns.

Scheme 4 shows methods useful for making the compounds of formula G18, which correspond to the Compounds of Formula (I).

Scheme 4

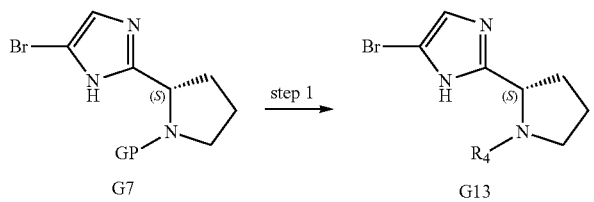

G7　　step 1　　G13

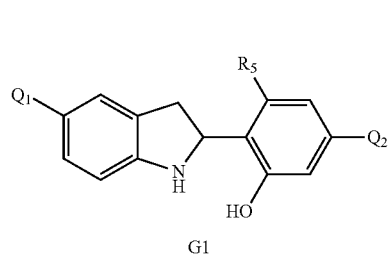 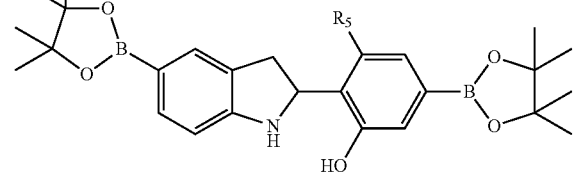 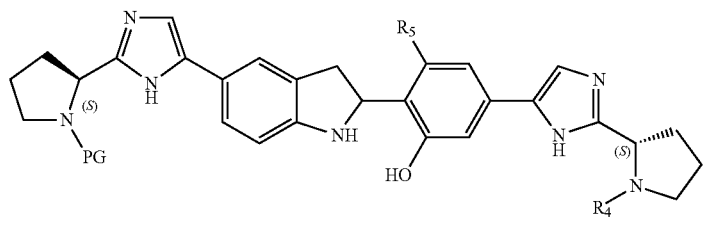 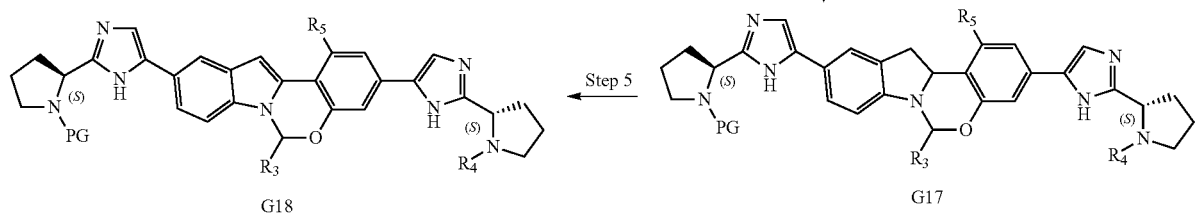

Wherein $R^3$, $R^4$ and $R^5$ are defined above for the Compounds of Formula (I), PG is a secondary amino protecting group, and $Q^1$ and $Q^2$ are each independently halo, hydroxyl, or a protected hydroxyl group, such as a methoxy or benzyloxy group.

A compounds of formula G7 can then be deprotected and subjected to an amide coupling with a desired cap compound to provide a compound of formula G12. A compound of formula G1 can be converted to compound of formula G14 via a Pd mediated coupling reaction with bis(pinacolato) diboron. A compound of formula G14 can then be subjected to a Pd-mediated coupling with 2 equivalents of G13 to provide the compounds of formula G15. A compound of formula G15 can then be converted to the compounds of formula G17 via reaction with an aldehyde of formula G16 in the presence of an acid. Compounds of formula G17 can then be oxidized to provide the tetracyclic compounds of formula G18. Diastereoisomers of G18 can be reparated by SFC using chiral columns.

In some of the Compounds of Formula (I) contemplated in Schemes 1-4, amino acids (such as, but not limited to proline, 4-(R)-fluoroproline, 4-(S)-fluoroproline, 4,4-difluoroproline, 4,4-dimethylsilylproline, aza-bicyclo[2.2.1]heptane carboxylic acid, aza-bicyclo[2.2.2]octane carboxylic acid, (S)-2-piperidine carboxylic acid, valine, alanine, norvaline, etc. . . . ) are incorporated as part of the structures. Methods have been described in the organic chemistry literature as well as in Banchard US 2009/0068140 (Published Mar. 9, 2009) for the preparation of such amino acid-derived intermediates.

One skilled in the art of organic synthesis will recognize that the synthesis of fused tetracyclic cores contained in Compounds of Formula (I) may require protection of certain functional groups (i.e., derivatization for the purpose of chemical compatibility with a particular reaction condition). Suitable protecting groups for the various functional groups of these Compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the fused tetracyclic cores of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

One skilled in the art of organic synthesis will recognize that the synthesis of certain fused tetracyclic cores of the Compounds of Formula (I) require the construction of an amide bond. Methods useful for making such amide bonds, include but are not limited to, the use of a reactive carboxy derivative (e.g., an acid halide, or ester at elevated temperatures) or the use of an acid with a coupling reagent (e.g., HOBt, EDCI, DCC, HATU, PyBrop) with an amine.

The preparation of multicyclic intermediates useful for making the fused tetracyclic ring systems of the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The Compounds Formula (I) may contain one or more silicon atoms. The Compounds contemplated in this invention in general can be prepared using the carba-analog methodology unless otherwise noted. A recent review of the synthesis of silicon containing Compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, J. Am. Chem. Soc., 128:8479 (2006)) and reduced metabolic processing of silyl containing Compounds have been described (Johansson et al., *Drug Metabolism & Disposition*, 38:73 (2009)).

The starting materials used and the intermediates prepared using the methods set forth in Schemes 1-5 may be isolated and purified if desired using conventional techniques, including but not limited to filtration, distillation, crystallization, chromatography and alike. Such materials can be characterized using conventional means, including physical constants and spectral data.

One skilled in the art will be aware of standard formulation techniques as set forth in the open literature as well as in textbooks such as Zheng, "Formulation and Analytical Development for Low-dose Oral Drug Products", Wiley, 2009, ISBN.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

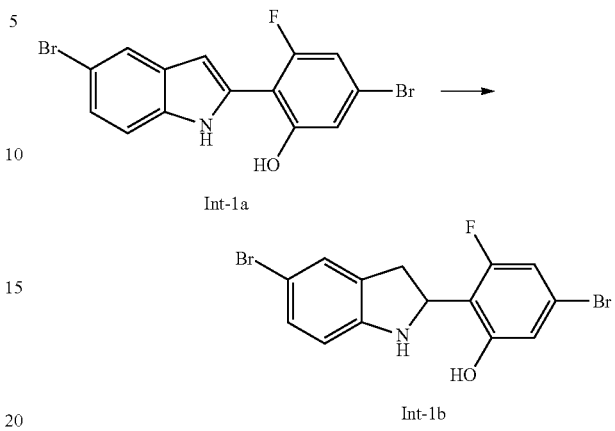

Compound Int-1a was prepared as described in Example 19 of WO 2012/040923 A1. Zn (80.0 g, 1.23 mol) was added to the solution of Int-1a (40.0 g, 0.104 mol) in TFA (400 mL) at 76° C. The mixture was stirred for 17 hours. Then it was cooled and concentrated in vacuo. The residue was washed with water (300 mL) and extracted with ethyl acetate (500 mL), washed with brine and dried over anhydrous sodium sulfate. After concentration in vacuo, Crude product was purified using SiO$_2$ chromatography (Hexane/EtOAc 10:1-5:1) to provide the product compound Int-1b (18.0 g, 44.8% yield). LC/MS: Anal. Calcd. For [M+H]$^+$ C14H10Br2FNO: 387.91. found 388.0.

Example 2

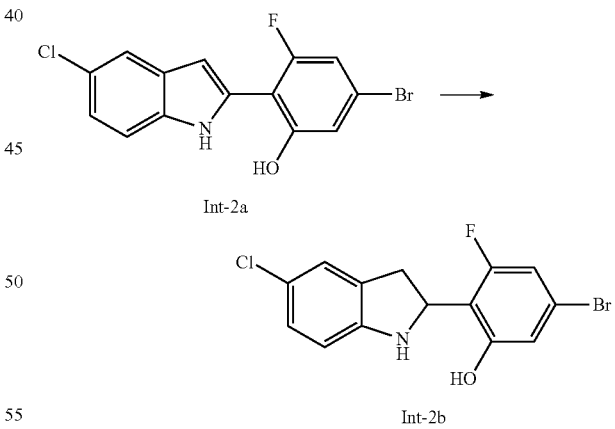

Compound Int-2a was prepared as described in Example 19 of WO 2012/040923 A1. To a mixture of Int-2a (10 g, 0.029 mol), Zn (20 g, 0.31 mol) in TFA (120 mL) was stirred at 70° C. under N$_2$ for about 15 hours. After cooling down, the mixture was filtered and concentrated in vacuo, extracted with EtoAc. Then added NaHCO$_3$ slowly to pH=8. The mixture was filtered and concentrated in vacuo. The residue was purified using SiO$_2$ chromatography (Hexane/EtOAc 10:1-5:1) to provide Int-2b (5 g, 50% yield). LC/MS: Anal. Calcd. For [M+H]$^+$ C14H10BrClFNO: 343.59. found 343.9.

Example 3

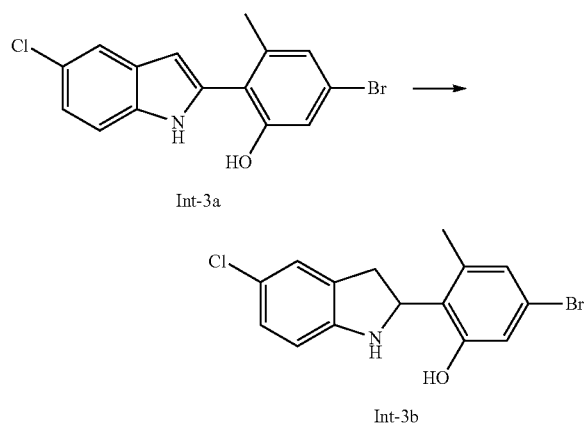

Compound Int-3a was prepared as described in Example 19 of WO 2012/040923 A1. To a 100 mL flask was added Int-3a (4 g, 11.88 mmol), zinc (7.77 g, 119 mmol), and TFA (59.4 mL). The solution was stirred at 65° C. for 16 hours. After cooling down, EtOAc (200 mL) and water (150 mL) were added. The organic layer was separated and washed with water two more times, Saturated NaHCO$_3$ twice, brine and dried over anhydrous Na$_2$SO$_4$. The solution was filtered and concentrated in vacuo. Product was purified using SiO$_2$ chromatography (120 g, Hexane/EtOAc 0% to 30%) to provide Int-3b (2.8 g, 69.6%).

Example 4

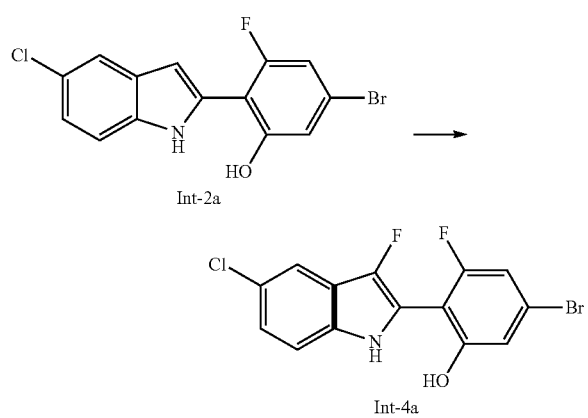

Int-2a (50 g, 0.15 mol) was dissolved in 300 ml of MeCN and DMSO (V$_1$:V$_2$=1:1) at 0° C. in an ice bath. Select F (42 g, 0.12 mol) was added into the solution in portions and the resulting mixture was stirred at 0° C. for 30 minutes. The mixture was poured into water and extracted with DCM, dried over anhydrous Na$_2$SO$_4$, removed the DCM under reduced pressure and gained the crude product. Then the crude product was purified using reverse HPLC to provide 24 g of Int-4a (24 g, yield 45%).

Example 5

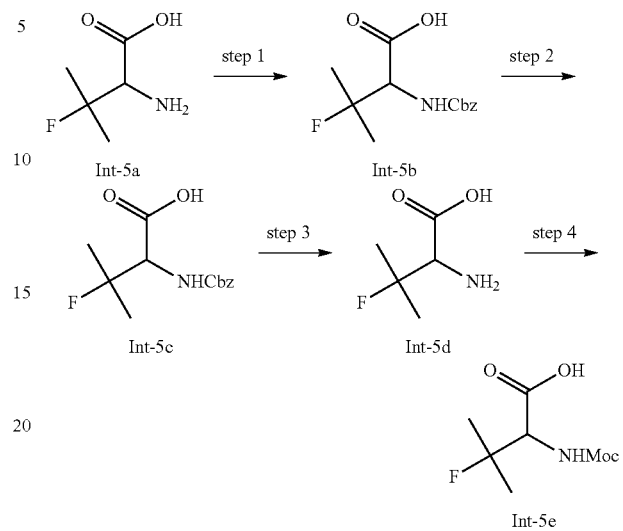

Step 1

To a solution of Int-5a (9 g, 66.7 mmol) in MeOH (100 mL) at 0° C. was added Et$_3$N (14.8 g, 146.7 mmol) and CbzCl (11.3 g, 66.7 mmol). The solution was stirred at 25° C. for about 15 hours. After completion of the reaction, the reaction mixture was adjusted pH=3 with HCl (1N in water), extracted with EtOAc, the organic phase was separated, washed with brine, dried over Na$_2$SO$_4$ and concentrated in vacuo to provide compound Int-5b (15 g, yield 89%). LC/MS: Anal. Calcd. For [M+H]$^+$ C13H16FNO4: 270.11. found 270.1.

Step 2

Int-5b was separated by SFC by using the following conditions to provide Int-5c as a mixture of isomers (7 g, yield 40%) and (7 g, yield 40%). LC/MS: Anal. Calcd. For [M+H]$^+$ C13H16FNO4: 270.11. found 270.12.

Column: Chiralpak AD-3 150×4.6 mm I.D.

Mobile phase: iso-propanol (0.05% DEA) in CO$_2$ from 5% to 40%

Flow rate: 2.5 mL/min

Wavelength: 220 nm

Step 3

To a solution of the product Int-5c (3.5 g, 13 mmol) in MeOH (50 mL) was added Pd/C (10%, 0.1 g) carefully. Then the reaction mixture was stirred at 25° C. under H$_2$ (15 psi) for 6 hours. After completion of the reaction, Pd/C was filtered and the solvent was removed in vacuo. The desired compound Int-5d was obtained as white solid (1.1 g, 67% yield).

Step 4

To a solution of Int-5d (0.87 g, 6.5 mmol) was added Et$_3$N (1.44 g, 14.3 mmol) at 0° C. After stirring for 10 minutes, methyl chloroformate (0.66 mg, 7.1 mmol) was added in dropwise at 0° C.; then the reaction mixture was stirred at room temperature for 3 hours. After completion of the reaction, the reaction mixture was adjusted to pH 3 using HCl (1N in water), extracted with ethyl acetate; the organic phase was separated, washed with brine, dried over Na$_2$SO$_4$ and concentrated in vacuo. The residue was purified using Pre-HPLC to provide compound Int-5e (1.2 g, 67% yield). LC/MS: Anal. Calcd. For [M+H]+ C5H8FO2: 120.05. found 120.25.

Example 6

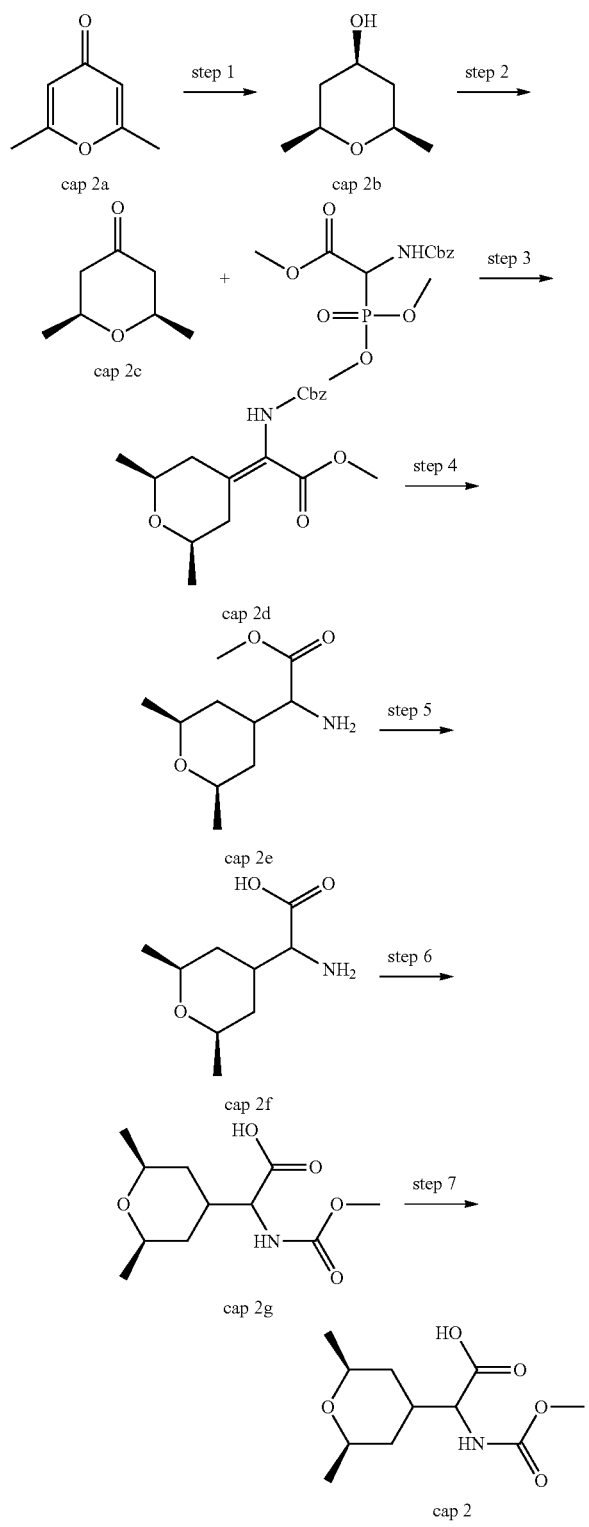

Step 1

The solution of compound cap 2a (73 g, 0.59 mol) in ethanol was added Pd/C (10%, 40 g) and the reaction was stirred at 35° C. under an $H_2$ (50 Psi) for 17 hours. The reaction was filtered through celite and the volatiles were removed in vacuo to provide compound cap 2b (76 g, 99% yield). $^1$H-NMR: (CDCl$_3$) δ: 3.75 (s, 1 H), 3.44-3.40 (m, 2 H), 1.88 (d, J=16 Hz, 2 H), 1.19 (d, J=8 Hz, 6 H), 1.14-1.08 (m, 2 H).

Step 2

To a solution of compound cap 2b (74.7 g, 0.57 mol) in DCM (750 mL) was added a solution of NaHCO$_3$ (4.83 g, 57 mmol) and KBr (6.84 g, 57 mmol) in water (200 mL). Then TEMPO (0.9 g, 5.7 mmol) was added. The mixture was treated at 0° C. under vigorous stirring with NaClO$_2$ aqueous (47.1 g, 0.63 mol, 5%~7%) over 1 hour. Then the whole system was stirred at 25° C. for 5 hours and the aqueous layer was extracted with DCM. The organic phase was washed with brine, dried over Na$_2$SO$_4$ and the solvent evaporated to provide compound cap 2c as pale yellow oil (72.2 g, 99% yield). $^1$H-NMR: (CDCl$_3$) δ: 3.75-3.70 (m, 2 H), 2.33 (d, J=16 Hz, 2 H), 2.19 (t, J=24 Hz, 2 H), 1.31 (d, J=6 Hz, 6 H).

Step 3

To a solution of benzyloxycarbonyl-α-phosphonoglycine trimethyl ester (124 g, 0.38 mol) in dry DCM (160 mL) was added DBU (57.2 g, 0.038 mol) dropwise at 0° C. Then a solution of compound cap 2c (72.2 g, 0.56 mol) in dry DCM (160 mL) was added dropwise at 0° C. The reaction mixture was stirred at 25° C. for 20 hours. After removal of the solvent, the residue was purified using SiO$_2$ chromatography to provide compound cap 2d (90 g, 71% yield). $^1$H-NMR: (J000205047 H14272-134-1 MeOD varian 400 MHz) δ: 7.35-7.31 (m, 5 H), 5.10 (s, 2 H), 3.68 (s, 3 H), 3.48-3.44 (m, 3 H), 2.63-2.60 (m, 1 H), 1.82-1.68 (m, 2 H), 1.25 (s, 6 H).

Step 4

To a solution of compound cap 2d (45 g, 0.135 mol) in MeOH (450 mL) was added Pd/C (10%, 30 g) carefully. Then the reaction mixture was stirred at 25° C. under H$_2$ (35 psi) for 8 hours. After completion of the reaction, Pd/C was filtered and the solvent was removed in vacuo. Compound cap 2e was obtained as colorless oil (27.8 g, 100% yield). $^1$H-NMR: (MeOD) δ: 3.71 (s, 3 H), 3.49-3.44 (m, 2 H), 3.25 (d, J=6 Hz, 1 H), 1.93-1.88 (m, 1 H), 1.62 (d, J=4 Hz, 1 H), 1.58 (d, J=4 Hz, 1 H), 1.15 (d, J=4 Hz, 6 H), 1.05-0.91 (m, 2 H).

Step 5

To a solution of compound cap 2e (27.8 g, 0.14 mol) in MeOH (300 mL) was added a solution of NaOH (11.05 g, 0.28 mol) in water (100 mL) and the reaction was refluxed for 35 hours. After completion of the reaction, the solvent was removed in vacuo and the crude compound cap 2f was used next step directly. LC/MS: Anal. Calcd. For [M+H]+ C9H17NFO3: 188.12. found: 188.1.

Step 6

To a solution of compound cap 2f (26.2 g, 0.14 mol) in H$_2$O (260 mL) was added NaOH (2.8 g, 0.07 mol) at 0° C. After stirring for 10 min, methyl chloroformate (14.4 g, 0.15 mol) was added in dropwise at 0° C.; then the reaction mixture was stirred at room temperature for 3 hours. After completion of the reaction, the reaction mixture was adjusted pH=3 with HCl (1N), extracted with EtOAc, the organic phase was separated, washed with brine, dried over Na$_2$SO$_4$ and concentrated in vacuo, and the resulting residue was purified using PRE-HPLC to provide the compound cap 2g (16 g, 53% yield). LC/MS: Anal. Calcd. For [M+H]+ C11H19NFO5: 246.13. found: 246.1.

Step 7

The compound cap 2g (16 g) was separated using SFC to provide compound cap 2 (5.4 g, 34% yield) by the following method:
Instrument: Thar SFC
Column: AY-5, 150×4.6 mm, 5 um
Mobile phase: A for $CO_2$ and B for EtOH (0.05% DEA)
Gradient: B 5% to 40 for A
Flow rate: 2.5 mL/min
Back pressure: 100 bar
Column temperature: 35° C.
Wavelength: 230 nm
Compounds cap 2 $^1$H-NMR (MeOD) δ: 4.01 (d, J=6 Hz, 1 H), 3.62 (s, 3 H), 3.46-3.43 (m, 2 H), 2.12-2.07 (m, 1 H), 1.61-1.52 (m, 2 H), 1.13 (d, J=6 Hz, 6 H), 1.03-0.94 (m, 2 H).

Example 7

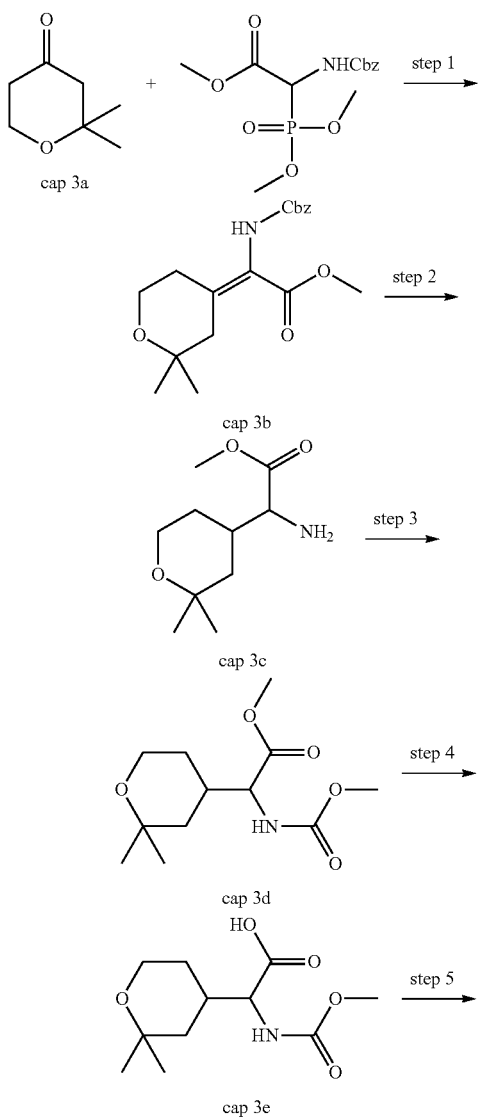

cap 3a cap 3b cap 3c cap 3d cap 3e

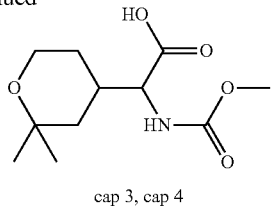

cap 3, cap 4

Step 1

To a solution of benzyloxycarbonyl-α-phosphonoglycine trimethyl ester (1.163 g, 3.52 mmol) in dry DCM (20 mL) was added DBU (0.534 g, 3.52 mmol) dropwise at 0° C. Then a solution of compound cap 3a (1.8 g, 14.08 mmol) in dry DCM (20 mL) was added dropwise at 0° C. The reaction mixture was stirred at 25° C. for 3 days. After removal of the solvent, the residue was purified using $SiO_2$ chromatography (eluting with petroleum ether/ethyl acetate=5:1 to 3:1) to provide compound cap 3b as white solid (0.15 g, 13% yield). $^1$H NMR (CDCl$_3$): δ 7.30-7.35 (m, 5 H), 5.11 (s, 2 H), 3.82-3.88 (m, 3 H), 3.09-3.16 (m, 2 H), 1.84 (s, 2 H), 1.48 (s, 2 H).

Step 2

To a solution of compound cap 3b (3 g, 9.01 mmol) in MeOH (100 mL) was added Pd/C (0.6 g) carefully under $N_2$. Then the reaction mixture was stirred at 25° C. under $H_2$ (45 psi) for 3 hours. After completion of the reaction, Pd/C was filtered and the solvent was removed in vacuo. Compound cap 3c was obtained as colorless oil (1.8 g, 99% yield). LC/MS: Anal. Calcd. For [M+H]$^+$ C10H19NFO3: 202.14. found: 202.1.

Step 3

To a solution of compound cap3c (1.7 g, 8.46 mmol) in dry DCM (40 mL) was added DIPEA (1.65 g, 12.69 mmol) and methyl chloroformate (0.964 g, 10.15 mmol) in dropwise at 0° C. Then the reaction mixture was stirred at 25° C. for 2 hours. After completion of the reaction, water and DCM was added. The organic phase was separated, washed with brine, dried over $Na_2SO_4$ and concentrated in vacuo. Compound cap 3d was obtained as colorless oil (1.9 g, 87% yield). LC/MS: Anal. Calcd. For [M+H]$^+$ C12H21NFO5: 260.14. found: 260.2.

Step 4

To a solution of compound cap 3d (1.9 g, 7.34 mmol) in THF/$H_2O$ (20 mL/4 mL) was added LiOH (0.264 g, 11.00 mL) at 25° C. for 4 hours. After completion of the reaction, 1 N HCl was added to adjust the solution to pH 6 and the organics were extracted using DCM. The organic phase was washed with brine, dried over $Na_2SO_4$. After removal of the solvent, the crude was purified using Pre-HPLC to provide compound cap 3e as white solid (1 g, 56%). LC/MS: Anal. Calcd. For [M+H]$^+$ C11H19NFO5: 246.13. found: 246.1.

Step 5

Compound cap 3e (1 g) was separated by SFC under the following condition to provide Cap 3 and Cap 4.
Instrument: Thar SFC
Column: AS-H, 150×4.6 mm, 5 um
Mobile phase: A for $CO_2$ and B for EtOH (0.05% DEA)
Gradient: B 5% to 40 for A
Flow rate: 2.5 mL/min
Back pressure: 100 bar
Column temperature: 35° C.
Wavelength: 230 nm
Cap 3 (170 mg, 17% yield). LC/MS: Anal. Calcd. For [M+H]$^+$ C11H19NFO5: 245.13. found: 246.1.

Cap 4 (230 mg, 23% yield). LC/MS: Anal. Calcd. For [M+H]+ C11H19NFO5: 245.13. found: 246.1.

Example 8

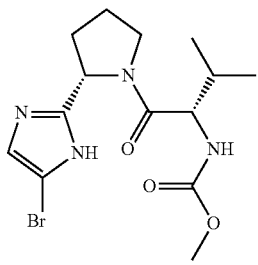

cap 5

Compound cap 5 was made using the methods described in International Application No. WO 2012/041014.

Example 9

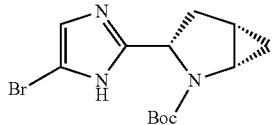

cap 6

Compound cap 6 was prepared using the methods described in International Publication No. WO 2012/041014.

Example 10

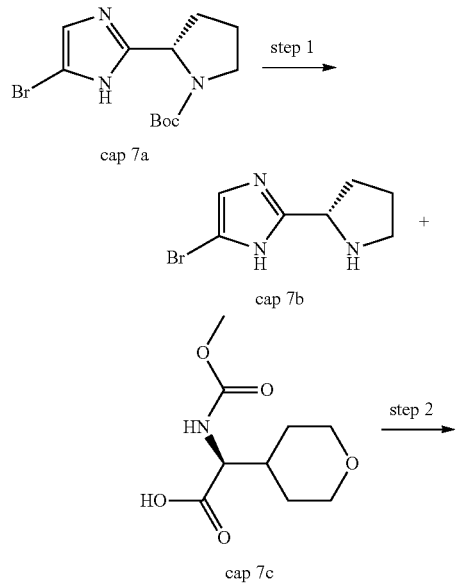

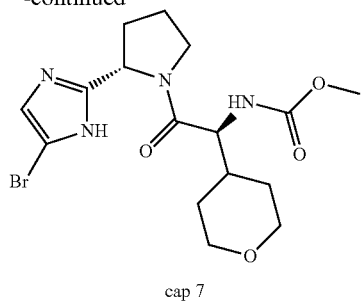

cap 7

Step 1

Compound cap 7a was prepared in Example 7 of WO 2012/040923 A1. Compound cap 7a (50 g, 0.16 mol) was added into TFA/DCM (1:1, 10 mL). The mixture was stirred at 25° C. for 2 hours; then concentrated in vacuo and dried under high vacuum to provide compound cap 7b (34.4 g, 100% yield). LC/MS: Anal. Calcd. For [M+H]+ C7H10BrN3: 216.01. found 216.1.

Step 2

Compound cap 7c was prepared as described in Example 4 of WO 2012/040923 A1. To a mixture of cap 7b (1.9 g, 9 mmol), cap 7c (1.9 g, 9 mmol) and DIPEA (4 mL) in CH2Cl2 (5 mL) was added HATU (3.5 g, 9 mmol). The resulting mixture was stirred at 25° C. for 2 hours. The reaction mixture was concentrated in vacuo, then purified using SiO2 chromatography (eluent: petroleum ether/ethyl acetate=5:1 to 1:2) to provide compound cap 7 (2 g, 54.1% yield). LC/MS: Anal. Calcd. For [M+H]+ C16H23BrN4O4: 415.09, 417.09. found 415.1, 417.1.

Example 11

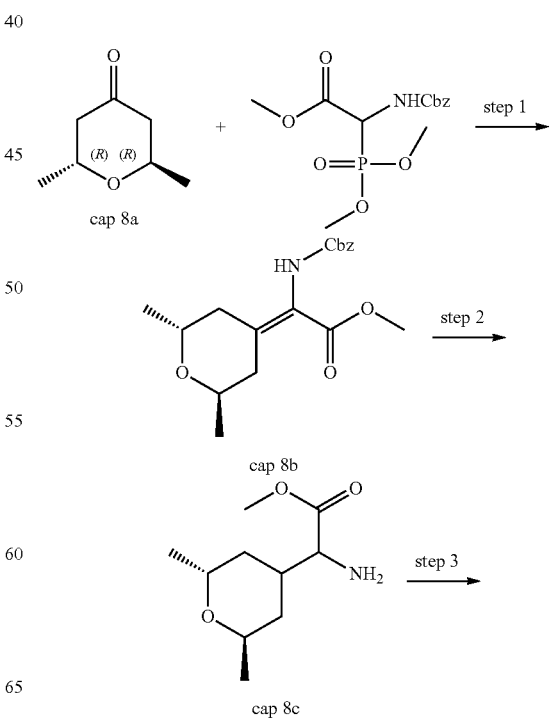

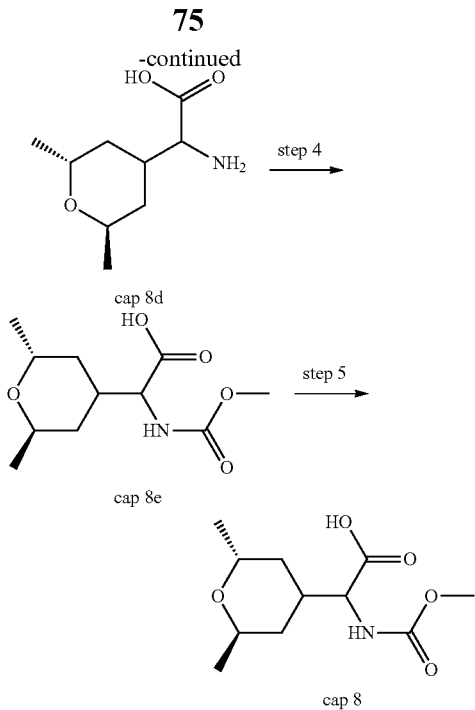

Step 1

To a solution of benzyloxycarbonyl-alpha-phosphonoglycine trimethyl ester (3.3 g, 10 mmol) in dry DCM (50 mL) was added DBU (1.52 g, 10 mmol) dropwise at 0° C. Then a solution of compound cap 8a (1.9 g, 14.7 mmol) in dry DCM (50 mL) was added dropwise at 0° C. The reaction mixture was stirred at room temperature for 20 hours. After removal of the solvent, the residue was purified using SiO$_2$ chromatography to provide compound cap 8b (3.6 g, 35% yield). LC/MS: Anal. Calcd. For [M+H]$^+$ C18H23NO5: 334.16. found 334.52.

Step 2

To a solution of compound cap 8b (3.6 g, 10.8 mmol) in MeOH (50 mL) was added Pd/C (10%, 0.2 g) carefully. Then the reaction mixture was stirred at 25° C. under H$_2$ (35 psi) for 8 hours. After completion of the reaction, Pd/C was filtered and the solvent was removed in vacuo. The desired compound cap 8c was obtained as a colorless oil (2 g, 99% yield). LC/MS: Anal. Calcd. For [M+H]$^+$ C10H19NO3: 202.14. found 202.24.

Step 3

To a solution of cap 8c (2 g, 10 mmol) in MeOH (21 mL) was added a solution of LiOH—H$_2$O (840 mg, 20 mmol) in water (7 mL) and the reaction mixture was stirred for 8 hours. After completion of the reaction, the solvent was removed in vacuo and the crude compound cap 8d was used next step directly.

Step 4

To a solution of cap 8d in H$_2$O was added LiOH—H$_2$O (0.42 g, 10 mmol) and Na$_2$CO$_3$ (3.2 g, 30 mmol) at 0° C. After stirring for 10 minutes, methyl chloroformate (1.1 g, 12 mmol) was added in dropwise at 0° C.; then the reaction mixture was stirred at 25° C. for 3 hours. After completion of the reaction, the reaction mixture was adjusted pH=3 with HCl (1N), extracted with ethyl acetate, the organic phase was separated, washed with brine, dried over Na$_2$SO$_4$ and concentrated in vacuo. The residue was purified using Pre-HPLC to provide compound cap 8e (1.4 g, 52% yield). LC/MS: Anal. Calcd. For [M+H]$^+$ C11H19NO5: 246.13. found 246.54.

Step 5

Compound cap 8e (1.4 g) was separated by SFC by using the following conditions to provide cap 8.

Column: Chiralpak AS-H 250×4.6 mm I.D.

Mobile phase: ethanol (0.05% DEA) in CO$_2$ from 5% to 40%

Flow rate: 2.35 mL/min

Wavelength: 220 nm

Cap 8 (0.5 g, 35% yield) LC/MS: Anal. Calcd. For [M+H]$^+$ C11H19NO5: 246.13. found 246.53.

Example 12

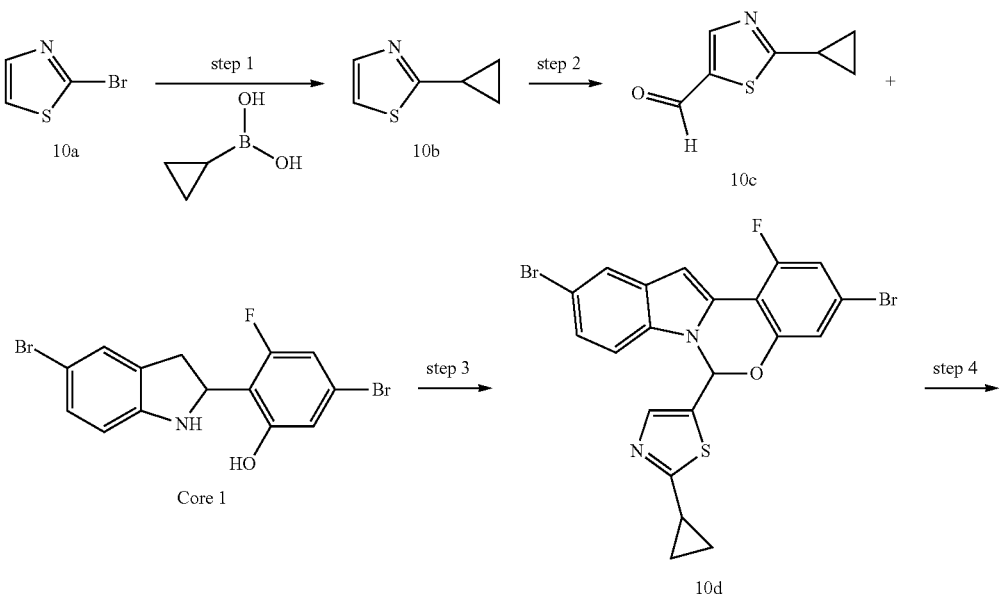

-continued

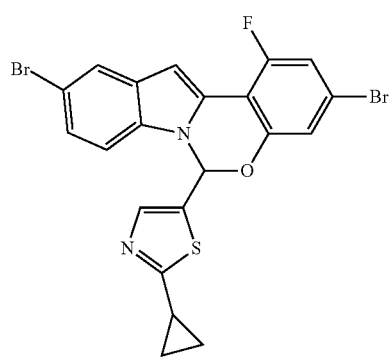

10e

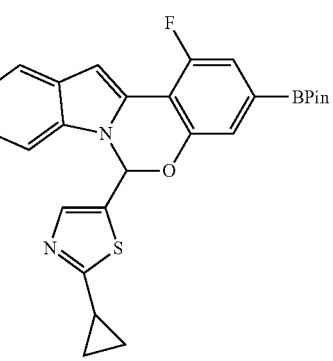

10f

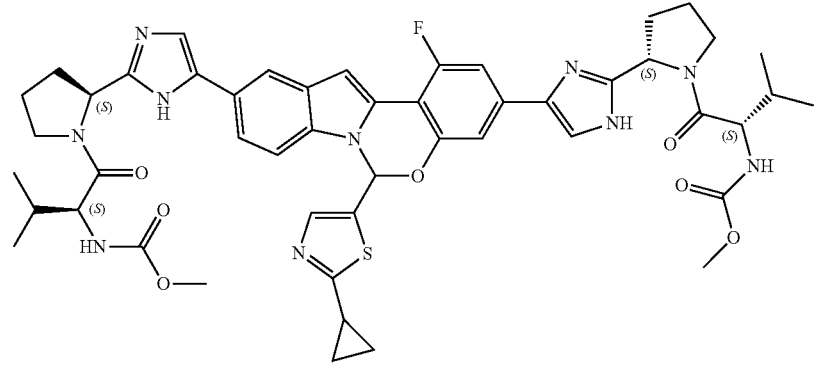

10g

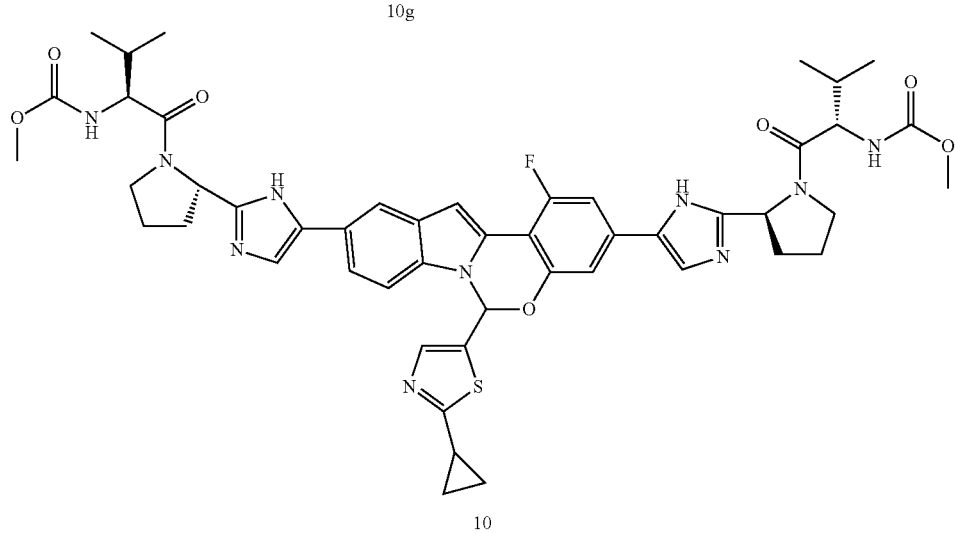

10

Step 1

A suspension of 10a (10 g, 61 mmol), cyclopropylboronic acid (21 g, 243 mmol), Pd(OAc)$_2$ (683 mg, 3 mmol), Cs$_2$CO$_3$ (79 g, 243 mmol), n-BuPACl$_2$ (79 g, 243 mmol) and in Toluene/H$_2$O (10:1, 200 mL) was refluxed at 100° C. for about 15 hours under N$_2$ atmosphere. After cooling to room temperature, the mixture was diluted with EtOAc and water. The organic layer was washed with brine and dried over anhydrous sodium sulfate. After concentration in vacuo, and the resulting residue was purified using SiO$_2$ chromatography, eluting with petroleum ether:ethyl acetate (100/1~40/1) to provide compound 10b (2 g, 32%).

Step 2

To a mixture of 10b (1.8 g, 14.4 mmol) in THF (30 mL) was added a 2.5 M solution of n-BuLi (6.3 mL, 15.8 mmol) at −78° C. under N$_2$. The mixture was agitated for 1 h at this temperature then DMF (1.6 g, 21.6 mmol) was added. The mixture was stirred at room temperature for 3 hours before quenched with NH$_4$Cl saturate solution and extracted with EtOAc. The organic layer was dried over sodium sulfate, and concentrated in vacuo and purified using SiO$_2$ chromatography, eluting with petroleum ether:ethyl acetate (50/1~20/1) to provide compound 10c (1.5 g, 49%).

Step 3

To a mixture of 10c (0.520 g, 3.4 mmol) and Int-1b (1 g, 2.6 mmol) in anhydrous CH$_3$CN (20 mL) was added TFA (0.089 g, 0.78 mmol) at room temperature. The mixture was agitated for 6 hours at ambient temperature. The reaction mixture became a clear solution and then solid appeared.

The solid was collected by filtration and washed with $CH_3CN$ to provide the desired compound 10d (0.9 g, 68%).
Step 4
The solution of 10d (0.86 g, 1.65 mmol) in dry toluene (20 mL) was added DDQ (0.560 g, 2.5 mmol). After refluxing for 2 hours, the solvent was removed in vacuo and diluted with EtOAc. The organic layer was washed with saturated $Na_2SO_3$ aqueous and brine, dried over $Na_2SO_4$, filtered and concentrated in vacuo. The residue was washed with MeOH (10 mL), filtered and the solid just was the product 10e (0.6 g, 82%).
Step 5
To a solution of 10e (0.6 g, 1.2 mmol) in 1,4-dioxane was added bis pinacol borate (0.88 g, 3.5 mmol) and $Pd(dppf)Cl_2$ (0.080 g, 0.12 mmol) and KOAc (0.470 g, 4.8 mmol). The reaction mixture was stirred under $N_2$ and heated to 110° C. for about 15 hours. After that, the solvent was removed in vacuo, and the residue was purified using $SiO_2$ chromatography, eluting with petroleum ether:ethyl acetate (5/1~1/1) to provide compound 10f (0.6 g, yield 82%).
Step 6
A suspension of 10f (614 mg, 1 mmol), Cap 5 (0.933 g, 2.5 mmol), $Pd(dppf)_2Cl_2$ (73 mg, 0.1 mmol), $Na_2CO_3$ (0.424 g, 4 mmol) and in $THF/H_2O$ (10:1, 27 mL) was refluxed at 95° C. for about 15 hours under $N_2$ atmosphere. After that, the mixture was filtered, and the filtrate was washed with water (50 mL) and extracted with EtOAc (100 mL). The organic layer was washed with brine and dried over anhydrous sodium sulfate. After filtration and concentration in vacuo, and the resulting residue was purified using HPLC to provide compound 10g.
Step 7
Compound 10g (90 mg, 45%) was purified by SFC by using the following conditions, to provide compound 10.
Column: Chiralpak AS-H 250×4.6 mm I.D.
40% of iso-propanol (0.05% DEA) in CO2
Flow rate: 2.5 mL/min
Wavelength: 340 nm
$^1$H NMR (MeOD) δ: 8.02 (s, 1 H), 7.97 (s, 1 H), 7.90 (s, 1 H), 7.76 (s, 1 H), 7.60-7.53 (m, 2 H), 7.40 (m, 1 H), 7.35 (s, 1 H), 7.21 (s, 1 H), 7.10 (s, 1 H), 5.24-5.12 (m, 2 H), 4.22-4.15 (m, 2 H), 4.15-4.05 (m, 2 H), 3.89-3.82 (m, 2 H), 3.63 (m, 6 H), 2.62-2.45 (m, 2 H), 2.30-2.21 (m, 2 H), 2.19-2.11 (m, 5 H), 2.05-1.95 (m, 2 H), 1.05-0.95 (m, 2 H), 0.98 (m, 2 H), 0.97-0.85 (m, 12 H). LC/MS: Anal. Calcd. For $[M+H]^+$ C49H55FN10O7S: 947.40. found 947.8.

Example 13

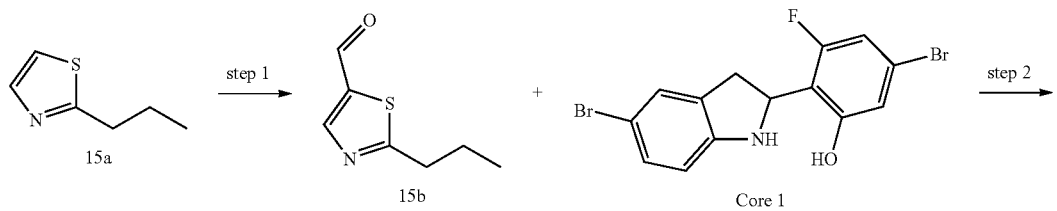

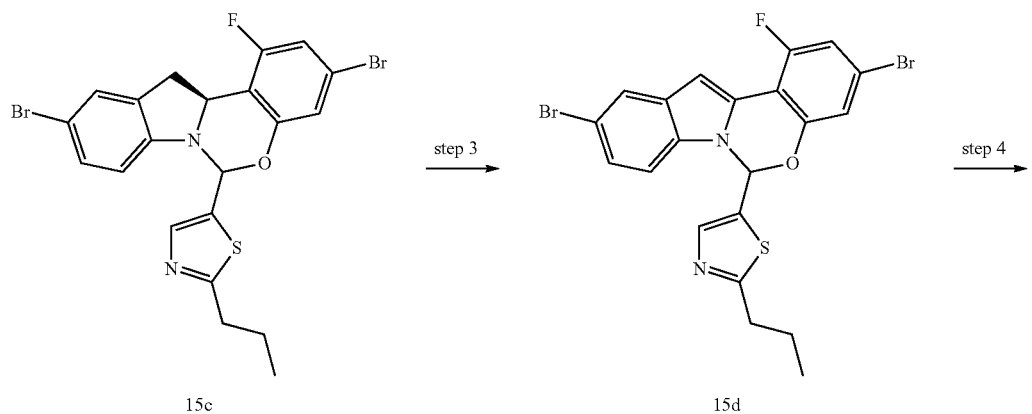

-continued
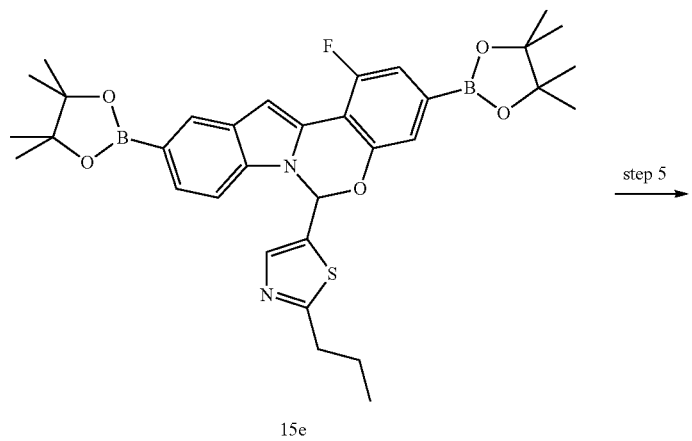
15e
step 5 →
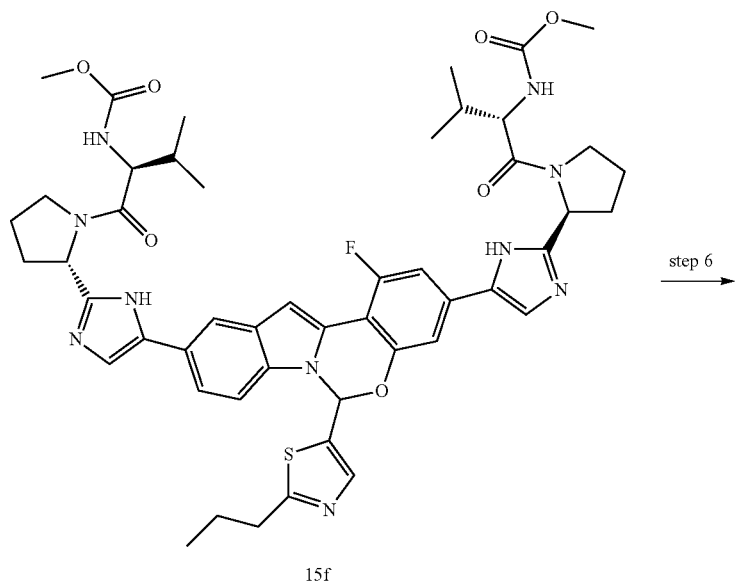
15f
step 6 →
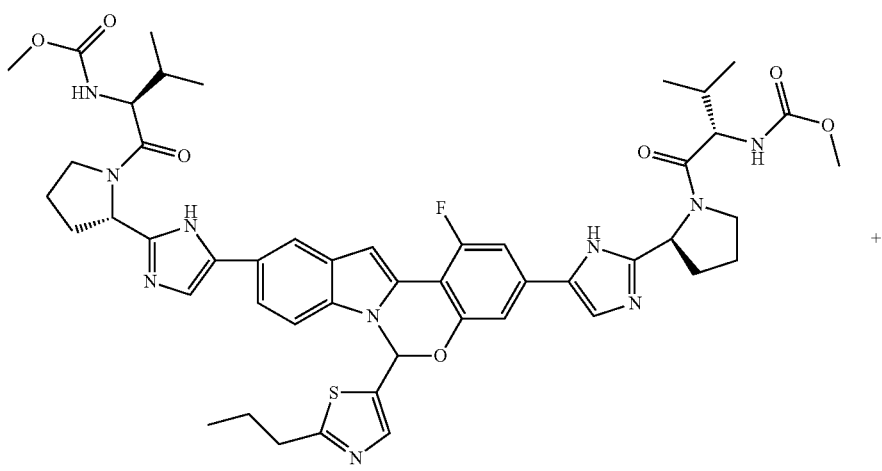
15
+

-continued

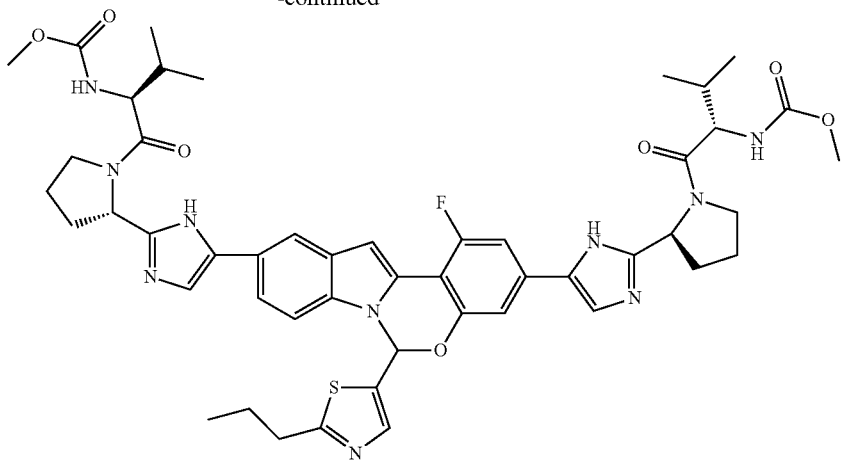

16

Step 1

Compound 15a (10 g, 78.7 mmol) was dissolved in anhydrous THF (100 mL). LDA (86.6 mL, 173.2 mmol) was added dropwised under −78° C. stirred for 1 hour. Then DMF (11.65 g, 157.4 mmol) was added and stirred at −78° C. for another 1 hour under $N_2$ atmosphere. The reaction mixture was quenched with saturated $NH_4Cl$ solution and extracted with EtOAc. The combined organic was dried over $Na_2SO_4$, purified using $SiO_2$ chromatography, eluting with petroleum ether:ethyl acetate (100/1~10/1) to provide 15b (10.5 g, 85%).

Step 2

To a mixture of 15b (6 g, 38.7 mmol) and Int-1b (14.9 g, 38.7 mmol) in anhydrous $CH_3CN$ (50 mL) was added TFA (1 mL). The mixture was stirred at room temperature for 6 hours. The reaction mixture became a clear solution and then solid appeared. The solid was collected by filtration and washed with $CH_3CN$ to provide 15c (13.1 g, 65%).

Step 3

The solution of 15c (10.5 g, 19.96 mmol) in dry toluene (100 mL) was added DDQ (4.5 g, 19.96 mmol). After refluxing for 2 hours, the solvent was removed in vacuo and diluted with EtOAc. The organic layer was washed with saturated $NaS_2O_3$ aqueous and brine, dried over $Na_2SO_4$, filtered and concentrated in vacuo. The residue was washed with MeOH (100 mL). The solid was collected by filtration to provide 15d (8.8 g, 85%).

Step 4

A suspension of 15d (8.24 g, 15.8 mmol), bis(pinacolato) diboron (8.83 g, 34.76 mmol), KOAc (7.7 g, 79 mmol) and Pd(dppf)Cl$_2$ (1.15 g, 3.16 mmol) in dioxane (80 mL) was stirred at 100° C. for 2 hours under $N_2$ atmosphere. The reaction mixture was cooled and concentrated in vacuo, and the residue was purified using $SiO_2$ chromatography, eluting with petroleum ether:ethyl acetate (100/1~10/1) to provide 15e (8.2 g, 85%).

Step 5

A suspension of 15e (8.2 g, 13.4 mmol), Cap 5 (11 g, 29.5 mmol), $Na_2CO_3$ (7.1 g, 67 mmol) and Pd(dppf)Cl$_2$ (1.47 g, 2.01 mmol) in THF/$H_2O$/DMF (v/v=5/2/1, 120 mL) was stirred at 80° C. for about 15 hours under $N_2$ atmosphere. After that, the mixture was washed with water and extracted with ethyl acetate, washed with brine and dried over anhydrous sodium sulfate. After concentration in vacuo, and the resulting residue was purified using $SiO_2$ chromatography, eluting with petroleum ether:ethyl acetate (10/1~1/5) to provide 15f (9.5 g, 75%). LC/MS: Anal. Calcd. For $[M+H]^+$ C49H57FN10O7S: 949.10. found 949.4.

Step 6

Compound 15f (4.0 g) was separated by SFC by using the following conditions to provide compounds 15 and 16 (1.05 g, 32%).

Instrument: Thar SFC

Column: AS-H,

Injection Volume: 5

Co-Solvent %: 40

Total Flow: 2.4

Co-Solvent: IPA (0.05% DEA)

Flow rate: 2.4 mL/min

Wavelength: 340 nm

Compound 15 (1.05 g, 32%). $^1$H-NMR (MeOD) δ: 7.99 (s, 1 H), 7.87 (s, 1 H), 7.75 (s, 2 H), 7.58 (s, 1 H), 7.42-7.40 (d, J=10.4 Hz 1 H), 7.28 (s, 1 H), 7.22 (s, 1 H), 7.17 (s, 1 H), 7.16 (s, 1 H), 5.27-5.19 (m, 2 H), 4.25-4.22 (m, 2 H), 4.10-3.92 (m, 2 H), 3.90-3.88 (m, 2 H), 3.65 (s, 6 H), 3.31-3.29 (m, 3H), 2.83-2.79 (m, 2H), 2.56-2.50 (m, 2 H), 2.28-2.05 (m, 6 H), 1.66-1.60 (m, 2 H), 0.95-0.93 (m, 7 H), 0.90-0.85 (m, 9 H). LC/MS: Anal. Calcd. For $[M+H]^+$ C49H57FN10O7S: 949.10. found 949.4.

Compound 16 (1.05 g, 32%). $^1$H-NMR (MeOD) δ: 8.02 (s, 1 H), 8.00 (s, 1 H), 7.98 (s, 1 H), 7.88 (s, 1 H), 7.75 (s, 2 H), 7.55-7.53 (d, J=10.4 Hz 1 H), 7.36-7.33 (d, J=10.4 Hz 1 H), 7.24-7.22 (d, J=10.4 Hz 1 H), 5.27-5.19 (m, 2 H), 4.25-4.22 (m, 2 H), 4.08-3.91 (m, 2 H), 3.88-3.84 (m, 2 H), 3.66 (s, 6 H), 3.31-3.29 (m, 3 H), 2.83-2.79 (m, 2 H), 2.58-2.50 (m, 2 H), 2.28-2.06 (m, 6 H), 1.66-1.61 (m, 2 H), 0.95-0.91 (m, 1 4H). LC/MS: Anal. Calcd. For $[M+H]^+$ C49H57FN10O7S: 949.10. found 949.4.

Example 14
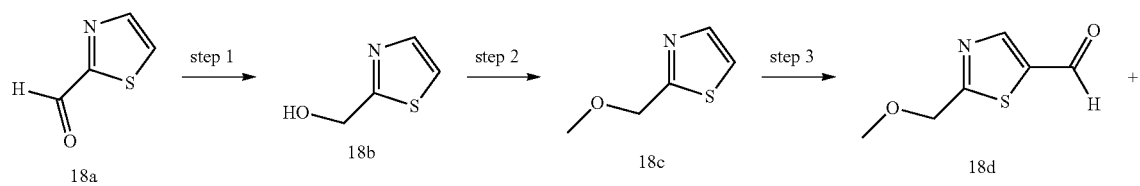
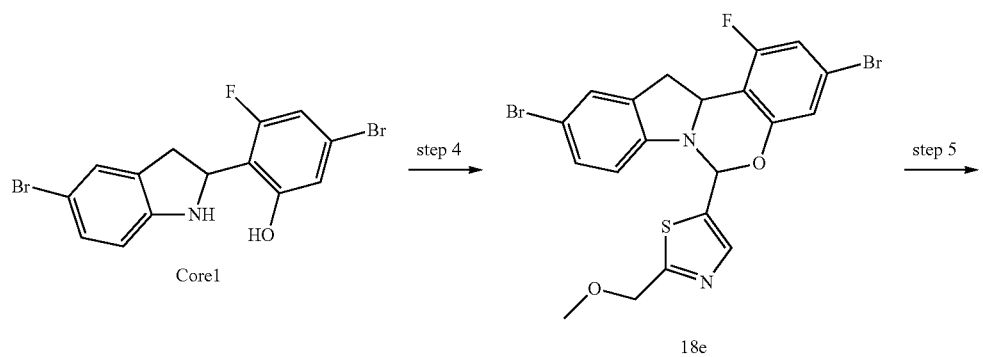
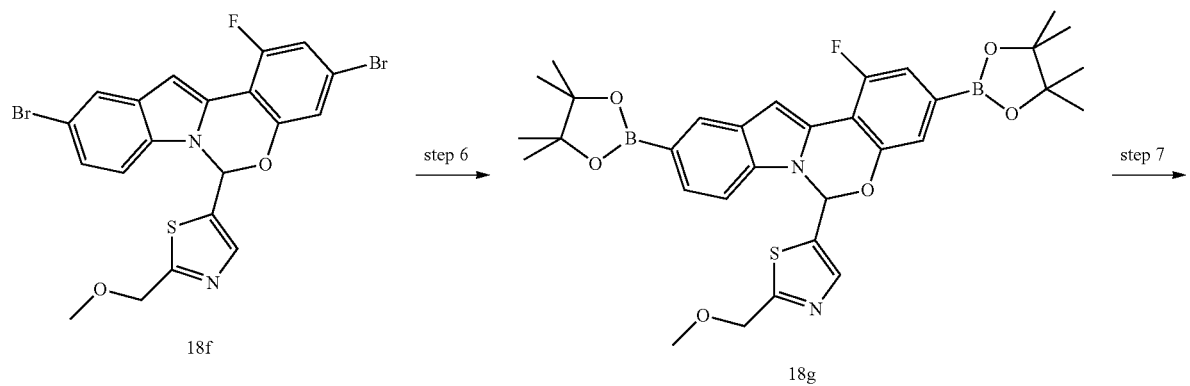
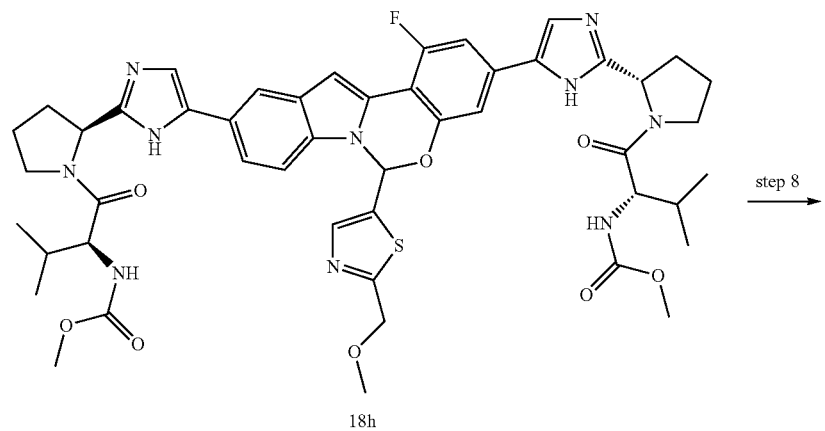

-continued

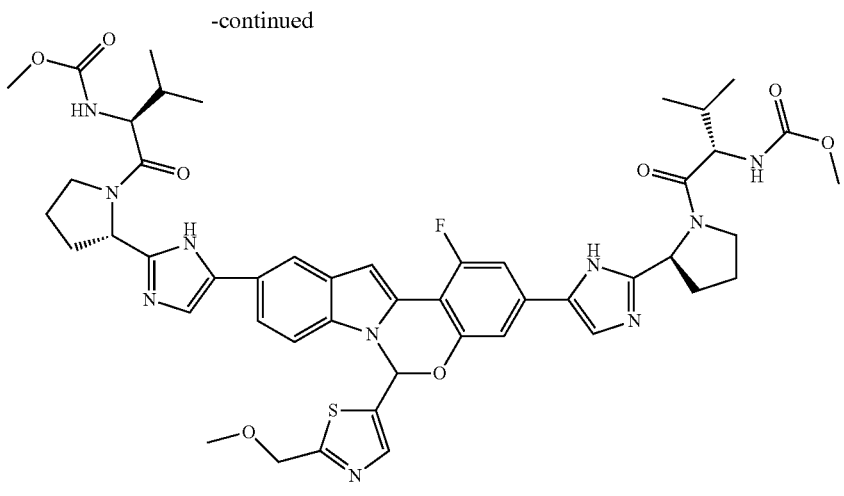

18

Step 1

To a solution of 18a (20.55 g, 0.18 mol) in MeOH (100 mL) was added NaBH$_4$ (7.6 g, 0.20 mol) at 0° C. The reaction mixture was stirred at 0° C. for 2 hours and monitored using TLC. Then, acetone (20 mL) was added into the solution and stirred for 20 minutes and the mixture was concentrated in vacuo. After that, the residue was washed with water (200 mL) and extracted with ethyl acetate (300 mL), washed with brine and dried over anhydrous sodium sulfate. After concentration in vacuo, and the resulting residue was purified using SiO$_2$ chromatography, eluting with petroleum ether:ethyl acetate (10/1~1/1) to provide 18b (3.18 g, 15.2%).

Step 2

To a solution of 18b (3.18 g, 27.7 mmol) in anhydrous DMF (50 mL) was added NaH (1.44 g, 36.00 mmol). The mixture was stirred at 0° C. for 20 minutes. Then, the CH$_3$I (9.410 g, 66.26 mmol) was added dropwise to the solution. The mixture was stirred at 0° C. for 2 hours. EtOAc (250 mL) and water (150 mL) were added. The organic layer was separated and washed with water three times, and dried over anhydrous Na$_2$SO$_4$. After filtration and concentration in vacuo, and the resulting residue was purified using SiO$_2$ chromatography, eluting with petroleum ether:ethyl acetate (20/1~5/1) to provide 18c (3.44 g, 96.3% yield).

Step 3

To a solution of 18c (1.18 g, 9.15 mmol) in anhydrous THF (25 mL) was added n-BuLi (4.40 mL, 10.98 mmol) at −78° C. After 30 minutes, DMF (1.34 g, 18.3 mmol) was added into the mixture and stirred at −78° C. for 2 hours under N$_2$ before quenched by NH$_4$C solution. The organic layer was separated and washed with water three times, and dried over anhydrous Na$_2$SO$_4$. After filtration and concentration in vacuo, and the resulting residue was purified using SiO$_2$ chromatography, eluting with petroleum ether:ethyl acetate (10/1~5/1) to provide 18d (0.45 g, 31.5%).

Step 4

To a mixture of 18d (0.45 g, 2.86 mmol) and Core1 (0.71 g, 1.85 mmol) in anhydrous CH$_3$CN (10 mL) was added TFA (0.3 mL). The mixture was stirred at room temperature for 6 hours. The reaction mixture became a clear solution and then solid appeared. The solid was collected by filtration and washed with MeOH to provide 18e (0.90 g, 92.7%).

Step 5

The solution of 18e (0.90 g, 1.71 mmol) in dry toluene (10 mL) was added DDQ (0.59 g, 2.57 mmol). After refluxing for 2 hours, the solvent was removed in vacuo and diluted with EtOAc. The organic layer was washed with saturated NaS$_2$O$_3$ aqueous and brine, dried over Na$_2$SO$_4$, filtered and concentrated in vacuo. The residue was washed with MeOH (20 mL). The solid was collected to provide 18f (0.60 g, 67.4%).

Step 6

A suspension of 18f (0.60 g, 1.14 mmol), bis(pinacolato)diboron (0.87 g, 3.43 mmol), KOAc (0.33 g, 3.43 mmol) and Pd(dppf)Cl$_2$ (80 mg, 0.11 mmol) in dioxane (20 mL) was stirred at 100° C. for 2 hours under N$_2$ atmosphere. The reaction mixture was cooled and concentrated in vacuo, and the residue was purified using SiO$_2$ chromatography, eluting with petroleum ether:ethyl acetate (20/1~5/1) to provide 18g (0.42, 60%).

Step 7

A suspension of 18g (0.42 g, 0.67 mmol), Cap 5 (0.63 g, 1.7 mmol), Na$_2$CO$_3$ (0.21 g, 2.04 mmol) and Pd(dppf)Cl$_2$ (50 mg, 0.068 mmol) in THF/H$_2$O (v/v=5/1, 24 mL) was stirred at 80° C. for about 15 hours under N$_2$ atmosphere. After that, the mixture was washed with water and extracted with ethyl acetate, washed with brine and dried over anhydrous sodium sulfate. After filtration, the filtrate was concentrated in vacuo, and the resulting residue was dissolved in DMF and purified using Pre-HPLC to provide 18f (69 mg, 23%).

Step 8

Compound 18 was obtained via purification of compound 18f (69 mg) by SFC separation using the following conditions:

Column: Chiralcel OJ-H 250×4.6 mm I.D., 5 um
Solvent: 40% of iso-propanol (0.05% DEA) in CO$_2$
Flow rate: 2.4 mL/min
Wavelength: 340 nm Compound 18 (20 mg, 58% yield). $^1$H NMR (MeOD) δ: 7.96-8.11 (m, 2H), 7.73-7.87 (m, 2 H), 7.53-7.64 (m, 2H), 7.37-7.43 (m, 1 H), 7.28 (s, 1H), 7.14-7.21 (m, 1 H), 5.14-5.29 (m, 2 H), 4.53 (s, 2 H), 4.18-4.29 (d, 2 H), 3.97-4.15 (m, 2 H), 3.38 (s, 1 H), 3.65 (s, 5 H), 3.39-3.44 (d, 1 H), 3.35 (s, 3 H), 2.44-2.63 (m, 2 H), 1.97-2.34 (m, 8 H), 0.84-1.03 (m, 12 H). LC/MS: Anal. Calcd. For [M+H]$^+$ C48H55FN10O8S: 951.39. found 951.6.

The following compounds of the present invention were prepared according to the methods described in the Example above.

| ID | Structures | Isomer | Observed [M + H]+ |
|---|---|---|---|
| 1<br>2 | 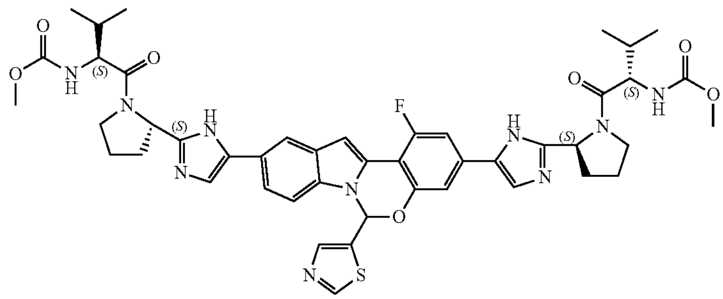 | Isomer 1<br>Isomer 2 | 907.6<br>907.4 |
| 3<br>4 | 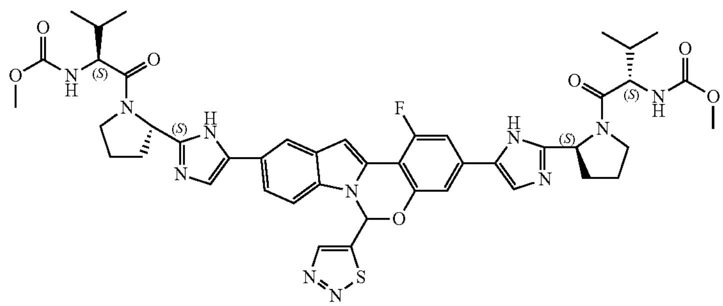 | Isomer 1<br>Isomer 2 | 908.6<br>908.6 |
| 5<br>6 | 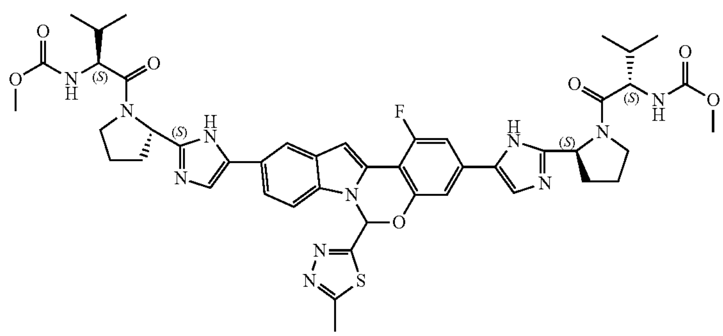 | Isomer 1<br>Isomer 2 | 922.6<br>922.4 |
| 7<br>8 | 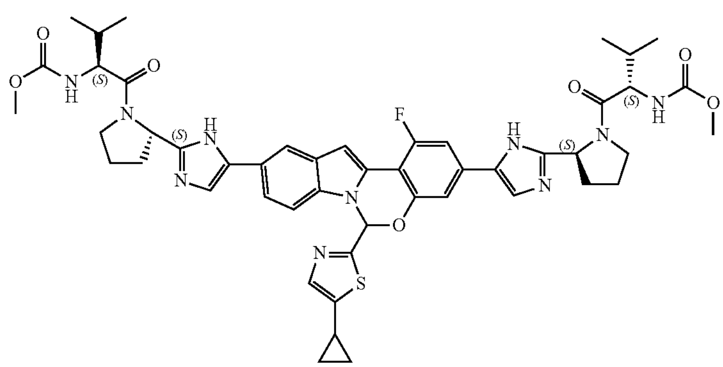 | Isomer 1<br>Isomer 2 | 947.6<br>947.6 |

-continued
| ID | Structures | Isomer | Observed [M + H]+ |
|---|---|---|---|
| 9 | 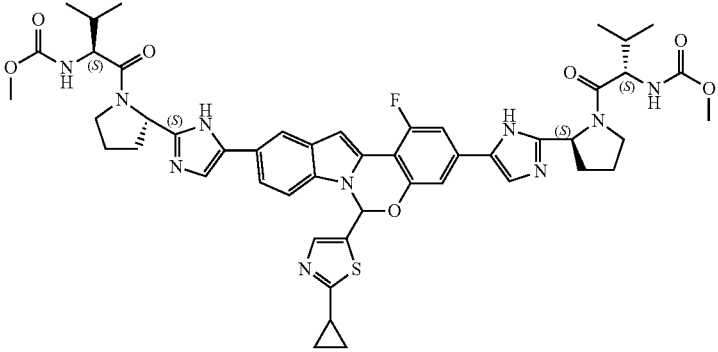 | Isomer 1 | 947.6 |
| 11 12 | 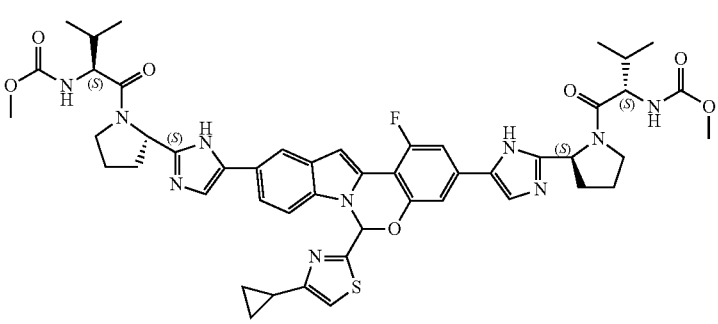 | Isomer 1 Isomer 2 | 947.6 947.6 |
| 13 14 | 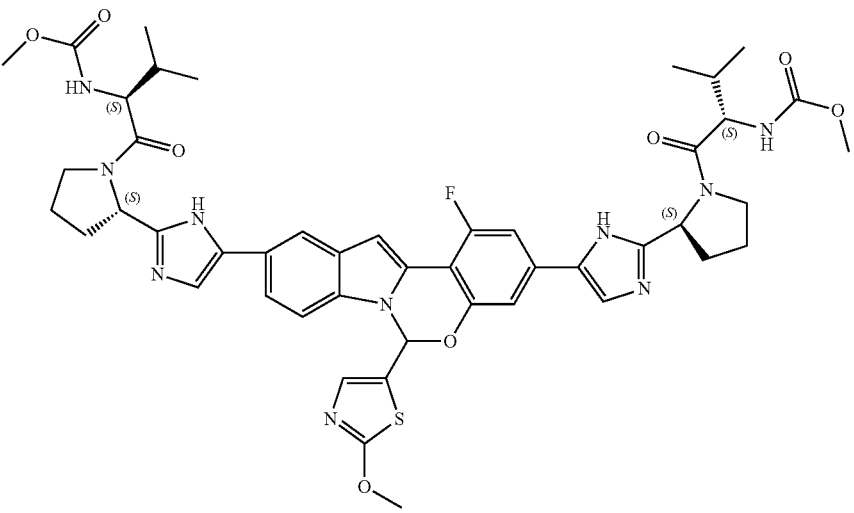 | Isomer 1 Isomer 2 | 937.6 937.6 |

-continued
| ID | Structures | Isomer | Observed [M + H]+ |
|---|---|---|---|
| 17 | 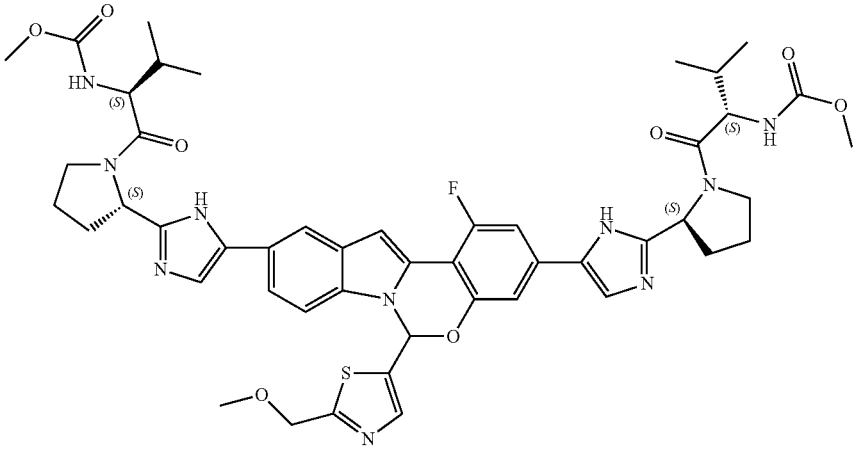 | Isomer 1 | 951.6 |
| 19 20 | 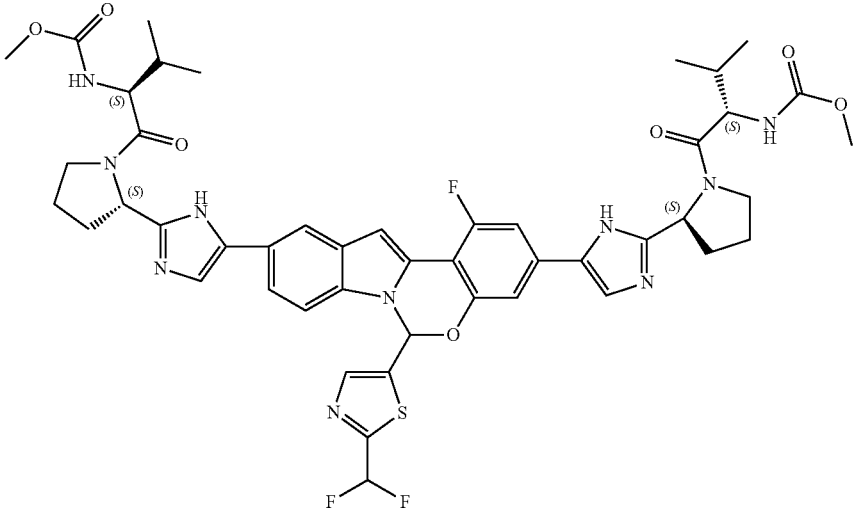 | Isomer 1 Isomer 2 | 957.8 957.4 |
| 22 | 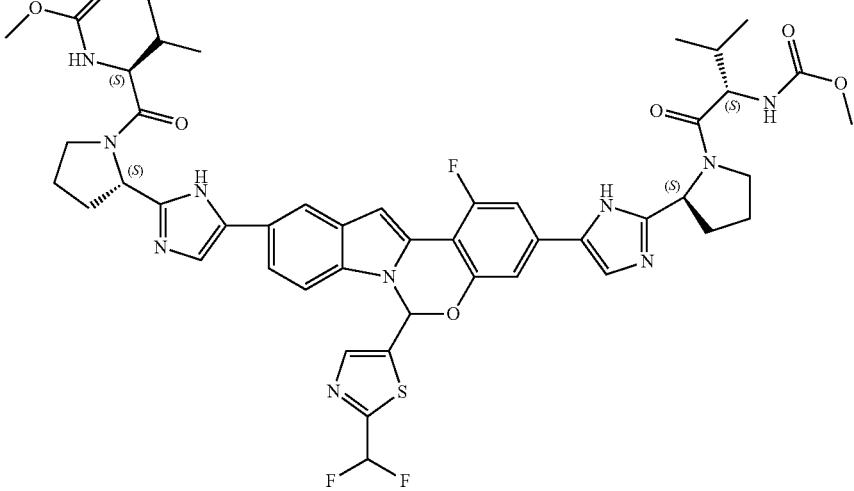 | Isomer 2 | 965.4 |

| ID | Structures | Isomer | Observed [M + H]+ |
|---|---|---|---|
| 23 | | Isomer 1 | 975.8 |
| 24 | | Isomer 2 | 975.6 |
| 26 | | Isomer 2 | 975.6 |

-continued

| ID | Structures | Isomer | Observed [M + H]⁺ |
|----|------------|--------|-------------------|
| 32 | | Isomer 2 | 1001.6 |
| 33 | | Isomer 1 | 1001.6 |
| 34 | | Isomer 2 | 1001.4 |

-continued

| ID | Structures | Isomer | Observed [M + H]+ |
|---|---|---|---|
| 43 | | Isomer 1 | 1008.8 |
| 44 | | Isomer 2 | 1008.6 |
| 45 | | Isomer 1 | 1013.6 |
| 46 | | Isomer 2 | 1013.8 |
| 48 | | Isomer 2 | 1013.8 |

-continued

| ID | Structures | Isomer | Observed [M + H]+ |
|---|---|---|---|
| 49 50 | | Isomer 1 Isomer 2 | 1017.8 1017.6 |
| 53 54 | | Isomer 1 Isomer 2 | 1017.8 1017.6 |

| ID | Structures | Isomer | Observed [M + H]+ |
|---|---|---|---|
| 55 | 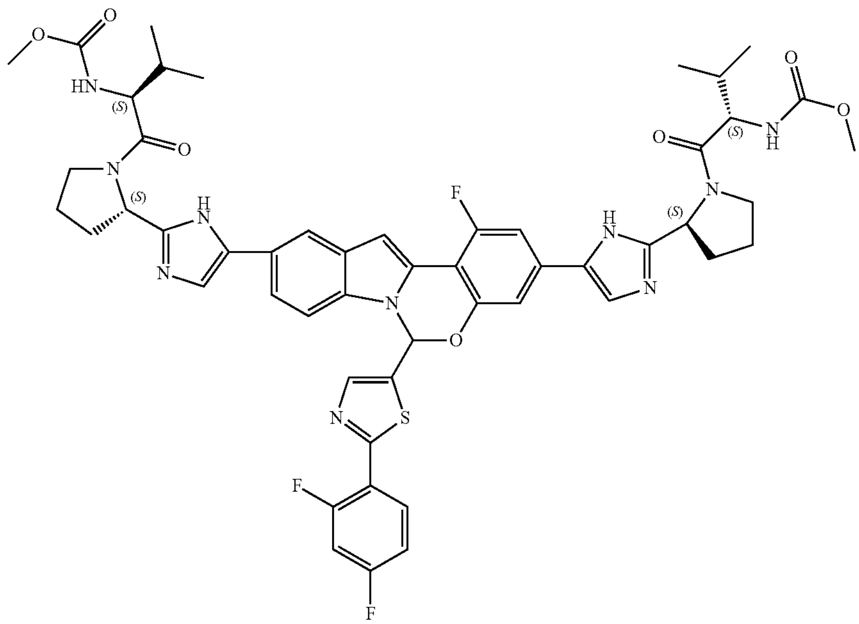 | | 1019.6 |
| 77 78 | | Isomer 1 Isomer 2 | 1067.6 1067.8 |

-continued

| ID | Structures | Isomer | Observed [M + H]+ |
|---|---|---|---|
| 81 | | Isomer 2 | 935.6 |
| 82 | | Isomer 1 | 935.4 |
| 85 | | Isomer 1 | 949.6 |
| 86 | | Isomer 2 | 949.6 |
| 87 | | Isomer 1 | 961.6 |
| 88 | | Isomer 2 | 961.4 |

-continued
| ID | Structures | Isomer | Observed [M + H]+ |
|---|---|---|---|
| 98 99 | 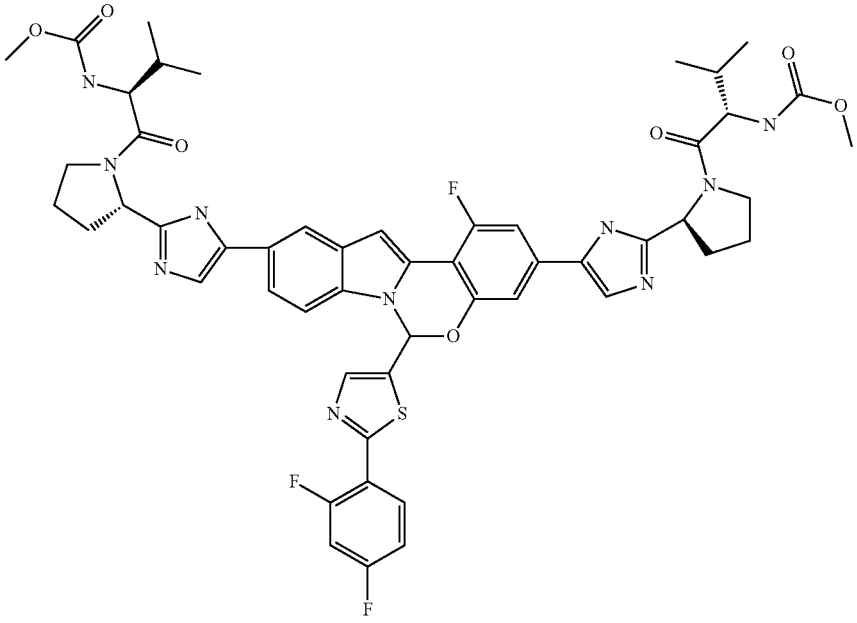 | Isomer 1<br>Isomer 2 | 1019.8<br>1019.8 |
| 114 115 | 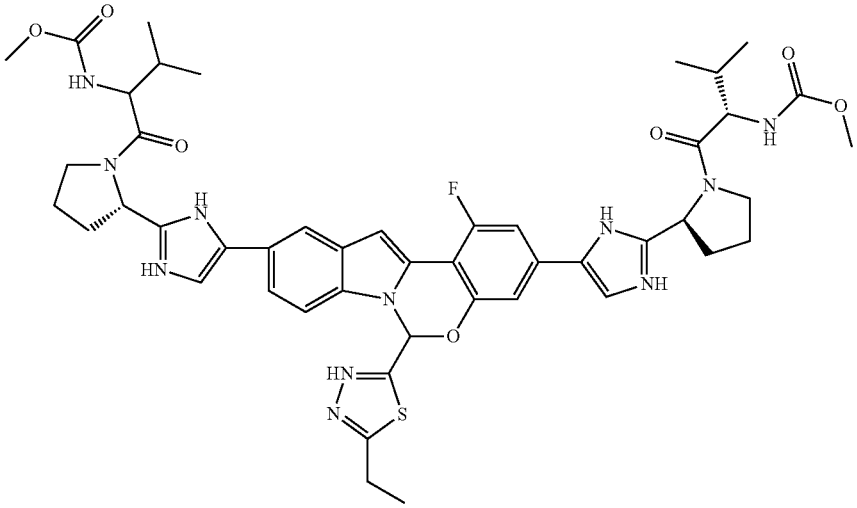 | Isomer 1<br>Isomer 2 | N/A<br>N/A |

Example 15
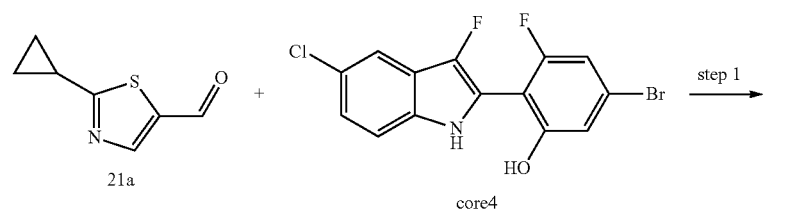
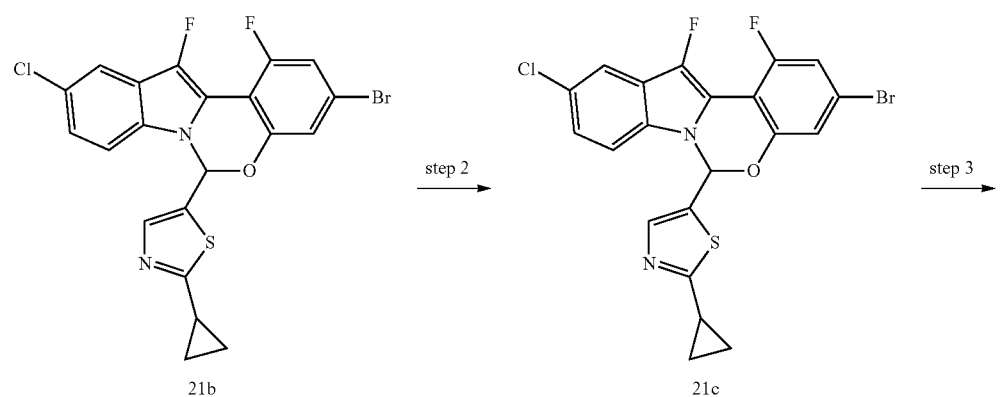
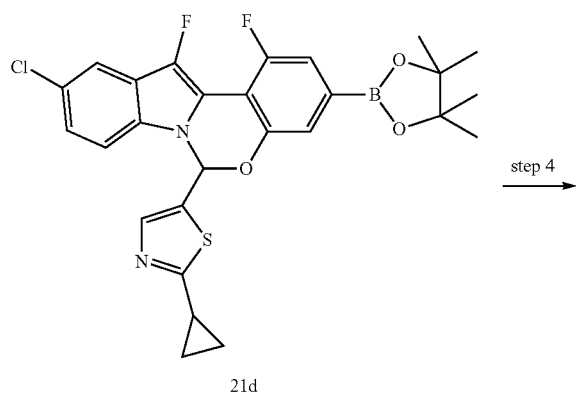
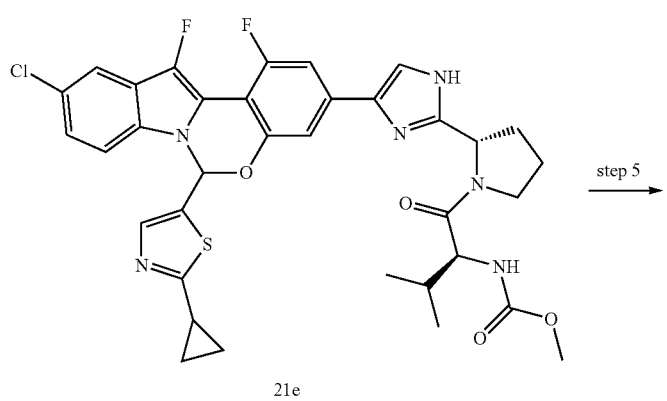

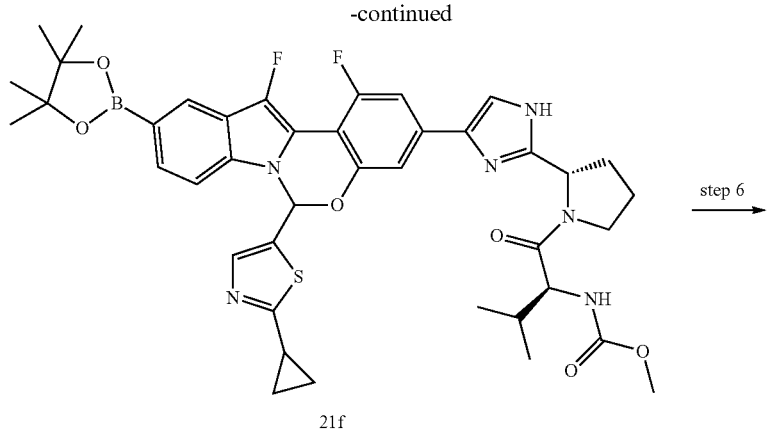
21f

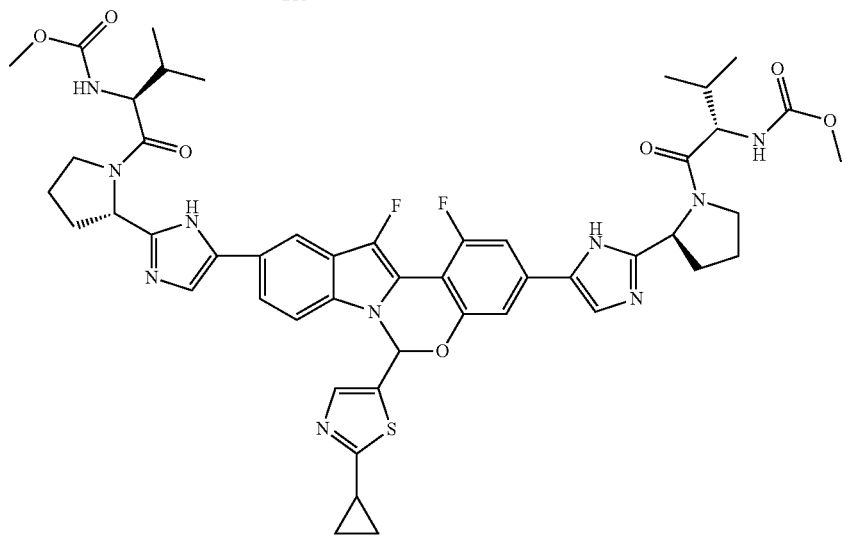
21

Step 1

21a (2.57 g, 16.7 mmol) and Int-4a (5 g, 13.9 mmol) were dissolved in 50 ml of toluene, MSA (catalyst equiv.) was added into it and the resulting mixture was stirred at 100° C. for about 15 hours under $N_2$ atmosphere. Cooled the mixture to room temperature and concentrated the mixture in vacuo. The crude product was washed with MeOH. The compound 21b (5.5 g, 81%) was collected by filtration.

Step 2

21b was purified using SFC separation to provide compound 21c (3.4 g).

Column: Chiralpak AD-3 150×4.6 mm I.D., 3 um
Mobile phase: 40% of methanol (0.05% DEA) in $CO_2$
Flow rate: 2.5 mL/min
Wavelength: 220 nm Step 3

A suspension of the compound 21c (3.4 g, 6.9 mmol), bis(pinacolato)diboron (2.1 g, 8.3 mmol), KOAc (1.35 g, 13.8 mmol) and Pd(dppf)Cl$_2$ (0.25 g, 0.34 mmol) in dioxane (120 mL) was stirred at 100° C. under $N_2$ atmosphere for 2 hours. The reaction mixture was cooled and concentrated in vacuo, purified using SiO$_2$ chromatography, eluting with petroleum ether:ethyl acetate (50/1~10/1) to provide the product compound 21e (3.7 g, 99%). LC/MS: Anal. Calcd. For [M+H]$^+$ C27H24BClF2N2O3S: 541.13. found 541.4.

Step 4

A suspension of the compound 21e (3.7 g, 6.85 mmol), Cap 5 (2.38 g, 7.54 mmol), Na$_2$CO$_3$ (1.45 g, 13.7 mmol) and Pd(dppf)Cl$_2$ (258 mg, 0.35 mmol) in THF/H$_2$O (v/v=5:1, 36 mL) was stirred at 100° C. under $N_2$ atmosphere for about 15 hours. LC-MS and TLC were detected the reaction. Separated the water phase via reparatory funnel, and the organic phase was concentrated in vacuo and purified using SiO$_2$ chromatography, eluting with petroleum ether:ethyl acetate (1/1~1/10) to provide the desired compound 21f (4.2 g, 89%).

Step 5

To a mixture of 21f (4.2 g, 6.5 mmol), bis(pinacolato) diboron (2.0 g, 7.8 mmol), KOAc (1.3 g, 13 mmol), Pd$_2$(dba)$_3$ (595 mg, 0.65 mmol), X-Phos (618 mg, 1.3 mmol) degassed and sealed under $N_2$ was added dioxane (80 mL). Following further $N_2$ purging. The mixture was stirred at 100° C. for about 15 hours. After cooling to room temperature, the solvent was concentrated in vacuo and the residue was purified using SiO$_2$ chromatography, eluting with DCM:MeOH (100/1~50/1) to provide 21g (4.2 g, 88%).

Step 6

A mixture of 21g (260 mg, 0.32 mmol), Cap 5 (84 mg, 0.32 mmol), Na$_2$CO$_3$ (120 mg, 1.1 mol) and Pd(dppf)Cl$_2$ (20 mg, 0.028 mmol) in THF/H$_2$O (v/v=5:1, 12 mL) was stirred at 100° C. under $N_2$ atmosphere for about 15 hours. After cooling to room temperature and filtration, the residue was purified using Pre-HPLC to provide 21 (220 mg, 70%). $^1$H NMR (MeOD) δ: 0.89-0.99 (m, 14 H), 1.06 (d, J=5.09 Hz, 2 H), 2.04-2.28 (m, 9 H), 2.54-2.57 (m, 2 H), 3.66 (s, 6 H), 3.88 (br. s., 2 H), 4.10 (br. s., 2 H), 4.23 (br. s., 2 H), 5.20-2.25 (m, 2 H), 7.18 (s, 1 H), 7.29 (s, 1 H), 7.43 (d, J=10.56 Hz, 1 H), 7.61-7.64 (m, 2 H), 7.82 (s, 1 H), 7.90-7.99 (m, 3 H). LC/MS: Anal. Calcd. For [M+H]$^+$ C49H54F2N10O7S: 965.39. found 965.8.
Example 16
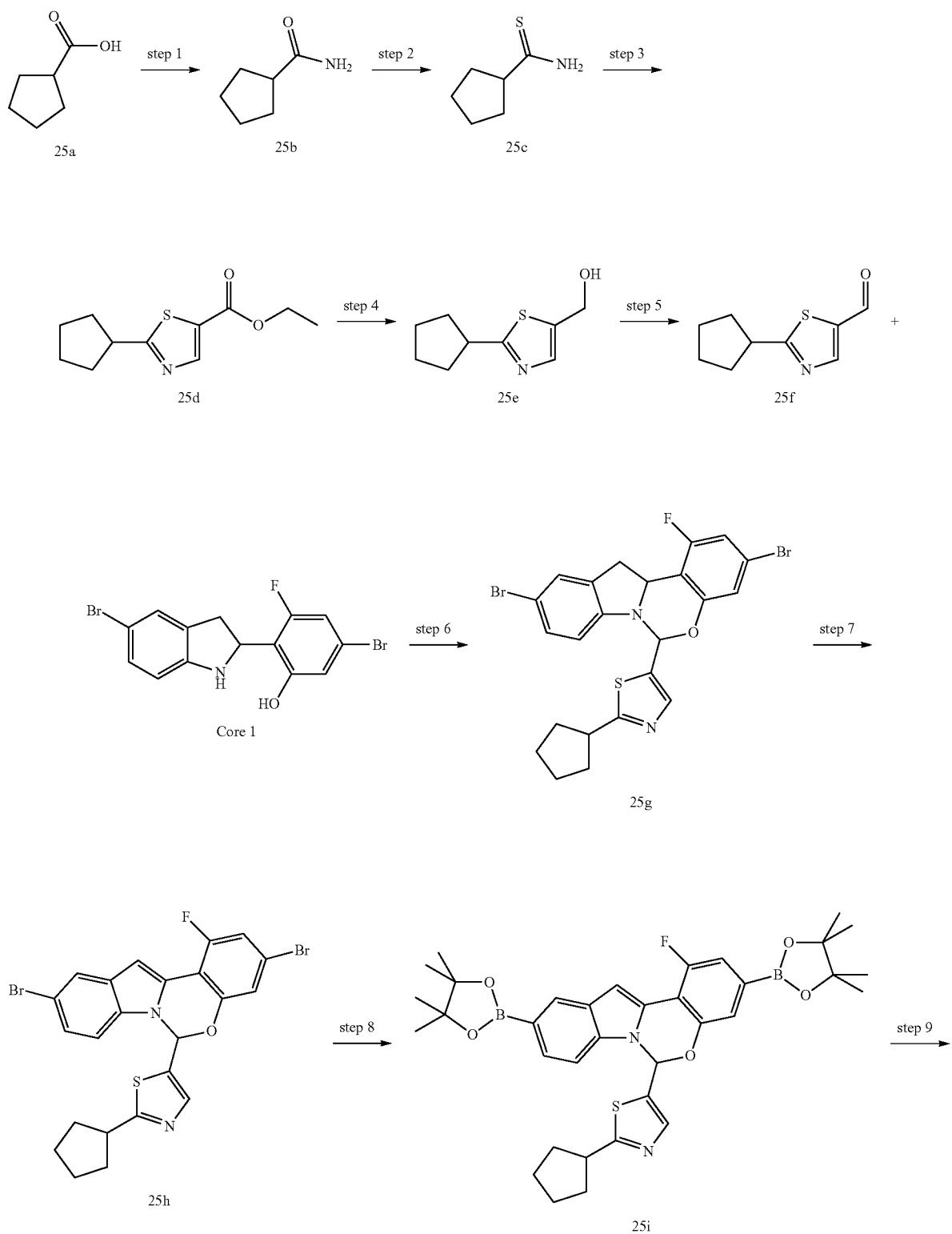

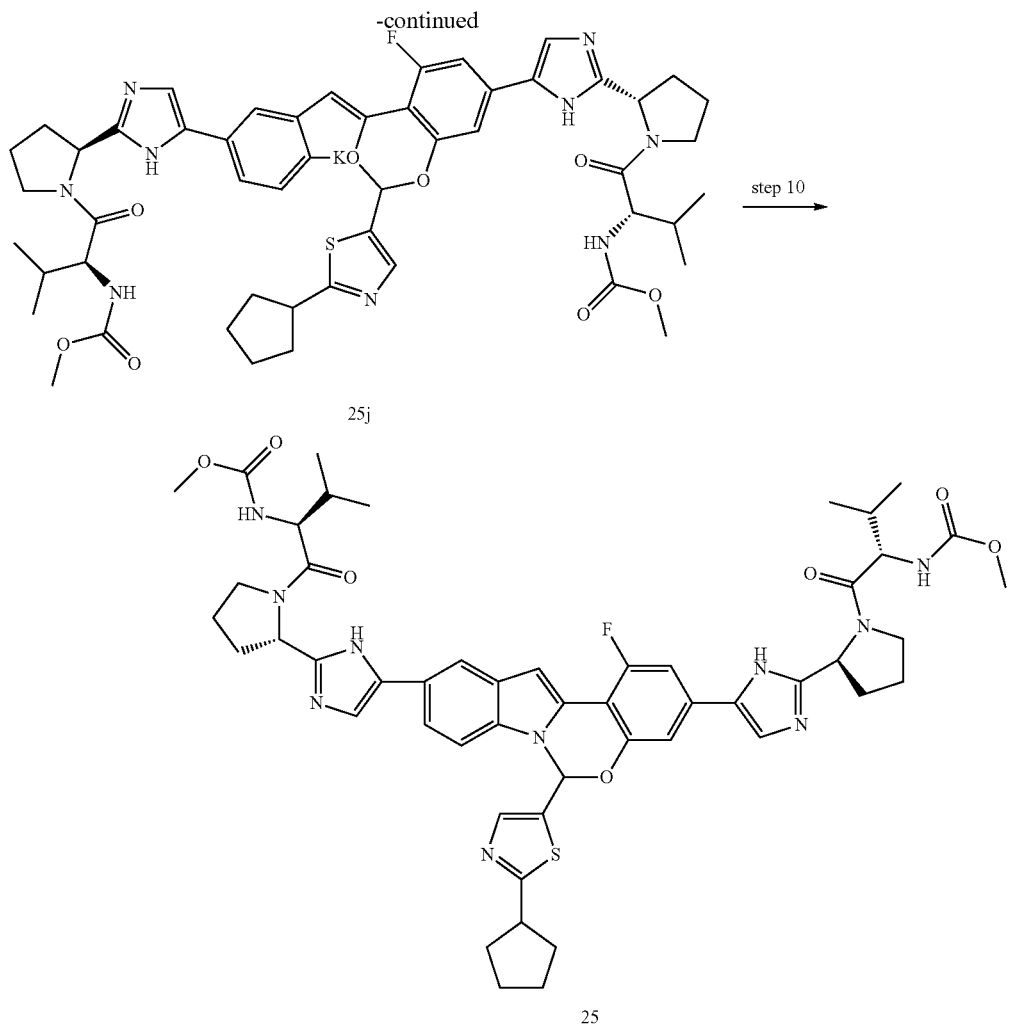

Step 1

A solution of 25a (15 g, 127 mmol) and CDI (22 g, 140 mmol) in EtOAc (200 mL) was stirred at room temperature for 2 hours. The mixture was then treated with ammonium hydroxide (8 mL) and heated at 45° C. for 2 hours. The solution was diluted with EtOAc (200 mL) and washed with water (200 mL), citric acid solution, dried over $Na_2SO_4$. After filtration, the solvent was removed in vacuo to provide 25b (13 g, 90%). $^1$H-NMR (400 MHz, $CDCl_3$) δ: 5.59 (br, 2H), 2.61 (q, J=8.0 Hz, 1H), 1.93-1.84 (m, 2H), 1.82-1.68 (m, 4H), 1.64-1.52 (m, 2H)

Step 2

To a mixture of 25b (13 g, 115 mmol) in toluene (150 mL) was added Lawesson Reagent (46.5 g, 115 mmol). The mixture was stirred at room temperature for about 15 hours. The reaction mixture was concentrated in vacuo, and the residue was purified using $SiO_2$ chromatography, eluting with petroleum ether:ethyl acetate (100/1~10/1) to provide 25c (10.8 g, 73%). $^1$H NMR ($CDCl_3$) δ: 4.99 (s, 1H), 2.92 (q, J=8.2 Hz, 1H), 1.96 (d, J=8.2 Hz, 2H), 1.87-1.72 (m, 4H), 1.64-1.53 (m, 2H)

Step 3

A suspension of ethyl 2-chloro-3-oxopropanoate (9.7 g, 52 mmol) in DMF (100 mL) was adjusted to pH=2 using $H_2SO_4$. To the mixture was added 25c (4.5 g, 35 mmol) and the mixture was stirred at 100° C. for 20 hours. The mixture was poured into $H_2O$, and extracted with ethyl acetate (100 mL). The organic layer was washed with brine and dried over anhydrous sodium sulfate. After filtration and concentration in vacuo, the crude product was purified using $SiO_2$ chromatography, eluting with petroleum ether:ethyl acetate (100/1~10/1) to provide 25d (3.7 g, 47%).

Step 4

To a mixture of 25d (3 g, 13.3 mmol) in THF (50 mL) was added $LiAlH_4$ (760 mg 20 mmol) in portions with stirring at 0° C. and then stirred at 30° C. for 3 hours. The mixture was quenched with water. After filtration and concentration in vacuo, and the resulting residue was purified using $SiO_2$ chromatography, eluting with petroleum ether:ethyl acetate (100/1~10/1) to provide 25e (2.1 g, 87%). $^1$H-NMR ($CDCl_3$) δ: 7.43 (s, 1H), 4.78 (s, 2H), 3.37 (q, J=7.8 Hz, 1H), 2.20-2.10 (m, 2H), 1.79 (d, J=3.5 Hz, 4H), 1.66 (d, J=3.5 Hz, 2H)

Step 5

To a mixture of 25e (2.1 g, 11.4 mmol) in DCM (50 mL) was added DMP (4.7 g, 12.5 mmol) in portions with stirring at 0° C. and then stirred at 30° C. for 5 hours, before the mixture was quenched with Sat $Na_2SO_3$ solution. After filtration and concentration in vacuo, and the resulting residue was purified using $SiO_2$ chromatography, eluting with petroleum ether:ethyl acetate (100/1~10/1) to provide 25f (1.8 g, 87%). ¹H NMR (CDCl₃) δ: 9.96 (s, 1H), 8.26 (s, 1H), 3.47 (q, J=7.7 Hz, 1H), 2.23-2.14 (m, 2H), 1.87-1.79 (m, 4H), 1.71 (s., 2H).

Step 6

To a mixture of 25f (1 g, 5.5 mmol) and Core 1 (1.9 g, 5 mmol) in anhydrous CH₃CN (50 mL) was added TFA (3 drops). The mixture was stirred at room temperature for about 15 hours. The reaction mixture became a clear solution and then solid appeared. The solid was collected by filtration and washed with CH₃CN to provide 25g (1.7 g, 57%). ¹H NMR (CDCl₃) δ: 7.51 (s, 1H), 7.07 (d, J=8.2 Hz, 1H), 7.03 (s, 1H), 6.79-6.71 (m, 4H), 5.01 (d, J=9.0 Hz, 1H), 3.51 (dd, J=9.8, 16.4 Hz, 1H), 3.36-3.26 (m, 1H), 3.21 (d, J=16.4 Hz, 1H), 2.15-2.05 (m, 2H), 1.78-1.69 (m, 4H), 1.62 (br. s., 2H).

Step 7

The solution of 25g (1.6 g, 2.9 mmol) in dry toluene (50 mL) was added DDQ (1 g, 4.4 mmol). After refluxing for 2 hours, the solvent was removed in vacuo and diluted with EtOAc. The organic layer was washed with saturated NaS₂O₃ aqueous and brine, dried over Na₂SO₄, filtered and concentrated in vacuo. The residue was washed with MeOH (20 mL) to provide 25h (1 g, 67%).

Step 8

The solution of 25h (540 mg, 0.98 mmol), bis(pinacolato)diboron (627 mg, 2.46 mmol), KOAc (480 mg, 4.9 mmol) and Pd(dppf)Cl₂ (73 mg, 0.1 mmol) in dioxane (20 mL) was stirred at 100° C. for 2 hours under N₂ atmosphere. The reaction mixture was cooled and concentrated in vacuo, and the residue was purified using SiO₂ chromatography, eluting with petroleum ether:ethyl acetate (5/1~1/1) to provide 25i (480 mg, 76%).

Step 9

To a solution of 25i (480 mg, 0.75 mmol), Cap 5 (697 mg, 1.87 mmol), Na₂CO₃ (397 mg, 3.75 mmol) and Pd(dppf)Cl₂ (54 mg, 0.075 mmol) in THF/H₂O (v/v=5/1, 20 mL) was stirred at 80° C. for about 15 hours under N₂ atmosphere. The mixture was then washed with water and extracted with ethyl acetate, washed with brine and dried over anhydrous sodium sulfate. After being concentrated in vacuo, and the resulting residue was purified using SiO₂ chromatography, eluting with petroleum ether:ethyl acetate (5/1~1/1) to provide 25j (480 mg, 66%). LC/MS: Anal. Calcd. For [M+H]⁺ C51H59FN10O7S: 975.4. found 975.6.

Step 10

Compound 25j (240 mg) was separated by SFC using the following conditions to provide 25 (55 mg, 46%).

Instrument: Thar SFC

Column: Chiralcel OJ-H, 250×4.6 mm, I.D. 5 um

Mobile phase: 40% of ios-propanol (0.05% DEA)

Co-SolventL: IPA (0.05% DEA)

Flow rate: 2.5 mL/min

Wavelength: 340 nm

¹H NMR ((MeOD)) δ: 8.03 (d, J=3.5 Hz, 2H), 7.91 (s, 1H), 7.77 (s, 1H), 7.63-7.54 (m, 2H), 7.41 (d, J=11.0 Hz, 1H), 7.35 (s, 1H), 7.21 (br. s., 2H), 5.26-5.16 (m, 2H), 4.20 (t, J=7.4 Hz, 2H), 4.08 (br. s., 2H), 3.88-3.80 (m, 2H), 3.64 (s, 6H), 2.54 (d, J=11.7 Hz, 3H), 2.25 (d, J=5.5 Hz, 2H), 2.15 (br. s., 4H), 2.08-1.97 (m, 4H), 1.75-1.54 (m, 6H), 1.05-0.77 (m, 12H).

Example 17

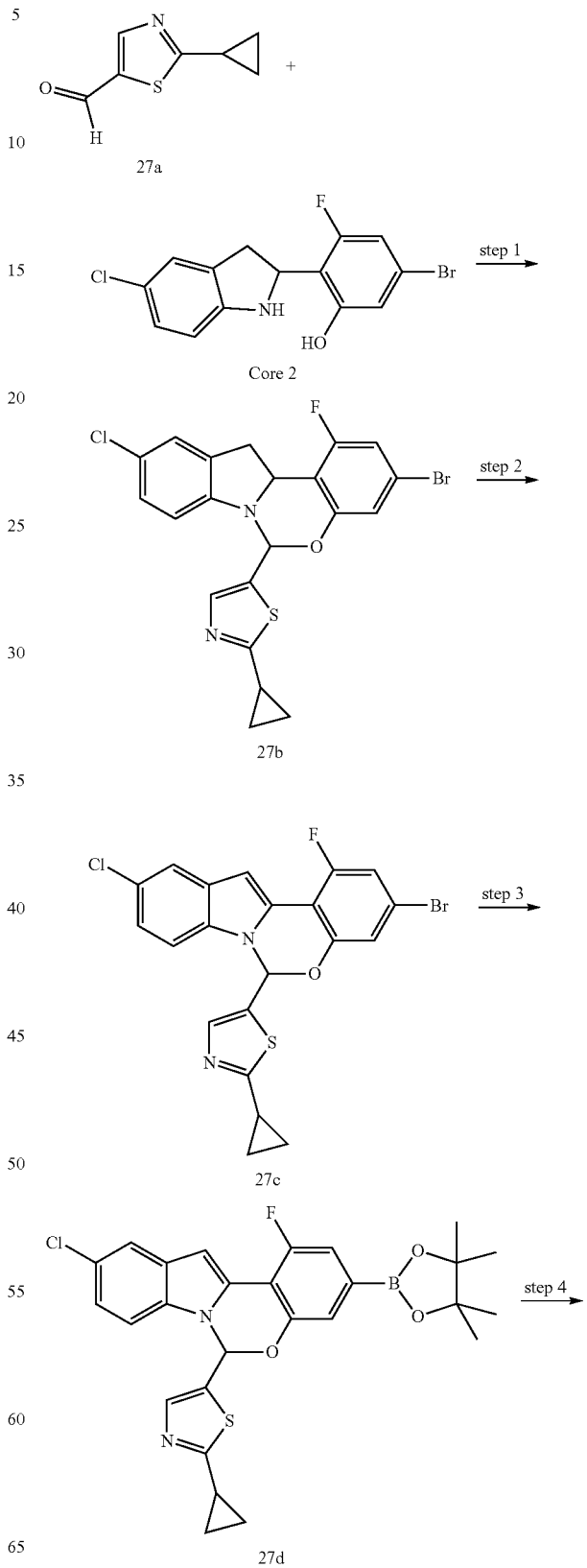

119

-continued

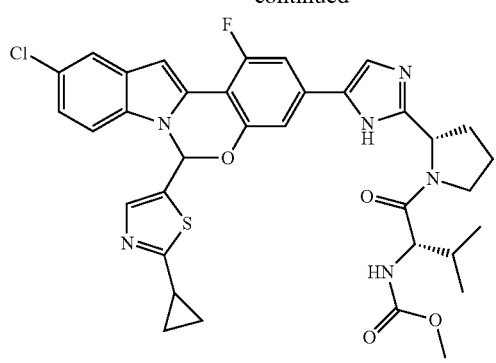
27e

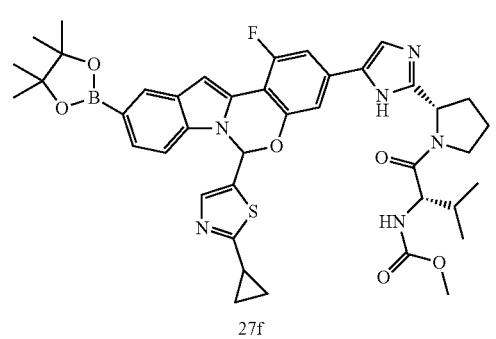
27f

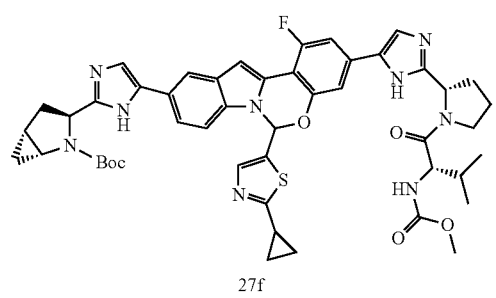
27f

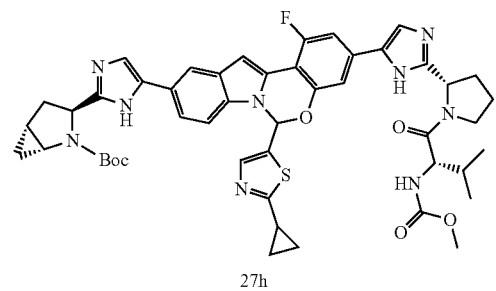
27h

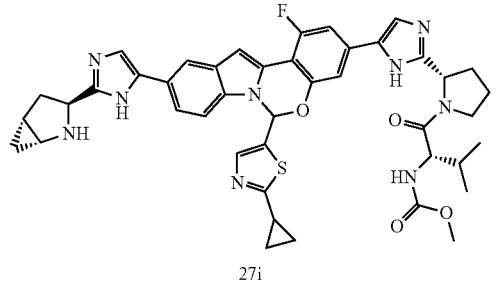
27i

120

-continued

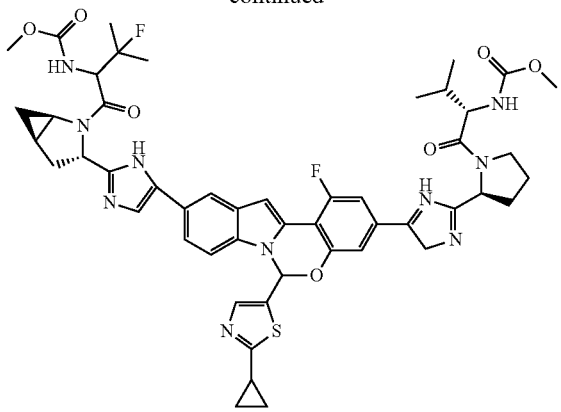
27

Step 1

To a mixture of 27a (2.7 g, 17.5 mmol) and Int-2b (4.0 g, 11.7 mmol) in anhydrous $CH_3CN$ (50 mL) was added TFA (1 mL). The mixture was stirred at room temperature for 6 hours. The reaction mixture became a clear solution and then solid appeared. The solid was collected by filtration and washed with $CH_3CN$ to provide 27b (4.5 g, 80%).

Step 2

The solution of 27b (4.5 g, 9.4 mmol) in dry toluene (50 mL) was added DDQ (3.2 g, 14.2 mmol). After refluxing for 2 hours, the solvent was removed in vacuo and diluted with EtOAc. The organic layer was washed with saturated $NaS_2O_3$ aqueous and brine, dried over $Na_2SO_4$, filtered and concentrated in vacuo. The residue was washed with MeOH (20 mL). The solid was collected to provide 27c (4.0 g, 88%).

Step 3

A suspension of 27c (4.0 g, 8.4 mmol), bis(pinacolato) diboron (2.6 g, 10.1 mmol), KOAc (2.1 g, 21.1 mmol) and Pd(dppf)$Cl_2$ (310 mg, 0.42 mmol) in dioxane (50 mL) was stirred at 100° C. for 2 hours under $N_2$ atmosphere. The reaction mixture was cooled and concentrated in vacuo, and the residue was purified using $SiO_2$ chromatography (80 g, EtOAc/Petroleum ether 0% to 5%) to provide 27d (4.2 g, 95%). LC/MS: Anal. Calcd. For $[M+H]^+$ C27H25BClFN2O3S: 523.14. found 523.2.

Step 4

A suspension of 27d (4.2 g, 8.0 mmol), Cap 5 (3.2 g, 8.4 mmol), $Na_2CO_3$ (2.2 g, 21.0 mmol) and Pd(dppf)$Cl_2$ (310 mg, 0.42 mmol) in THF/$H_2O$ (v/v=5/1, 120 mL) was stirred at 80° C. for about 15 hours under $N_2$ atmosphere. After that, the mixture was washed with water and extracted with ethyl acetate, washed with brine and dried over anhydrous sodium sulfate. After concentration in vacuo, and the resulting residue was purified using $SiO_2$ chromatography (80 g, EtOAc/Hexane 10% to 50%) to provide 27e (4.5 g, 81%). LC/MS: Anal. Calcd. For $[M+H]^+$ C35H34ClFN6O4S: 689.20. found 689.2.

Step 5

To a mixture of 27e (4.5 g, 6.5 mmol), bis(pinacolato) diboron (2.0 g, 7.8 mmol), KOAc (1.6 g, 16.3 mmol), $Pd_2(dba)_3$ (338 mg, 0.33 mmol), X-Phos (312 mg 0.65 mmol) degassed and sealed under $N_2$ was added dry dioxane. The mixture was stirred at 100° C. for about 15 hours. After cooling to room temperature, the solvent was concentrated in vacuo and the residue was purified using $SiO_2$ chromatography, eluting with petroleum ether:ethyl acetate (5/1~1/1) to provide 27f (4.6 g, 90%). LC/MS: Anal. Calcd. For [M+H]+ C41H46BFN6O6S: 781.33. found 781.4.

Step 6

A mixture of 27f (4.6 g, 5.9 mmol), Cap 6 (2.0 g, 6.4 mmol), Na2CO3 (1.7 g, 16.0 mol) and Pd(dppf)Cl2 (234 mg, 0.33 mmol) in THF/H2O (v/v=5/1, 120 mL) was stirred at 80° C. under N2 atmosphere for about 15 hours. After that, the mixture was washed with water and extracted with ethyl acetate, washed with brine and dried over anhydrous sodium sulfate. After concentration in vacuo, and the resulting residue was purified using SiO2 chromatography, eluting with petroleum ether:ethyl acetate (3/1~1/2) (100 g, Hexane/EtOAc 30% to 200%) to provide 27g (4.0 g, 74%). LC/MS: Anal. Calcd. For [M+H]+ C48H52FN9O6S: 902.37. found 902.6.

Step 7

The compound of 27g (4.0 g) was separated by SFC by using the following conditions to provide 27h (1.3 g, 32%).
Instrument: Thar SFC
Column: OJ-H, 250×4.6 mm, 5 um
Mobile phase: 40% of iso-propanol (0.05% DEA) in CO2
Flow rate: 2.4 mL/min
Wavelength: 340 nm Step 8

To a solution of 27h (1.3 g, 1.4 mmol) in 1,4-dioxane (15 mL) was added HCl/1,4-dioxane (15 mL, 4M). Then the mixture was stirred at room temperature for 1-2 hours. When the reaction completed, the mixture was concentrated in vacuo to provide 27i (1.1 g, 99%). LC/MS: Anal. Calcd. For [M+H]+ C43H44FN9O4S: 802.32. found 802.4.

Step 9

To a mixture of 27i (500 mg, 0.62 mmol), Cap 1 (186 mg, 0.76 mmol) and HATU (289 mg, 0.76 mmol) in DMF (5 mL) was added DIEA (164 mg, 1.26 mmol). The resulting mixture was stirred at room temperature for 30 minutes, and LC-MS judged the material was consumed up. After filtration, the filtrate was purified using Pre-HPLC to provide 27 (290 mg, 48%). $^1$H NMR (MeOD) δ: 8.01-8.05 (m, 1H), 7.97 (br, 1H), 7.90 (s, 1H), 7.76 (s, 1H), 7.60 (s, 2H), 7.43 (d, J=10.5 Hz, 1H), 7.33 (br, 1H), 7.21 (br, 1H), 7.13 (s, 1H), 5.15-5.27 (m, 2H), 5.05 (d, J=8.5 Hz, 2H), 5.00-5.09 (m, 2H), 4.25 (d, J=7.0 Hz, 1H), 4.10 (br, 1H), 3.83-3.98 (m, 2H), 3.69 (d, J=10.5 Hz, 6H), 2.70 (dd, J=9.3, 13.8 Hz, 1H), 2.45-2.60 (m, 2H), 2.30 (br, 1H), 2.21 (dd, J=4.3, 8.3 Hz, 3H), 2.10 (td, J=6.8, 13.6 Hz, 2H), 1.47-1.57 (m, 3H), 1.28-1.39 (m, 3H), 1.06-1.17 (m, 3H), 0.94 (dd, J=6.8, 18.3 Hz, 9H). LC/MS: Anal. Calcd. For [M+H]+ C50H54F2N10O7S: 977.39. found 977.8.

Example 18

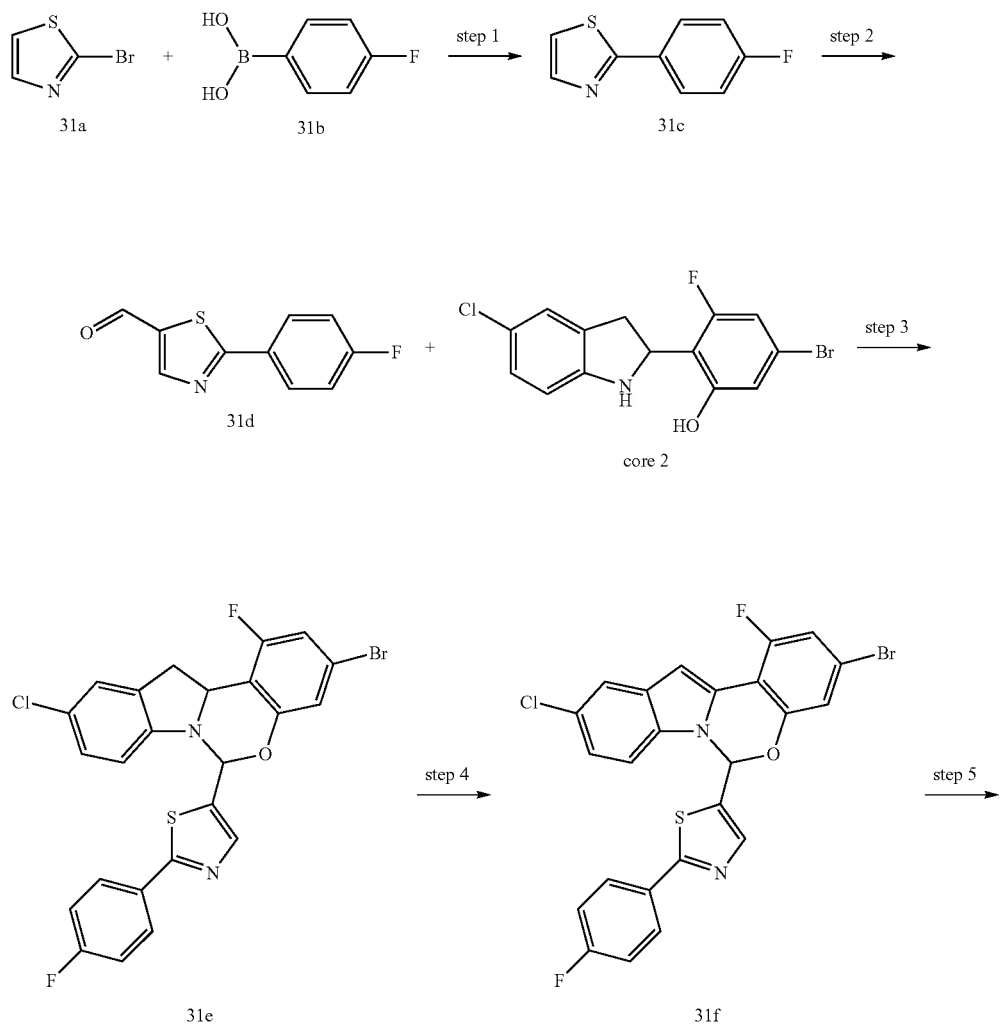

-continued
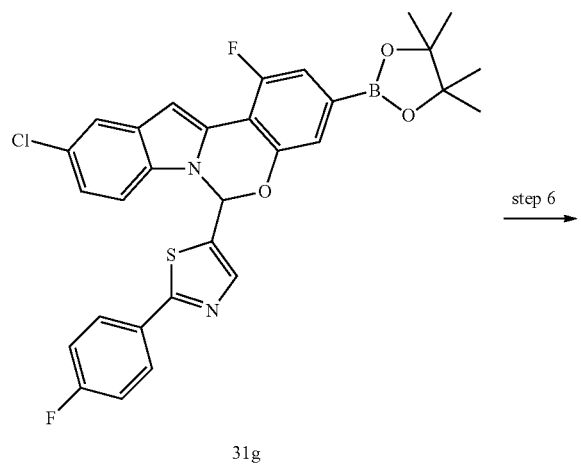
31g
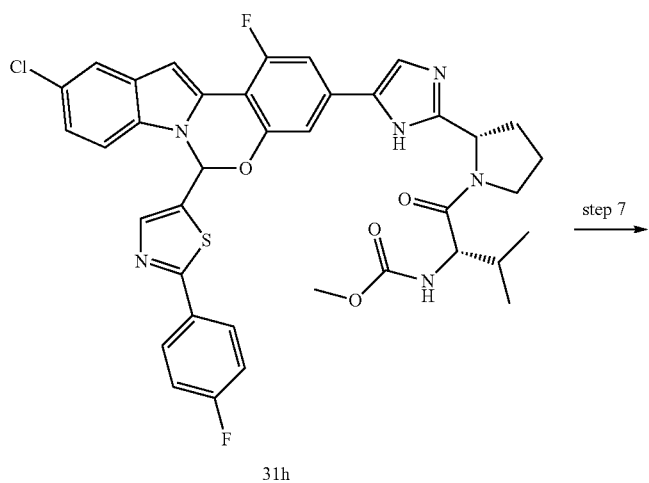
31h
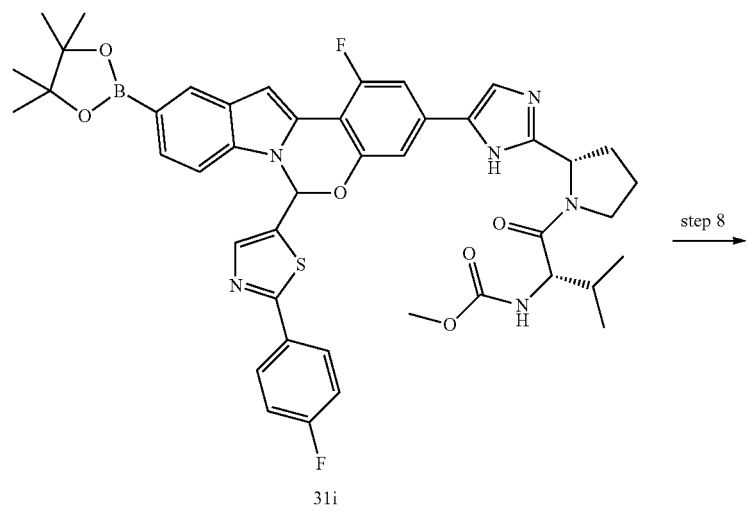
31i

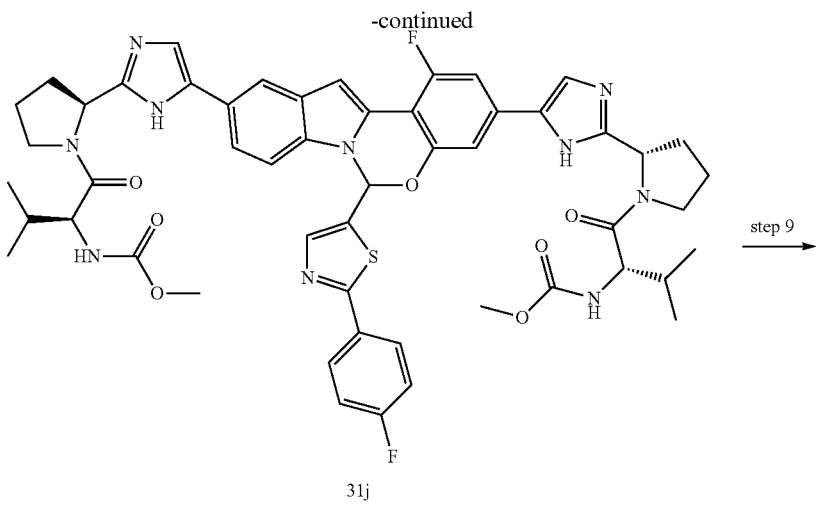

31j

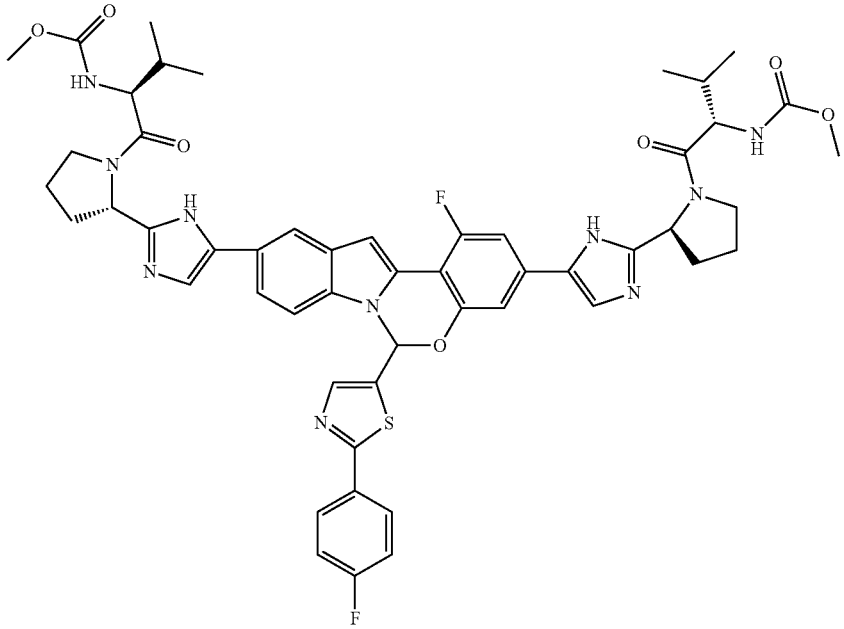

31

Step 1

A solution of 31a (2 g, 12.2 mmol), 31b (5 g, 36.6 mmol), Pd(OAc)$_2$ (0.16 g, 0.73 mmol), cataCXium® A (0.52 g, 1.46 mmol) and Cs$_2$CO$_3$ (12 g, 36.6 mmol) in toluene/H$_2$O (88 mL, toluene:H$_2$O=10:1) was stirred at 100° C. for 16 hours under N$_2$ atmosphere. The solution was extracted with EtOAc. The combined organic was dried over Na$_2$SO$_4$, purified using SiO$_2$ chromatography, eluting with petroleum ether:ethyl acetate (100/1~40/1) to provide 31c (2 g, 92% yield). $^1$H NMR (CDCl$_3$) δ: 7.95-7.91 (m, 2 H), 7.82 (d, J=4 Hz, 1 H), 7.29 (d, J=4 Hz, 1 H), 7.11 (t, J=16 Hz, 2 H).

Step 2

To a mixture of 31c (1.56 g, 8.76 mmol) in THF (60 mL) was added a 2.5 M solution of n-BuLi (3.86 mL, 9.64 mmol) at −78° C. under N$_2$. The mixture was agitated for 2 hours at this temperature then DMF (0.83 g, 11.4 mmol) was added. The mixture was stirred at 25° C. for 1 hour. Quenched with NH$_4$Cl saturate solution and extracted with EtOAc. The organic layer was dried over sodium sulfate, and concentrated in vacuo and purified using SiO$_2$ chromatography to provide compound 31d (1.8 g, 100% yield). $^1$H NMR (CDCl$_3$) δ:10.03 (s, 1 H), 8.40 (s, 1 H), 8.03-8.00 (m, 2 H), 7.24-7.15 (m, 2 H).

Step 3

To a mixture of 31d (2.2 g, 10.7 mmol) and Core2 (3.66 g, 10.7 mmol) in anhydrous CH$_3$CN (60 mL) was added TFA (0.37 g, 3.2 mmol). The mixture was stirred at 25° C. for 1 hour. The reaction mixture became a clear solution and then solid appeared. The solid was collected by filtration and washed with CH$_3$CN to provide 31e (4.35 g, 76% yield). $^1$H NMR (CDCl$_3$) δ: 7.83-7.79 (m, 2 H), 7.69 (s, 1 H), 7.24 (d, J=8 Hz, 1 H), 7.20 (s, 1 H), 7.05 (t, J=16 Hz, 2 H), 6.82 (s, 1 H), 6.77 (d, J=8 Hz, 1 H), 6.65 (s, 1 H), 6.59 (d, J=12 Hz, 1 H), 5.07 (d, J=8 Hz, 1 H), 3.57-3.51 (m, 1 H), 3.23 (d, J=16 Hz, 1 H).

Step 4

The solution of 31e (4.35 g, 8.2 mmol) in dry toluene (80 mL) was added DDQ (2.8 g, 12.3 mmol). After refluxing for 3 hours, the solvent was removed in vacuo and diluted with EtOAc. The organic layer was washed with saturated Na$_2$SO$_3$ aqueous and brine, dried over Na$_2$SO$_4$, filtered and concentrated in vacuo. The residue was washed with MeOH (30 mL), filtered and the collected solid was dried under vacuum to provide compound 31f (2.55 g, 59% yield). LC/MS: Anal. Calcd. For [M+H]$^+$ C24H12BrClF2N2OS: 530.95. found 531.04.

Step 5

To a solution of 31f (2.55 g, 4.82 mmol) in 1,4-dioxane (70 mL) was added bis pinacol borate (1.35 g, 5.3 mmol) and Pd(dppf)Cl$_2$ (0.35 g, 0.48 mmol) and KOAc (0.94 g, 9.64 mmol). The reaction mixture was stirred under N$_2$ and heated to 110° C. for 2 hours. After that, the solvent was removed in vacuo, and the residue was purified using SiO$_2$ chromatography to provide compound 31g (1.7 g, 61% yield). LC/MS: Anal. Calcd. For [M+H]$^+$ C30H24BClF2N2O3S: 577.13. found 577.04.

Step 6

A suspension of 31g (1.7 g, 2.95 mmol), Cap 5 (1.1 g, 2.95 mmol), Pd(dppf)Cl$_2$ (0.22 g, 0.3 mmol), Na$_2$CO$_3$ (0.63 g, 5.9 mmol) and in THF/H$_2$O (8:1, 72 mL) was refluxed at 75° C. for about 15 hours under N$_2$ atmosphere. After that, the solvent was removed; the residue was purified using SiO$_2$ chromatography, eluting with petroleum ether:ethyl acetate (10/1~1/2) to provide 31h (1.26 g, 58% yield). LC/MS: Anal. Calcd. For [M+H]$^+$ C38H33ClF2N6O4S: 743.19. found 743.04.

Step 7

To a solution of 31h (1.26 g, 1.7 mmol) in 1,4-dioxane (60 mL) was added bis pinacol borate (0.52 g, 2 mmol), Pd$_2$(dba)$_3$ (0.13 g, 0.14 mmol), X-phos (0.13 g, 0.27 mmol) and KOAc (0.33 g, 3.4 mmol). The reaction mixture was stirred under N$_2$ and heated to 110° C. for about 15 hours. After that, the solvent was removed in vacuo, and the residue was purified using SiO$_2$ chromatography eluting with petroleum ether:ethyl acetate (10/1~1/2) to provide compound 31i (1.17 g, 82% yield). LC/MS: Anal. Calcd. For [M+H]$^+$ C44H45BF2N6O6S: 835.32. found 835.04.

Step 8

A suspension of 31i (1.17 g, 1.4 mmol), Cap 5 (0.52 g, 1.4 mmol), Pd(dppf)Cl$_2$ (0.1 g, 0.14 mmol), Na$_2$CO$_3$ (0.3 g, 2.8 mmol) and in THF/H$_2$O (8:1, 63 mL) was refluxed at 75° C. for about 15 hours under N$_2$ atmosphere. After that, the solvent was removed; the residue was purified using SiO$_2$ chromatography, eluting with petroleum ether:ethyl acetate (10/1~1/2) to provide 31j (0.6 g, 43% yield). LC/MS: Anal. Calcd. For [M+H]$^+$ C52H54F2N10O7S: 1001.39. found 1001.04.

Step 9

Compound 31i was separated using SFC separation to provide compound 31 by using the following conditions:
Column: Chiralcel OJ-H 250×4.6 mm I.D., 5 um
Solvent: 40% of iso-propanol (0.05% DEA) in CO$_2$
Flow rate: 2.4 mL/min
Wavelength: 340 nm
Compound 31 (170 mg, 57% yield). $^1$H-NMR (MeOD) δ:8.02 (s, 1H), 7.95 (s, 1 H), 7.83 (s, 1 H), 7.72-7.80 (m, 3 H), 7.55-7.65 (m, 2 H), 7.35-7.40 (m, 2 H), 7.24 (s, 1 H), 7.07-7.13 (m, 3 H), 5.26-5.16 (m, 2 H), 4.22 (m, 2 H), 4.08-4.06 (m, 2 H), 3.89-3.86 (m, 2 H), 3.64 (s, 6 H), 2.57-2.48 (m, 2 H), 2.26-2.02 (m, 8 H), 0.94-0.84 (m, 12H). LC/MS: Anal. Calcd. For [M+H]$^+$ C$_{51}$H$_{58}$FN$_9$O$_7$S: C52H54F2N10O7S: 1001.39. found 1001.04.

Example 19

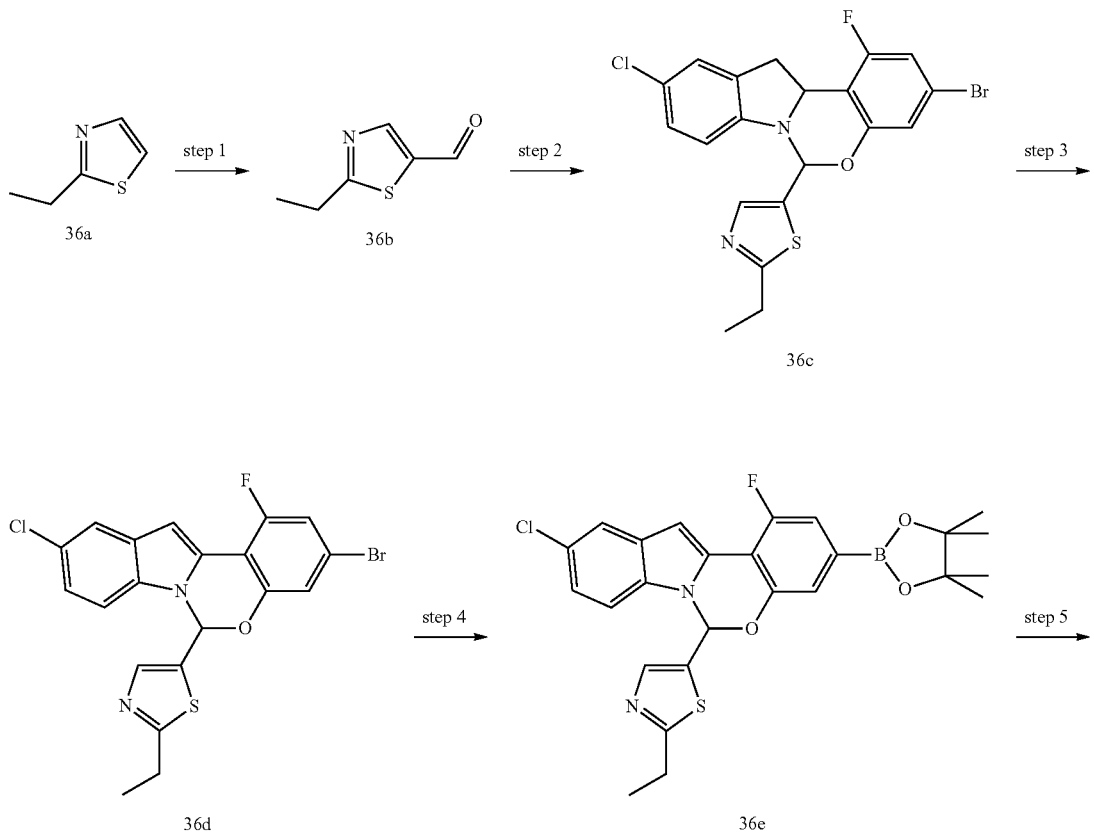

-continued
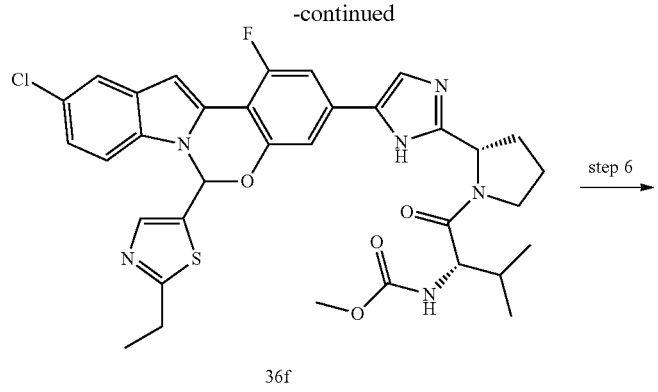
36f
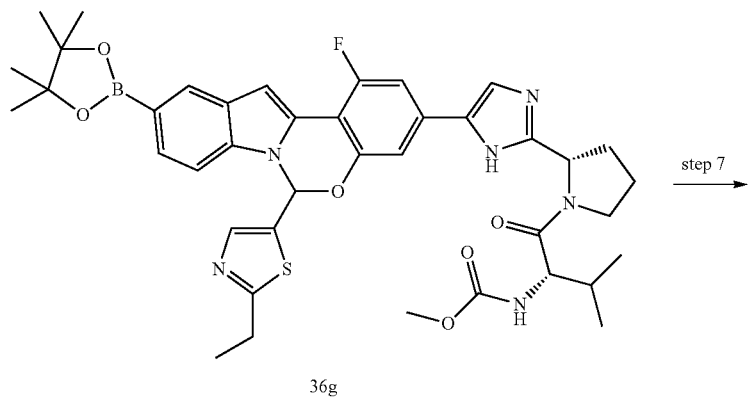
36g
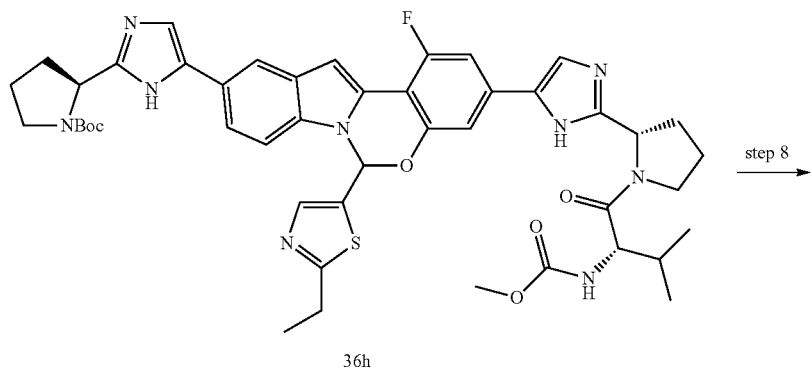
36h
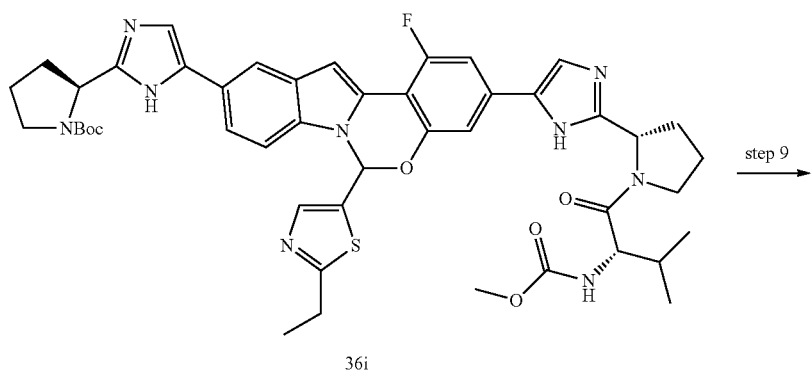
36i

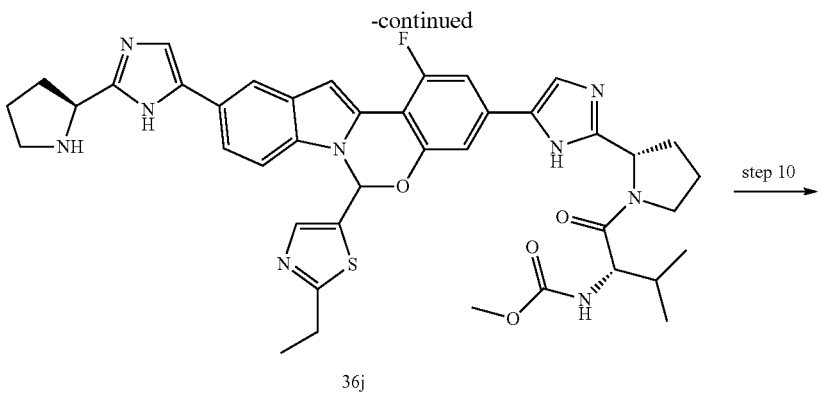

36j

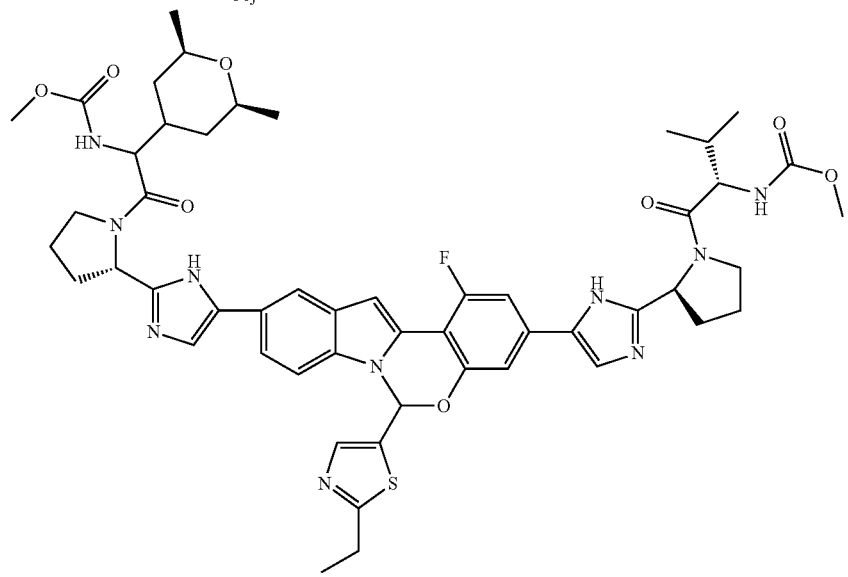

36

Step 1

To a solution of 36a (5 g, 44.2 mmol) in THF (50 mL) at −78° C. under N₂ was added dropwise LDA (26.5 mL, 53 mmol). The mixture was stirred for 30 minutes and DMF (6.4 g, 88 mmol) was added in dropwise. The reaction was stirred at the same temperature for half an hour and then quenched with saturated ammonium chloride solution and extracted with EtOAc. The organic layer was combined and dried over Na₂SO₄, filtered and concentrated in vacuo. The residue was purified using SiO₂ chromatography, eluting with petroleum ether:ethyl acetate (100/1~40/1) to provide 36b (3.5 g, 57%). ¹H NMR (CDCl₃) δ: 9.97 (s, 1H), 8.27 (s, 1H), 3.09 (q, J=7.4 Hz, 2H), 1.42 (t, J=7.4 Hz, 3H).

Step 2

To a mixture of 36b (2.3 g, 16.3 mmol) and Core2 (3.7 g, 10.9 mmol) in anhydrous CH₃CN (20 mL) was added TFA (1 d) at room temperature. The mixture was agitated for about 15 hours at room temperature. The reaction mixture became a clear solution and then solid appeared. The solid was collected by filtration and washed with CH₃CN to provide 36c (5 g, 98%).

Step 3

The solution of 36c (4.2 g, 9.01 mmol) in dry toluene (50 mL) was added DDQ (3.07 g, 13.5 mmol). After refluxing for 2 hours, the solvent was removed in vacuo and diluted with EtOAc. The organic layer was washed with saturated NaS₂O₃ aqueous and brine, dried over Na₂SO₄, filtered and concentrated in vacuo. The residue was washed with MeOH (50 mL), filtered to provide 36d (3.4 g, 81%).

Step 4

To a solution of 36d (3.7 g, 8 mmol) in 1,4-dioxane (40 mL) was added bis pinacol borate (2.43 g, 9.57 mmol) and Pd(dppf)Cl₂ (585 mg, 0.8 mmol) and KOAc (2.3 g, 24 mmol). The reaction mixture was stirred under N₂ and heated to 100° C. for about 15 hours. After that, the solvent was removed in vacuo, and the residue was purified using SiO₂ chromatography, eluting with petroleum ether:ethyl acetate (5/1~1/1) to provide 36e (2.3 g, 57.5%).

Step 5

A suspension of 36e (2.8 g, 4.5 mmol), Cap 5 (2.25 g, 6 mmol), Pd(dppf)₂Cl₂ (400 mg, 0.547 mmol) and Na₂CO₃ (1.8 g, 16.6 mmol) in THF/H₂O (5:1, 54 mL) was refluxed at 75° C. for about 15 hours under N₂ atmosphere. After that, the mixture was filtered, and the filtrate was washed with water (50 mL) and extracted with ethyl acetate (150 mL), washed with brine and dried over anhydrous sodium sulfate. After concentration in vacuo, and the resulting residue was purified using SiO₂ chromatography, eluting with petroleum ether:ethyl acetate (5/1~1/1) to provide 36f (2.9 g, 78.3%).

Step 6

To a mixture of 36f (2.6 g, 3.8 mmol), bis(pinacolato) diboron (1.17 g, 4.6 mmol), KOAc (1.12 g, 11.5 mmol), pd₂(dba)₃ (351 mg, 0.38 mmol), x-Phos (180 mg, 0.38 mmol) degassed and sealed under N₂ was added dry dioxane. Following further N₂ purging. The mixture was stirred at 120° C. for about 15 hours. Under standard work-up to provide the residue which was purified using SiO₂ chromatography, eluting with petroleum ether:ethyl acetate (5/1~1/1) to provide 36g (2.7 g, 91.5%).

Step 7

A suspension of 36g (2.7 g, 3.51 mmol), Cap 7a (1.22 g, 3.86 mmol), Pd(dppf)₂Cl₂ (256 mg, 0.35 mmol) and Na₂CO₃ (1.2 g, 10.5 mmol) in THF/H₂O (5:1, 36 mL) was refluxed at 75.deg. C. for about 15 hours under N₂ atmosphere. After that, the mixture was filtered, and the filtrate was washed with water (50 mL) and extracted with ethyl acetate (100 mL), washed with brine and dried over anhydrous sodium sulfate. After concentration in vacuo, and the resulting residue was purified using SiO₂ chromatography, eluting with DCM:MeOH (5/1~3/1) to provide 36h (2.0 g, 65.2%).

Step 8

36h (2 g) was separated by SFC by using the following conditions to provide 36i.

Column: Chiral OZ 150×4.6 mm I.D., 5 um
Mobile phase: 50% of methanol (0.05% DEA) in CO2
Flow rate: 2.0 mL/min
Wavelength: 220 nm Step 9

36i (400 mg, 0.45 mmol) was added into HCl/dioxane (15 mL). Then the mixture was stirred at room temperature for 2-3 hr. When the reaction completed, the mixture was concentrated in vacuo to provide 36j (350 mg, 96.1%).

Step 10

To a mixture of 36j (100 mg, 0.128 mmol), Cap 2 (32 mg, 0.128 mmol) and HATU (50 mg, 0.128 mmol) in DMF (10 mL) was added DIPEA (0.5 mL). The resulting mixture was stirred at room temperature for 16 hours before the solution was subjected directly to HPLC to provide 36. ¹H NMR (MeOH) δ: 8.11-8.00 (m, 2H), 7.94 (s, 1H), 7.83-7.75 (m, 1H), 7.66-7.55 (m, 2H), 7.49-7.32 (m, 2H), 7.21 (br. s., 2H), 5.21 (d, J=7.3, 14.3 Hz, 2H), 4.27-4.02 (m, 4H), 3.84 (br. s., 2H), 3.64 (d, J=2.3 Hz, 6H), 3.49-3.33 (m, 3H), 2.86 (q, J=7.4 Hz, 2H), 2.54 (d, J=7.0 Hz, 2H), 2.32-2.07 (m, 5H), 2.06-1.93 (m, 2H), 1.56 (d, J=12.1 Hz, 1H), 1.28 (d, J=12.5 Hz, 1H), 1.20 (t, J=7.4 Hz, 3H), 1.07 (dd, J=6.5, 8.0 Hz, 6H), 0.99-0.81 (m, 8H). LC/MS: Anal. Calcd. For [M+H]⁺ C52H61FN10O8S: 1005.2. found 1005.4.

Example 20

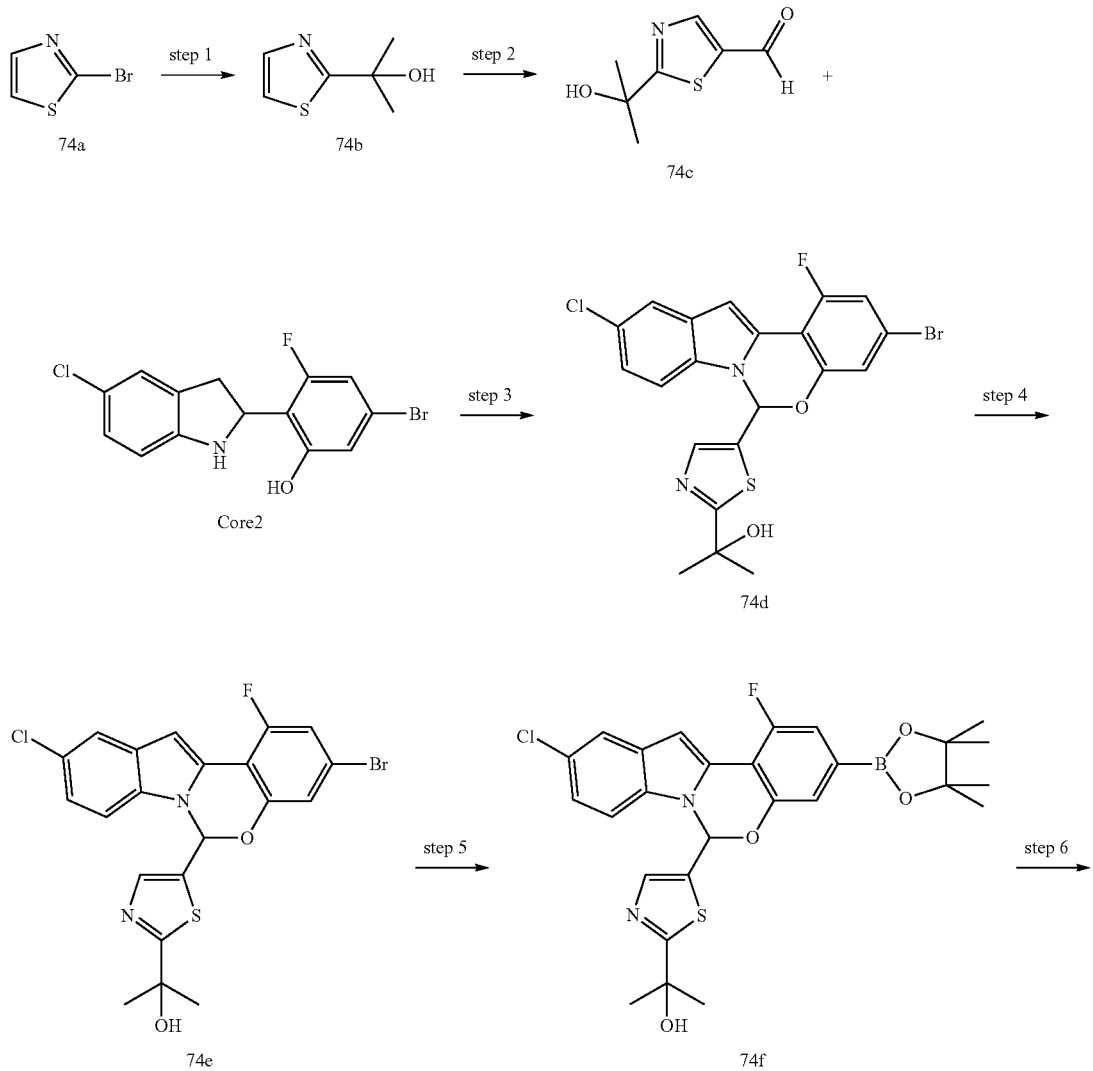

-continued
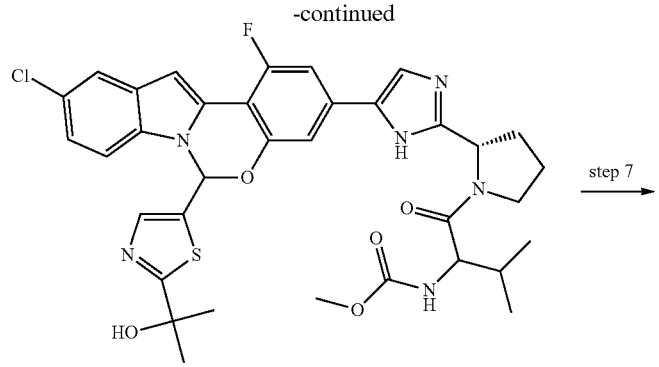
74g
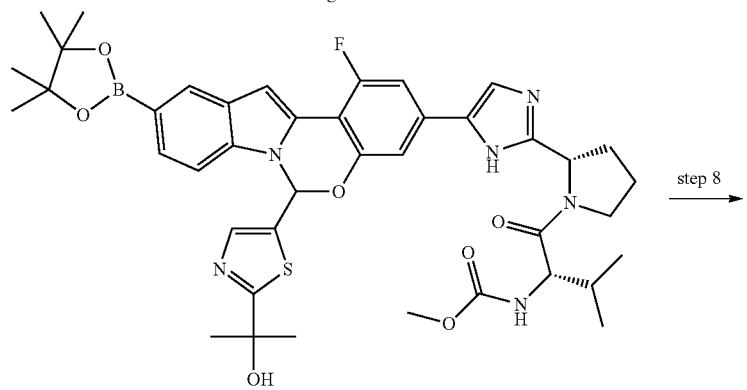
74h
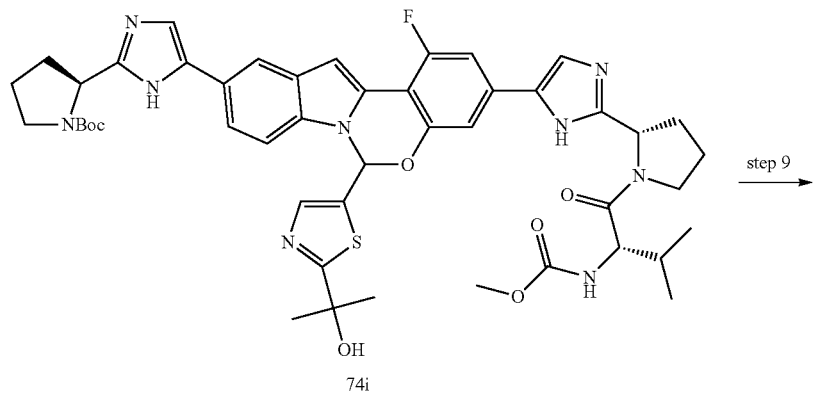
74i
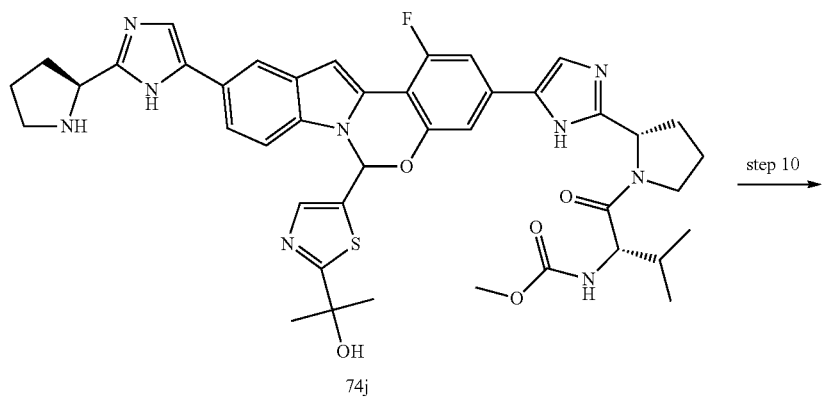
74j

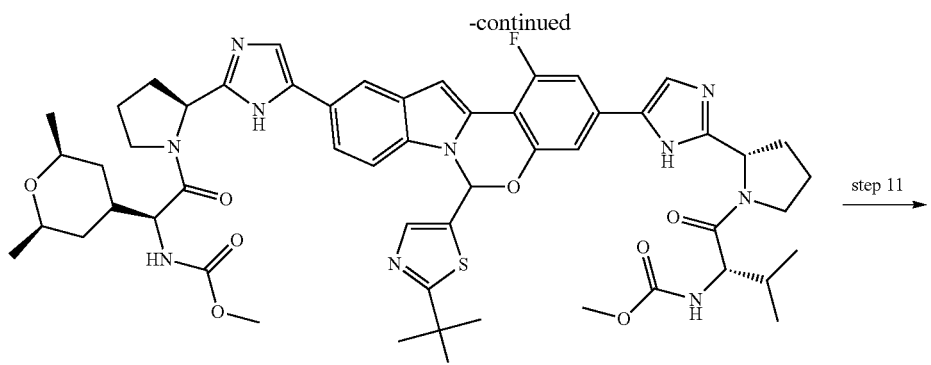

74k

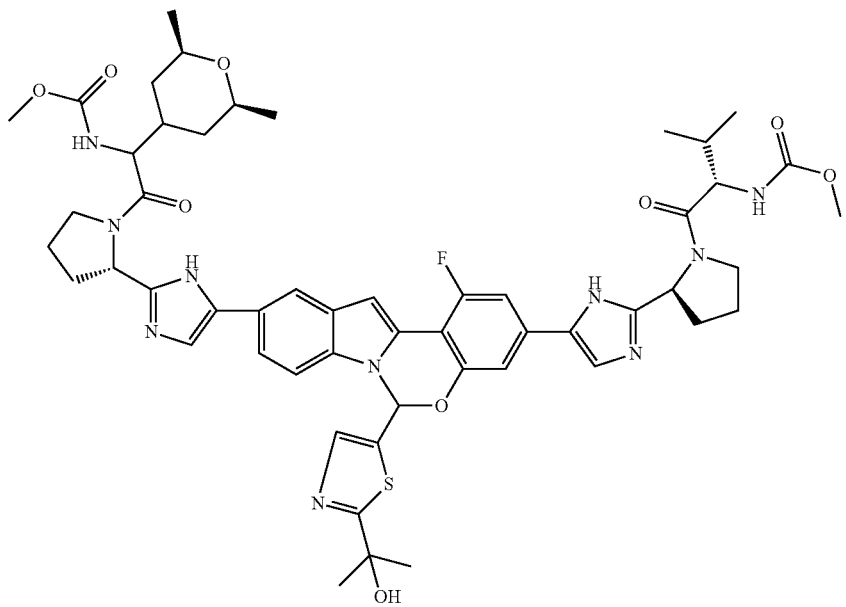

74

Step 1

To a solution of compound 74a (6.4 g, 40 mmol) in THF (100 mL) was added n-BuLi (17.6 mL, 44 mol) at −78° C. The mixture was stirred at −78° C. for 30 minutes, acetone (2.5 g, 44 mmol) was added dropwise at −78° C. and was stirred at −78° C. for 90 minutes. The mixture was poured into $H_2O$, extracted with ethyl acetate (100 mL), washed with brine and dried over anhydrous sodium sulfate. After concentration in vacuo, the crude product was purified using $SiO_2$ chromatography, eluting with petroleum ether:ethyl acetate (10/1~3/1) to provide compound 74b (1.2 g, Yield: 25%).

Step 2

To solution of compound 74b (1.1 g. 10 mmol) in THF (20 mL) was added n-BuLi (12 mL, 30 mol) at −78° C. The mixture was stirred at −78° C. for 30 minutes, and then to it was added DMF (1.4 g, 20 mmol) dropwise at −78° C. The mixture was stirred another 3 h at −78° C. before poured into $H_2O$ (50 mL), extracted with ethyl acetate (50 mL×2), washed with brine and dried over anhydrous sodium sulfate. The resulting solution was then filtered, concentrated in vacuo, the crude product was purified using $SiO_2$ chromatography, eluting with petroleum ether:ethyl acetate (10/1~3/1) to provide compound 74c (1.05 g, Yield: 75%).

Step 3

To a mixture of 74c (1.4 g, 10 mmol) and Core2 (1.7 g, 5 mmol) in anhydrous $CH_3CN$ (30 mL) was added TFA (0.2 mL). The mixture was stirred at room temperature for 30 hours. The resulting solution was then filtered, concentrated in vacuo, the crude product was purified using $SiO_2$ chromatography, eluting with petroleum ether:ethyl acetate (10/1~2/1) to provide compound 74d (1.6 g, Yield: 67%). LC/MS: Anal. Calcd. For $[M+H]^+$ C21H17C1FN2O2S: 494.98. found 494.6

Step 4

The solution of 74d (1.2 g, 2.4 mmol) in dry toluene (25 mL) was added DDQ (0.9 g, 4.0 mmol). After refluxing for 2 hours, the solvent was removed in vacuo and diluted with EtOAc. The organic layer was washed with saturated $NaS_2O_3$ aqueous and brine, dried over $Na_2SO_4$, filtered and concentrated in vacuo. The residue was washed with MeOH (20 mL). The solid was collected by filtration to provide 74e (0.6 g, 50%). LC/MS: Anal. Calcd. For $[M+H]^+$ C21H15C1FN2O2S: 492.97. found 492.6

Step 5

A suspension of 74e (1.0 g, 2 mmol), bis(pinacolato) diboron (0.63 g, 2.5 mmol), KOAc (0.6 g, 6 mmol) and $Pd(dppf)Cl_2$ (150 mg, 0.2 mmol) in dioxane (20 mL) was stirred at 100° C. for 2 hours under $N_2$ atmosphere. The reaction mixture was cooled and concentrated in vacuo, and the residue was purified using $SiO_2$ chromatography, eluting with petroleum ether:ethyl acetate (100/1~4/1) to provide 74f (0.9 g, 83%). LC/MS: Anal. Calcd. For $[M+H]^+$ C27H27BClFN2O4S: 541.15; found 541.2.

Step 6

A suspension of 74f (1.1 g, 2 mmol), Cap 5 (1.2 g, 3.2 mmol), $Na_2CO_3$ (0.6 g, 6 mmol) and Pd(dppf)Cl$_2$ (150 mg, 0.2 mmol) in THF/$H_2O$ (v/v=5/1, 20 mL) was stirred at 80° C. for about 15 hours under $N_2$ atmosphere. After that, the mixture was washed with water and extracted with ethyl acetate, washed with brine and dried over anhydrous sodium sulfate. The resulting solution was then filtered, concentrated in vacuo, and the resulting residue was purified using $SiO_2$ chromatography, eluting with petroleum ether:ethyl acetate (1/1~1/4) to provide 74g (0.9 g, 64%). LC/MS: Anal. Calcd. For $[M+H]^+$ C35H36ClFN6O5S: 707.21. found 707.3.

Step 7

To a mixture of 74g (1.05 g, 1.5 mmol), bis(pinacolato)diboron (0.5 g, 2.0 mmol), KOAc (0.6 g, 6.0 mmol), Pd$_2$(dba)$_3$ (68 mg, 0.075 mmol), X-Phos (72 mg 0.15 mmol) degassed and sealed under $N_2$ was added dry dioxane. Following further $N_2$ purging. The mixture was stirred at 100° C. for about 15 hours. After cooling to room temperature, the solvent was concentrated in vacuo and the residue was purified using $SiO_2$ chromatography, eluting with petroleum ether:ethyl acetate (1/1~1/3) to provide 74h (0.8 g, 69%). LC/MS: Anal. Calcd. For $[M+H]^+$ C41H48BFN6O7S: 799.34. found 799.4.

Step 8

A mixture of 74h (0.8 g, 1 mol), Cap 7a (0.46 g, 1.5 mmol), $Na_2CO_3$ (0.3 g, 3 mol) and Pd(dppf)Cl$_2$ (150 mg, 0.2 mmol) in THF/$H_2O$ (v/v=5/1, 9 mL) was stirred at 80° C. under $N_2$ atmosphere for about 15 hours. After that, the mixture was washed with water and extracted with ethyl acetate, washed with brine and dried over anhydrous sodium sulfate. The resulting solution was then filtered, concentrated in vacuo, the residue was purified using $SiO_2$ chromatography, eluting with petroleum ether:ethyl acetate (1/1~1/4) to provide 74i (0.7 g, 78%). LC/MS: Anal. Calcd. For $[M+H]^+$ C47H54FN9O7S: 908.39. found 908.5.

Step 9

To a solution of 74i (0.45 g, 0.5 mmol) in 1,4-dioxane (10 mL) was added HCl/1,4-dioxane (10 mL, 3M). Then the mixture was stirred at room temperature for 1 hour. When the reaction completed, the mixture was concentrated in vacuo to provide 74j (0.4 g, 99%). LC/MS: Anal. Calcd. For $[M+H]^+$ C42H46FN9O5S: 808.33. found 808.5.

Step 10

To a mixture of 74j (400 mg, 0.5 mmol), Cap 2 (123 mg, 0.5 mmol) and HATU (195 mg, 0.5 mmol) in DMF (5 mL) was added DIEA (600 mg, 5 mmol). The resulting mixture was stirred at room temperature for 30 minutes, and LC-MS judged the material was consumed up. After filtration, the filtrate was purified using Pre-HPLC to provide 74k (200 mg, 40%).

Step 11

The compound 74k (0.26 g) was separated by SFC by using the following conditions to provide compound 74 (0.08 g, 61.5%). LC/MS: Anal. Calcd. For $[M+H]^+$ C53H63FN10O9S: 1035.45. found 1035.5.

Instrument: Thar SFC

Column: AS-H, 250×4.6 mm, 5 um

Mobile phase: A for $CO_2$ and B for iso-propanol (0.05% DEA)

Gradient: B 5% to 40 for A

Flow rate: 2.5 mL/min

Wavelength: 340 nm $^1$H NMR (MeOD) δ: 8.02-8.04 (m, 2 H), 7.91 (s, 1 H), 7.79 (s, 1 H), 7.57-7.62 (m, 2 H), 7.28-7.40 (m, 3 H), 7.19 (s, 1 H), 5.18-5.25 (m, 2 H), 4.20-4.27 (m, 2 H), 3.85-4.09 (m, 4 H), 3.65 (s, 6 H), 3.40-3.46 (m, 2 H), 2.50-2.59 (m, 2 H), 2.05-2.26 (m, 8 H), 1.30-1.57 (m, 8 H), 0.80-1.09 (m, 14 H).

The following compounds of the present invention were prepared according to the methods described in the Example above.

| ID | Structures | Isomer | Observed [M + H]$^+$ |
|---|---|---|---|
| 28 | 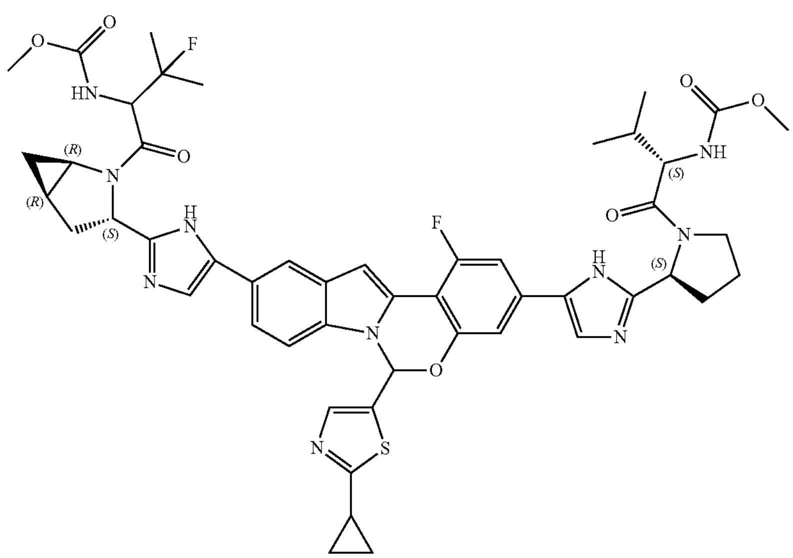 | Isomer 2 | 977.6 |

-continued

| ID | Structures | Isomer | Observed [M + H]+ |
|---|---|---|---|
| 29 | | Isomer 1 | 991.6 |
| 30 | | Isomer 2 | 991.6 |
| 35 | | Isomer 1 | 1005.6 |

-continued

| ID | Structures | Isomer | Observed [M + H]+ |
|---|---|---|---|
| 37 | | Isomer 2 | 1005.6 |
| 38 | | Isomer 1 | 1005.8 |
| 39 | | Isomer 3 | 1005.6 |
| 40 | | Isomer 4 | 1005.8 |
| 41 | | Isomer 1 | 1007.6 |
| 42 | | Isomer 2 | 1007.6 |

| ID | Structures | Isomer | Observed [M + H]+ |
|---|---|---|---|
| 47 | | Isomer 1 | 1013.6 |
| 48 | | Isomer 2 | 1013.8 |
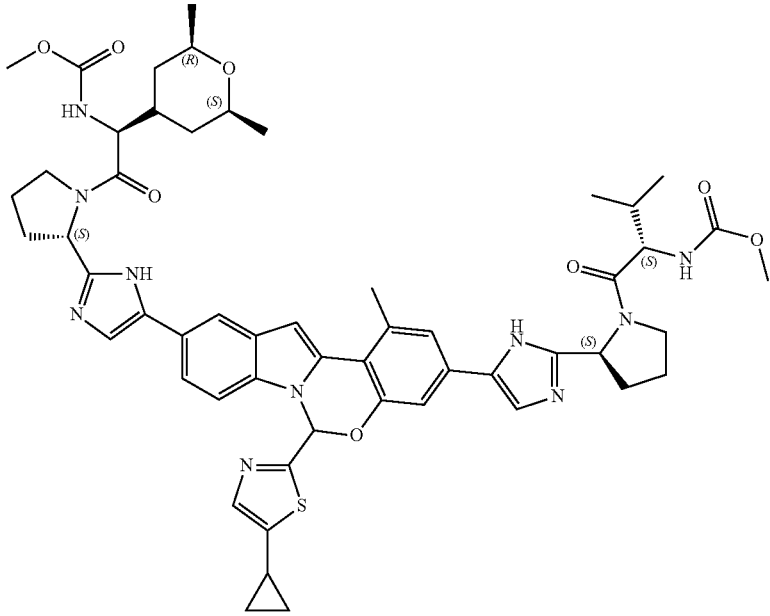
| | | | |
|---|---|---|---|
| 51 | | Isomer 2 | 1017.6 |
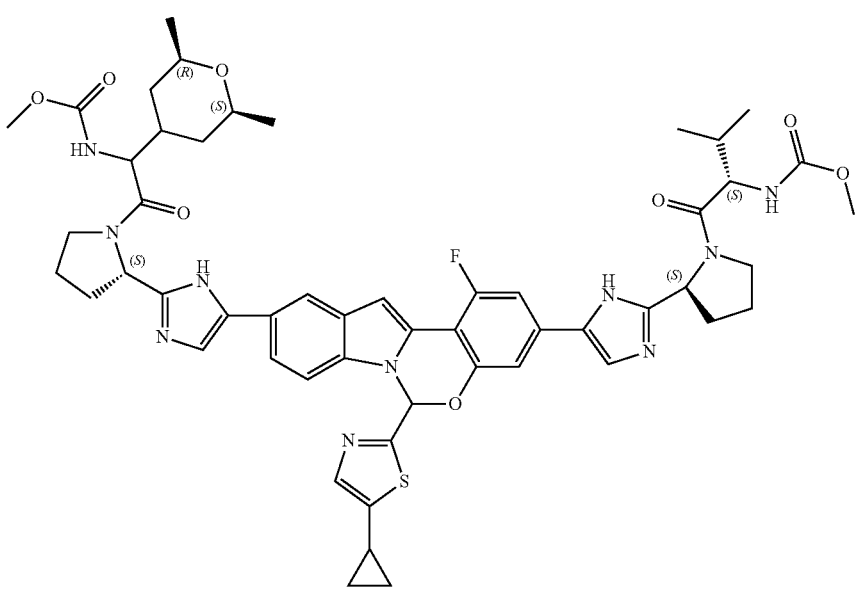

-continued

| ID | Structures | Isomer | Observed [M + H]+ |
|---|---|---|---|
| 56 | | Isomer 1 | 1019.4 |
| 57 | | Isomer 2 | 1019.6 |
| 58 | | Isomer 4 | 1019.6 |
| 59 | | Isomer 2 | 1019.8 |
| 60 | | Isomer 1 | 1019.6 |
| 61 | | Isomer 3 | 1019.8 |

| ID | Structures | Isomer | Observed [M + H]+ |
|---|---|---|---|
| 62 | | Isomer 1 | 1019.6 |
| 63 | | Isomer 2 | 1019.6 |
| 64 | | Isomer 1 | 1029.8 |
| 65 | | Isomer 2 | 1029.6 |

-continued
| ID | Structures | Isomer | Observed [M + H]+ |
|---|---|---|---|
| 66 | | Isomer 1 | 1031.6 |
| 67 | 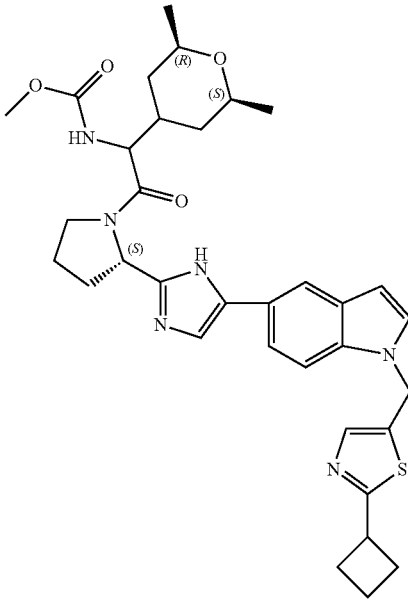 | Isomer 2 | 1031.8 |
| 68 | | Isomer 1 | 1031.6 |
| 69 | 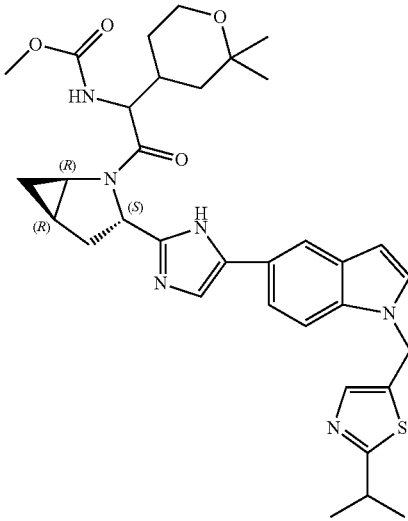 | Isomer 2 | 1031.4 |

-continued

| ID | Structures | Isomer | Observed [M + H]+ |
|---|---|---|---|
| 70 71 | | Isomer 1 Isomer 2 | 1031.8 1031.6 |
| 72 | 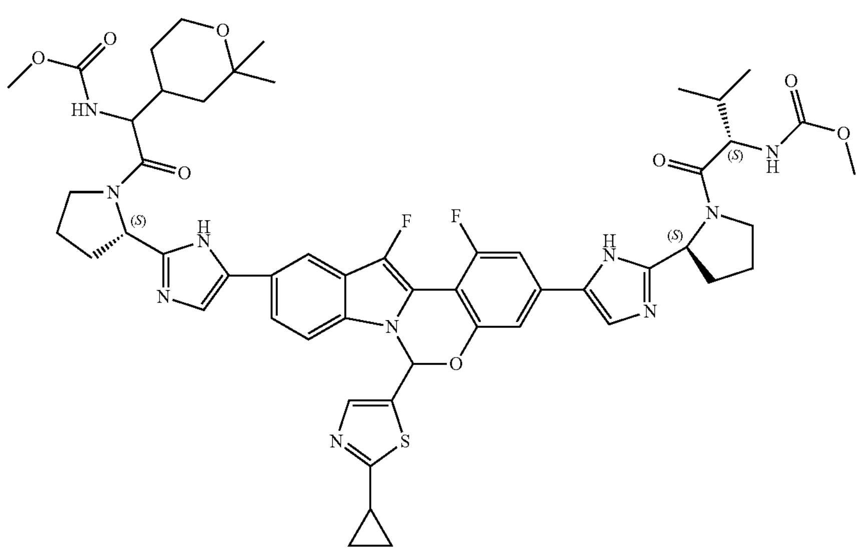 | Isomer 1 | 1035.6 |

| ID | Structures | Isomer | Observed [M + H]+ |
|---|---|---|---|
| 73 | 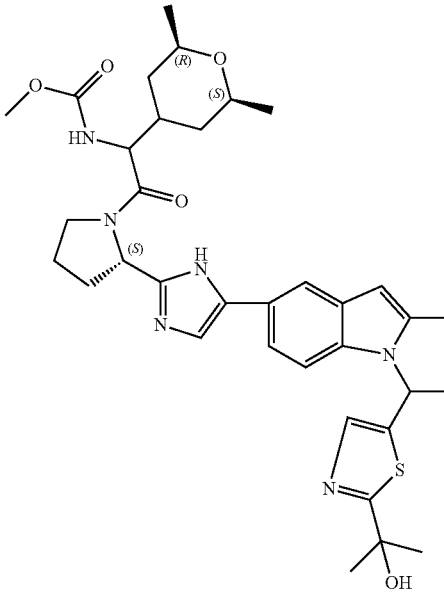 | Isomer 1 | 1035.8 |
| 75<br>76 | 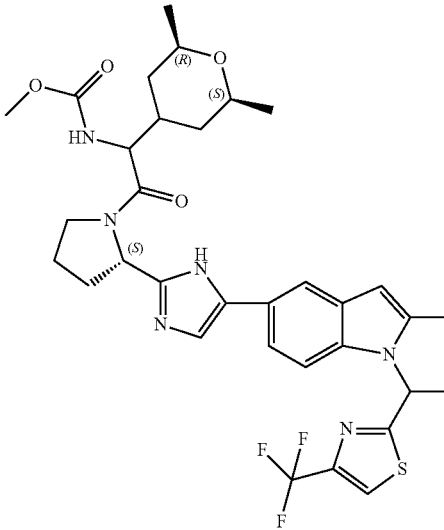 | Isomer 1<br>Isomer 2 | 1045.6<br>1045.8 |

-continued

| ID | Structures | Isomer | Observed [M + H]+ |
|---|---|---|---|
| 79 | | Isomer 1 | 1071.6 |
| 80 | | Isomer 2 | 1071.8 |
| 83 | | Isomer 1 | 947.4 |
| 84 | | Isomer 2 | 947.6 |

-continued
| ID | Structures | Isomer | Observed [M + H]+ |
|---|---|---|---|
| 89 | 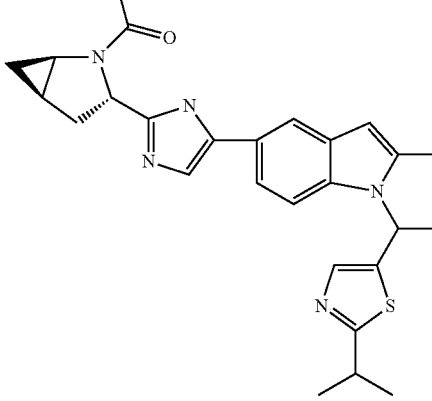 | Isomer 2 | 961.4 |
| 90 91 | 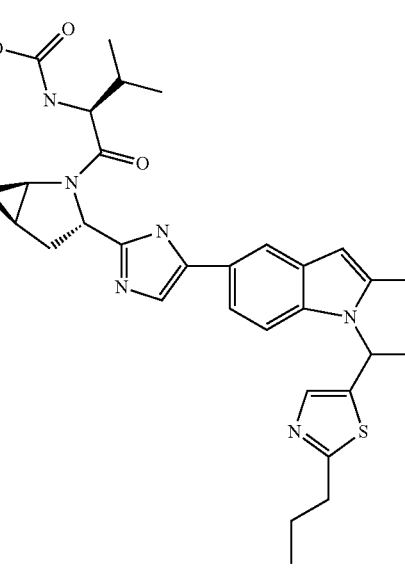 | Isomer 1 Isomer 2 | 961.6 961.6 |
| 92 93 94 95 | 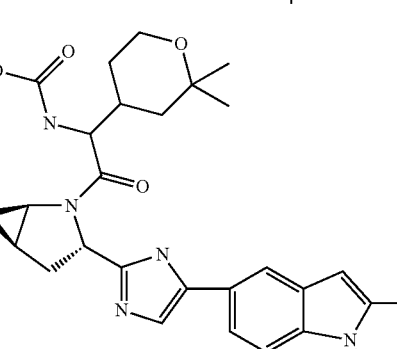 | Isomer 1 Isomer 2 Isomer 3 Isomer 4 | 1017.6 1017.6 1017.8 1017.8 |

-continued

| ID | Structures | Isomer | Observed [M + H]+ |
|---|---|---|---|
| 96 | | Isomer 1 | 1017.6 |
| 97 | | Isomer 2 | 1017.6 |
| 102 | | Isomer 1 | 1019.8 |
| 103 | | Isomer 2 | 1019.6 |

-continued

| ID | Structures | Isomer | Observed [M + H]+ |
|---|---|---|---|
| 104 | | Isomer 1 | 1031.6 |
| 105 | | Isomer 3 | 1031.8 |
| 106 | | Isomer 2 | 1031.8 |
| 107 | | Isomer 4 | 1031.8 |
| 108 | | Isomer 1 | 1031.8 |
| 109 | | Isomer 2 | 1031.6 |

| ID | Structures | Isomer | Observed [M + H]+ |
|---|---|---|---|
| 110 | 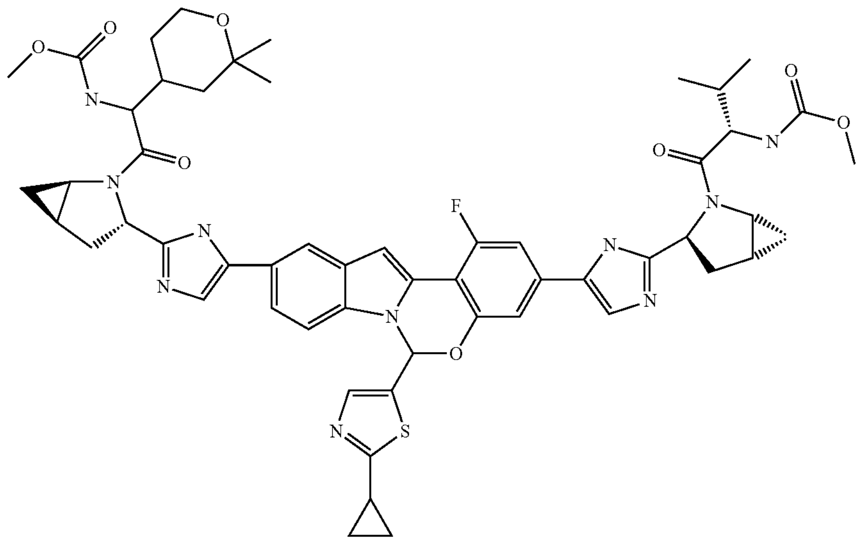 | Isomer 1 | 1041.8 |
| 111 | 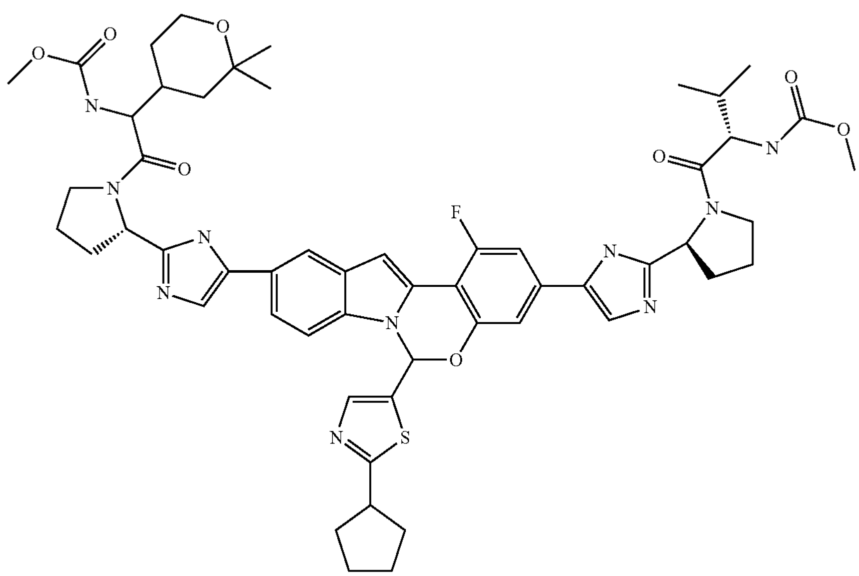 | Isomer 1 | 1045.8 |

-continued
| ID | Structures | Isomer | Observed [M + H]+ |
|---|---|---|---|
| 112 | | Isomer 1 | 1047.6 |
| 113 | | Isomer 2 | 1047.8 |
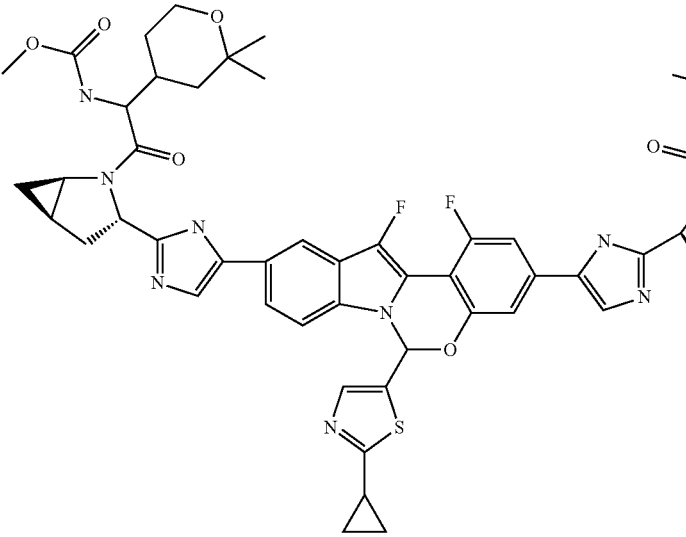
Example 21
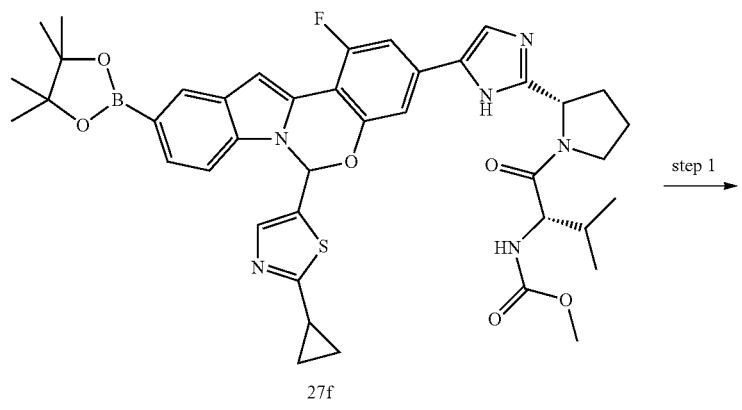
27f
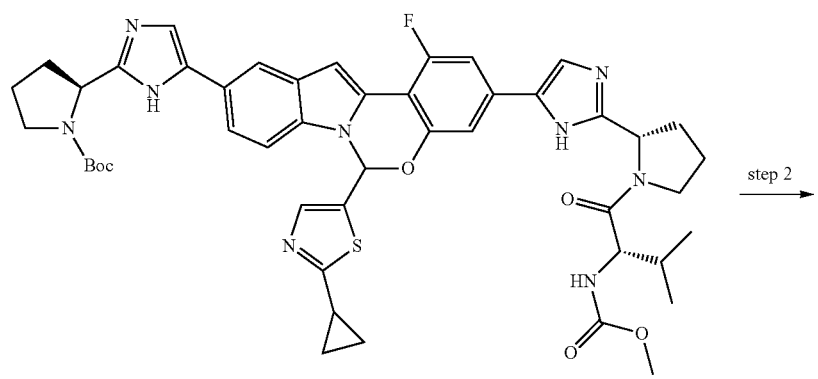
305a

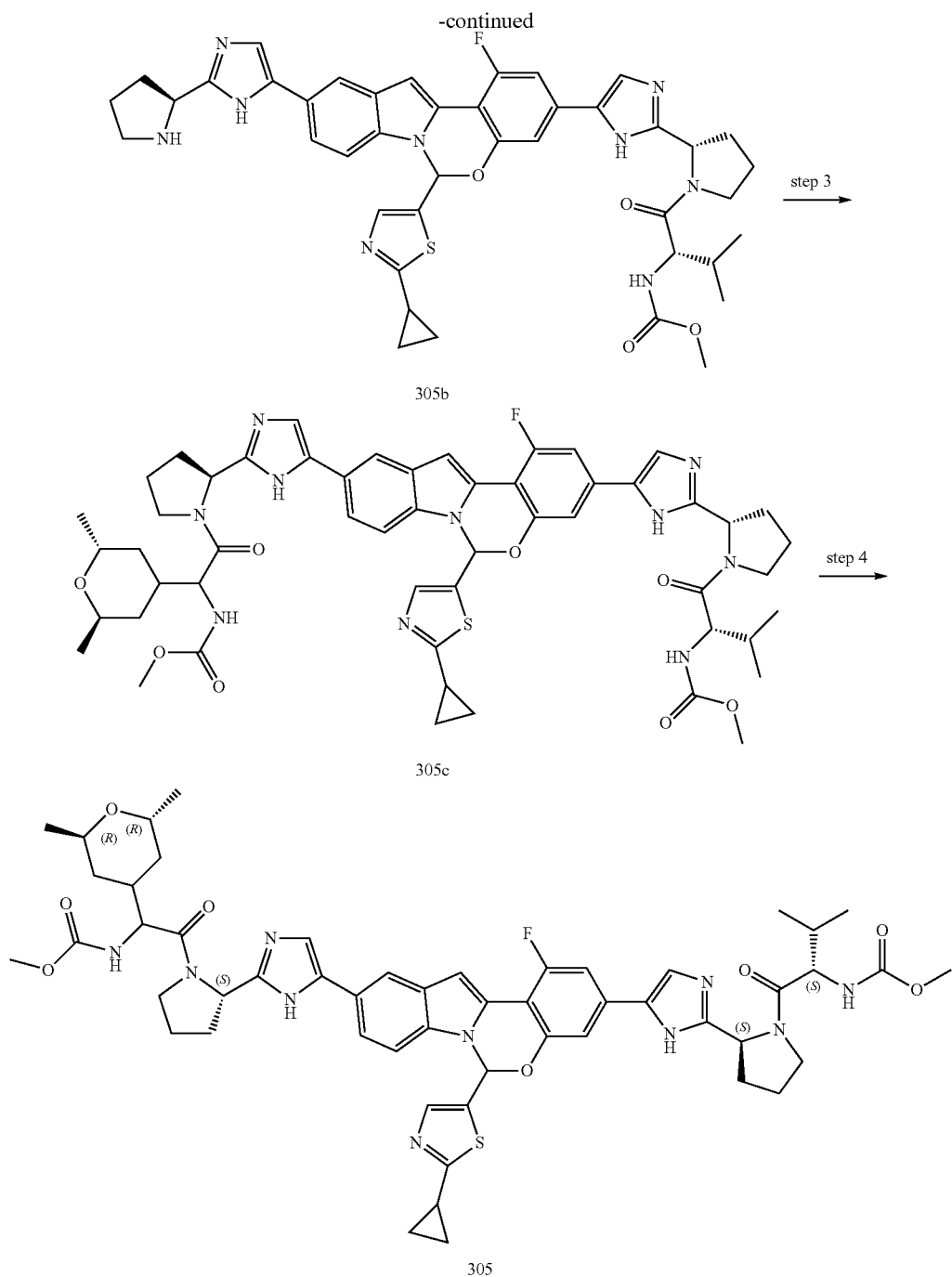

305

Step 1

A mixture of 27f (1.6 g, 2.322 mmol, Cap7a (0.881 g, 2.79 mmol), K$_2$CO$_3$ (962 mg, 6.96 mmol) and Pd(dppf)Cl$_2$ (284 mg, 0.348 mmol), 15 ml Dioxane/2 ml H$_2$O in pressure tube was purged with nitrogen and vacuumed 2 times and stirred at 90° C. for 5 hours. After that, the mixture was washed with water and extracted with ethyl acetate, washed with brine and dried over anhydrous sodium sulfate. The resulting solution was then filtered, concentrated in vacuo, and the residue was purified using SiO$_2$ chromatography, eluting with chromatography Ethyl acetate/Hexane (0% to 100%) to provide 305a (1.1 g, 53.2% yield). LC/MS: Anal. Calcd. For [M+H]$^+$ C47H52FN9O6S: 890.37. found 890.75

Step 2

To a solution of the compound 305a (1100 mg, 1.236 mmol) in dry dioxane (10 mL) was added HCl-dioxane 4M (3.09 mL) through syringe and stirred at 25° C. for 6 hours, then concentrated in vacuo and dried under high vacuum to provideHCl salt of compound 305b (1110 mg, 100%). LC/MS: Anal. Calcd. For [M+H]$^+$ C42H44FN9O4S: 790.32. found 790.39.

Step 3

305b (200 mg, 0.222 mmol), Cap 8 (54.5 mg, 0.222 mmol), HATU (85 mg, 0.222 mmol), and DMF (3 mL) were added into a 20 mL tube, cooled down to 0° C. by ice-water bath, Diisopropylethylamine (0.198 mL, 1.112 mmol) were added. The solution was stirred at 0° C. for 30 minutes. LC-MS showed no SM. The mixture was warmed up to room temp and to that was added water (10 mL). The mixture was filtered, washing with water (~5 mL) to provide the solid as 305c (165 mg, 69.3% yield). LC/MS: Anal. Calcd. For [M+H]$^+$ C53H61FN10O8S: 1018.38. found 1018.47

Step 4

SFC conditions:
ChiralPak AS-H, 250×30 mm I.D.

Mobile phase: A for $CO_2$ and B for IPA (0.1% NH3.H2O)
Gradient: B 30%
Flow rate: 50 mL/min
Isomer B (305) was obtained 40 mg.
LC/MS: Anal. Calcd. For [M+H]$^+$ C53H61FN10O8S: 1018.18. found 1018.2

The following compounds of the present invention were prepared according to the methods described in the Example above.

| ID | Structures | Isomer | Observed [M + H]$^+$ |
|---|---|---|---|
| 300 | | Isomer 1 | 960.3 |
| 301 | | Isomer 2 | 960.3 |
| 302 | | Isomer 1 | 964.1 |
| 303 | | Isomer 2 | 964.2 |
| 304 | | Isomer 1 | 1018.01 |
| 305 | | Isomer 2 | 1017.97 |

Example 22
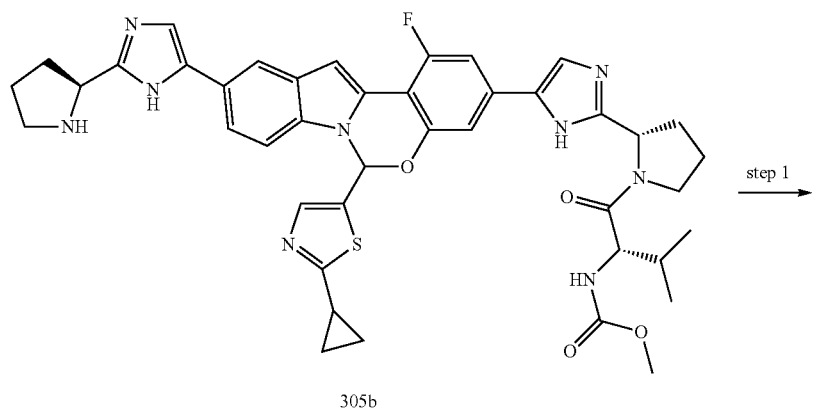
305b
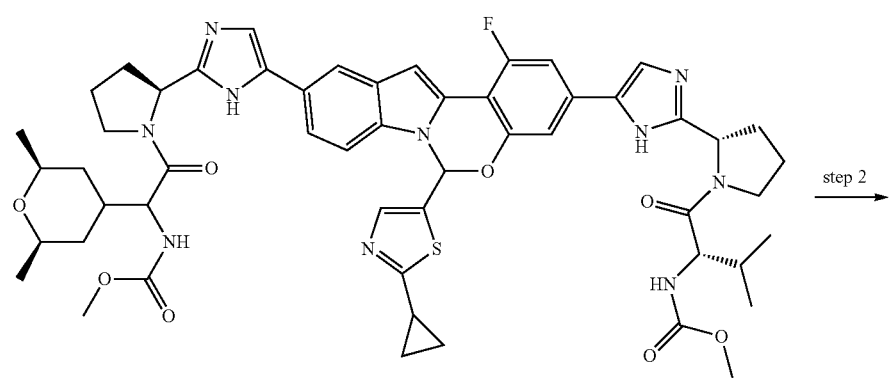
307a
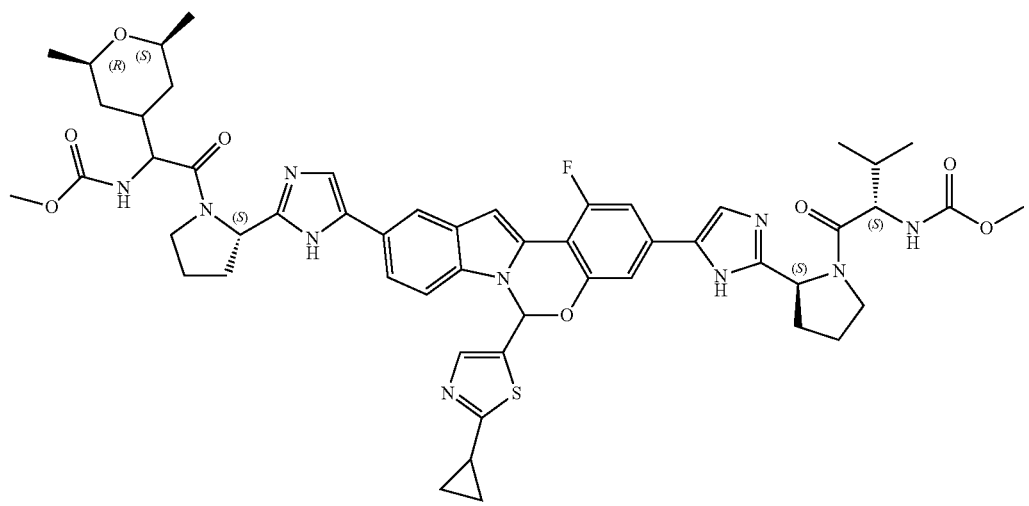
307

Step 1

305b (200 mg, 0.222 mmol), Cap2 (54.5 mg, 0.222 mmol), HATU (85 mg, 0.222 mmol), and DMF (3 mL) were added into a 20 mL tube, cooled down to 0° C. by ice-water bath, Diisopropylethylamine (0.198 mL, 1.112 mmol) were added. The solution was stirred at 0° C. for 30 minutes. LC-MS showed no SM, water and EtOAc were added and organic layer was separated and washed with brine, dried under $Na_2SO_4$. After the solvent was evaporated, 307a (188 mg, 83% yield) was provided using purification on 24 g silica column 0% to 40% MeOH in $CH_2Cl_2$. LC/MS: Anal. Calcd. For $[M+H]^+$ C53H61FN10O8S: 1018.18. found 1018.38

Step 2

SFC conditions:
Column: ChiralPark AS-H, 250×30 mm I.D.
Mobile phase: A for $CO_2$ and B for IPA (0.1% NH3.H2O)
Gradient: B 35%
Flow rate: 60 mL/min
Isomer B (307) was obtained 40 mg.
LC/MS: Anal. Calcd. For $[M+H]^+$ C53H61FN10O8S: 1017.18. found 1018.2

The following compounds of the present invention were prepared according to the methods described in the Example above.

| ID | Structures | Isomer | Observed [M + H]$^+$ |
|---|---|---|---|
| 306 307 | | Isomer 1 Isomer 2 | 1018.27 1018.35 |
| 308 309 | | Isomer 1 Isomer 2 | 1018.3 1018.3 |

-continued
| ID | Structures | Isomer | Observed [M + H]+ |
|---|---|---|---|
| 315 316 | 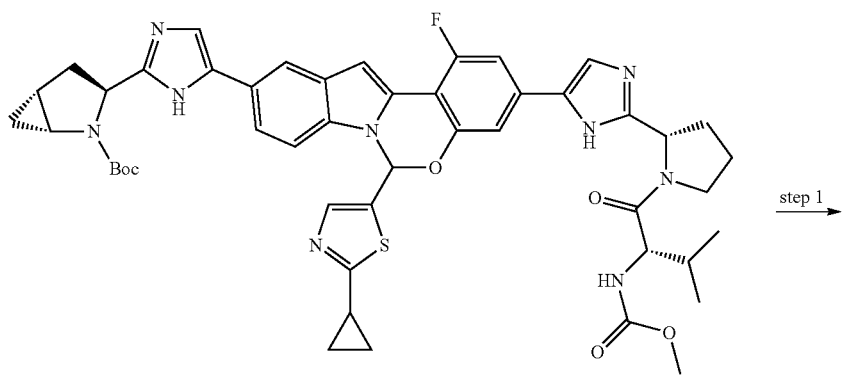 | Isomer 1 Isomer 2 | 1034.41 1034.38 |
Example 23
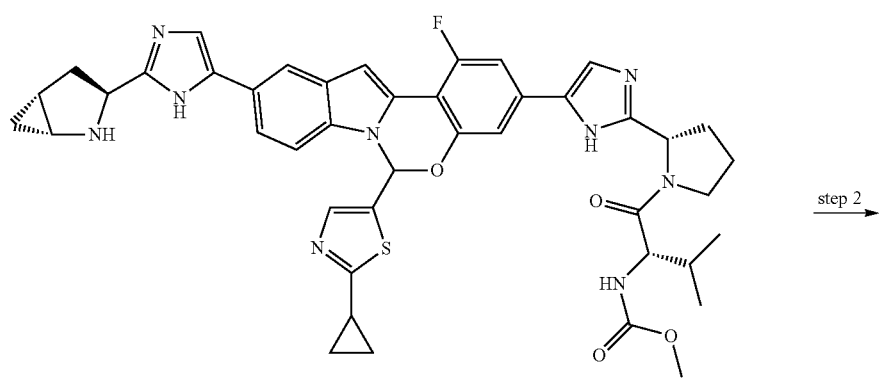

-continued

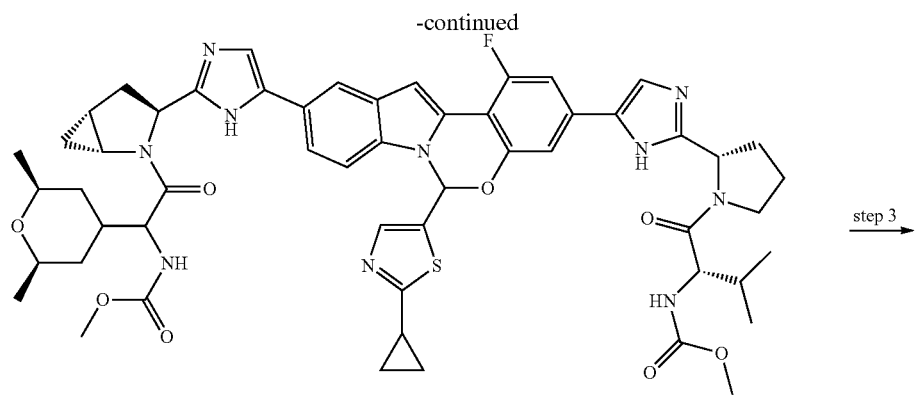

311b

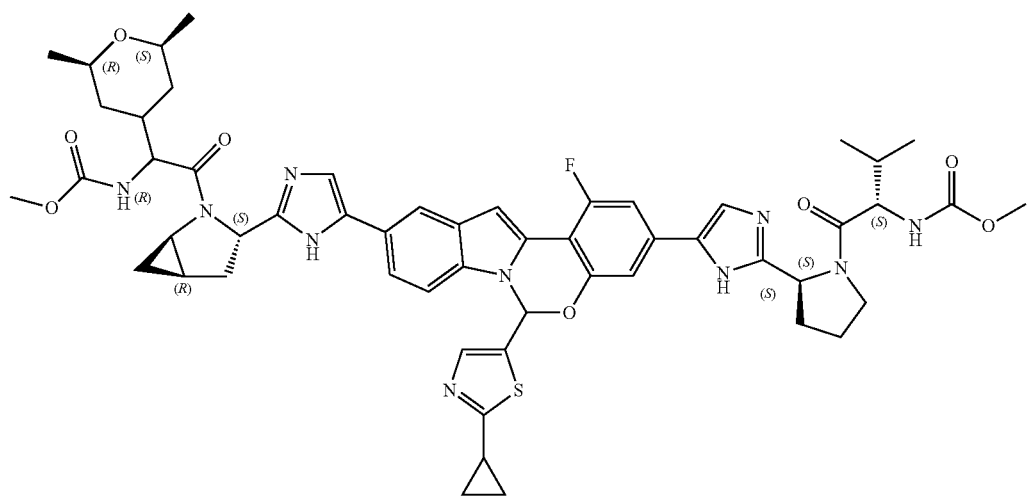

311

Step 1

To a solution of the compound 27g (300 mg, 0.333 mmol) in dry dioxane (10 mL) was added HCl-dioxane 4M (0.831 mL) through syringe and stirred at 25° C. for 6 hours, then concentrated in vacuo and dried under high vacuum to provide the HCl salt of the desired product compound 311a (303 mg, 98%). LC/MS: Anal. Calcd. For [M+H]+ C43H44FN9O4S: 801.93. found 803.00.

Step 2

HATU (84 mg, 0.222 mmol), 311a (202 mg, 0.222 mmol), Cap 2 (54.4 mg, 0.222 mmol), and DMF (3 mL) were added into a 20 mL tube, cooled to 0° C. by ice-water bath, to the mixture was added N-ethyl-N-isopropylpropan-2-amine (143 mg, 1.108 mmol). The solution was stirred at 0° C. for 30 minutes. LC-MS showed no SM, water and EtOAc were added and the organic layer was separated and washed with brine, dried under Na2SO4. After the solvent was evaporated, 311b (148 mg, 61.6% yield) was provided using purification on 24 g silica column 0% to 40% MeOH in CH2Cl2. LC/MS: Anal. Calcd. For [M+H]+ C54H61FN10O8S: 1029.19; found 1030.29

Step 3

SFC conditions:

Column: ChiralPark AS-H, 250×30 mm I.D.

Mobile phase: A for CO2 and B for IPA (0.1% NH3.H2O)

Gradient: B 40%

Flow rate: 50 mL/min

Isomer B (311) was obtained 28 mg.

LC/MS: Anal. Calcd. For [M+H]+ C54H61FN10O8S: 1029.19. found 1030.31

The following compounds of the present invention were prepared according to the methods described in the Example above.

| ID | Structures | Isomer | Observed [M + H]+ |
|---|---|---|---|
| 310 | | Isomer 1 | 1030.30 |
| 311 | 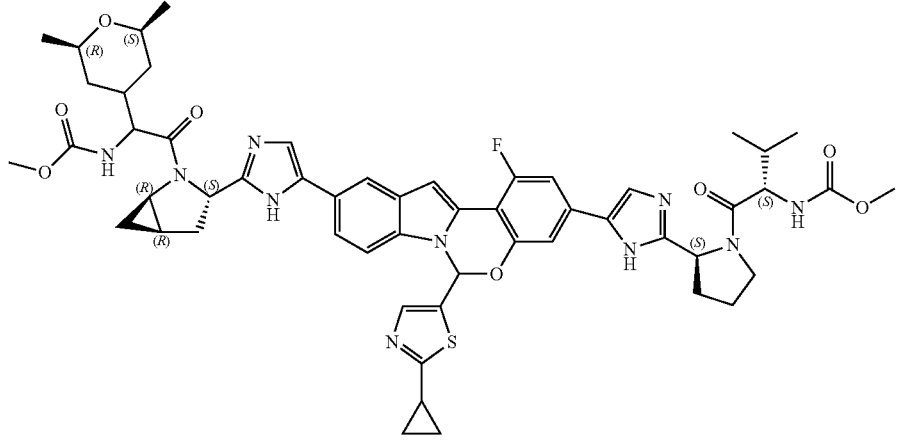 | Isomer 2 | 1030.31 |
| 312 | | Isomer 1 | 1030.42 |
| 312 | 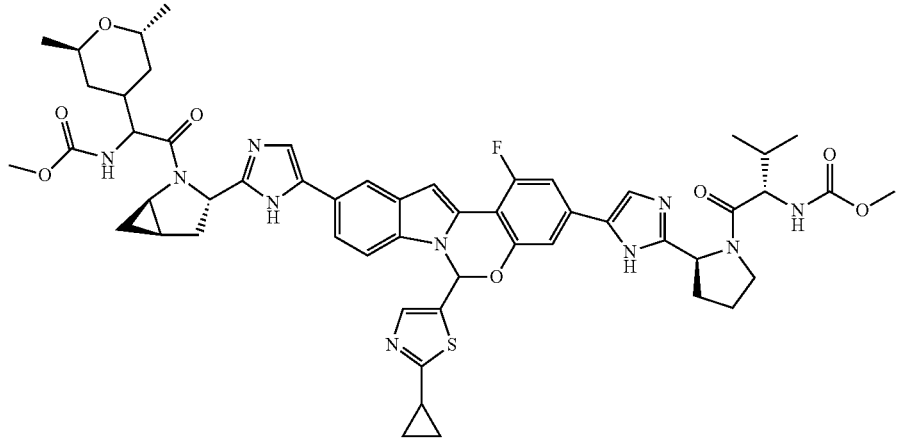 | Isomer 2 | 1031.32 |
| 313 | | Isomer 1 | 1030.41 |
| 314 | 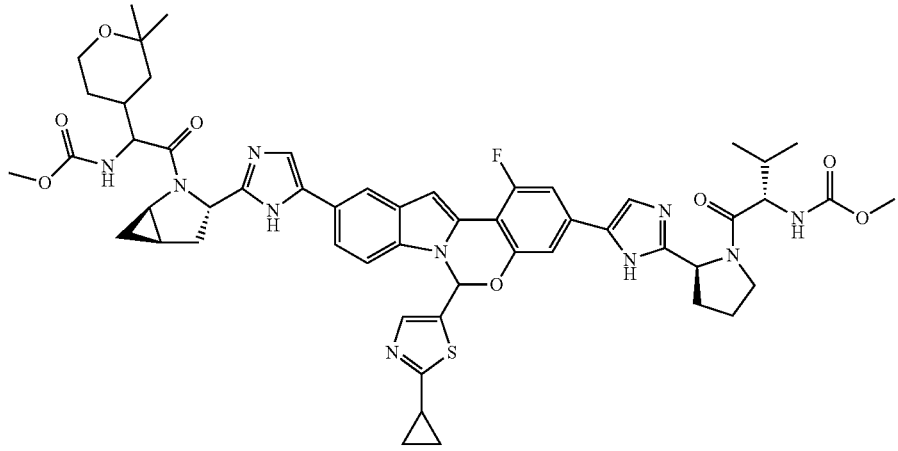 | Isomer 2 | 1030.83 |

-continued
| ID | Structures | Isomer | Observed [M + H]+ |
|---|---|---|---|
| 319 320 | 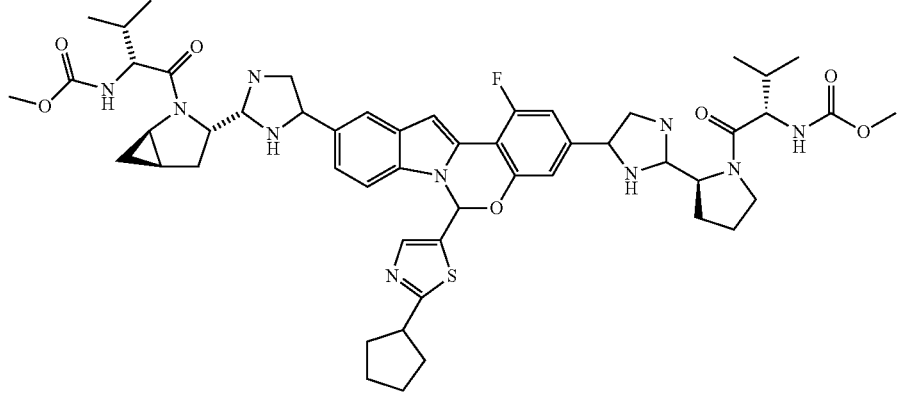 | Isomer 1 Isomer 2 | 988.11 988.3 |
| 321 322 | 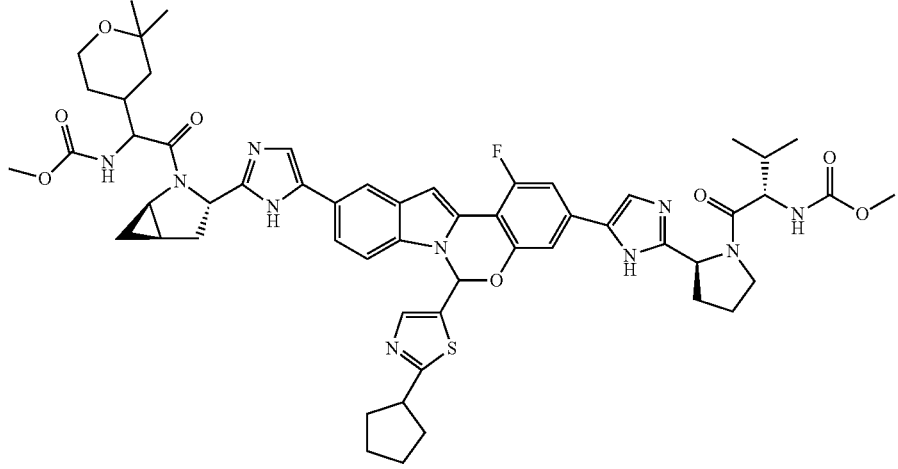 | Isomer 1 Isomer 2 | 1058.3 1058.3 |
| 323 324 | 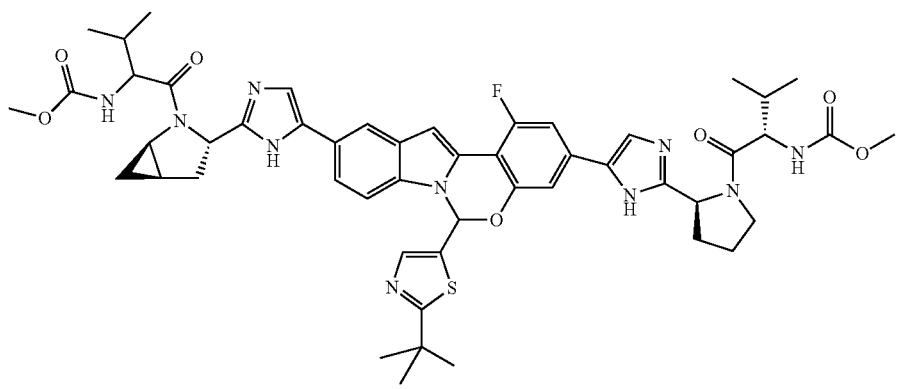 | Isomer 1 Isomer 2 | 976.3 976.3 |

| ID | Structures | Isomer | Observed [M + H]+ |
|---|---|---|---|
| 325 | | Isomer 1 | 990.2 |
| 326 | | Isomer 2 | 990.2 |
| 327 | | Isomer 2 | 1006.8 |
| 328 | | Isomer 2 | 1006.8 |
| 329 | | Isomer 1 | 1046.4 |
| 330 | | Isomer 2 | 1046.0 |

Example 24
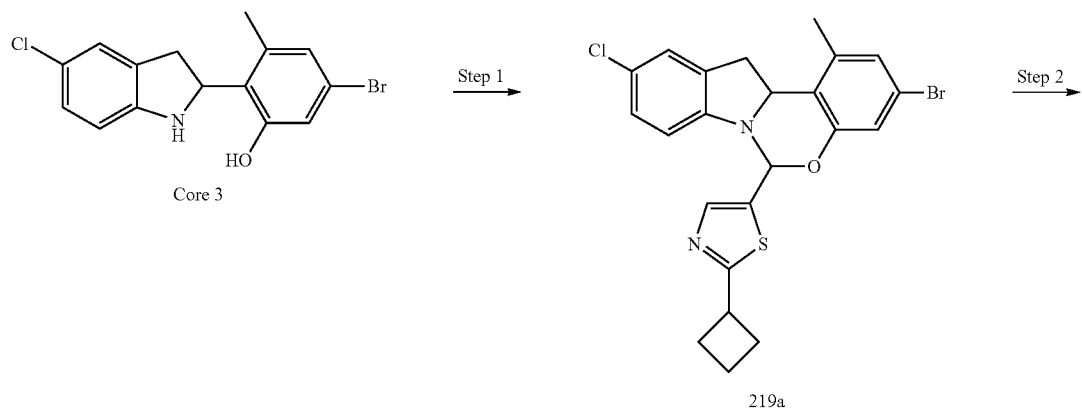
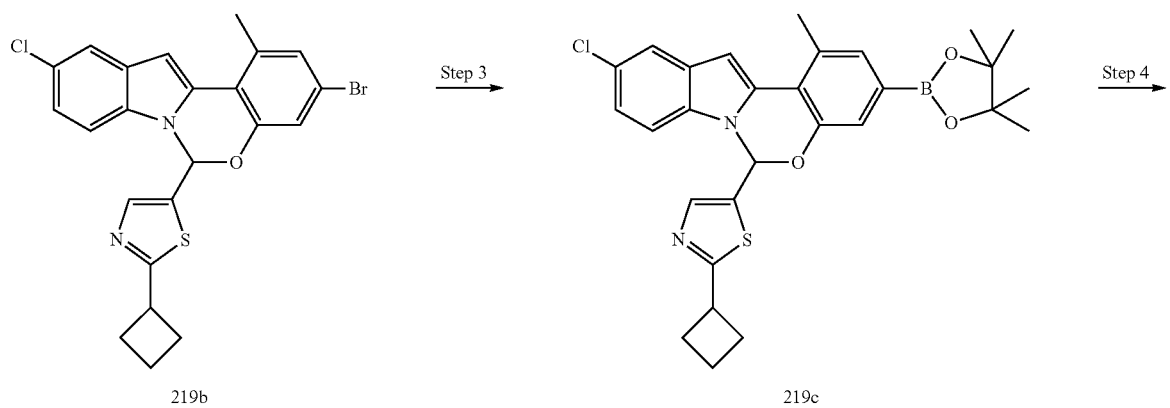
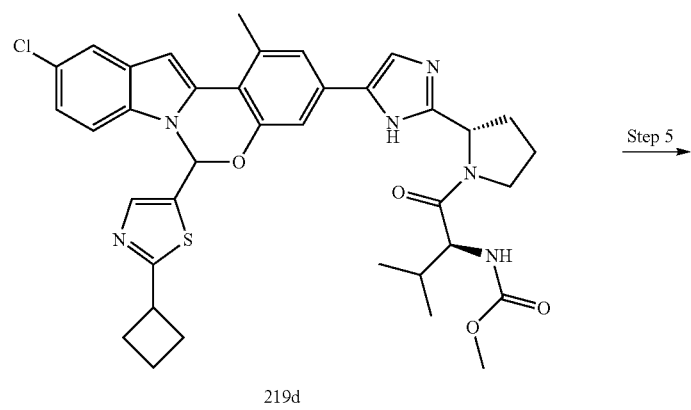

-continued
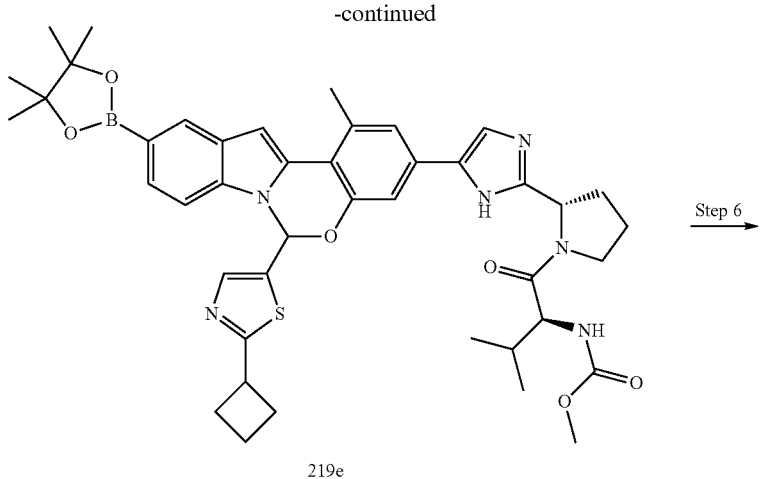
219e
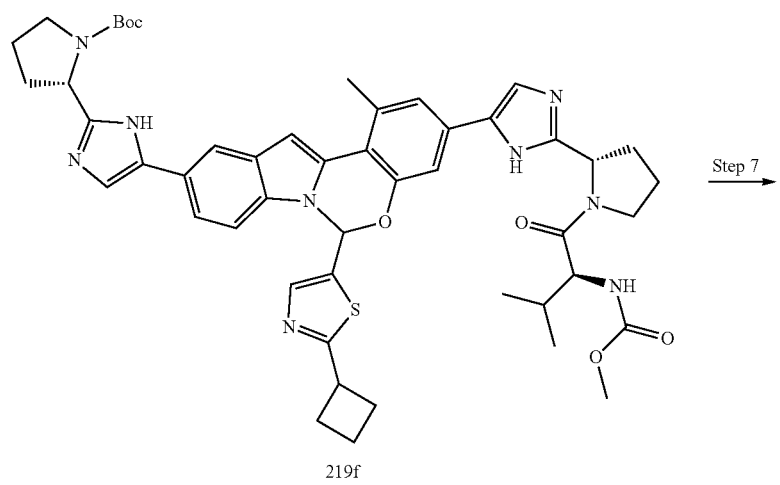
219f
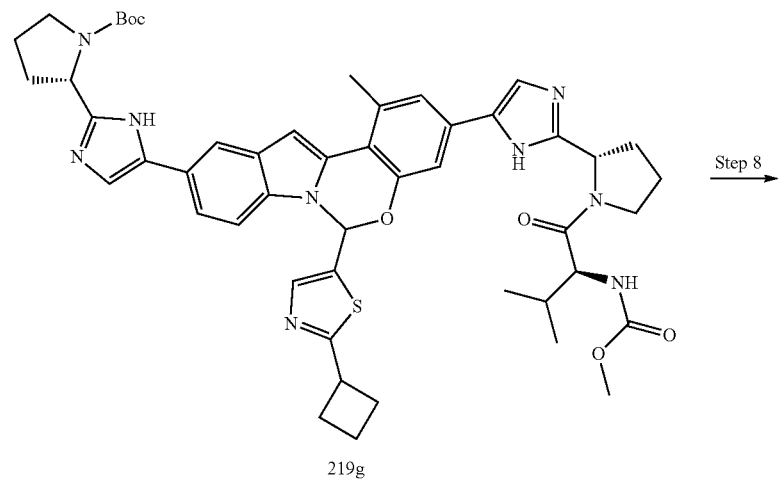
219g

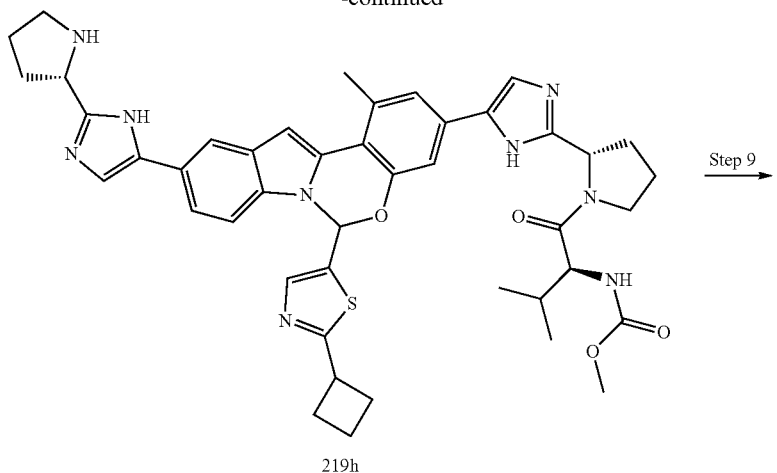

219h

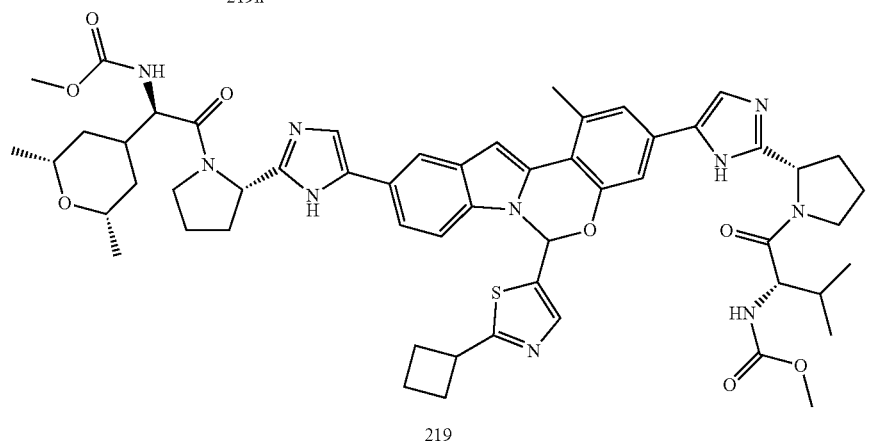

219

Step 1

To a 20 ml tube was added 2-cyclobutylthiazole-5-carbaldehyde (0.619 g, 3.70 mmol), Int-3b (1.0440 g, 3.08 mmol), Acetonitrile (15.42 mL), and TFA (0.071 mL, 0.925 mmol) and the mixture was stirred at room temperature for about 15 hours. The solied was collected by filtration, and washed with AcCN (~2 mL) to provide 219a (1.38 g, 92% yield) as a colorless solid, which was used in the next step without purification.

Step 2

DDQ (0.642 g, 2.83 mmol) was added to a stirred mixture of 219a (1.38 g, 2.83 mmol) in toluene (10 mL) and the mixture was stirred at 110° C. for 1 hour. The mixture was cooled, the solvent was removed in vacuo and the residue was diluted with EtOAc (~50 mL). The organic fractions were washed with sat. $Na_2S_2O_3$ (20 mL) and brine (saturated, 20 mL), dried over $Na_2SO_4$. After filtration and concentration in vacuo, and the resulting residue was tauturated with DCM/Hexane (~10 mL/10 mL), filtered to provide brown solid. The mother liquid was concentrated in vacuo and the residue was purified using column chromatography on silica gel ISCO 24 g, eluting with 0-10%-20% EtOAc in Hex to provide a white solid. The two batches were combined to provide 219b (1.6 g, 116% yield) as a yellow solid.

Step 3

Pinacol Diborane (0.690 g, 2.72 mmol), Potassium Acetate (0.667 g, 6.79 mmol), Pd(dppf)$Cl_2$ (0.166 g, 0.226 mmol) was added to a stirred solution of 219b (1.1 g, 2.264 mmol) in Dioxane (11.32 mL). The tube was de-gassed three times and the mixture was stirred at 110° C. for 2 hours. LCMS confirmed completion of reaction and the crude reaction mixture, which contained compound 219c (1.207 g, 100% yield) was used in the next reaction without further purification.

Step 4

To the reaction mixture of 219c (1.207 g, 2.265 mmol) in Dioxane (2.5 mL) was added Cap 7a (1.057 g, 2.83 mmol), aqueous $K_2CO_3$ solution (6.80 mL, 6.80 mmol) and PdCl$_2$dppf (0.185 g, 0.227 mmol) in a pressure tube. The tube was sealed and degassed following with purging of nitrogen for three times, stirred at 85° C. for 20 hr. The mixture was cooled, aqueous phase was removed by syringe, and the organic layer was purified using column chromatography on silica gel (ISCO 125 g) and eluting with EtOAc in Hex (0-50%-85%), to provide 219d (730 mg, 46.1% yield) as yellow foam.

Step 5

219d (513 mg, 0.734 mmol) was taken in pressure vial, KOAc (216 mg, 2.201 mmol), Pd$_2$(dba)$_3$ (91 mg, 0.088 mmol), X-Phos (87 mg, 0.183 mmol) and bis(pinacolato) diboron (224 mg, 0.880 mmol) in Dioxane (3668 μl) were added and purged with nitrogen for 3 minutes, then vacuumed for 3 minutes. The mixture was stirred at 110° C. for 3 hours. LC-MS shows completion of the reaction. After coolant to room temperature, the mixture of 219e in solvent was used in next step without purification.

Step 6

To the mixture of 219e (580 mg, 0.733 mmol) in dioxane, was added Cap7a (348 mg, 1.100 mmol), PdCl$_2$(dppf)$_2$ (53.7 mg, 0.073 mmol), aqueous K$_2$CO$_3$ solution (2.93 mL, 2.93 mmol). The mixture was placed in a sealed tube and heated at 85° C. for 16 h. The mixture was cooled and separated. The organic layer was purified using column chromatography on silica gel (50 g supelco), eluting with DCM/EtOAc/MeOH (60/46/4 then 20/72/8), to provide 219f (360 mg, 54.5% yield) as a yellow gum.

Step 7

219f (696 mg, 0.773 mmol) was resolved by SFC using the following conditions: Column: ChiralCel OZ-H, 250×30 mm I.D.

Mobile phase: A for CO$_2$ and B for Methanol (0.1% NH3.H2O)
- Gradient: B 50%
- Flow rate: 70 mL/min
- Wavelength: 220 nm The solvent was concentrated in vacuo to provide diastereomer A and 219g (204 mg, 0.227 mmol, 58.6% yield) as diastereomer B.

Step 8

To the CH$_2$Cl$_2$ (10 mL) solution of 219g (204 mg, 0.227 mmol) was added hydrogen chloride (1.133 mL, 4.53 mmol) and the mixture stirred at room temperature for 0.5 hour. The solvent was evaporated to provide 219h (182 mg, 88% yield), which was used in the next step without purification.

Step 9

219h (46.3 mg, 0.051 mmol), Cap 2 (13.11 mg, 0.053 mmol), HATU (21.30 mg, 0.056 mmol), and DMF (1 mL) were added into a 10 mL tube, cooled down to 0° C. by ice-water bath, Diisopropylethylamine (0.036 mL, 0.204 mmol) were added. The solution was stirred at 0° C. for 30 minutes. The mixture was warmed up to room temperature, and then was added water (~5 mL) and the mixture filtered. The solid was collected and converted to HCl salt by adding ~0.1 ml 1M HCl in Et$_2$O and evaporating the volatile to provide 219 (45.5 mg, 0.041 mmol, 81% yield) as a yellow solid.

The following compounds of the present invention were prepared according to the methods described in the Example above.

| ID | Structures | Observed Isomer | [M + H]+ |
|---|---|---|---|
| 200 | | Isomer 2 | 944.26 |
| 201 | | Isomer 1 | 947.18 |
| 202 | | Isomer 2 | 947.23 |

-continued

| ID | Structures | Isomer | Observed [M + H]+ |
|---|---|---|---|
| 203 | 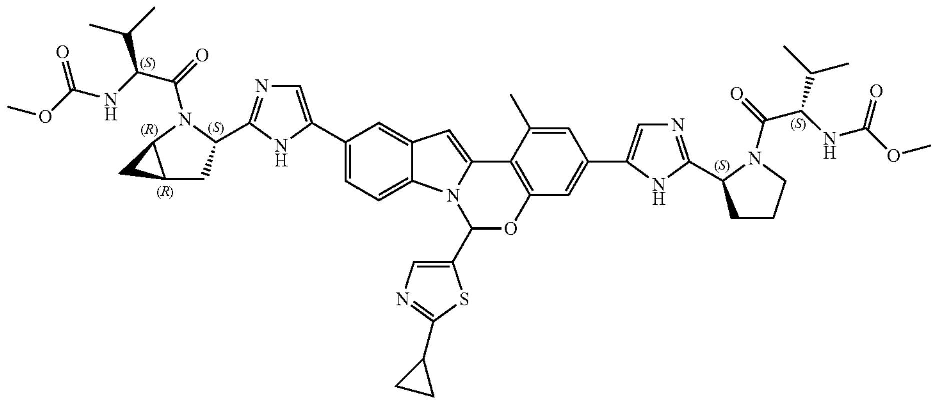 | Isomer 2 | 956.29 |
| 204 | 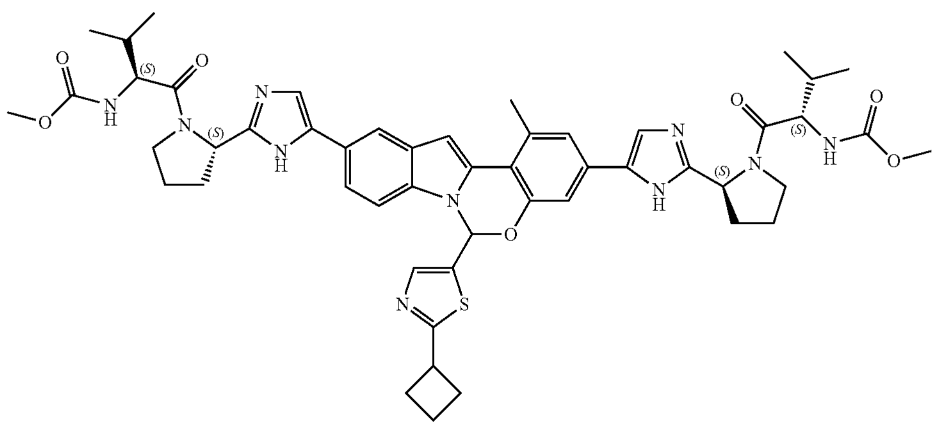 | Isomer 2 | 958.43 |
| 205 | | Isomer 1 | 980.77 |
| 206 | | Isomer 2 | 958.25 |

-continued

| ID | Structures | Isomer | Observed [M + H]+ |
|---|---|---|---|
| 207 | 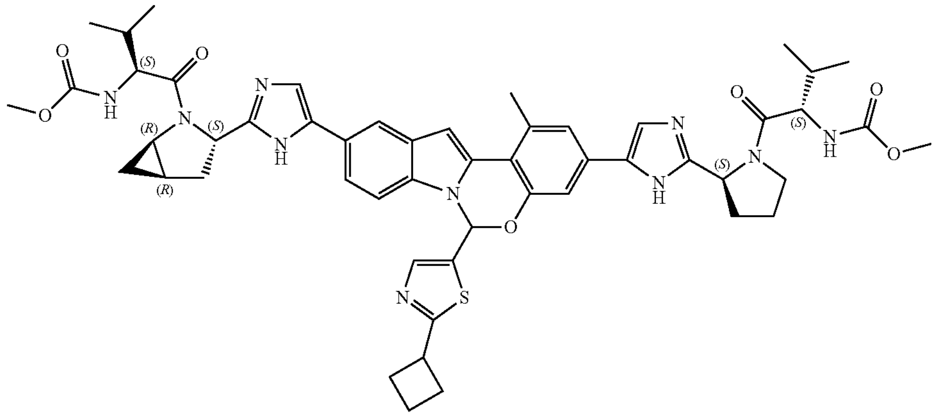 | Isomer 2 | 970.44 |
| 208 | | Isomer 2 | 974.36 |
| 209 | | Isomer 1 | 974.35 |
| 210 | 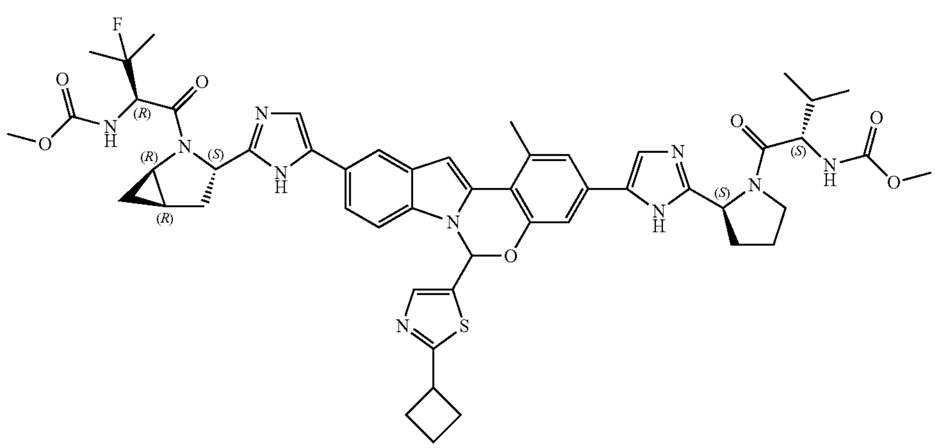 | Isomer 1 | 987.87 |

-continued

| ID | Structures | Isomer | Observed [M + H]+ |
|---|---|---|---|
| 212 | 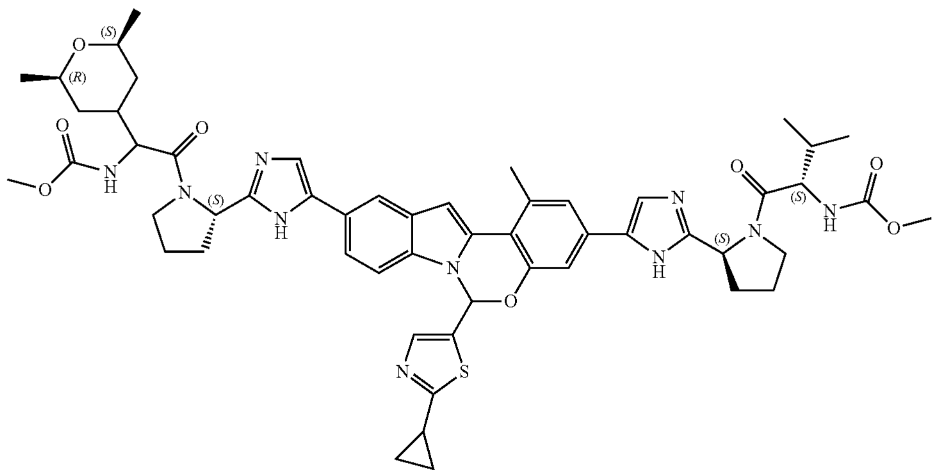 | Isomer 2 | 1014.91 |
| 213 | 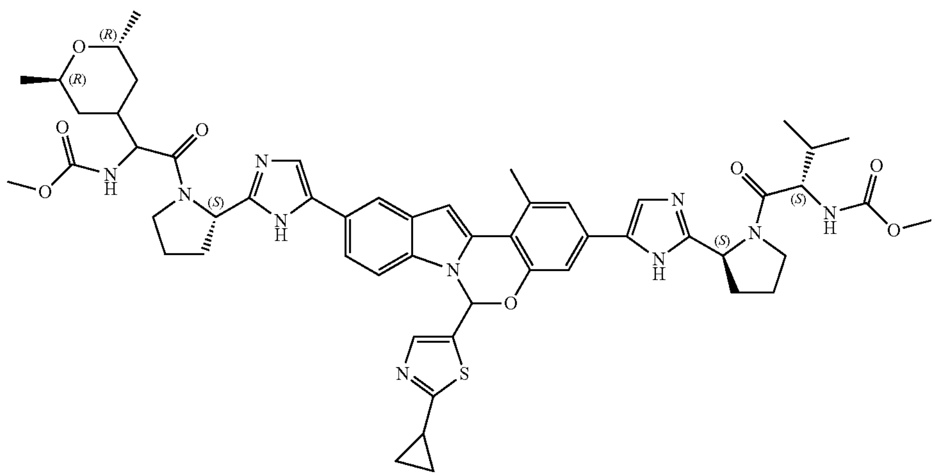 | Isomer 2 | 1014.27 |
| 214 | 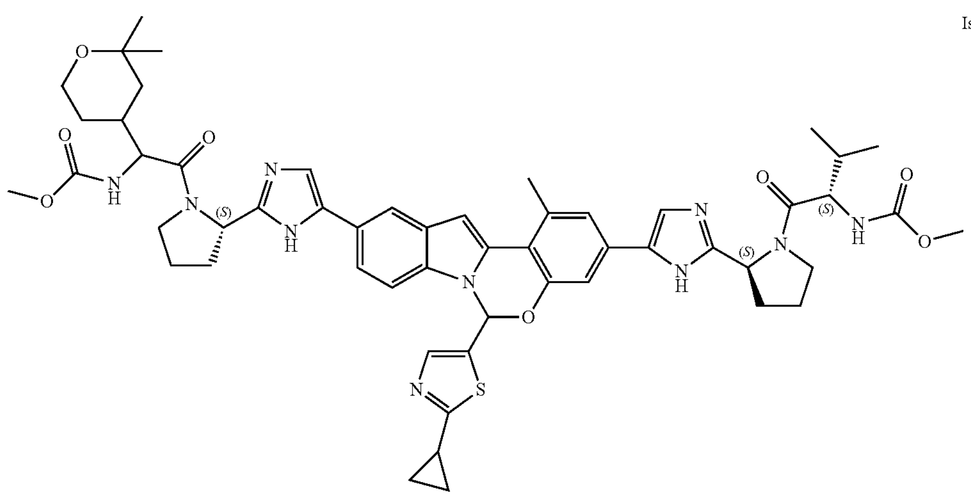 | Isomer 2 | 1014.39 |

-continued
| ID | Structures | Isomer | Observed [M + H]+ |
|---|---|---|---|
| 215 | 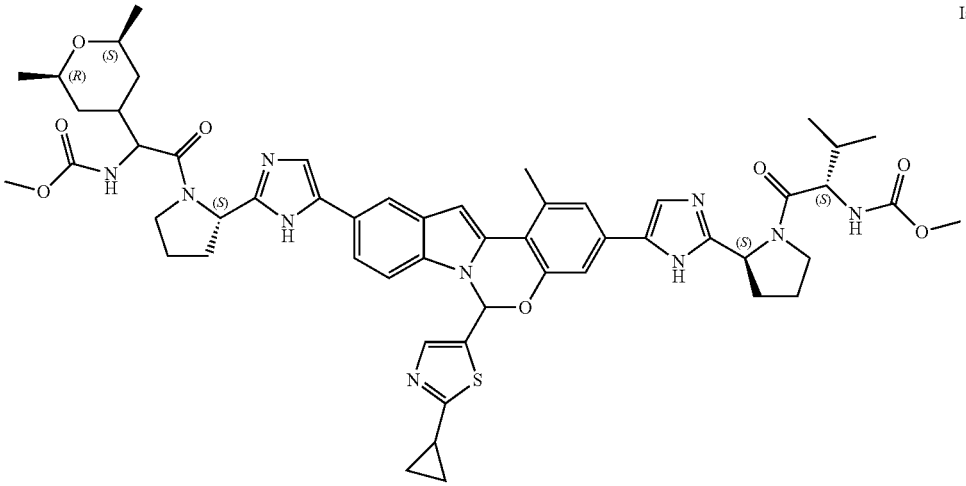 | Isomer 1 | 1014.28 |
| 216<br>217 | 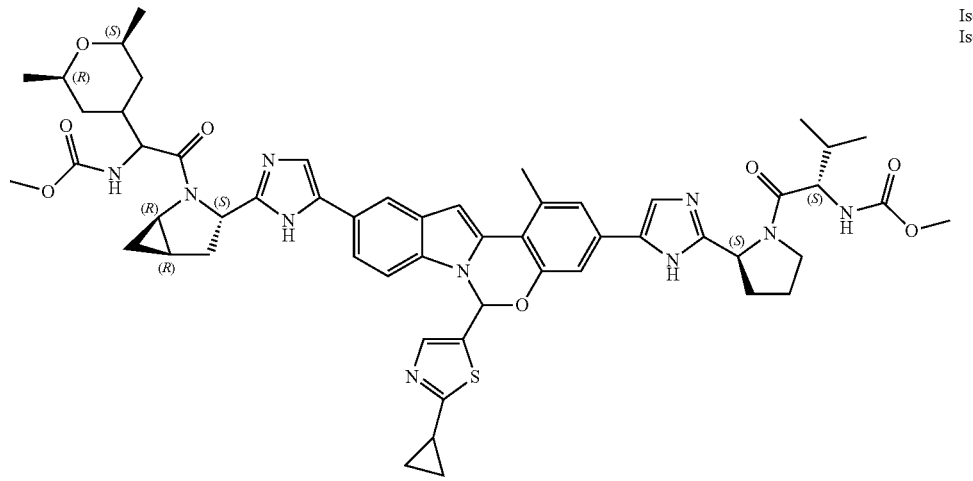 | Isomer 1<br>Isomer 2 | 1026.81<br>1026.62 |
| 218<br>219 | 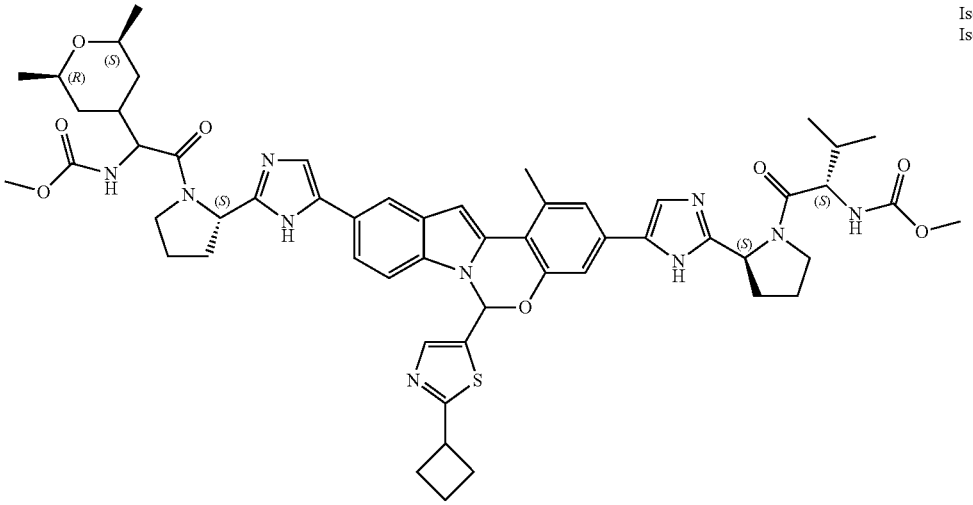 | Isomer 1<br>Isomer 2 | 1028.38<br>1028.44 |

-continued

| ID | Structures | Isomer | Observed [M + H]+ |
|---|---|---|---|
| 220 | 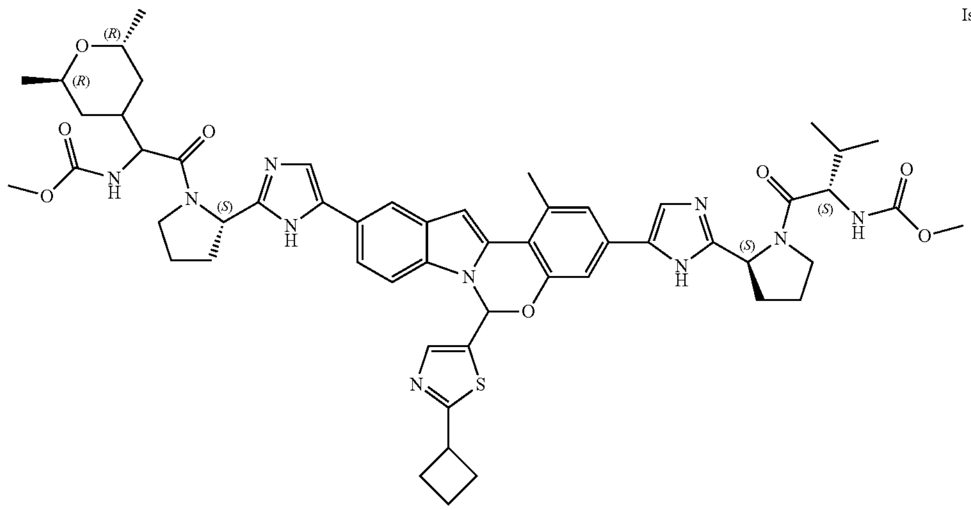 | Isomer 2 | 1028.38 |
| 221 | 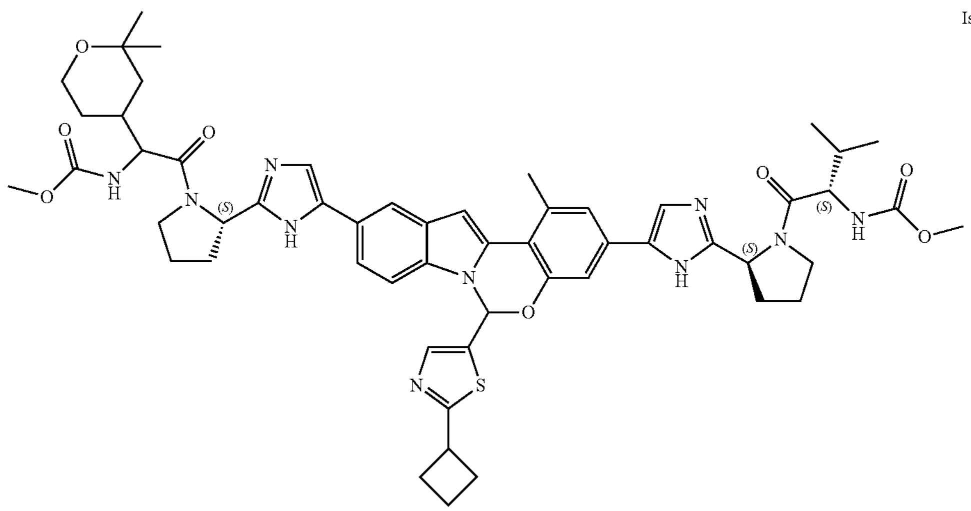 | Isomer 2 | 1028.37 |
| 222 | 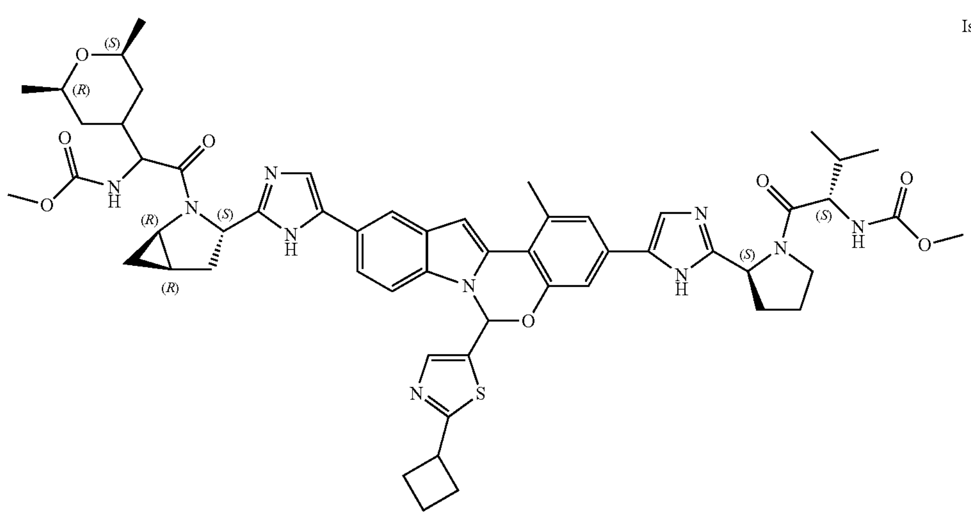 | Isomer 1 | 1039.41 |

-continued

| ID | Structures | Isomer | Observed [M + H]+ |
|---|---|---|---|
| 223 | 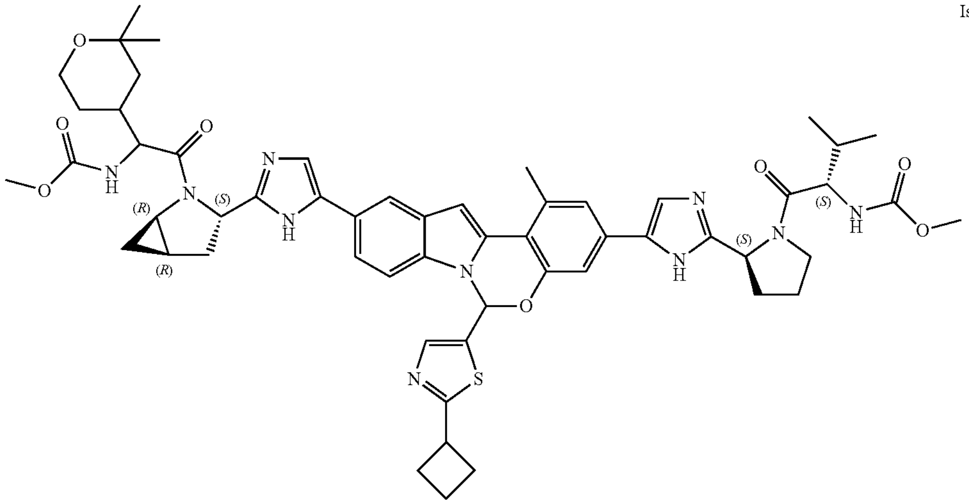 | Isomer 1 | 1040.50 |
| 224 | 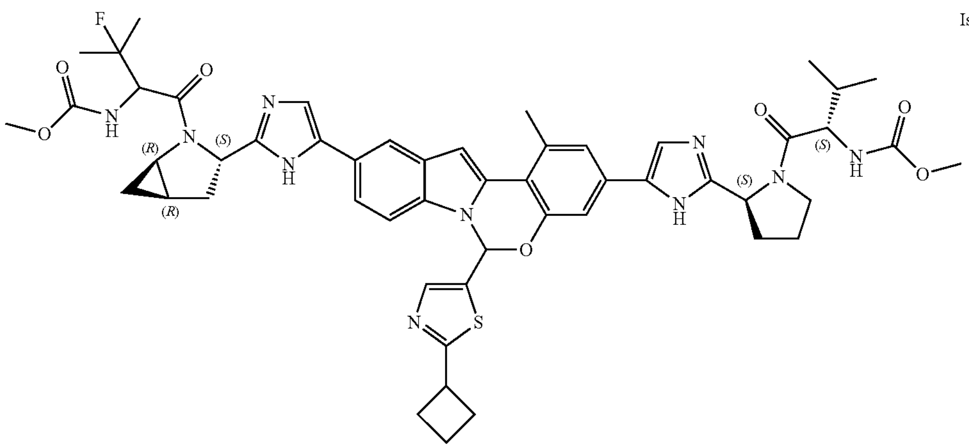 | Isomer 2 | 988.38 |
| 225 | 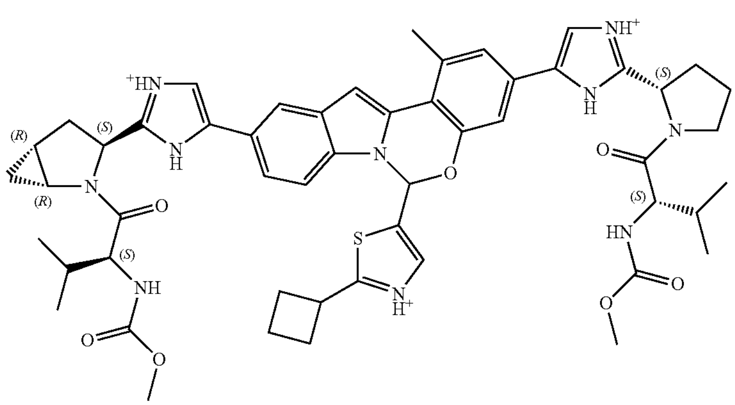 | Isomer 1 | 970.29 |

-continued
| ID | Structures | Isomer | Observed [M + H]+ |
|---|---|---|---|
| 226 | 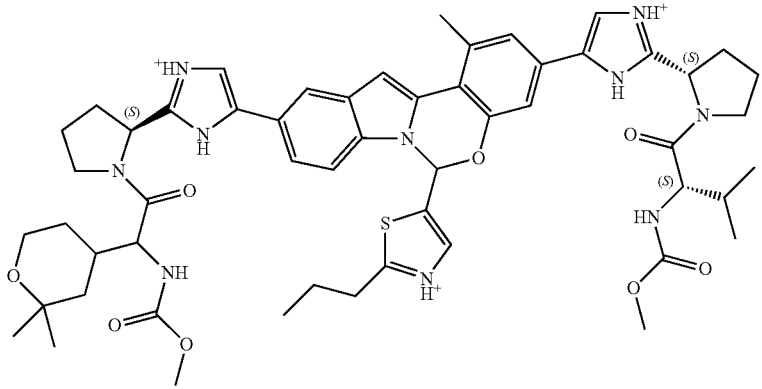 | Isomer 2 | 1016.24 |
| 227 | 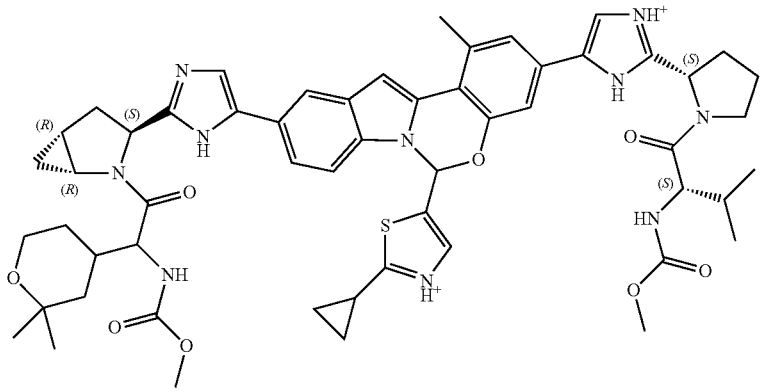 | Isomer 2 | 513.70 |
| 228 | 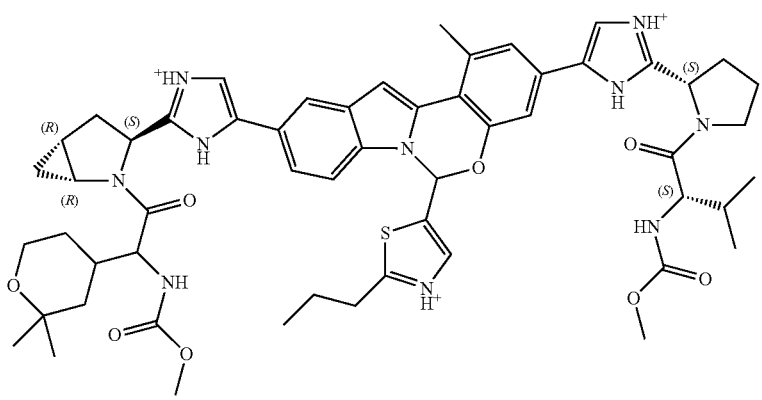 | Isomer 2 | 1029.29 |

-continued
| ID | Structures | Isomer | Observed [M + H]+ |
|---|---|---|---|
| 229 | 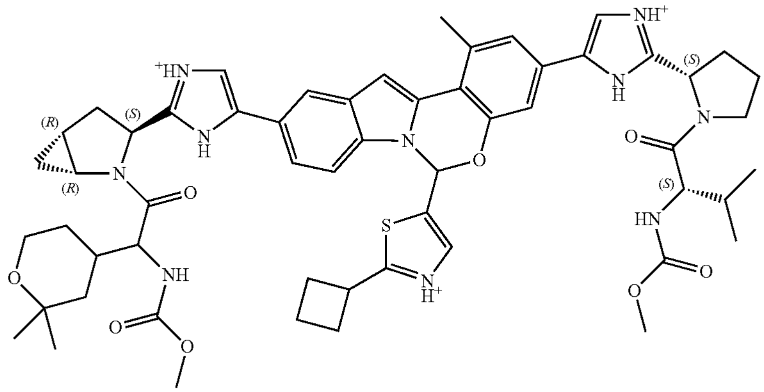 | Isomer 1 | 1041.42 |
Example 25
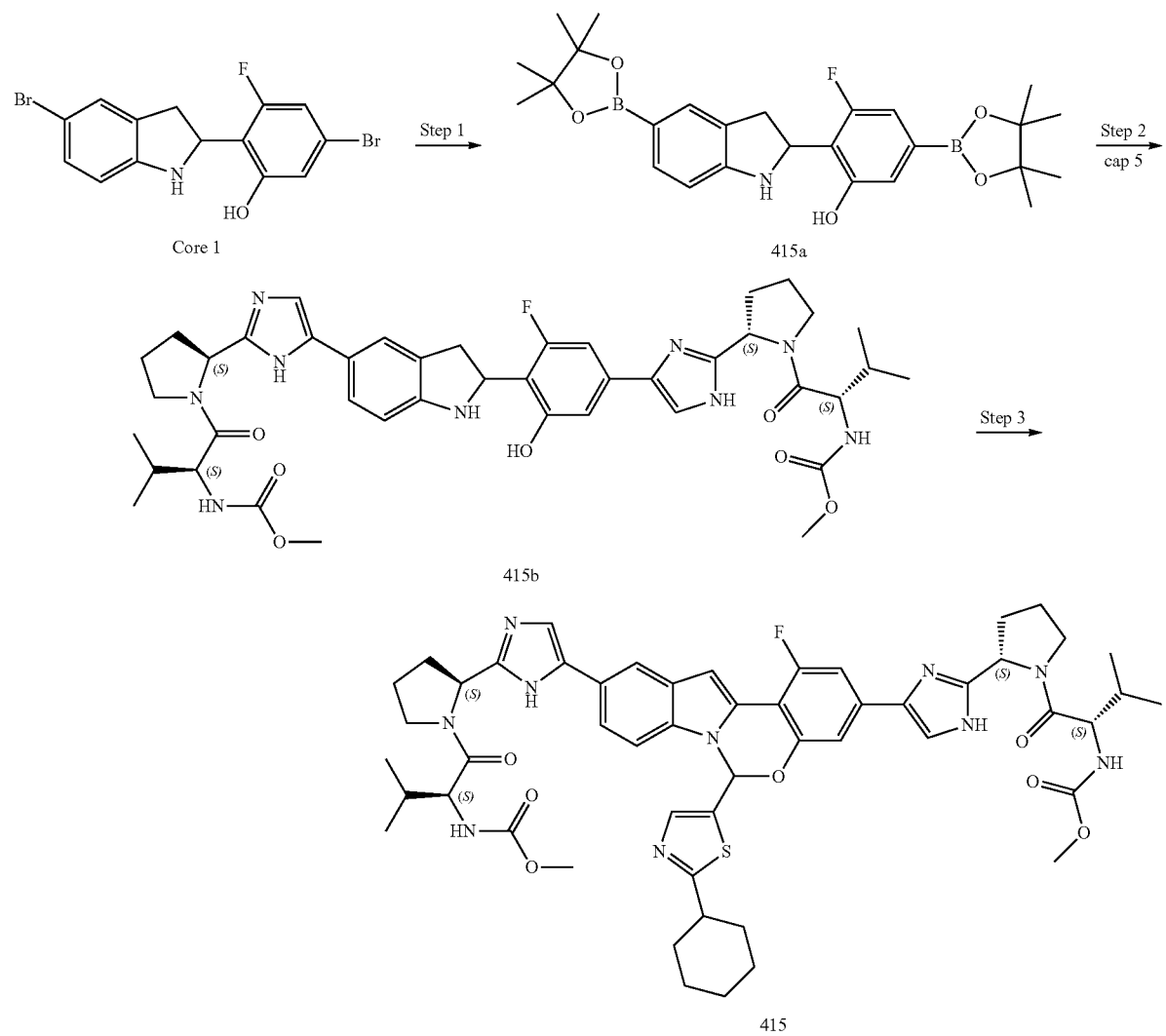

Step 1

To a solution of Int-1b (7.0 g, 18 mmol) in dioxane (140 mL) was added bis(pinacolato)diboron (18.4 g, 72 mmol, 4 eq), Pd(dppf)Cl$_2$ (658 mg, 0.9 mmol, 0.05 eq) and KOAc (7.1 g, 72 mmol, 4 eq) under nitrogen atmosphere, and then the mixture was heated to 120° C. for 3 hours. After the reaction was completed by LCMS, then the mixture was cooled down to room temperature. The reaction was quenched with water (50 mL) and the resulting mixture was extracted with EtOAc (100 mL×3). The organic layers were combined and washed with brine (50 mL), dried over Na$_2$SO$_4$, filtered and concentrated in vacuo. The residue was purified using flash chromatography on silica gel (10 to 15% EtOAc/Petroleum ether) to provide compound 415a (5.0 g, 57%). $^1$H NMR (CDCl$_3$, 400 MHz) δ: 9.98 (s, 1H), 7.61 (t, J=5.6 Hz, 2H), 7.24 (s, 1H), 6.96-6.98 (m, 1H), 6.84 (d, J=7.6 Hz, 1H), 5.32-5.37 (m, 1H), 4.42 (s, 1H), 3.38-3.44 (m, 1H), 2.97-3.04 (m, 1H), 1.31 (s, 24H). M+1: 482

Step 2

To a solution of compound 415a (5.0 g, 10.40 mmol) and Cap 5 (8.5 g, 22.88 mmol, 2.2 eq) and Na$_2$CO$_3$ (4.4 g, 41.60 mmol, 4.0 eq) in THF/DMF/H$_2$O (250 mL/50 mL/100 mL) was added Pd(dppf)Cl$_2$ (1.5 g, 2.08 mmol, 0.2 eq) at room temperature under nitrogen atmosphere, and then the mixture was heated to 100° C. for 5 hours. The reaction was monitored using LCMS. After the reaction was completed, then the mixture was cooled down to room temperature. The resulting mixture was extracted with EtOAc (500 mL×3). The organic layers were combined and washed with water (300 mL), brine (250 mL), dried over Na$_2$SO$_4$, filtered and concentrated in vacuo. The residue was purified using Prep-HPLC to provide compound 415b (3.7 g, 44%) as a brown solid. $^1$H NMR (MeOD, 400 MHz) δ: 7.21-7.50 (m, 5H), 6.80-7.00 (m, 2H), 5.00-5.41 (m, 4H), 3.80-4.25 (m, 6H), 3.60 (s, 6H), 3.46-3.49 (m, 1H), 2.98 (t, J=5.6 Hz, 1H), 1.90-2.40 (m, 14H), 0.80-1.00 (m, 12H). M+1: 814

Step 3

To a stirring solution of the compound 415b (50 mg, 0.06 mmol) in NMP (1.0 mL) was added 2-cyclohexylthiazole-5-carbaldehyde (35 mg, 0.18 mmol, 3.0 eq), MP-TsOH (30 mg, 2 eq). The resulting mixture was heated to 100° C. for about 15 hours. The reaction was monitored using LCMS. After the mixture was cooled to room temperature added DDQ (42 mg, 0.18 mmol, 3 eq) and the resulting mixture was heated at 110° C. for about 15 hours before cooling down to room temperature. The mixture was filtered through sintered glass funnel and the filtrate was purified using prep-HPLC to provide compound 415. M+1: 990

Compounds in the following table were prepared by parallel synthesis using the similar procedure described for compound 415.

Compound 419 and 420 in the following table were obtained from SFC separation of the parent compound under the following condition.

Column: ChiralPak AS-H, 250×4.6 mm I.D.
Mobile phase: 40% Ethanol (0.05% DEA) in CO$_2$
Flow rate: 2.4 mL/min
Wavelength: 210 nm The following compounds of the present invention were prepared according to the methods described in the Example above.

| ID | Structures | Observed Isomer | [M + H]+ |
|---|---|---|---|
| 403 | 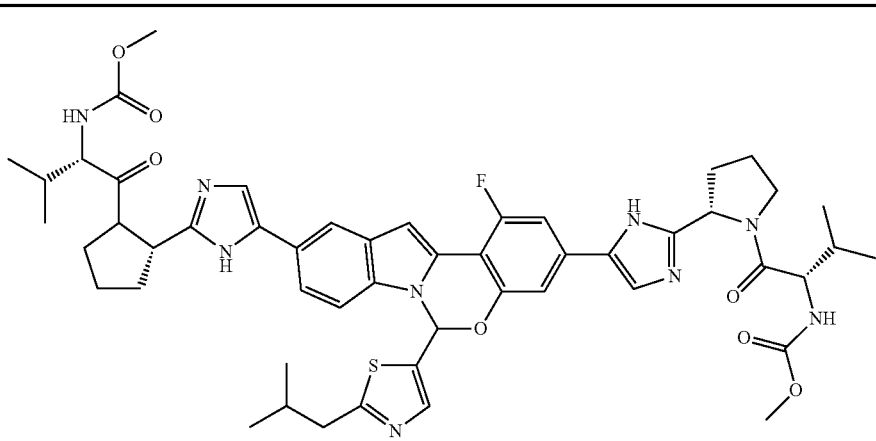 | racemic | 963.4 |

-continued

| ID | Structures | Isomer | Observed [M + H]+ |
|---|---|---|---|
| 407 | 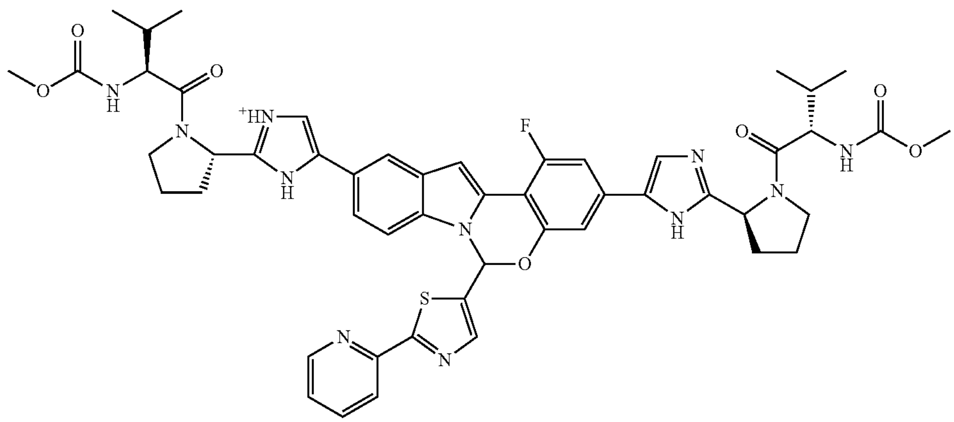 | racemic | 984.58 |
| 411 | 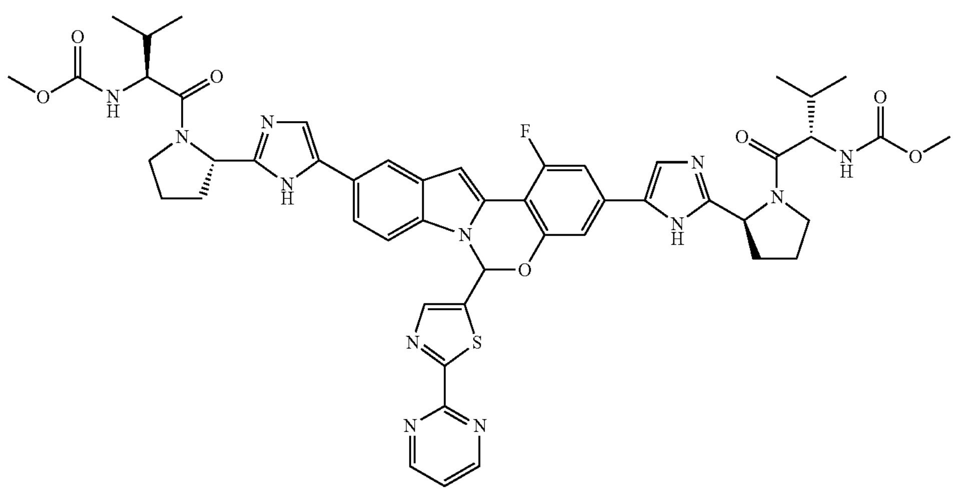 | racemic | 986.0 |
| 416 | 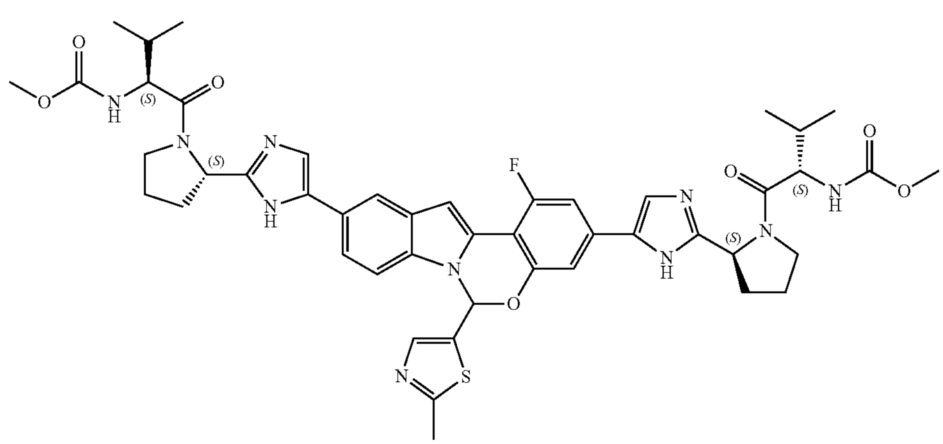 | racemic | 921.66 |

-continued

| ID | Structures | Isomer | Observed [M + H]+ |
|---|---|---|---|
| 417 | 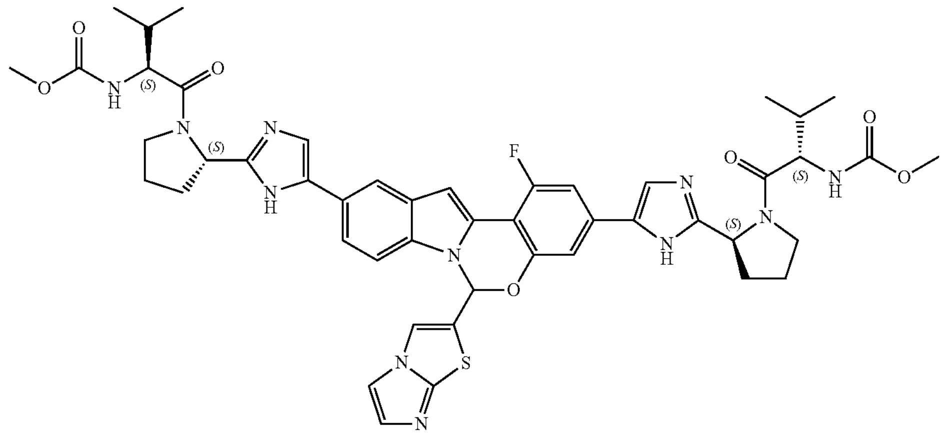 | racemic | 946.67 |
| 418 | 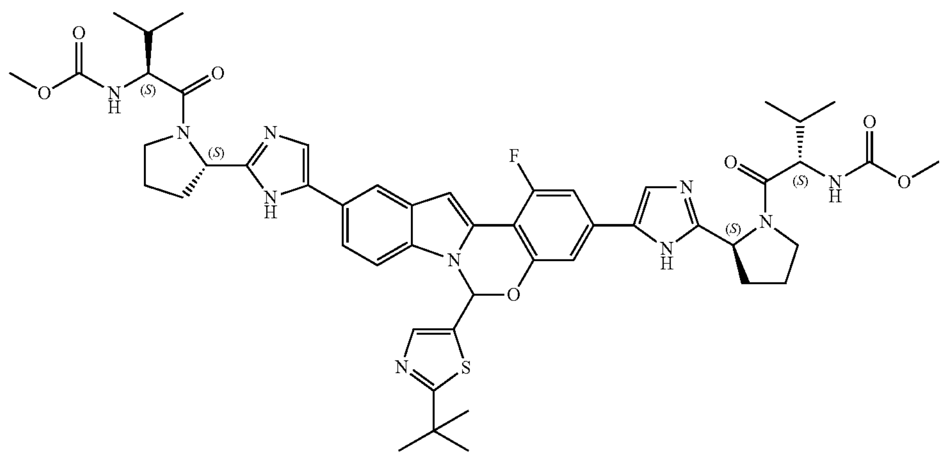 | racemic | 963.75 |
| 419 | | isomer 1 | 975.30 |
| 420 | | isomer 2 | 975.30 |

-continued
| ID | Structures | Isomer | Observed [M + H]+ |
|---|---|---|---|
| 422 | 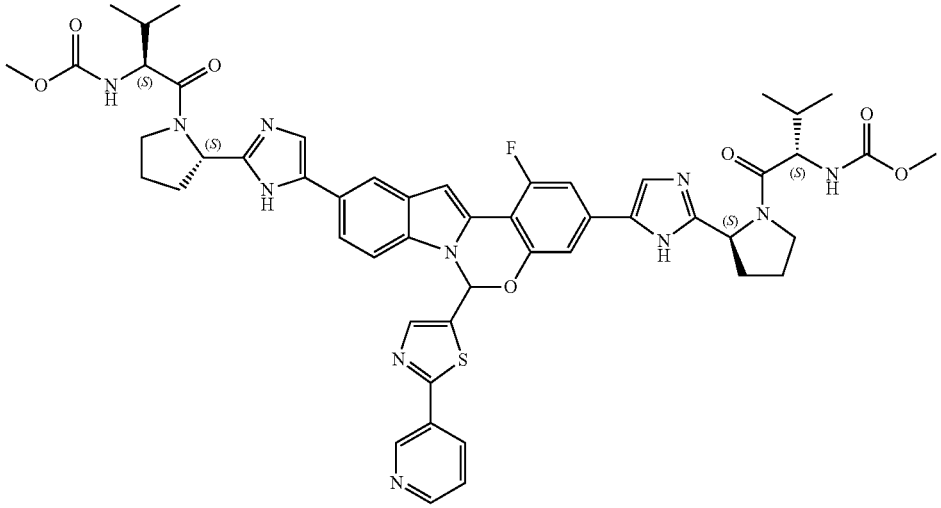 | racemic | 984.68 |
| 423 | 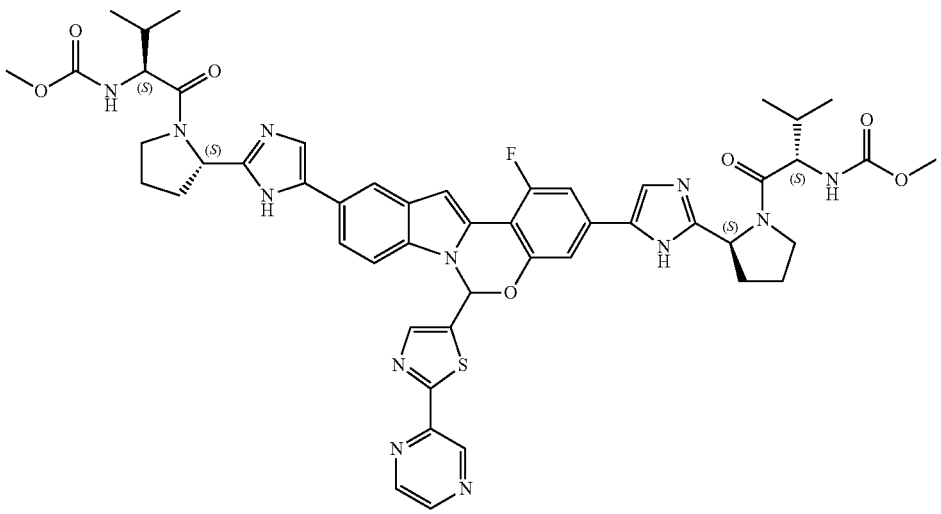 | racemic | 985.74 |
| 425 | 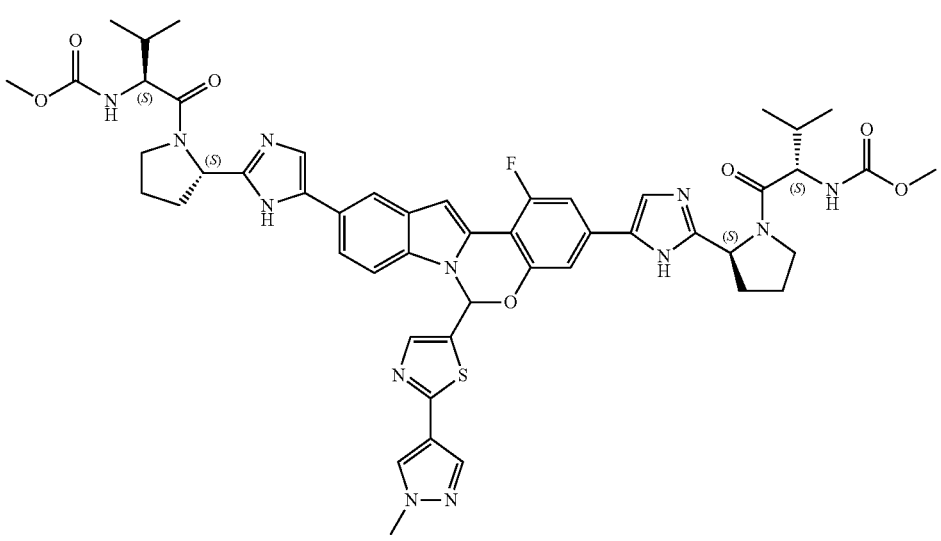 | racemic | 987.78 |

Example 26

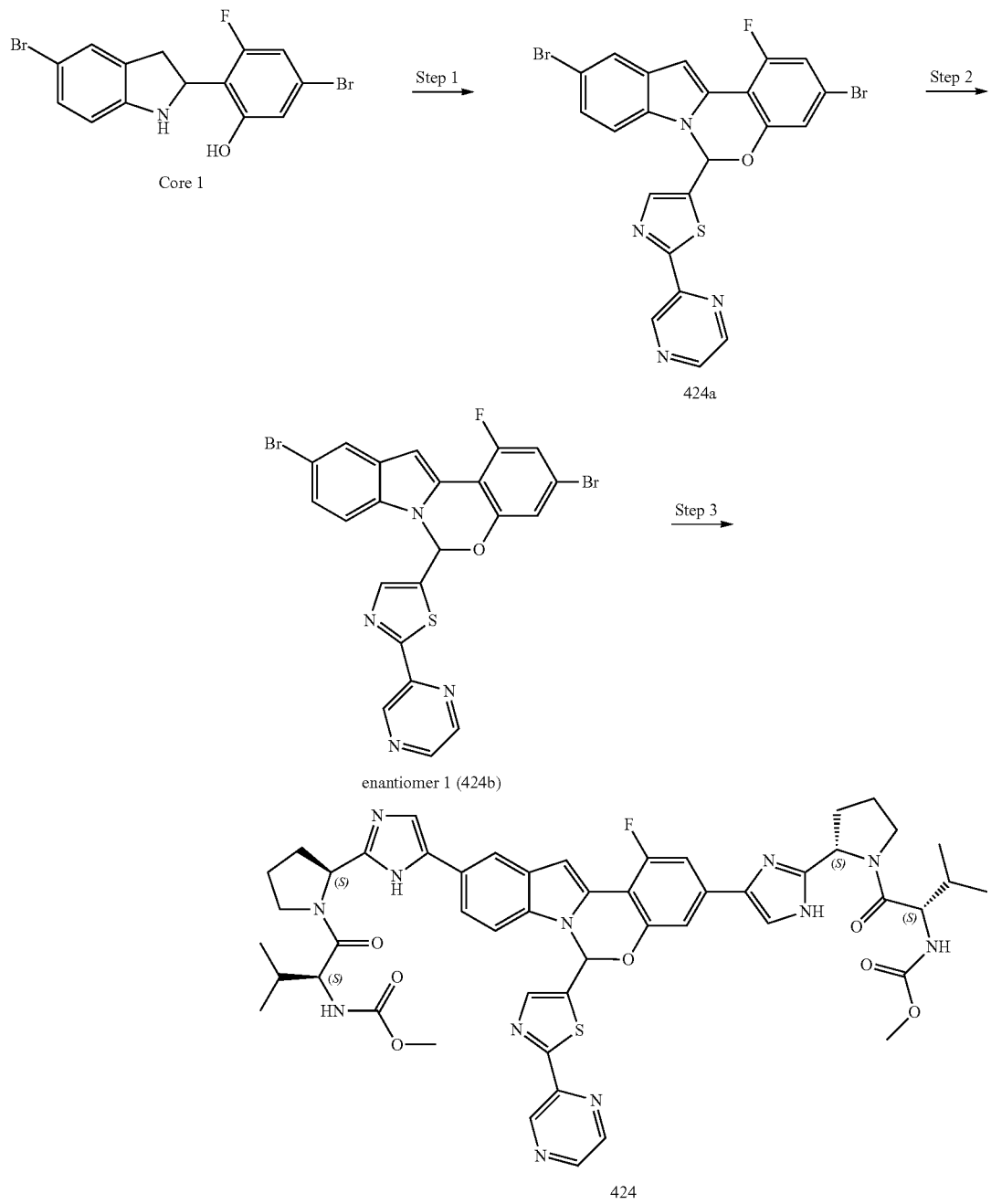

Step 1

To a stirring solution of Int-1b (0.5 g, 1.29 mmol) in ACN (6.0 mL) was added 2-(pyrazin-2-yl)thiazole-5-carbaldehyde (450 mg, 2.0 eq), MP-TsOH (0.5 g, 2 eq). The resulting mixture was heated to 80° C. for about 15 hours. The reaction was monitored using LCMS. After dilution with DCM followed by filtration and rinsed with DCM, the resulting filtrate was concentrated in vacuo. The residue was taken up in toluene and was further treated with DDQ at 100° C. for 2 h and after this period the reaction mixture was cooled to room temperature, diluted with EtOAc, washed with aq-NaHCO3 soln and brine, dried over Na2SO4, filtered, concentrated in vacuo. The crude material was purified over SiO2 column (0 to 100% EtOAc containing 0.5% DEA/Hex) to provide compound 424a (0.15 g, 15%) as a light brown solid. $^{1}$H NMR (DMSO d6, 500 MHz) δ: 9.19 (s, 1H), 8.73 (d, J=3.0 Hz, 1H), 8.62 (d, J=1.5 Hz, 1H), 8.42 (s, 1H), 7.95 (s, 1H), 7.88 (s, 1H), 7.69 (d, J=8.5 Hz, 1H), 7.55 (d, J=9.5 Hz, 1H), 7.44-7.43 (m, 2H), 7.15 (d, J=3.0 Hz, 1H). M+1: 531

Step 2

Compound 424a (105 mg) was separated by SFC by using the following conditions to provide 424b (50 mg, 48%).

Column: IC-H 250×4.6 mm I.D.

Mobile phase: 55% Methanol (0.2% DEA) in CO$_2$

Step 3

To a solution of 424b (50 mg) and bis(pinacolato)diboron (76 mg, 3 eq) and KOAc (39 mg, 4.0 eq) in dioxane (2.0 mL) was added 2nd generation Pd-XPHOS precatalyst (7.9 mg, 0.1 eq) at room temperature under nitrogen atmosphere, and then the mixture was heated to 100° C. for 5 hours. The reaction was monitored using LCMS. After the starting material was consumed, to this mixture was added Cap 5, Pd(dppf)Cl$_2$.CH2Cl2 (8.2 mg, 0.1 eq) and 1M-K3PO4 (0.4 mL, 4 eq). The resulting mixture was further stirred at 100° C. until bis-boronate intermediate was disappeared by LCMS monitoring. The mixture was cooled down to the room temperature and was diluted with EtOAc and brine. The resulting mixture was filtered through a celite pad and was separated. The organic layer was washed with brine, dried, concentrated in vacuo. The residue was purified using Prep-HPLC to provide compound 424 (5.1 mg, 5.2%) as a brown solid. $^1$H NMR (MeOD, 500 MHz) δ: 9.23 (s, 1H), 8.62 (d, J=2.5 Hz, 1H), 8.56-8.55 (m, 1H), 8.42 (s, 1H), 8.20 (s, 1H), 8.10 (s, 1H), 7.94 (s, 1H), 7.81 (s, 1H), 7.74 (d, J=8.5 Hz, 1H), 7.65-7.63 (m, 1H), 7.57 (s, 1H), 7.47-7.44 (m, 1H), 7.31 (d, J=3.0 Hz, 1H), 5.28 (t, J=2.5 Hz, 1 H), 5.23 (t, J=2.5 Hz, 1 H), 4.26-4.21 (m, 2 H), 4.16-4.08 (m, 2 H), 3.90-3.85 (m, 2 H), 3.68 (s, 3H), 3.67 (s, 3H), 2.60-2.54 (m, 2 H), 2.30-2.02 (m, 8 H), 1.02-0.89 (m, 12 H). M+1: 956

The following compounds of the present invention were prepared according to the methods described in the Example above.

| ID | Structures | Isomer | Observed [M + H]+ |
|---|---|---|---|
| 406 | | isomer 1 | 985.4 |
| 408 | | isomer 2 | 985.4 |
| 421 | | isomer 1 | 977.72 |

US 9,555,038 B2
223                                                                                       224
-continued
| ID | Structures | Isomer | Observed [M + H]+ |
|---|---|---|---|
| 427 | | isomer 1 | 989.59 |
| 428 | | isomer 2 | 990.23 |
| 429 | | isomer 2 | 977.72 |
Example 27
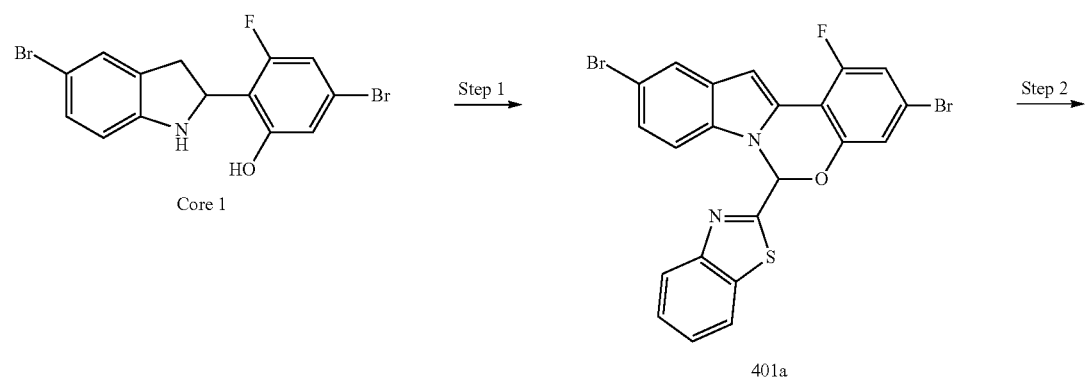
401a

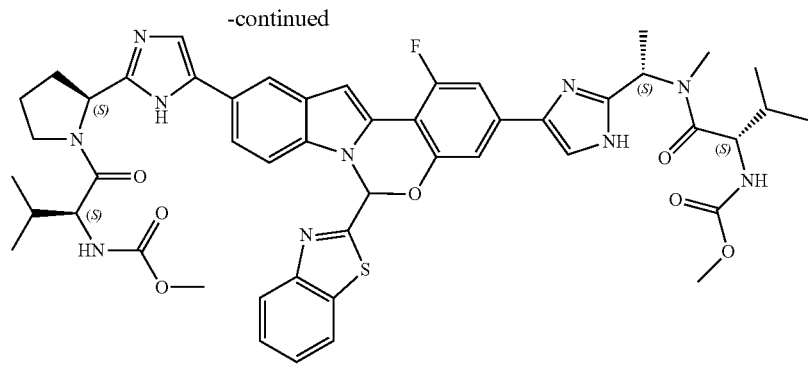

401

Step 1

To a stirring solution of Int-1b (0.5 g, 1.29 mmol) in ACN (6.0 mL) was added 2-(pyrazin-2-yl)thiazole-5-carbaldehyde (450 mg, 2.0 eq), MP-TsOH (0.5 g, 2 eq). The resulting mixture was heated to 80° C. for about 15 hours. The reaction was monitored using LCMS. After dilution with DCM followed by filtration and rinsed with DCM, the resulting filtrate was concentrated in vacuo. The residue was taken up in toluene and was further treated with DDQ at 100° C. for 2 h and after this period the reaction mixture was cooled to room temperature, diluted with EtOAc, washed with aq-NaHCO3 soln and brine, dried over Na2SO4, filtered, concentrated in vacuo. The crude material was purified over SiO2 column (0 to 100% EtOAc containing 0.5% DEA/Hex) to provide compound 401a (0.15 g, 15%) as a light brown solid. $^1$H NMR (CDCl3, 500 MHz) δ: 8.07 (d, J=8.0 Hz, 1H), 7.87 (s, 1H), 7.76 (d, J=8.0 Hz, 1H), 7.64 (s, 1H), 7.53-7.50 (m, 1H), 7.43-7.378 (m, 2H), 7.30-7.28 (m, 1H), 7.19 (s, 1H), 7.16-7.15 (m, 2H). M+1: 531

Step 2

To a solution of 401a (50 mg) and bis(pinacolato)diboron (76 mg, 3 eq) and KOAc (39 mg, 4.0 eq) in dioxane (2.0 mL) was added 2nd generation Pd-XPHOS precatalyst (7.9 mg, 0.1 eq) at room temperature under nitrogen atmosphere, and then the mixture was heated to 100° C. for 5 hours. The reaction was monitored using LCMS. After the starting material was consumed, to this mixture was added Cap 5, Pd(dppf)Cl$_2$.CH2Cl2 (8.2 mg, 0.1 eq) and 1M-K3PO4 (0.4 mL, 4 eq). The resulting mixture was further stirred at 100° C. until bis-boronate intermediate was disappeared by LCMS monitoring. The mixture was cooled down to the room temperature and was diluted with EtOAc and brine. The resulting mixture was filtered through a celite pad and was separated. The organic layer was washed with brine, dried, concentrated in vacuo. The residue was purified using Prep-HPLC to provide compound 401 (9.2 mg, 9.6%) as a brown solid. $^1$H NMR (MeOD, 500 MHz) δ: 8.17 (s, 1H), 8.08 (d, J=8.5, 1H), 7.93-7.87 (m, 3H), 7.80 (s, 1H), 7.76 (dd, J=8.5, 4.5 Hz, 1H), 7.63-7.42 (m, 1H), 7.50-7.42 (m, 4H), 7.28 (d, J=3.5 Hz, 1H), 5.28 (t, J=7.5 Hz, 1 H), 5.22 (t, J=7.5 Hz, 1 H), 4.27-4.22 (m, 2 H), 4.12-4.11 (m, 2 H), 3.91-3.87 (m, 2 H), 3.68 (s, 3H), 3.67 (s, 3H), 2.60-2.54 (m, 2 H), 2.30-2.05 (m, 8 H), 1.00-0.89 (m, 12 H). M+1: 957

Compounds 400 and 402 were obtained from SFC separation of the parent compound 401 under the following condition.

Column: ChiralPak AS-H, 250×30 mm I.D.

Solvent: 0 to 40% of EtOH (0.05% DEA) in CO$_2$

Compound 408 and 410 were obtained from SFC separation of the parent compound 409 under the following condition.

Column: ChiralCel OJ-H, 250×30 mm I.D.

Solvent: 0 to 40% of iPrOH (0.1% NH3.H2O) in CO$_2$

Compound 412 and 414 were obtained from SFC separation of the parent compound 413 under the following condition.

Column: ChiralCel OJ-H, 250×30 mm I.D.

Solvent: 0 to 40% of iPrOH (0.1% NH3.H2O) in CO$_2$

The following compounds of the present invention were prepared according to the methods described in the Example above.

| ID | Structures | Isomer | Observed [M + H]+ |
|---|---|---|---|
| 400 | | isomer 1 | 958.2 |
| 402 | | isomer 2 | 958.3 |

| ID | Structures | Isomer | Observed [M + H]+ |
|---|---|---|---|
| 404 | | racemic | 979.4 |
| 409 | | racemic | 985.3 |
| 410 | | Isomer 2 | 985.2 |
| 412 | | isomer 1 | 988.0 |
| 413 | | racemic | 988.6 |
| 414 | | isomer 2 | 987.3 |

| ID | Structures | Isomer | Observed [M + H]+ |
|---|---|---|---|
| 426 | 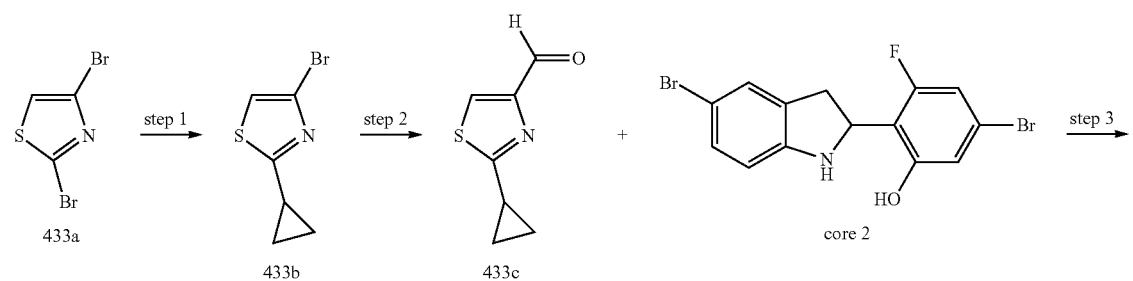 | racemic | 989.70 |
Example 28
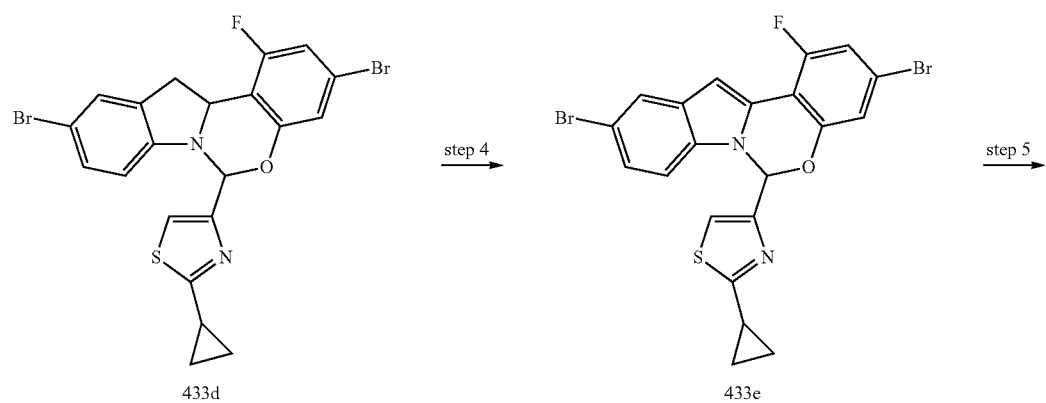

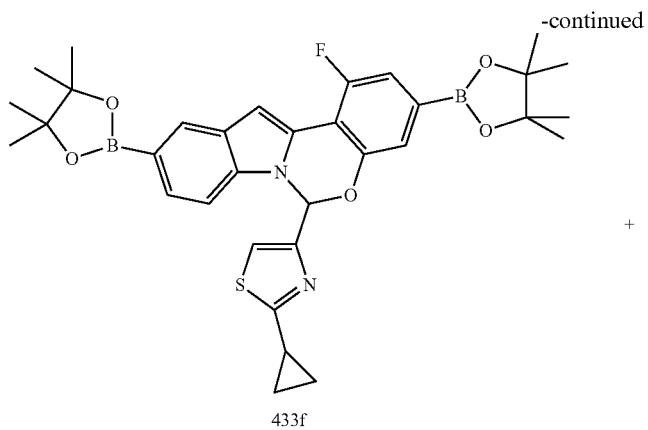

433f

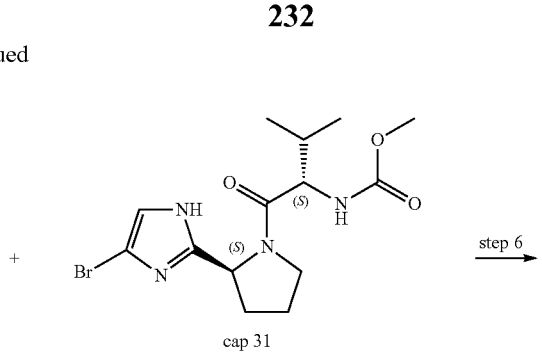

cap 31 step 6

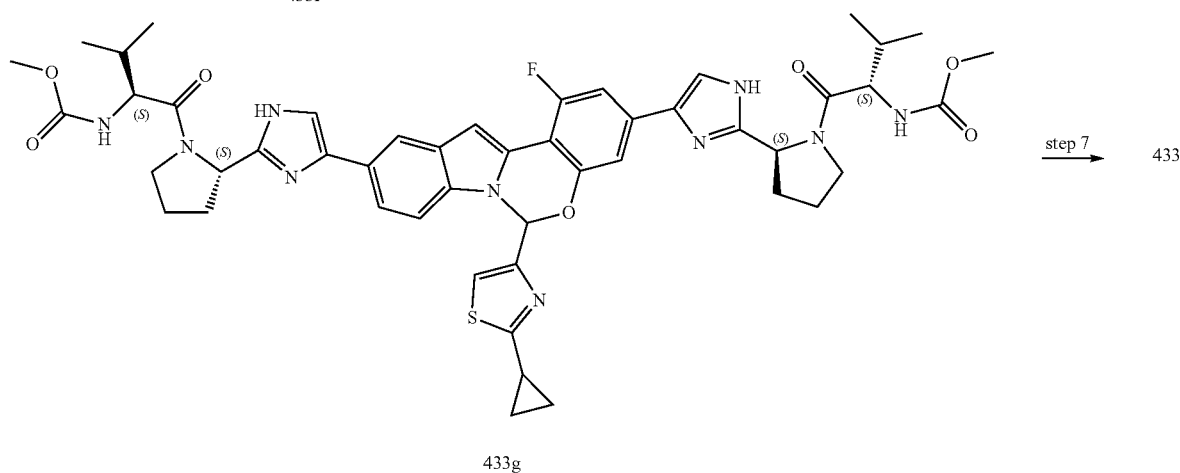

433g step 7  433

Step 1

The mixture of compound 433a (5 g, 20.5 mmol), cyclopropyl boronic acid (2.12 g, 24.7 mmol), $K_3PO_4$ (13.1 g, 61.7 mmol), Xantphos (0.6 g, 1.04 mmol) and $Pd(OAc)_2$ (0.23 g, 1.04 mmol) in THF (140 mL) was stirred at 80° C. under $N_2$ for about 15 hours. The reaction was complete detected by TLC (Petroleum Ether/EtOAc=30:1) and LCMS. The mixture was extracted with EtOAc (100 mL), water (50 mL). The combined organics was dried over $Na_2SO_4$, purified with silica gel (Petroleum Ether/EtOAc=50:1) to provide compound 433b as oil (3.48 g, yield: 83.3%).

Step 2

To a solution of compound 433b (1 g, 4.9 mmol) in 2-isopropxypropane (20 mL) was added a 2.5 M solution of t-BuLi (11.3 mL, 14.7 mmol) at −60° C. under $N_2$. The mixture was agitated for 1 hour at this temperature then DMF (1.05 g, 14.7 mmol) was added. The mixture was stirred at this temperature for 1 hour. Quenched with $NH_4Cl$ saturate solution and extracted with EtOAc. The organic layer was dried over $Na_2SO_4$, and concentrated in vacuo and purified using column chromatography to provide compound 433c (735 mg, 97.9% yield). LC/MS: Anal. Calcd. For $[M+H]^+$ C7H7NOS: 154.0. found 154.1

Step 3

To a mixture of 433c (735 mg, 4.8 mmol) and Int-2b (1.33 g, 3.43 mmol) in anhydrous $CH_3CN$ (15 mL) was added TFA (117 mg, 1.03 mmol) at 25° C. The mixture was stirred at 25° C. for 3 hours. The reaction mixture became a clear solution and then solid appeared. The solid was collected by filtration and washed with $CH_3CN$ to provide compound 433d (1.02 g, 57% yield). LC/MS: Anal. Calcd. For $[M+H]^+$ C21H15BrFN2OS: 521.9. found 523.

Step 4

The solution of compound 433d (1 g, 1.9 mmol) in dry toluene (25 mL) was added DDQ (0.65 g, 2.87 mmol). After refluxing for 2 hours, the solvent was removed in vacuo and diluted with EtOAc. The organic layer was washed with saturated $Na_2S_2O_3$ aqueous and brine, dried over $Na_2SO_4$, filtered and concentrated in vacuo. The residue was washed with MeOH (5 mL), filtered and the solid just was the product 433e (740 mg, 74.7% yield). LC/MS: Anal. Calcd. For $[M+H]^+$ C21H13BrFN2OS: 519.9. found 521.

Step 5

To a solution of compound 433e (0.74 g, 1.42 mmol) in 1,4-dioxane was added bis pinacol borate (0.9 g, 3.56 mmol) and $Pd(dppf)Cl_2$ (0.1 g, 0.14 mmol) and KOAc (0.56 mg, 0.57 mmol). The reaction mixture was stirred under $N_2$ and heated to 110° C. for about 15 hours. After that, the solvent was removed in vacuo, and the residue was purified using column chromatography with silica gel to provide compound 433f (720 mg, 82.7% yield). LC/MS: Anal. Calcd. For $[M+H]^+$ C33H37B2FN2O5S: 615.26. found 615.3.

Step 6

A suspension of compound 433f (0.7 g, 1.14 mmol), cap 31 (0.94 g, 2.5 mmol), $Pd(dppf)Cl_2$ (166 mg, 0.23 mmol) and $Na_2CO_3$ (0.48 g, 4.56 mmol) in $THF/H_2O$ (8:1, 30 mL) was refluxed at 100° C. for about 15 hours under $N_2$ atmosphere. After that, the mixture was filtered, the filtrate was washed with water (10 mL) and extracted with EtOAc (50 mL), washed with brine and dried over anhydrous sodium sulfate. The resulting solution was then filtered, concentrated in vacuo, and the residue was purified using column chromatography (Petroleum Ether/EtOAc=5:1→1:1) to provide compound 433g (0.41 g, 38% yield). LC/MS: Anal. Calcd. For [M+H]+ C49H55FN10O7S: 947.40. found 947.5.

Step 7

Compound 433 was prepared from compound 433g (0.41 g) by SFC by using the following conditions:
Instrument: Thar SFC
Column: OD-3, 150×4.6 mm, 3 um
Mobile phase: A for CO2 and B for MeOH (0.05% DEA)
Gradient: 40% for A
Flow rate: 2.5 mL/min
Wavelength: 340 nm Compound 433 (180 mg, 45% yield). $^1$H NMR (MeOD) δ: 8.07-8.03 (m, 1H), 7.93-7.90 (m, 1H), 7.78 (s, 1H), 7.63 (s, 1H), 7.57-7.52 (m, 1H), 7.50-7.45 (m, 1H), 7.41-7.35 (m, 1H), 7.33-7.30 (m, 1H), 7.24-7.20 (m, 1H), 6.73 (s, 1H), 5.30-5.20 (m, 2H), 4.28-4.22 (m, 2H), 4.17-4.07 (m, 2H), 3.94-3.83 (m, 2H), 3.68 (s, 6H), 2.62-2.51 (m, 2H), 2.34-2.25 (m, 3H), 2.24-2.13 (m, 4H), 2.11-2.03 (m, 2H), 1.14-1.07 (m, 2H), 1.03-0.86 (m, 14H). LC/MS: Anal. Calcd. For [M+H]+ C49H55FN10O7S: 947.40. found 947.5.

The following compounds of the present invention were prepared according to the methods described in the Example above.

| ID | Structures | Isomer | Observed [M + H]+ |
|---|---|---|---|
| 114 | 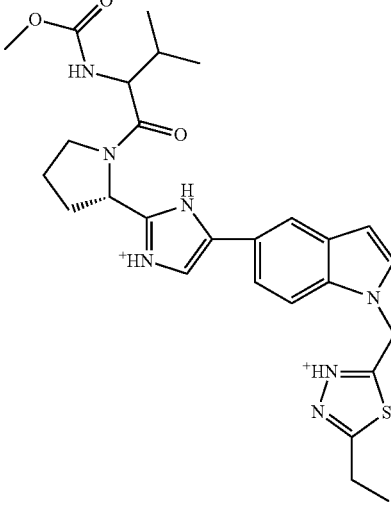 | Isomer 1 | N/A |
| 115 | | Isomer 2 | N/A |
| 430 | 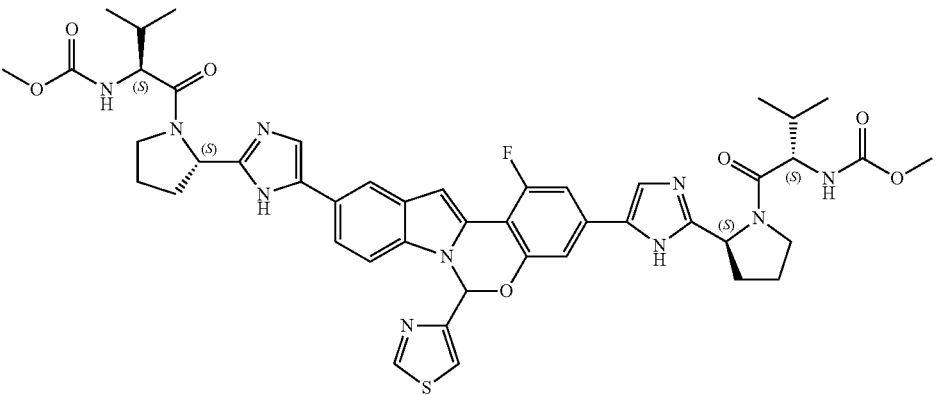 | Isomer 1 | 907.4 |
| 431 | | Isomer 2 | 907.4 |

-continued
| ID | Structures | Isomer | Observed [M + H]+ |
|---|---|---|---|
| 432 |  | Isomer 1 | 947.5 |
| 433 |  | Isomer 2 | 947.5 |
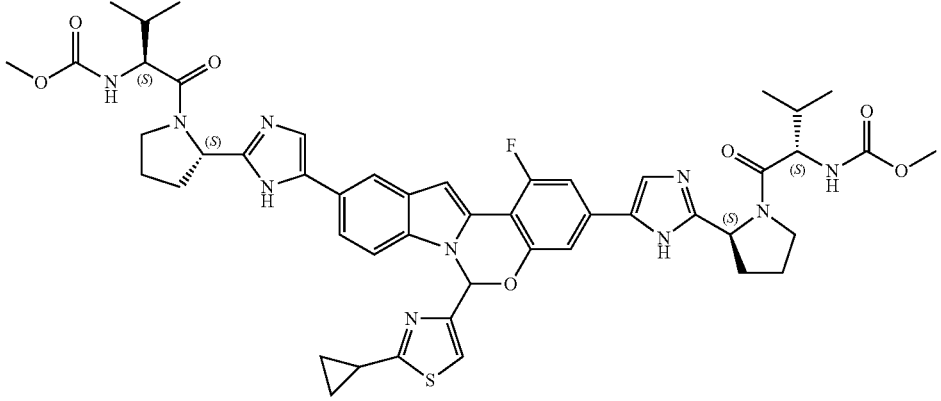
Example 29
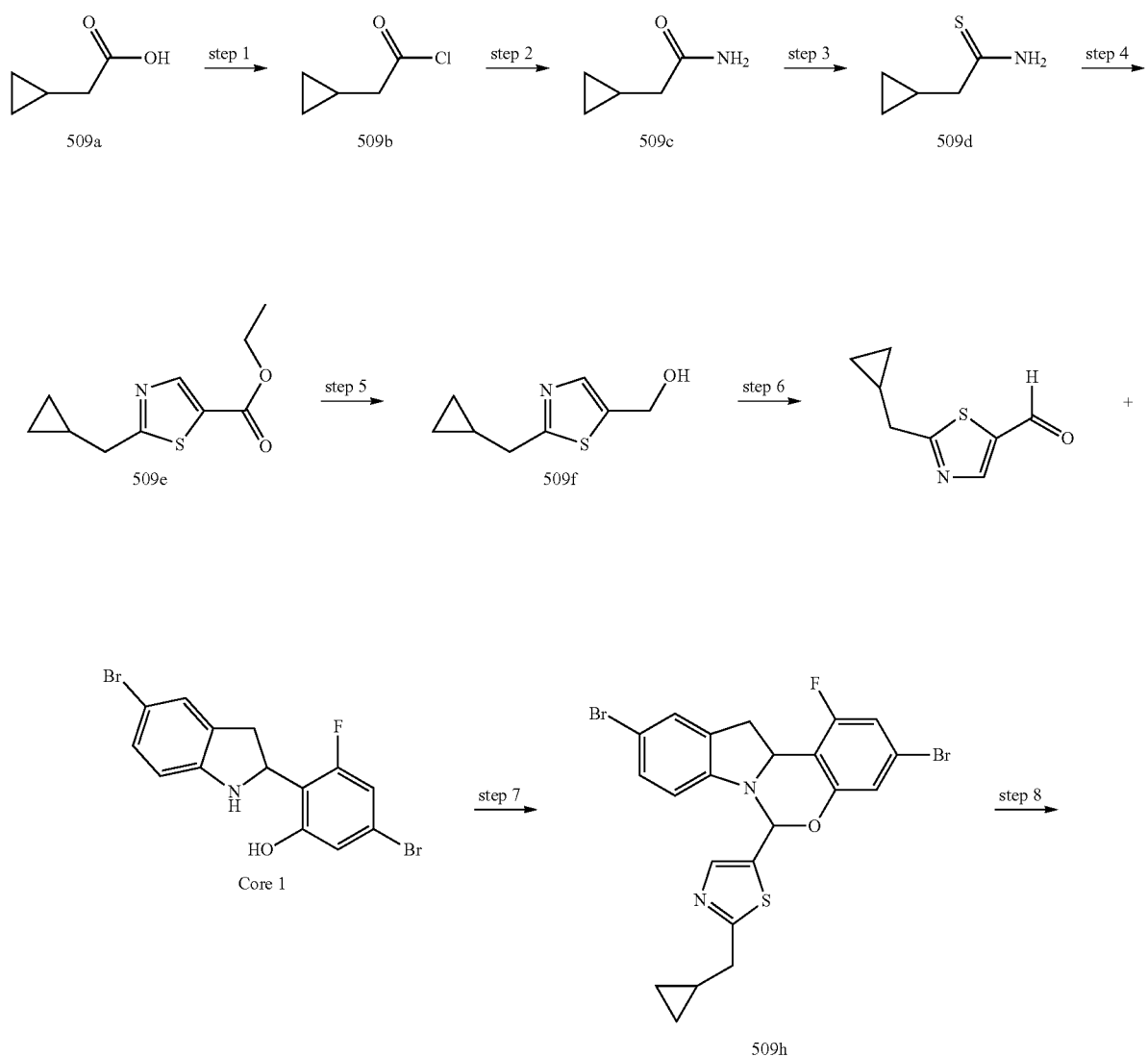

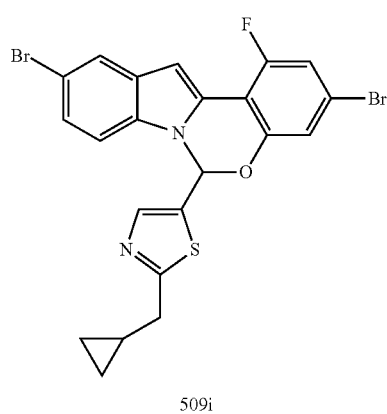

509i

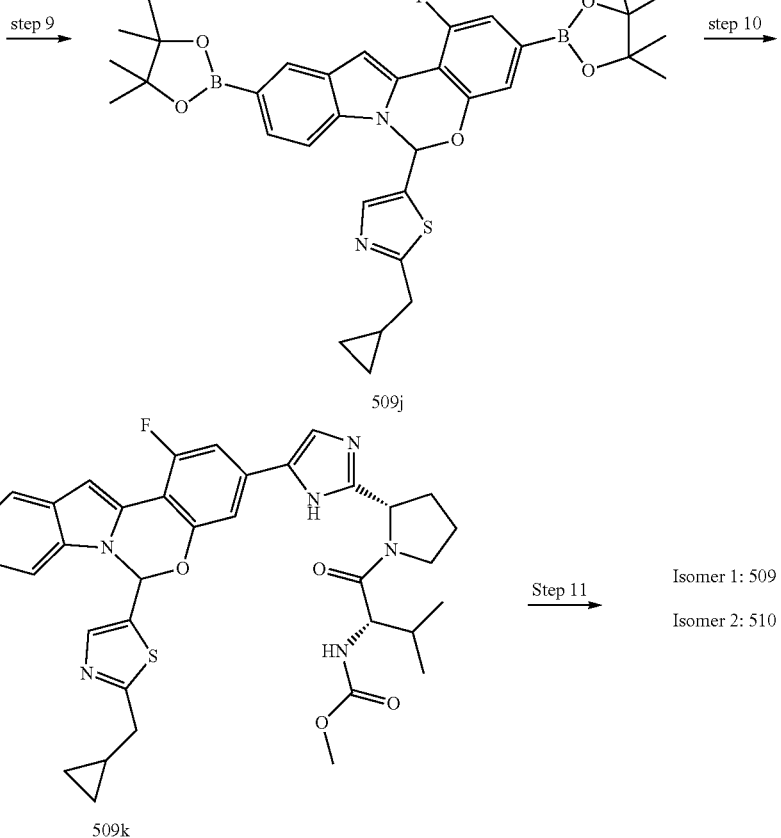

509j

509k

Isomer 1: 509
Isomer 2: 510

Step 1

The solution of 509a (10 g, 0.1 mol) in $SOCl_2$ (100 mL) was heated to 80° C. for 2 hours. After that, the reaction mixture was concentrated to remove the solvent and the crude 509b was used directly.

Step 2

To a solution of ammonia in DCM (30 mL) was added 509b (10 g, 84.74 mmol) at 0° C. The reaction mixture was allowed to stir at 20° C. for 2 h before poured into water, extracted with EtOAc, dried over $Na_2SO_4$, filtered and concentrated to provide 509c (8 g, 94.45%).

Step 3

To a solution of 509c (8 g, 84.74 mmol) in anhydrous THF (100 mL) was added Lawesson Reagent (33 g, 84.74 mmol). The mixture was allowed to stir at 18° C. for 16 hours. After that, the reaction mixture was filtered and concentrated in vacuo The residue obtained was purified using flash column chromatography on silica gel, eluting with petroleum ether:ethyl acetate (10/1~5/1) to provide 509d (5 g, 53.82%).

Step 4

To a suspension of ethyl 2-chloro-3-oxopropanoate (12.3 g, 84.74 mmol) in DMF (50 mL) was added con. $H_2SO_4$ to adjusted pH=2. To the mixture was added 509d (5 g, 43.47 mmol) and the mixture was allowed to stir at 100° C. for 20 hours. After cooling to room temperature, the mixture was poured into water and extracted with ethyl acetate. The organic layer was washed with brine and dried over anhydrous $Na_2SO_4$. After concentrated in vacuo, the resulting residue was purified using flash column chromatography on silica gel, eluting with petroleum ether:ethyl acetate (20/1~5/1) to provide 509e (6.8 g, 74.15%).

Step 5

To a mixture of 509e (6.8 g, 32.22 mmol) in THF (50 mL) was added $LiAlH_4$ (2.45 g, 64.45 mmol) in portions with stirring at 0° C. and then stirred at 30° C. for 3 hours. The mixture was cooled to 0° C. and quenched with water. After filtration and concentration in vacuo, the resulting residue was purified using flash column chromatography on silica gel, eluting with petroleum ether:ethyl acetate (10/1~3/1) to provide 509f (5.2 g, 95.48%).

Step 6

To a mixture of 509f (5.2 g, 30.76 mmol) in DCM (50 mL) was added DMP (13 g, 30.76 mmol) in portions with stirring at 0° C. and then stirred at 30° C. for 5 hours, before quenched with saturated $Na_2SO_3$ solution. The organic layer was concentrated in vacuo and the resulting residue was purified using flash column chromatography on silica gel, eluting with petroleum ether:ethyl acetate (20/1~5/1) to provide 509g (5 g, 97.31%).

Step 7

To a mixture of 509g (1.24 g, 7.46 mmol) and Core1 (1.44 g, 3.73 mmol) in anhydrous $CH_3CN$ (10 mL) was added TFA (0.3 mL). The mixture was allowed to stir at room temperature for about 15 hours. The reaction mixture became a clear solution and then solid appeared. The solid was collected by filtration and washed with $CH_3CN$ to provide 509h (1 g, 50.16%).

Step 8

To the solution of 509h (1 g, 1.86 mmol) in dry toluene (10 mL) was added DDQ (633 mg, 2.79 mmol). After refluxing for 2 hours, the solvent was removed in vacuo and diluted with EtOAc. The organic layer was washed with saturated $Na_2S_2O_3$ solution and brine, dried over $Na_2SO_4$, filtered and concentrated in vacuo. The residue obtained was washed with MeOH. The solid was collected to provide 509i (0.42 g, 42.16%).

Step 9

The solution of 509i (0.42 g, 0.786 mmol), bis(pinacolato)diboron (0.6 g, 2.4 mmol), (0.231 g, 2.4 mmol) and Pd(dppf)Cl₂ (173 mg, 0.24 mmol) in dioxane (15 mL) was allowed to stir at 100° C. for 2 hours under $N_2$ atmosphere. The reaction mixture was cooled and concentrated in vacuo, and the resulting residue was purified using flash column chromatography on silica gel, eluting with petroleum ether:ethyl acetate (5/1) to provide 509j (0.3 g, 60.73%).

Step 10

The mixture of 509j (0.3 g, 0.48 mmol), Cap5 (0.534 g, 1.43 mmol), $Na_2CO_3$ (0.152 g, 1.43 mmol) and Pd(dppf)Cl₂ (102 mg, 0.14 mmol) in THF/DMF/$H_2O$ (v/v=5/1/1, 14 mL) was allowed to stir at 80° C. for about 15 hours under $N_2$ atmosphere. After cooling to room temperature, the mixture was washed with water and extracted with ethyl acetate. The organic layer was washed with brine and dried over anhydrous $Na_2SO_4$. After concentrated in vacuo, the resulting residue was purified using preparative HPLC to provide 509k (255 mg, 55.67%).

Step 10

The compound of 509k (250 mg) was separated by SFC by using the following conditions to provide 509 (60 mg, 48%) and 510 (40 mg, 48%).

Column: Chiralcel OJ-3 150×4.6 mm I.D., 3 um
Solvent: 40% iso-propanol (0.05% DEA) in $CO_2$
Flow rate: 2.5 mL/min
Wavelength: 220 nm 509: 1H NMR (400 MHz, METHANOL-d4) δ: 7.78 (d, 2 H), 7.77 (s, 1 H), 7.61 (s, 1 H), 7.42 (m, 2 H), 7.22 (m, 2 H), 7.04 (m, 2 H), 5.03 (m, 2 H), 4.02-3.91 (m, 4 H), 3.66 (m, 2 H), 3.43 (s, 8 H), 2.55 (m, 2 H), 2.37 (s, 2 H), 2.07-1.86 (m, 8 H), 1.30 (m, 1 H), 1.03 (m, 3 H), 0.89-0.68 (m, 12 H), 0.32 (m, 2 H), 0.01 (m, 2 H). LC/MS: Anal. Calcd. For [M+H]⁺ C50H57FN10O7S: 961.11. found 961.6.

510: 1H NMR (400 MHz, MeOH-d4) δ: 7.84 (m, 2 H), 7.44 (m, 1 H), 7.35 (m, 2 H), 7.17 (m, 2 H), 7.04 (d, 2 H), 6.98 (m, 1 H), 5.15 (m, 2 H), 4.22 (m, 3 H), 4.05 (m, 3H), 3.89 (m, 6H), 3.63 (s, 10H), 3.41 (s, 2H), 2.70 (d, 4 H), 1.27 (m, 12 H), 0.47 (d, 3 H), 0.16 (d, 3 H). LC/MS: Anal. Calcd. For [M+H]⁺ C50H57FN10O7S: 961.11. found 961.8.

Example 30

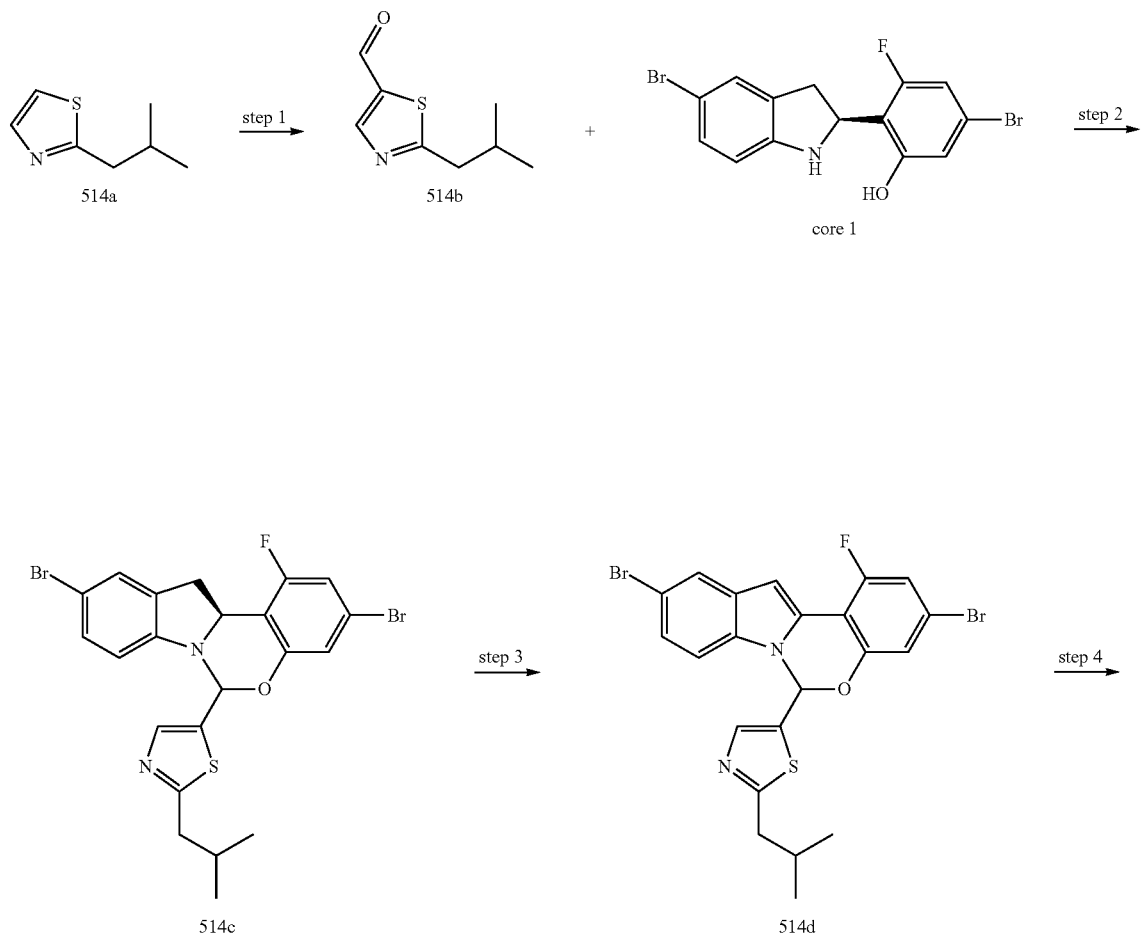

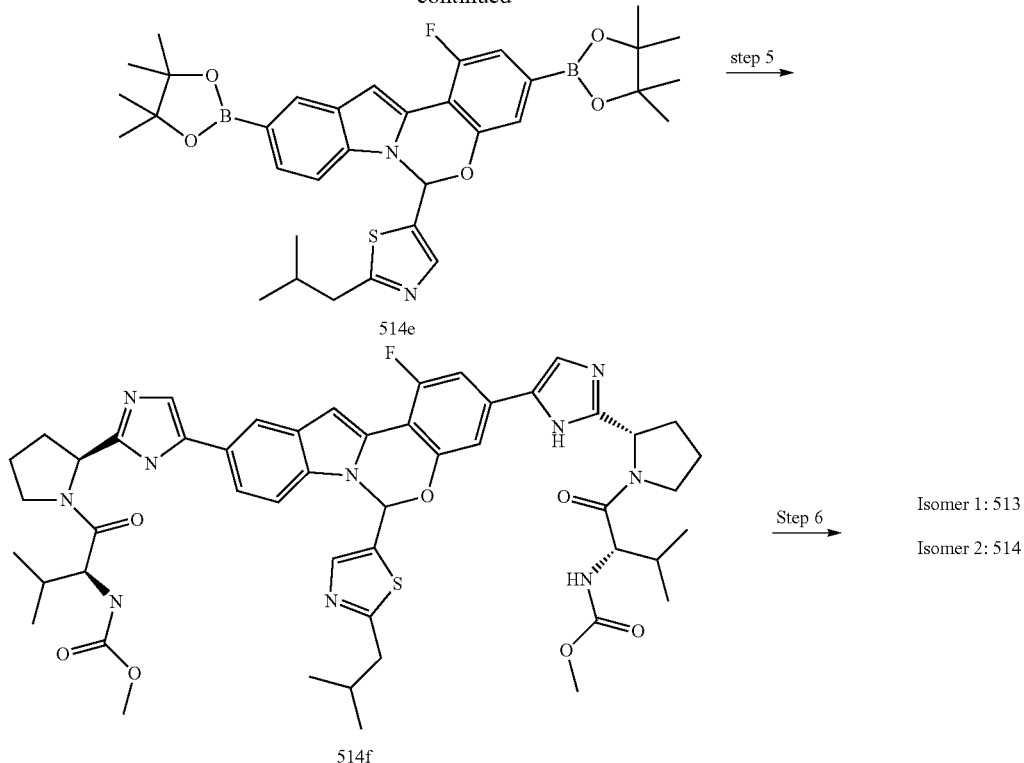

Step 1

To a solution of 514a (1 g, 7.09 mmol) in anhydrous THF (20 mL) was added LDA (4.6 mL, 9.2 mmol) at −78° C. After being stirred for 30 min, to the mixture was added DMF (0.78 g, 10.6 mmol). The mixture was allowed to stir at −78° C. for 2 hours under $N_2$ before quenched by $NH_4Cl$ solution. The organic layer was separated and washed with water, and dried over anhydrous $Na_2SO_4$. After filtration and concentration in vacuo, the resulting residue was purified using flash column chromatography on silica gel, eluting with petroleum ether:ethyl acetate (0~10/1) to provide 514b (1 g, 83.4%).

Step 2

To a mixture of 514b (1 g, 5.91 mmol) and Core1 (1.47 g, 3.84 mmol) in anhydrous $CH_3CN$ (20 mL) was added TFA (0.6 mL). The mixture was allowed to stir at room temperature for 12 hours. The reaction mixture became a clear solution and then solid appeared. The solid was collected by filtration and washed with MeOH to provide 514c (1.5 g, 47.3%).

Step 3

The solution of 514c (1.5 g, 2.78 mmol) in dry toluene (20 mL) was added DDQ (0.59 g, 4.17 mmol). After refluxing for 2 hours, the solvent was removed in vacuo and re-dissolved with EtOAc. The organic layer was washed with saturated $Na_2S_2O_3$ solution and brine, dried over $Na_2SO_4$. After filtration and concentration in vacuo, the solid was washed with MeOH and collected to provide 514d (1.2 g, 80.5%).

Step 4

A suspension of 514d (1.2 g, 2.23 mmol), bis pinacol borate (1.42 g, 5.6 mmol), KOAc (1.09 g, 11.15 mmol) and $Pd(dppf)Cl_2$ (160 mg, 0.22 mmol) in dioxane (30 mL) was allowed to stir at 100° C. for 2 hours under $N_2$ atmosphere. The reaction mixture was cooled and concentrated in vacuo. The residue obtained was purified using flash column chromatography on silica gel, eluting with petroleum ether:ethyl acetate (20/1~5/1) to provide 514e (1.3 g, 92.8%).

Step 5

A suspension of 514e (1.3 g, 2.06 mmol), Cap5 (1.68 g, 4.54 mmol), $Na_2CO_3$ (1.09 g, 10.3 mmol) and $Pd(dppf)Cl_2$ (146 mg, 0.2 mmol) in $THF/H_2O/DMF$ (v/v=5/2/1, 32 mL) was allowed to stir at 80° C. for about 15 hours under $N_2$ atmosphere. The resulting reaction was then washed with water and extracted with ethyl acetate, washed with brine and dried over anhydrous $Na_2SO_4$. After filtration, the filtrate was concentrated in vacuo, and the resulting residue was dissolved in DMF and purified using preparative HPLC to provide 514f (792 mg, 40%).

Step 6

513 (70 mg, 35%) and 514 (80 mg, 40%) was separated from compound 514f (200 mg) by SFC by using the following conditions:

Injection Volume: 5;
Co-Solvent: 50% IPA (0.05% DEA) in $CO_2$;
Column: AS-H;
Flow rate: 2.5 mL/min
Wavelength: 340 nm 513: $^1H$ NMR (MeOD) δ: 7.95 (s, 1 H), 7.80 (s, 1 H), 7.70 (s, 1 H), 7.38-7.12 (m, 6 H), 6.92 (s, 1 H), 5.18-5.10 (m, 2 H), 4.22-4.08 (m, 2H), 3.98-3.67 (m, 4 H), 3.63 (s, 6 H), 2.67-2.28 (m, 2 H), 2.04-1.99 (m, 5 H), 1.29-1.23 (m, 7 H), 0.98-0.79 (m, 8 H). LC/MS: Anal. Calcd. For $[M+H]^+$ C50H59FN10O7S: 963.13. found 963.6.

514: $^1H$ NMR (MeOD) δ: 7.72 (s, 2 H), 7.44 (s, 1 H), 7.32-7.19 (m, 5 H), 7.00-6.85 (m, 2 H), 5.19-5.12 (m, 2 H), 4.23-4.22 (m, 2 H), 3.99-3.58 (m, 4 H), 3.54 (s, 8 H), 2.65-2.64 (m, 3 H), 2.32-1.70 (m, 5 H), 1.28-1.10 (m, 6 H), 0.96-0.78 (m, 15 H). LC/MS: Anal. Calcd. For $[M+H]^+$ C50H59FN10O7S: 963.13. found 963.8.

The following compounds of the present invention were made using the methods described in the Example above and substituting the appropriate reactants and/or reagents.

| ID | Structures | Isomer info | Observed [M + H]+ |
|---|---|---|---|
| 491 | 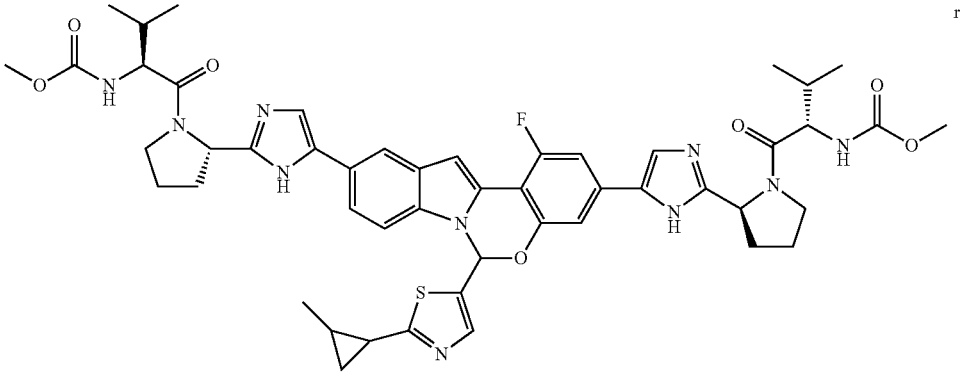 | racemic | 961.84 |
| 492 499 500 | 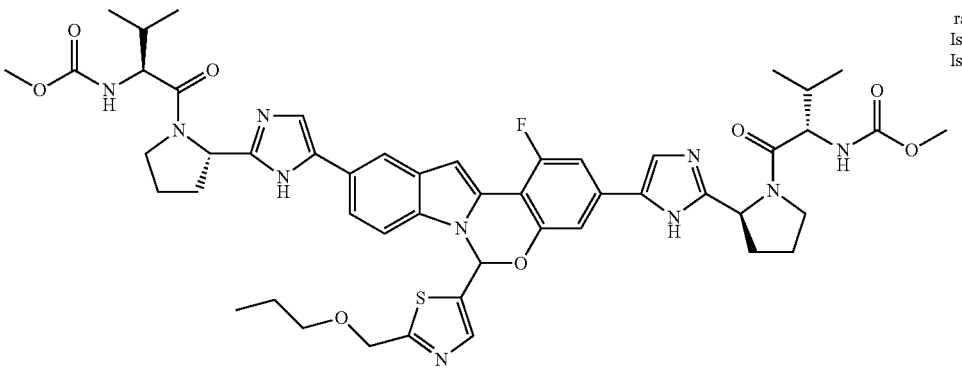 | racemic Isomer 1 Isomer 2 | 979.31 979.00 979.00 |
| 503 | 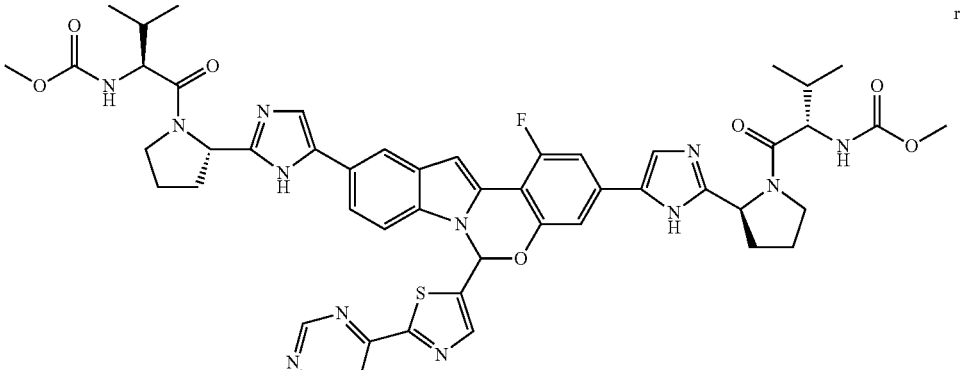 | racemic | 985.57 |
| 507 508 | 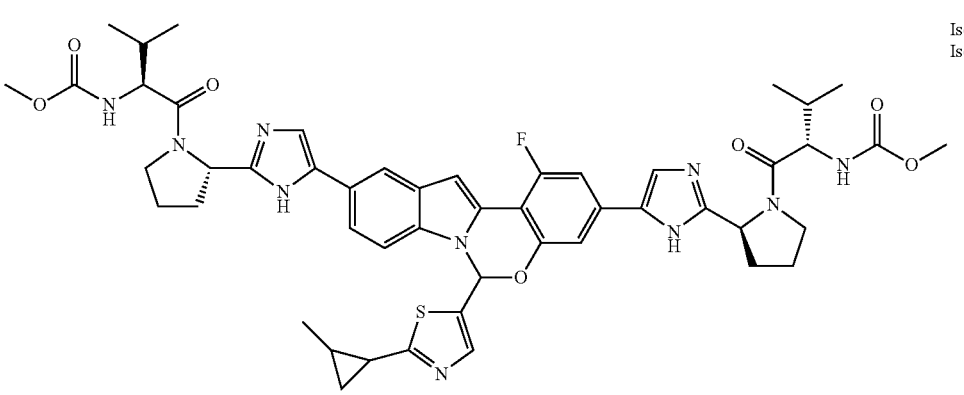 | Isomer 1 Isomer 2 | 961.00 961.00 |

Example 31

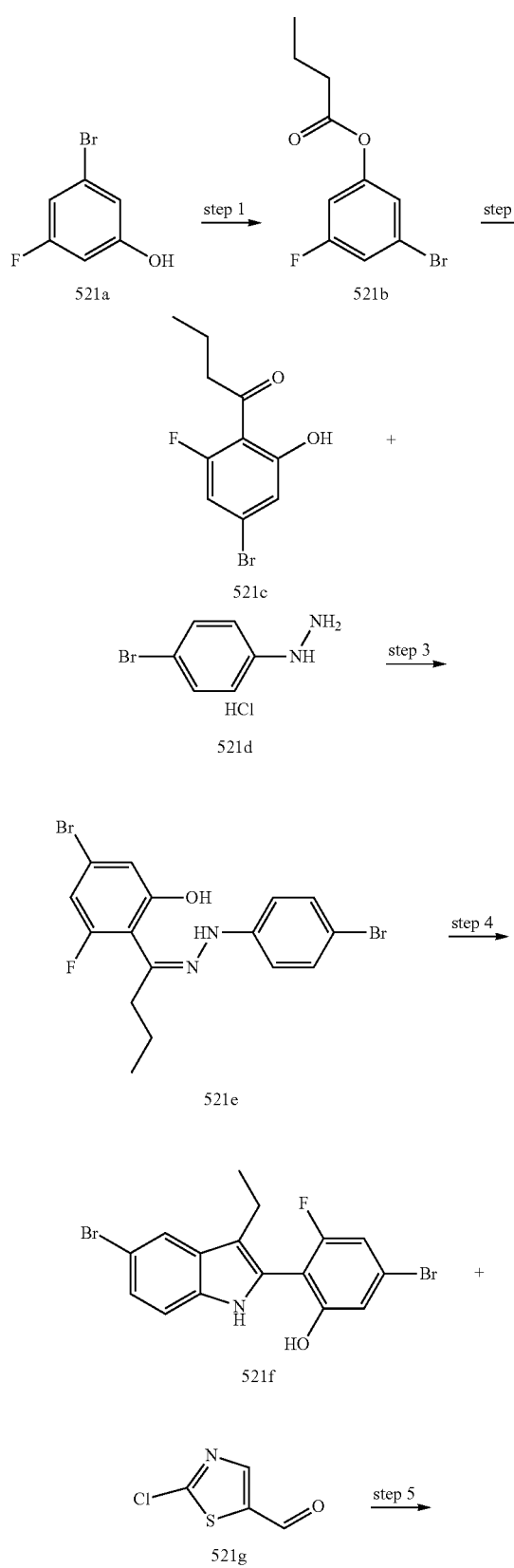

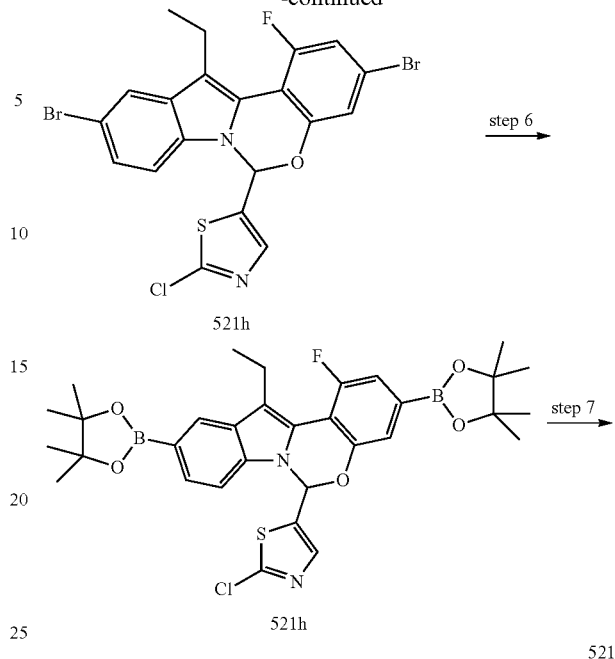

Step 1

To a solution of compound 521a (15.8 g, 0.083 mol), Et$_3$N (12.1 g, 0.12 mol) in DCM (125 mL) was added butyryl chloride (10.6 g, 0.1 mol) at 0° C. The mixture was allowed to stir for 1 hour. The crude product was washed with 1N HCl, NaHCO$_3$, and brine. The organics were separated, dried over Na$_2$SO$_4$, filtered, and the filtrate was concentrated in vacuo, evaporated in vacuo to provide compound 521b (18.5 g, 85.6% yield). LC/MS: Anal. Calcd. For [M+H]$^+$ C10H10BrFO2: 259.98. found 262.1.

Step 2

The compound 521b was heated at 80-100° C., then AlCl$_3$ (28 g, 0.21 mol) was added, the temperature was heated to 140° C. for 1 hour. The mixture was poured into ice water and extracted with DCM, the crude product was washed with NaHCO$_3$ and brine, dried over Na$_2$SO$_4$, evaporated in vacuo to provide compound 521c (8.56 g, 46.3% yield). LC/MS: Anal. Calcd. For [M+H]$^+$ C10H10BrFO2: 259.98. found 262.1

Step 3

To a solution of compound 521c (8.56 g, 0.033 mol), 521d (8.85 g, 0.04 mol) in MeOH (90 mL) was added AcOH (9 mL), the mixture was allowed to stir at 60-64° C. for 15 hours. The solvent was removed in vacuo to provide crude compound 521e (14 g, 100% yield).

LC/MS: Anal. Calcd. For [M+H]$^+$ C16H15Br2FN2O: 427.95. found 431.1.

Step 4

Compound 521e (16 g, 0.037 mol) in CH$_3$SO$_3$H (80 mL) was stirring at 85° C. for 2 hours. The mixture was poured into ice water, extracted with MTBE. The organic layer was separated and washed with NaHCO$_3$ and NaCl solution, dried over anhydrous Na$_2$SO$_4$, and concentrated under reduced pressure. The residue obtained was purified using flash column chromatography on silica gel, eluting with petroleum ether:ethyl acetate (3:1) to provide compound 521f (9.5 g, 59.7% yield). LC/MS: Anal. Calcd. For [M+H]$^+$ C16H12Br2FNO 412.93. found 414.1.

Step 5

Compound 521f (1 g, 2.42 mmol), compound 521g (0.402 g, 2.66 mmol) and TosCl (139 mg, 0.73 mmol) in xylenes (20 mL) was allowed to stir at 170° C. for 16 hours. After that, the solvent was removed in vacuo under vacuum, and the resulting residue was purified using flash column chromatography on silica gel, eluting with petroleum ether:ethyl acetate (3:1) to provide compound 521h (170 mg, 12.8% yield). LC/MS: Anal. Calcd. For [M+H]$^+$ C23H17Br2FN2OS: 547.94. found 549.2.

Step 6

To a solution of compound 521h (170 mg, 0.31 mmol) in 1,4-dioxane was added bis pinacol borate (165 mg, 0.65 mmol) and Pd(dppf)Cl$_2$ (22 mg, 0.03 mmol) and KOAc (182 mg, 1.86 mmol). The reaction mixture was allowed to stir under N$_2$ and heated to 110° C. for about 15 hours. After that, the solvent was removed in vacuo under vacuum, and the resulting residue was purified using flash column chromatography on silica gel, eluting with petroleum ether:ethyl acetate (2:1) to provide compound 521i (170 mg, 85.4% yield). LC/MS: Anal. Calcd. For [M+H]$^+$ C35H41B2FN2O5S: 642.30. found 643.1.

Step 7

A suspension of compound 521i (210 mg, 0.327 mmol), Cap5 (256 mg, 0.687 mmol), Pd(dppf)Cl$_2$ (24 mg, 0.033 mmol), Na$_2$CO$_3$ (208 mg, 1.96 mmol) and in THF/H$_2$O (5:1, 20 mL) was refluxed at 90° C. for about 15 hours under N$_2$ atmosphere. The resulting reaction was then filtered, the filtrate was washed with water and extracted with ethyl acetate, washed with brine and dried over anhydrous sodium sulfate. After concentration in vacuo, the resulting residue was purified using flash column chromatography on silica gel, eluting with ethyl acetate to provide compound 521 (286 mg, 89.9% yield). $^1$H NMR (400 MHz, METHANOL-d4) δ: 8.08-8.13 (m, 1 H), 7.88-7.98 (m, 2 H), 7.78-7.84 (m, 1 H), 7.55-7.64 (m, 2 H), 7.40-7.48 (m, 1 H), 7.35-7.39 (m, 1 H), 7.13-7.20 (m, 1 H), 5.17-5.29 (m, 2 H), 4.23 (m, 2 H), 4.04-4.16 (m, 2 H), 3.82-3.91 (m, 2 H), 3.65 (s, 6 H), 3.09-3.18 (m, 2 H), 2.50-2.61 (m, 2 H), 2.25-2.32 (m, 2 H), 2.14-2.23 (m, 4 H), 2.01-2.10 (m, 2 H), 1.27-1.45 (m, 4 H), 1.04-1.11 (m, 2 H), 0.75-1.03 (m, 14 H). LC/MS: Anal. Calcd. For [M+H]$^+$ C51H59FN10O7S: 975.16. found 975.6.

The following compounds of the present invention were made using the methods described in the Example above and substituting the appropriate reactants and/or reagents.

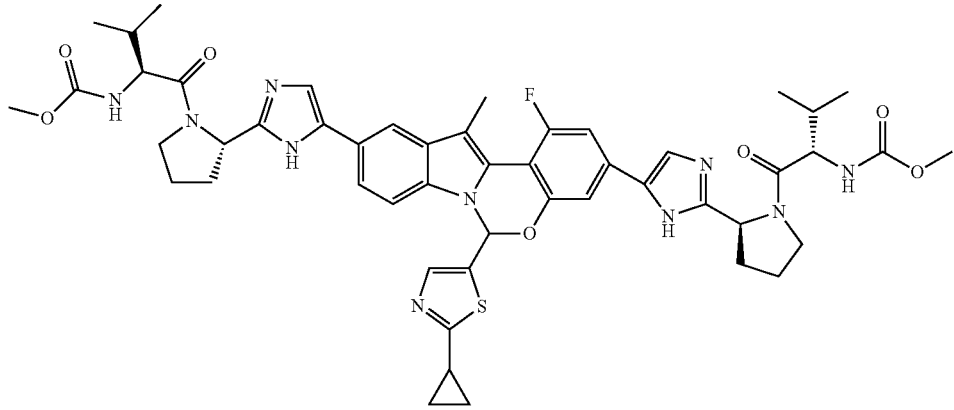

| ID | Structures | Isomer info | Observed [M + H]$^+$ |
|---|---|---|---|
| 494 | | racemic | 962.3 |
| 495 | | Isomer 1 | 962.3 |
| 496 | | Isomer 2 | 962.2 |

Example 32

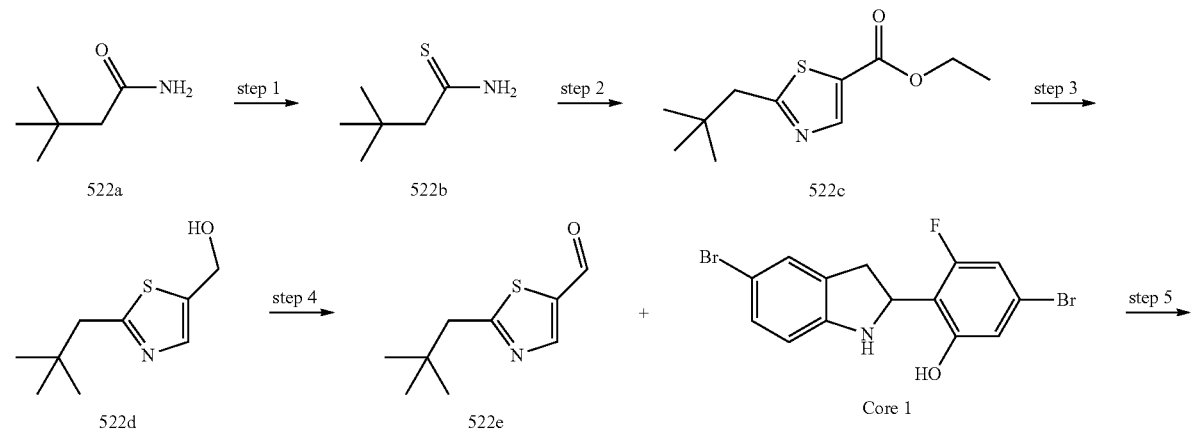

-continued

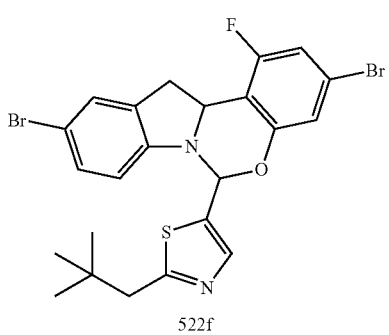

522f step 6

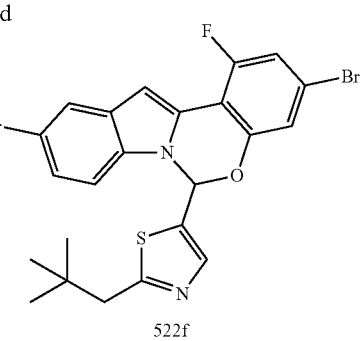

522f step 7

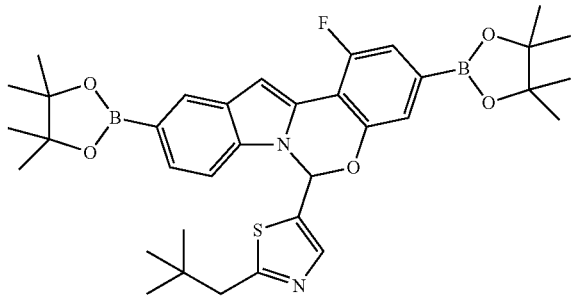

522h step 8

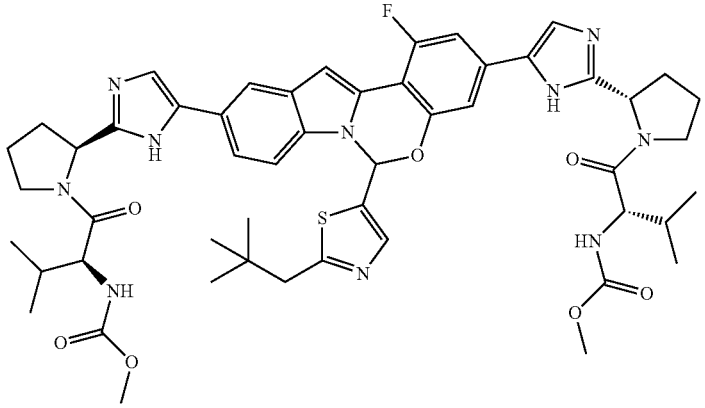

522i step 9

Isomer 1: 522
Isomer 2: 523

Step 1

To a mixture of 522a (5.4 g, 47 mmol) in toluene (100 mL) was added Lawesson Reagent (19 g, 47 mmol). The mixture was allowed to stir at room temperature for about 15 hours. The reaction mixture was concentrated in vacuo, and the resulting residue was purified using flash column chromatography on silica gel, eluting with petroleum ether:ethyl acetate (10/1~1/1) to provide 522b (10.8 g, 96%).

Step 2

To a suspension of ethyl 2-chloro-3-oxopropanoate (11.8 g, 63 mmol) in DMF (150 mL) was added con. $H_2SO_4$ until the solution was ~pH 2. To the mixture was added 522b (5.5 g, 42 mmol) and the mixture was allowed to stir at 100° C. for 20 hours. After cooling to room temperature, the mixture was poured into water and extracted with ethyl acetate. The organic layer was washed with brine and dried over anhydrous $Na_2SO_4$. After concentrated in vacuo, the resulting residue was purified using flash column chromatography on silica gel, eluting with petroleum ether:ethyl acetate (20/1~5/1) to provide 522c (4.3 g, 45%).

Step 3

To a mixture of 522c (4.3 g, 19 mmol) in THF (100 mL) was added $LiAlH_4$ (1.1 g, 28 mmol) in portions with stirring at 0° C. and then stirred at 30° C. for 3 hours. The mixture was cooled to 0° C. and quenched with water. After filtration and concentration in vacuo, the resulting residue was purified using flash column chromatography on silica gel, eluting with petroleum ether:ethyl acetate (10/1~3/1) to provide 522d (3.4 g, 97%).

Step 4

To a mixture of 522d (3.4 g, 18 mmol) in DCM (70 mL) was added DMP (7.6 g, 20 mmol) in portions with stirring at 0° C. and then stirred at 30° C. for 5 hours, before quenched with saturated $Na_2SO_3$ solution. The organic layer was concentrated in vacuo and the resulting residue was purified using flash column chromatography on silica gel, eluting with petroleum ether:ethyl acetate (20/1~5/1) to provide 522e (3.1 g, 90%).

Step 5

To a mixture of 522e (3 g, 16.4 mmol) and Core1 (5.8 g, 14.9 mmol) in anhydrous $CH_3CN$ (60 mL) was added TFA (5 drops). The mixture was allowed to stir at room temperature for about 15 hours. The reaction mixture became a clear solution and then a solid precipitate appeared. The solid was collected by filtration and washed with CH₃CN to provide 522f (5.2 g, 58%).
Step 6
To the solution of 522f (5.2 g, 9.4 mmol) in dry toluene (80 mL) was added DDQ (3.2 g, 14.1 mmol). After refluxing for 2 hours, the solvent was removed in vacuo and diluted with EtOAc. The organic layer was washed with saturated $Na_2S_2O_3$ solution and brine, dried over $Na_2SO_4$, filtered and concentrated in vacuo. The residue obtained was washed with MeOH (20 mL). The solid was collected to provide 522g (3.5 g, 68%).
Step 7
The solution of 522g (3 g, 5.4 mmol), bis(pinacolato) diboron (3.5 g, 13.6 mmol), KOAc (2.6 g, 27 mmol) and Pd(dppf)Cl₂ (349 mg, 0.54 mmol) in dioxane (50 mL) was allowed to stir at 100° C. for 2 hours under N₂ atmosphere. The reaction mixture was cooled and concentrated in vacuo, and the resulting residue was purified using flash column chromatography on silica gel, eluting with petroleum ether: ethyl acetate (20/1~5/1) to provide 522h (2.4 g, 68%).
Step 8
The mixture of 522h (2.4 g, 3.7 mmol), Cap 5 (3.5 g, 9.3 mmol), Na₂CO₃ (1.9 g, 18.5 mmol) and Pd(dppf)Cl₂ (270 mg, 0.37 mmol) in THF/H₂O (v/v=5/1, 50 mL) was allowed to stir at 80° C. for about 15 hours under N₂ atmosphere. After cooling to room temperature, the mixture was washed with water and extracted with ethyl acetate. The organic layer was washed with brine and dried over anhydrous Na₂SO₄. After concentrated in vacuo, the resulting residue was purified using flash column chromatography on silica gel, eluting with petroleum ether:ethyl acetate (5/1~1/2) to provide 522i (1.8 g, 50% yield).
Step 9
The compound of 522i (1.8 g) was separated by SFC by using the following conditions to provide 522 (0.64 g, 71%) and 523 (0.6 g, 67%).
Column: Chiralcel OJ-H 250×4.6 mm I.D., 5 um
Mobile phase: 40% ethanol (0.05% DEA) in CO₂
Flow rate: 2.5 mL/min
Wavelength: 220 nm
522: ¹H NMR (MeOD) δ: 8.09 (s, 1H), 8.06 (s, 1H), 7.99 (s, 1H), 7.78 (s, 1H), 7.67-7.58 (m, 2H), 7.46 (d, J=11.0 Hz, 1H), 7.41 (s, 2H), 7.25 (br. s., 1H), 5.22 (m, 2H), 4.21 (t, J=7.4 Hz, 2H), 4.08 (br. s., 2H), 3.89 (br. s., 2H), 3.70-3.56 (m, 6H), 2.81 (s, 2H), 2.55 (br. s., 2H), 2.27 (br. s., 2H), 2.17 (d, J=3.9 Hz, 4H), 2.09-2.02 (m, 2H), 1.01-0.82 (m, 21H). LC/MS: Anal. Calcd. For [M+H]⁺ C51H61FN10O7S: 977.16. found 977.8.

523: ¹H NMR (MeOD) δ: 8.07 (s, 1H), 8.03 (s, 1H), 7.95 (s, 1H), 7.72 (s, 1H), 7.62-7.54 (m, 2H), 7.42 (m, 1H), 7.40 (s, 2H), 7.24 (m, 1H), 5.13 (m, 2H), 4.20 (m, 2H), 4.01 (m, 2H), 3.82 (br. s., 2H), 3.72-3.54 (m, 6H), 2.84 (s, 2H), 2.50 (m, 2H), 2.20 (m, 2H), 2.10 (m, 4H), 2.02 (m, 2H), 0.98-0.80 (m, 21H). LC/MS: Anal. Calcd. For [M+H]⁺ C51H61FN10O7S: 977.16. found 977.8.

Example 33

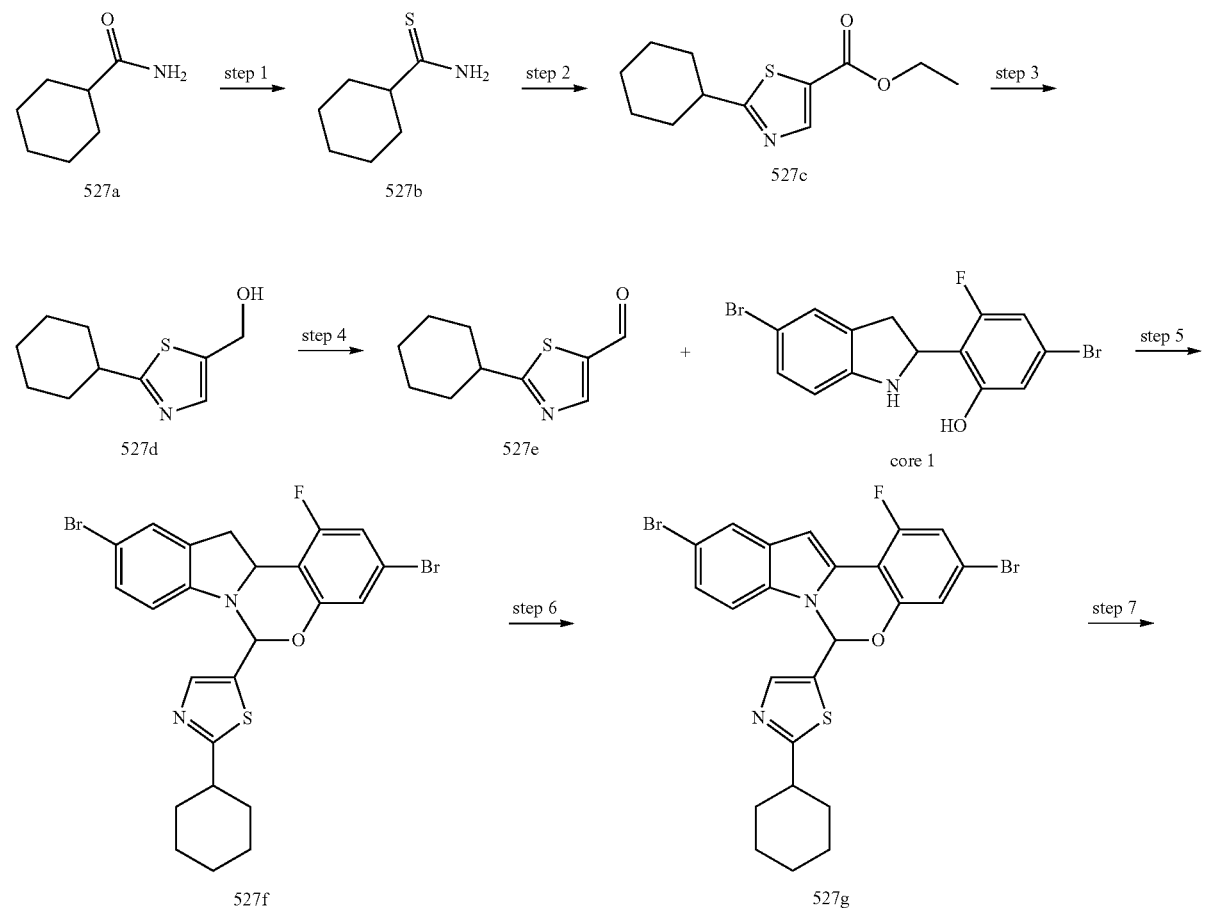

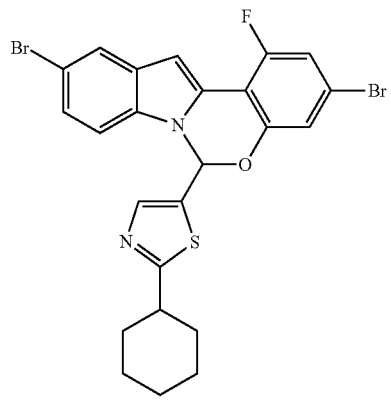

527h

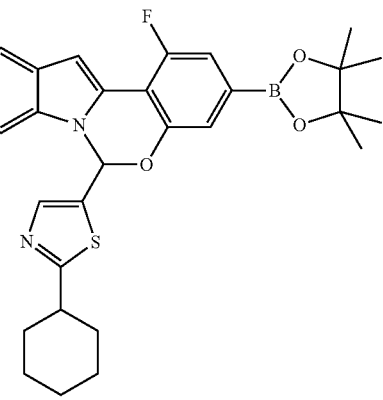

527i

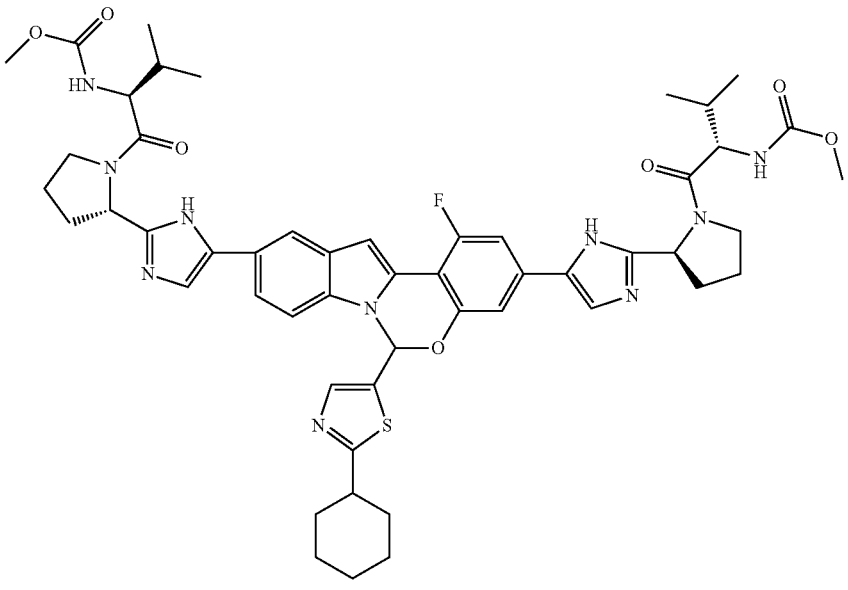

527

Step 1

To a mixture of 527a (7 g, 0.55 mol) in toluene (100 mL) was added Lawesson Reagent (22.3 g, 55 mmol). The mixture was allowed to stir at room temperature for about 15 hours. The reaction mixture was concentrated in vacuo, and the resulting residue was purified using flash column chromatography on silica gel, eluting with petroleum ether:ethyl acetate (15/1~5/1) to provide 527b (8 g, 97%).

Step 2

To a suspension of ethyl 2-chloro-3-oxopropanoate (15.8 g, 84 mmol) in DMF (500 mL) was added con. $H_2SO_4$ to adjusted pH=2. To the mixture was added 527b (8 g, 56 mmol) and the mixture was allowed to stir at 100° C. for 20 hours. After cooling to room temperature, the mixture was poured into water and extracted with ethyl acetate. The organic layer was washed with brine and dried over anhydrous $Na_2SO_4$. After concentrated in vacuo, the resulting residue was purified using flash column chromatography on silica gel, eluting with petroleum ether:ethyl acetate (20/1~5/1) to provide 527c (7 g, 52%).

Step 3

To a mixture of 527c (7.15 g, 30 mmol) in THF (100 mL) was added $LiAlH_4$ (3.8 g, 30 mmol) in portions with stirring at 0° C. and then stirred at 30° C. for 3 hours. The mixture was cooled to 0° C. and quenched with water. After filtration and concentration in vacuo, the resulting residue was purified using flash column chromatography on silica gel, eluting with petroleum ether:ethyl acetate (10/1~3/1) to provide 527d (4 g, 68%).

Step 4

To a mixture of 527d (4 g, 16.9 mmol) in DCM (70 mL) was added DMP (7.0 g, 18.5 mmol) in portions with stirring at 0° C. and then stirred at 30° C. for 5 hours, before quenched with saturated $Na_2SO_3$ solution. The organic layer was concentrated in vacuo and the resulting residue was purified using flash column chromatography on silica gel, eluting with petroleum ether:ethyl acetate (20/1~5/1) to provide 527e (3.5 g, 92%).

Step 5

To a mixture of 527e (1.82 g, 7.8 mmol) and Core1 (2 g, 5.1 mmol) in anhydrous $CH_3CN$ (15 mL) was added TFA (0.2 mL). The mixture was allowed to stir at room temperature for about 15 hours. The reaction mixture became a clear solution and then solid appeared. The solid was collected by filtration and washed with $CH_3CN$ to provide 527f (1.5 g, 52%).

Step 6
To the solution of 527f (1 g, 1.8 mmol) in dry toluene (15 mL) was added DDQ (0.6 g, 2.6 mmol). After refluxing for 2 hours, the solvent was removed in vacuo and diluted with EtOAc. The organic layer was washed with saturated $Na_2S_2O_3$ solution and brine, dried over $Na_2SO_4$, filtered and concentrated in vacuo The residue obtained was washed with MeOH (20 mL). The solid was collected to provide 527g (760 mg, 76%).

Step 7
The compound of 527g (760 mg) was separated by SFC by using the following conditions to provide 527h (300 mg, 39%).
Column: Chiralpak AS-H 250×4.6 mm I.D., 5 um
Mobile phase: methanol (0.05% DEA) in CO2 from 5% to 40%
Flow rate: 2.35 mL/min
Wavelength: 220 nm Step 8
The solution of 527h (400 mg, 0.7 mmol), bis(pinacolato) diboron (397 mg, 1.57 mmol), KOAc (350 mg, 3.56 mmol) and $Pd(dppf)Cl_2$ (52 mg, 0.07 mmol) in dioxane (20 mL) was allowed to stir at 100° C. for 2 hours under $N_2$ atmosphere. The reaction mixture was cooled and concentrated in vacuo, and the resulting residue was purified using flash column chromatography on silica gel, eluting with petroleum ether:ethyl acetate (20/1~5/1) to provide 527i (350 mg, 75%).

Step 9
The mixture of 527i (350 mg, 0.53 mmol), Cap 5 (437 mg, 1.17 mmol), $Na_2CO_3$ (282 g, 2.67 mmol) and $Pd(dppf)Cl_2$ (39 mg, 0.053 mmol) in THF/$H_2O$ (v/v=5/1, 24 mL) was allowed to stir at 80° C. for about 15 hours under $N_2$ atmosphere. After cooling to room temperature, the mixture was washed with water and extracted with ethyl acetate. The organic layer was washed with brine and dried over anhydrous sodium sulfate. After concentrated in vacuo, the resulting residue was purified using preparative HPLC to provide compound 527 (60 mg, 11%).

$^1$H NMR (400 MHz, METHANOL-$d_4$): 8.12-7.94 (m, 3H), 7.83-7.76 (m, 1H), 7.68-7.57 (m, 2H), 7.46 (d, J=10.6 Hz, 1H), 7.42-7.31 (m, 2H), 7.17 (br. s., 1H), 5.23 (m, 2H), 4.22 (t, J=6.7 Hz, 2H), 4.14-4.01 (m, 2H), 3.99-3.87 (m, 2H), 3.83-3.49 (m, 6H), 2.90 (br. s., 1H), 2.55 (br. s., 2H), 2.41-2.01 (m, 8H), 1.93 (br. s., 2H), 1.81-1.63 (m, 3H), 1.44-1.10 (m, 6H), 1.06-0.75 (m, 11H). LC/MS: Anal. Calcd. For $[M+H]^+$ C52H61FN10O7S: 989.17. found 989.6.

The following compounds of the present invention were made using the methods described in the Example above and substituting the appropriate reactants and/or reagents.

| ID | Structures | Isomer info | Observed $[M + H]^+$ |
|---|---|---|---|
| 528 | 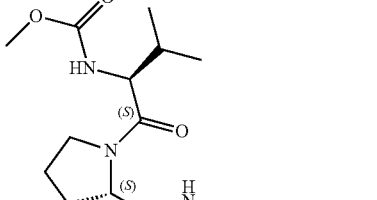 | Isomer 2 | 989.6 |

Example 34

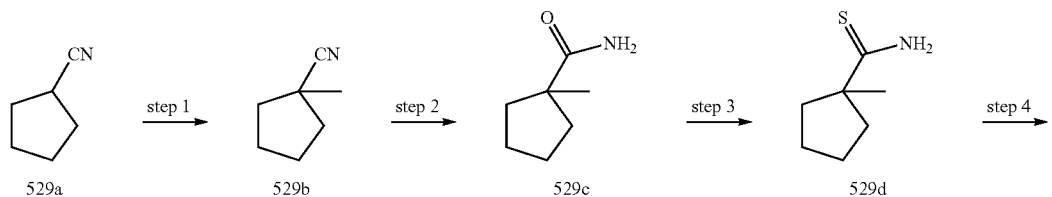

-continued
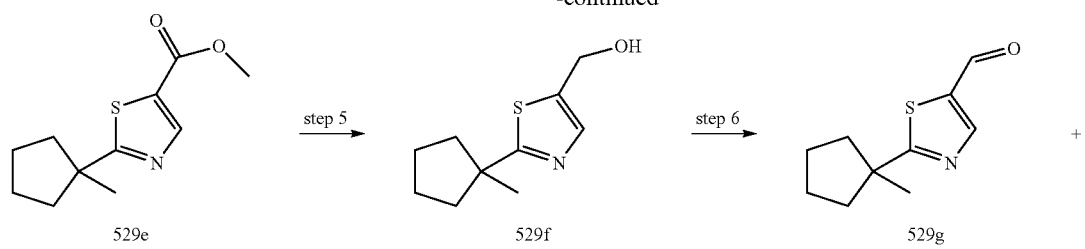
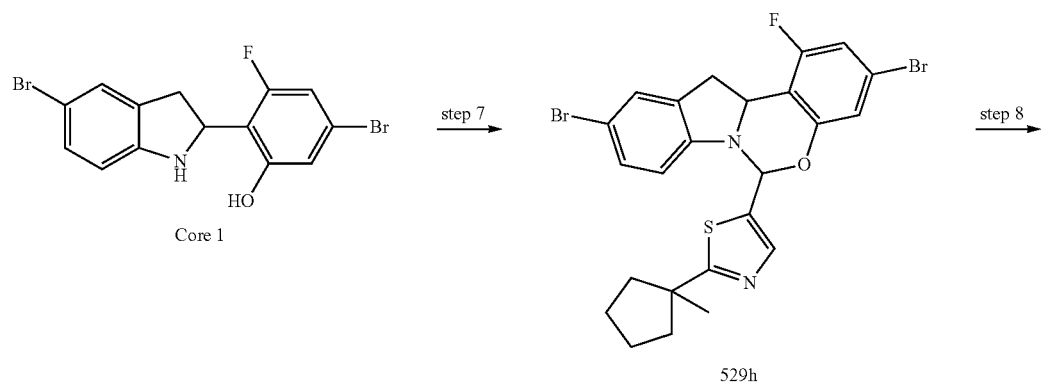
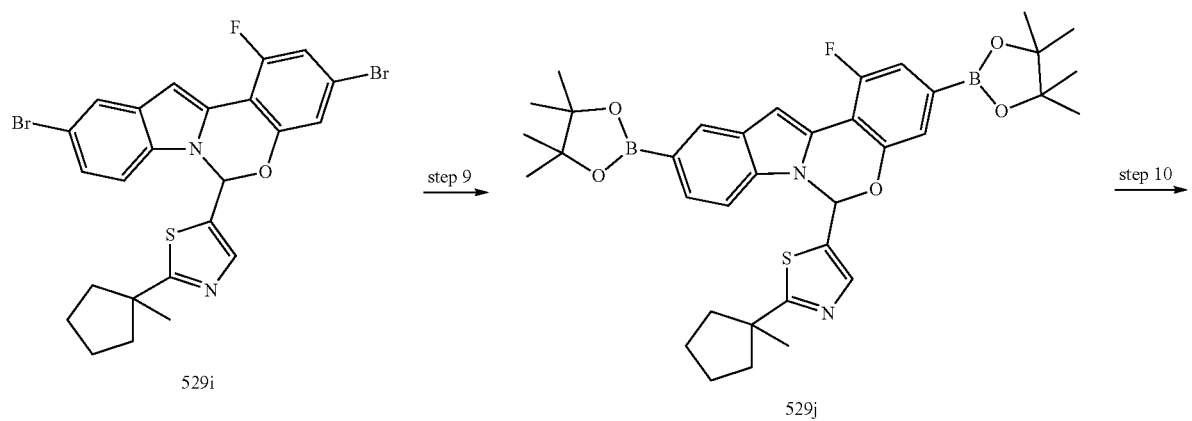
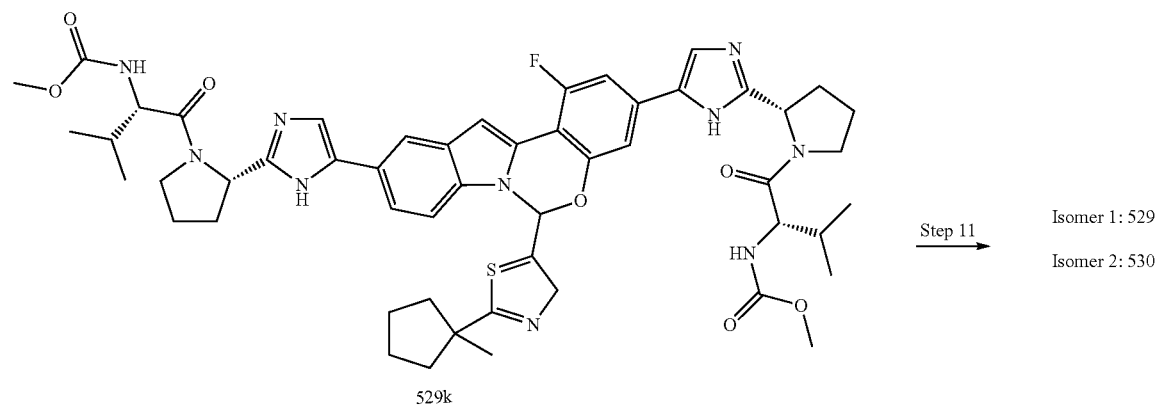
Step 11 → Isomer 1: 529
Isomer 2: 530

Step 1

To a solution of the 529a (4.13 g, 43.5 mmol) in THF (100 mL) was added LDA (1M, 87 ml, 87 mmol) dropwise at −78° C. The mixture was allowed to stir at −78° C. for 1 hour, and then to the mixture was added MeI (12.3 g, 87 mmol). The mixture was allowed to stir at −78° C. for 1 hour before quenched with $NH_4Cl$ solution, extracted with ethyl acetate. The organic layer was washed with water and dried over $Na_2SO_4$. After concentrated in vacuo, the resulting residue was purified using flash column chromatography on silica gel, eluting with petroleum ether:ethyl acetate (20/1~10/1) to provide 529b (3.1 g, 65.4%).

Step 2

To a solution of the 529b (4.74 g, 43.42 mmol) in MeOH (110 mL) was added DMSO (4.4 mL), NaOH (1N, 52 mL) and $H_2O_2$ (30%, 17.6 mL) at room temperature. The mixture was allowed to stir at 50° C. for 3 hours. After cooling to room temperature, the mixture was partitioned between DCM and water. The organic layer was washed with brine and dried over $Na_2SO_4$. After concentrated in vacuo, the resulting residue was purified using flash column chromatography on silica gel, eluting with petroleum ether:ethyl acetate (10/1~2/1) to provide 529c (3 g, 54%).

Step 3

To a mixture of 529c (3 g, 23.6 mmol) in THF (80 mL) was added Lawesson Reagent (11.5 g, 28 mmol). The mixture was allowed to stir at room temperature for about 15 hours. The reaction mixture was concentrated in vacuo, and the resulting residue was purified using flash column chromatography on silica gel, eluting with petroleum ether:ethyl acetate (10/1~2/1) to provide 529d (1.7 g, 50.3%).

Step 4

To a suspension of ethyl 2-chloro-3-oxopropanoate (6.72 g, 35.6 mmol) in DMF (40 mL) was added con. $H_2SO_4$ to adjusted pH=2. To the mixture was added 529d (1.7 g, 11.87 mmol) and the mixture was allowed to stir at 100° C. for 20 hours. After cooling to room temperature, the mixture was poured into water and extracted with ethyl acetate. The organic layer was washed with brine and dried over anhydrous $Na_2SO_4$. After concentrated in vacuo, the resulting residue was purified using flash column chromatography on silica gel, eluting with petroleum ether:ethyl acetate (20/1~5/1) to provide 529e (400 mg, 14%).

Step 5

To a mixture of 529e (400 mg, 1.67 mmol) in THF (5 mL) was added $LiAlH_4$ (127 mg, 3.34 mmol) in portions with stirring at 0° C. and then stirred at 30° C. for 3 hours. The mixture was cooled to 0° C. and quenched with water. After filtration and concentration in vacuo, the resulting residue was purified using flash column chromatography on silica gel, eluting with petroleum ether:ethyl acetate (10/1~3/1) to provide 529f (330 mg, 91%).

Step 6

To a mixture of 529f (300 mg, 1.52 mmol) in DCM (5 mL) was added DMP (1.27 g, 3 mmol) in portions with stirring at 0° C. and then stirred at 30° C. for 5 hours, before quenched with saturated $Na_2SO_3$ solution. The organic layer was concentrated in vacuo and the resulting residue was purified using flash column chromatography on silica gel, eluting with petroleum ether:ethyl acetate (20/1~5/1) to provide 529g (250 mg, 84%).

Step 7

To a mixture of 529g (125 mg, 0.638 mmol) and Core1 (0.2 g, 0.5 mmol) in anhydrous $CH_3CN$ (3 mL) was added TFA (2 drops). The mixture was allowed to stir at room temperature for about 15 hours. The reaction mixture became a clear solution and then solid appeared. The solid was collected by filtration and washed with $CH_3CN$ to provide 529h (0.2 g, 69%).

Step 8

To the solution of 529h (0.2 g, 0.36 mmol) in dry toluene (5 mL) was added DDQ (0.11 g, 0.5 mmol). After refluxing for 2 hours, the solvent was removed in vacuo and diluted with EtOAc. The organic layer was washed with saturated $Na_2S_2O_3$ solution and brine, dried over $Na_2SO_4$, filtered and concentrated in vacuo. The residue obtained was washed with MeOH and dried in vacuo to provide 529i (0.15 g, 74%).

Step 9

The solution of 529i (0.15 g, 0.27 mmol), bis(pinacolato)diboron (0.17 g, 0.68 mmol), KOAc (0.13 g, 1.4 mmol) and $Pd(dppf)Cl_2$ (30 mg, 0.054 mmol) in dioxane (3 mL) was allowed to stir at 100° C. for 2 hours under $N_2$ atmosphere. The reaction mixture was cooled and concentrated in vacuo, and the resulting residue was purified using flash column chromatography on silica gel, eluting with petroleum ether:ethyl acetate (5/1) to provide 529j (0.12 g, 65%).

Step 10

The mixture of 529j (0.12 g, 0.18 mmol), Cap 5 (0.18 g, 0.46 mmol), $Na_2CO_3$ (0.1 g, 0.9 mmol) and $Pd(dppf)Cl_2$ (27 mg, 0.037 mmol) in $THF/H_2O$ (v/v=5/1, 3 mL) was allowed to stir at 80° C. for about 15 hours under $N_2$ atmosphere. After cooling to room temperature, the mixture was washed with water and extracted with ethyl acetate. The organic layer was washed with brine and dried over anhydrous $Na_2SO_4$. After concentrated in vacuo, the resulting residue was purified using preparative HPLC to provide 529k (60 mg, 33% yield).

Step 11

The compound of 529k (60 mg) was separated by SFC by using the following conditions to provide 529 (20 mg, 67%) and 530 (20 mg, 67%).

Column: Chiralcel OJ-3 150×4.6 mm

Mobile phase: ethanol (0.05% DEA) in $CO_2$ from 5% to 40%

Flow rate: 2.5 mL/min

Wavelength: 220 nm

529: 1H NMR (400 MHz, METHANOL-d4) δ: 7.89 (d, J=13.7 Hz, 2H), 7.72 (s, 1H), 7.58-7.49 (m, 3H), 7.38-7.30 (m, 1H), 7.19 (s, 1H), 7.15-7.08 (m, 1H), 7.02 (br. s., 1H), 5.28-5.09 (m, 2H), 4.23 (d, J=7.0 Hz, 2H), 4.09-4.05 (m, 2H), 3.88 (d, J=5.9 Hz, 2H), 3.64 (s, 6H), 2.26 (d, J=5.5 Hz, 2H), 2.18-2.10 (m, 4H), 2.09-2.03 (m, 3H), 1.92 (br. s., 2H), 1.25 (br. s., 3H), 1.22 (s, 2H), 1.16 (t, J=7.0 Hz, 2H), 0.99-0.85 (m, 16H). LC/MS: Anal. Calcd. For $[M+H]^+$ C52H61FN10O7S: 989.17. found 989.6.

530: LC/MS: Anal. Calcd. For $[M+H]^+$ C52H61FN10O7S: 989.17. found 989.6.

The following compounds of the present invention were made using the methods described in the Example above and substituting the appropriate reactants and/or reagents.

| ID | Structures | Isomer info | Observed [M + H]+ |
|---|---|---|---|
| 501 | | Racemic | 908.4 |
| 502 503 | | Isomer 2 Isomer 1 | 921.6 921.6 |
| 504 505 | | Isomer 1 Isomer 2 | 947.4 947.6 |

-continued
| ID | Structures | Isomer info | Observed [M + H]+ |
|---|---|---|---|
| 511 512 | 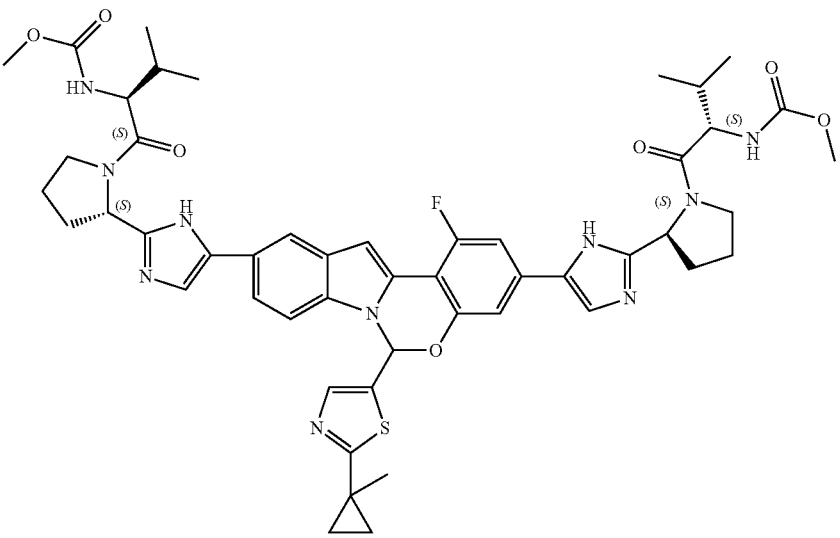 | Isomer 1 Isomer 2 | 961.6 961.6 |
| 515 516 | 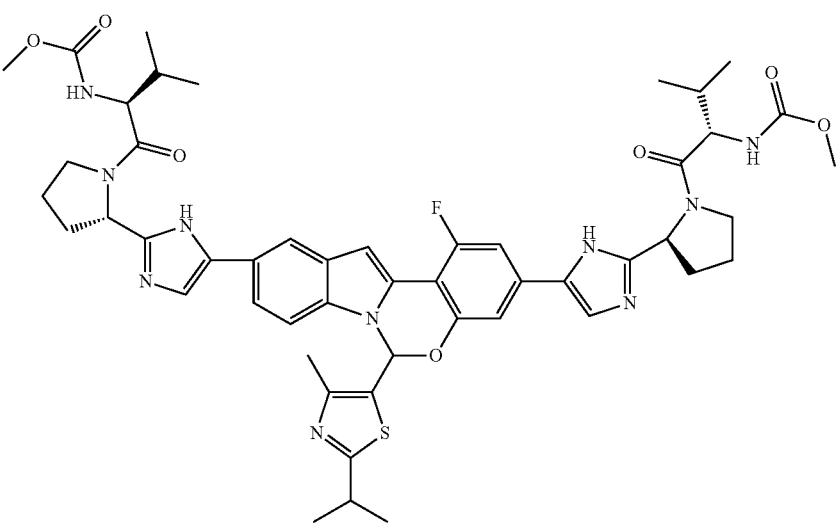 | Isomer 1 Isomer 2 | 963.6 963.4 |
| 524 | 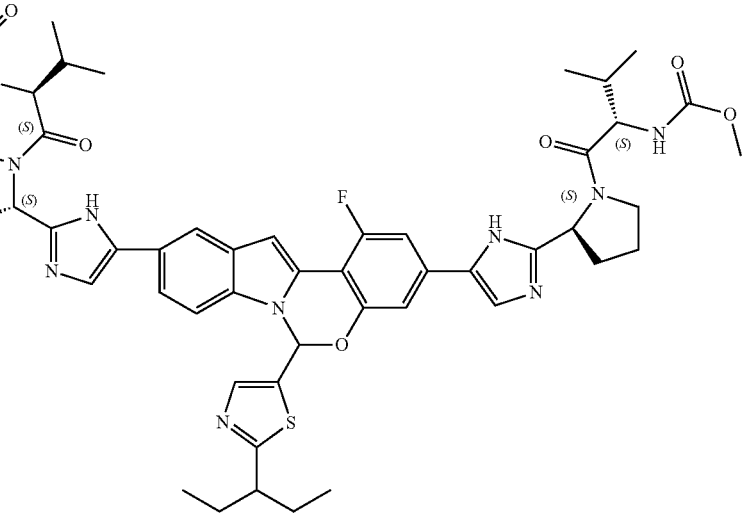 | Racemic | 977.4 |

| ID | Structures | Isomer info | Observed [M + H]+ |
|---|---|---|---|
| 525 526 | 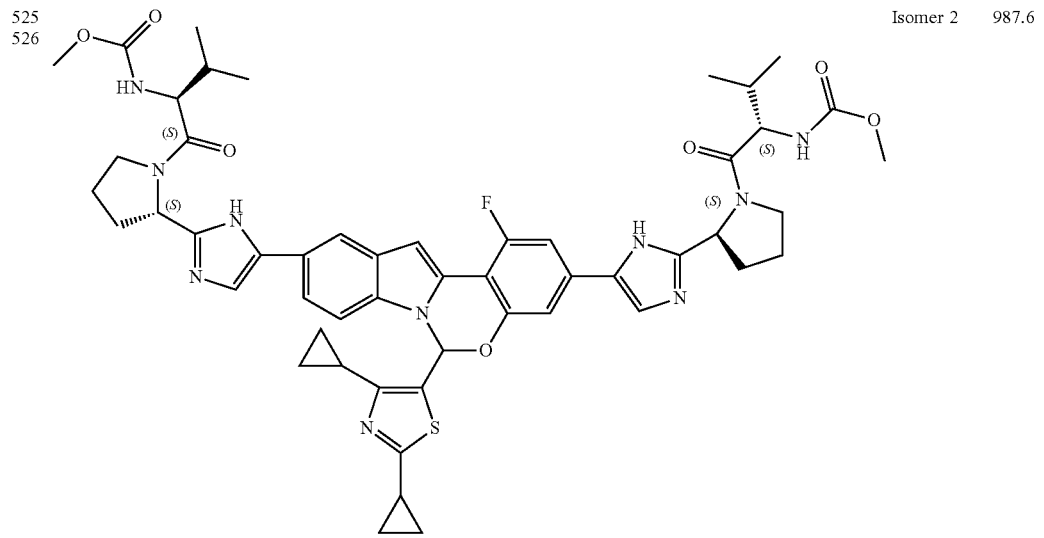 | Isomer 2 | 987.6 |
| 531 532 | 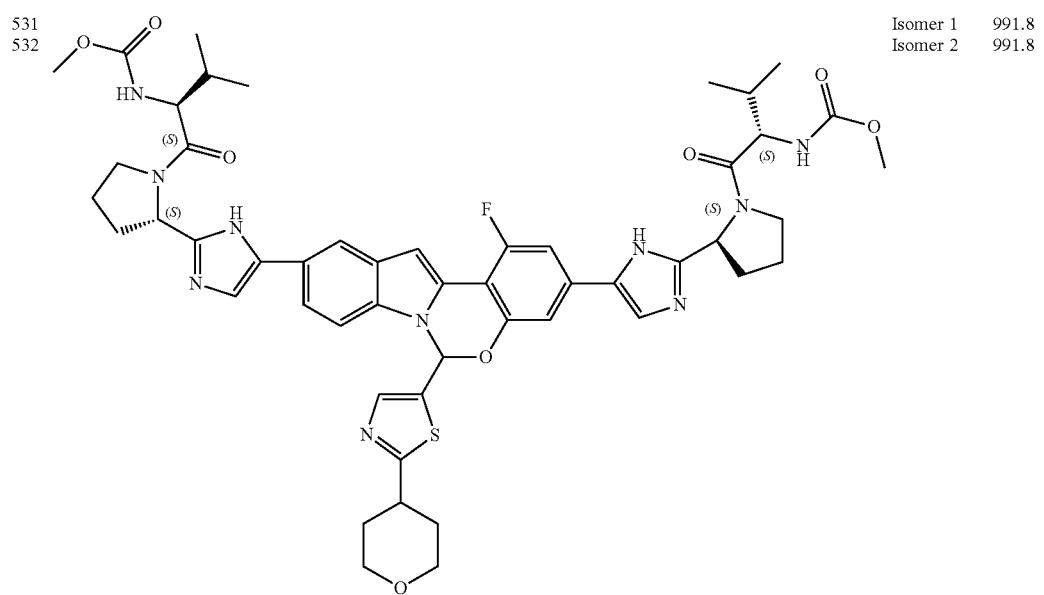 | Isomer 1 Isomer 2 | 991.8 991.8 |

| ID | Structures | Isomer info | Observed [M + H]+ |
|---|---|---|---|
| 534 535 | 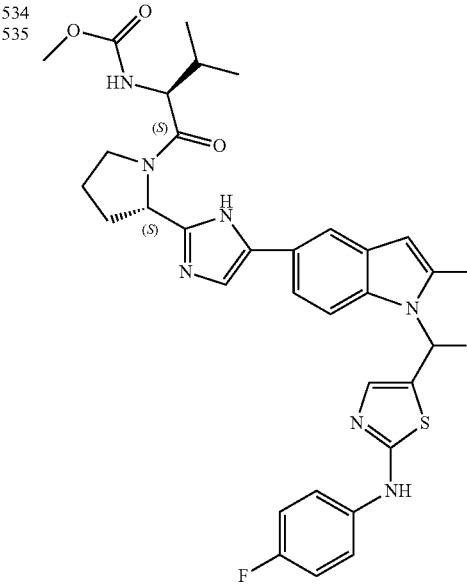 | Isomer 1 Isomer 2 | 1016.6 1016.6 |
| 451 | 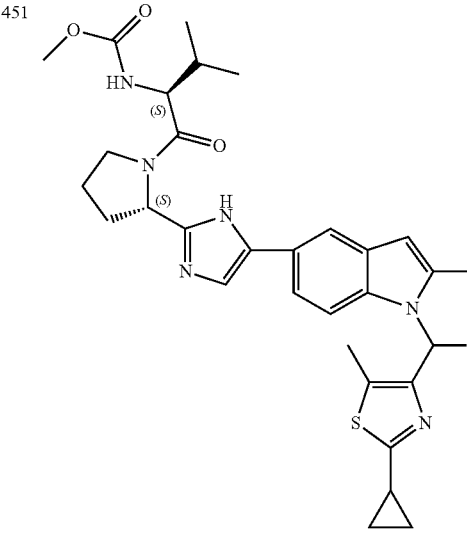 | Racemic | 961.6 |

| ID | Structures | Isomer info | Observed [M + H]+ |
|---|---|---|---|
| 456 | 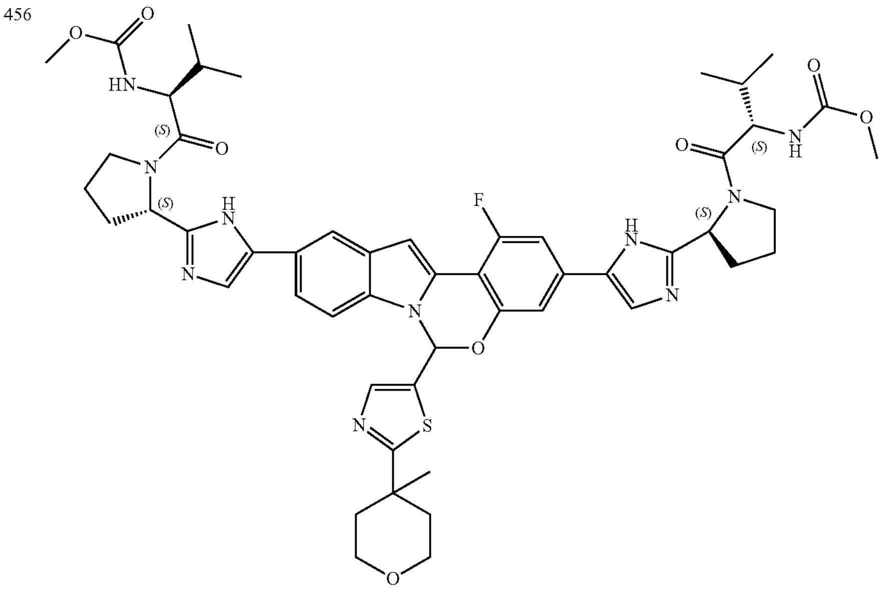 | Racemic | 1005.8 |
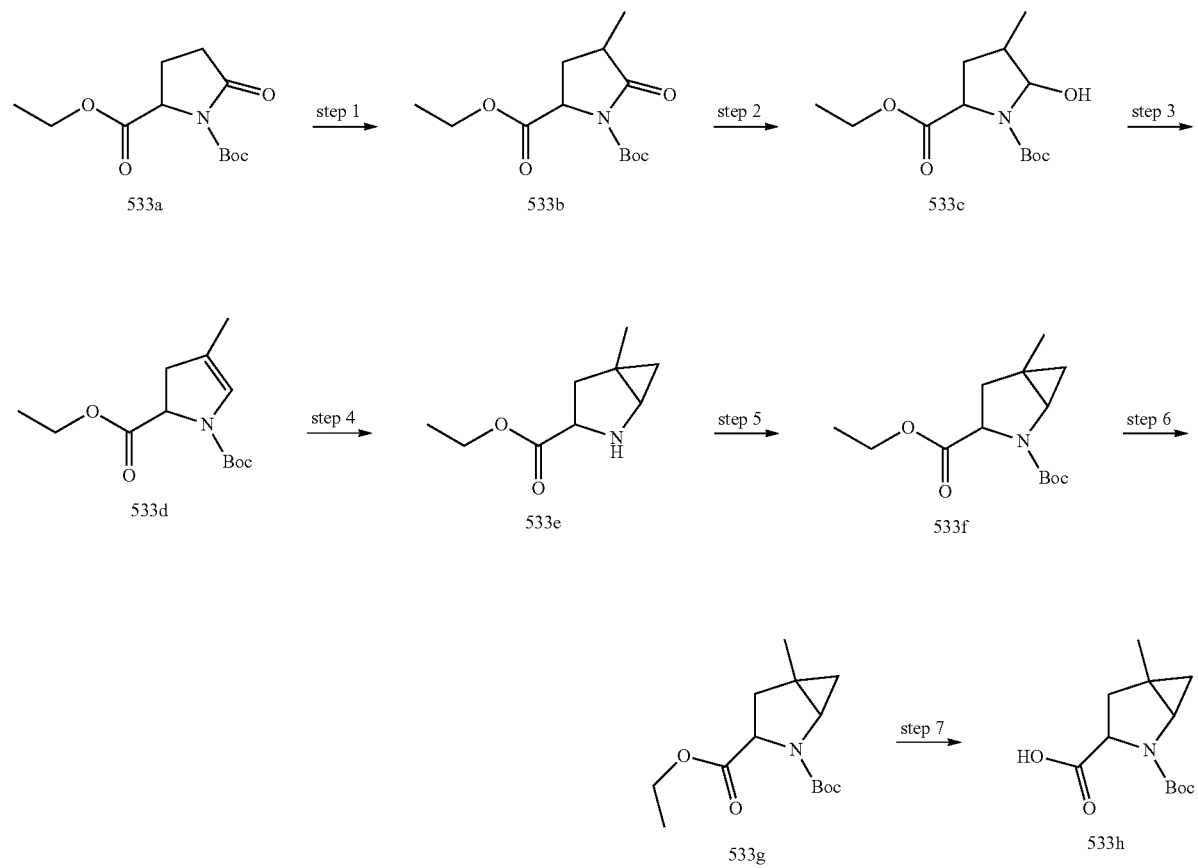
Example 35

271
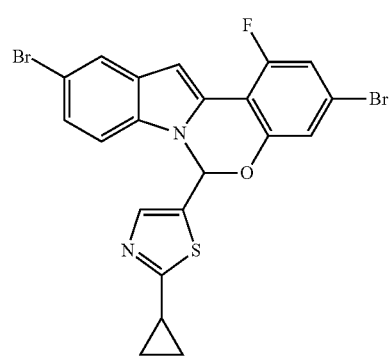
533i
272
-continued
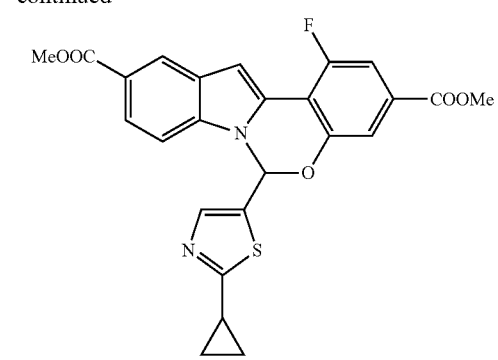
533j
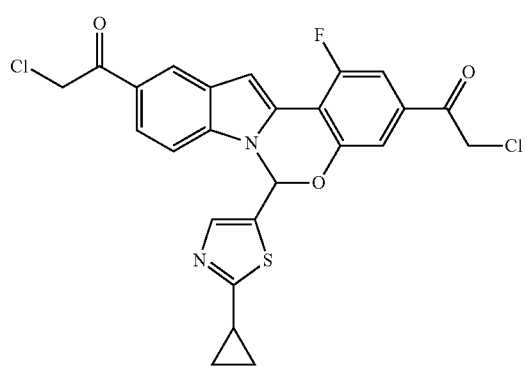
533k
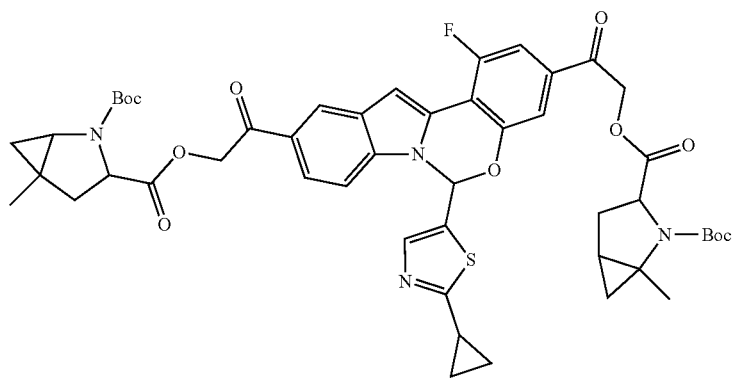
533l

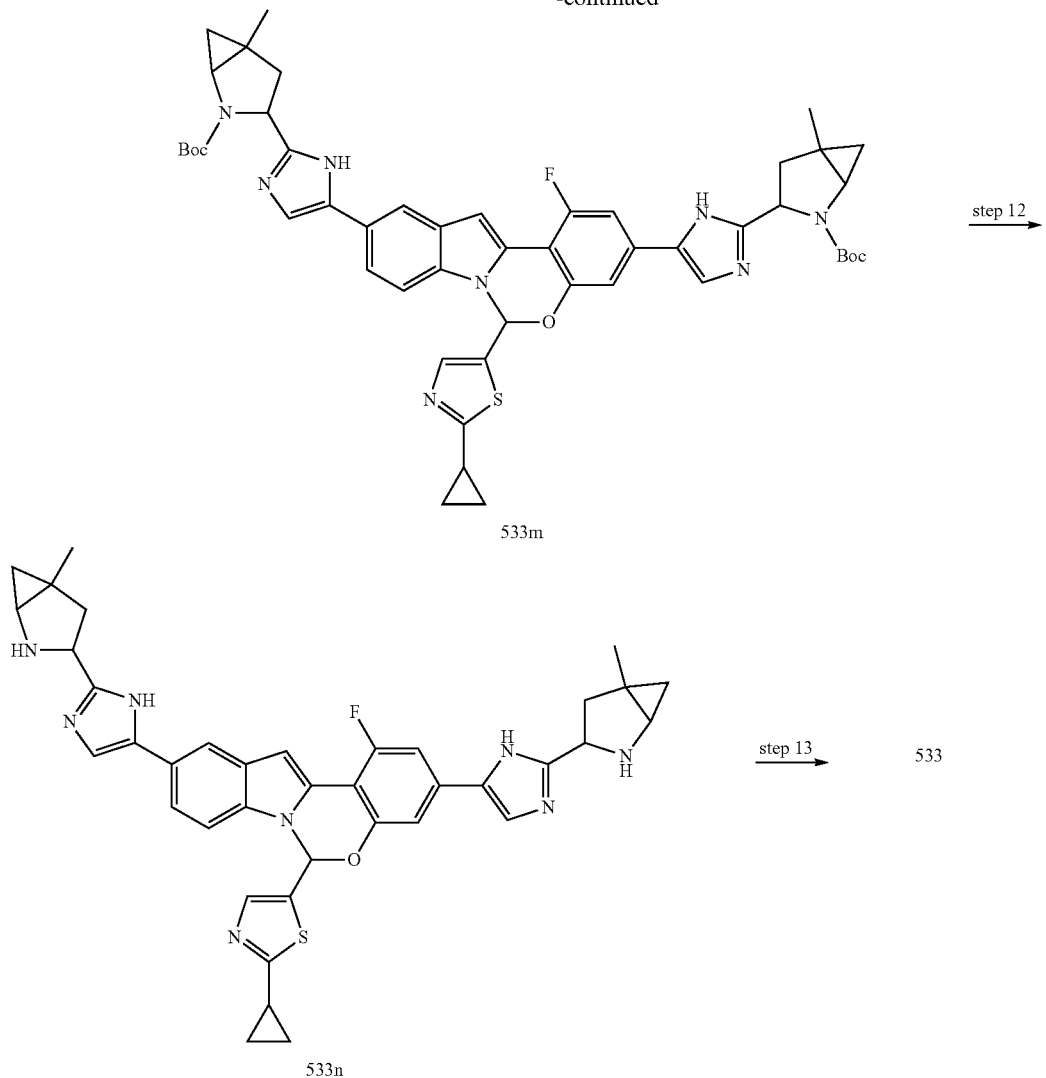

Step 1

To a solution of 533a (1.03 g, 4 mmol) in anhydrous THF (20 ml) was added LiHMDS (4.12 ml, 4.12 mmol) under −78° C. The mixture was allowed to stir for 1 hour at the same temperature, to the mixture was added MeI (1.2 g, 8 mmol). After stirring at −78° C. for 1 hour, the mixture was poured into water and extracted with ethyl acetate. The organic layer was washed with brine, dried over $Na_2SO_4$. After filtration and concentration in vacuo, the resulting residue was purified using flash column chromatography on silica gel, eluting with petroleum ether:ethyl acetate (5/1~1/1) to provide 533b (0.8 g, 76.3%).

Step 2

To a solution of 533b (6.9 g, 25.5 mmol) in anhydrous toluene (60 ml) was added Lithium triethylborohydride (40 ml, 38.25 mmol) under −78° C. The mixture was allowed to stir at the same temperature for 1 hour, before poured into water and extracted with ethyl acetate. The organic layer was washed with water and brine, dried over $Na_2SO_4$, filtrated and concentrated to provide compound 533c (6.95 g, 100%), which was used to the next step directly.

Step 3

To a solution of 533c (6.95 g, 25.5 mmol) in anhydrous toluene (60 ml) was added Trifluoroacetic anhydride (3.6 ml, 25.5 mmol) and 2,6-lutidine (4.09 g, 38.25 mmol). The mixture was heated to 80° C. and stirred for 4 hours. After cooling to room temperature, the mixture was poured into water and extracted with ethyl acetate. The organic layer was washed with water and brine, then dried over Na2SO4, filtrated and concentrated in vacuo The residue obtained was purified using flash column chromatography on silica gel, eluting with petroleum ether:ethyl acetate (5/1~1/1) to provide 533d (4.26 g, 65.54%).

Step 4

To the solution of $Et_2Zn$ (126 ml, 0.126 mol) in anhydrous DCM (100 ml) was added diiodomethane (65.62 g, 0.252 mol) at −78° C. The mixture was allowed to stir at −78° C. for 0.5 hour, and then warmed to 0° C. To the mixture was added 533d (5 g, 15.8 mmol) in 10 ml of anhydrous DCM in drop wise. The mixture was allowed to stir at room temperature for about 15 hours, before quenched by sat. $Na_2EDTA$. The organic layer was washed with water and brine, then dried over $Na_2SO_4$, filtrated and concentrated to obtained crude product 533e (3.64 g, 100%).

Step 5

To the solution of 533e (3.64 g, 15.8 mmol) in anhydrous DCM (50 ml) was added Boc$_2$O (5.1 g, 23.6 mmol). The mixture was allowed to stir at room temperature for 1 hour, and then poured into water and extracted with DCM. The organic layer was washed with water and brine, dried over Na2SO4, filtrated and concentrated in vacuo The residue obtained was purified using flash column chromatography on silica gel, eluting with petroleum ether:ethyl acetate (5/1~1/1) to provide 533f (2.13 g, 41.03%).

Step 6

To a solution of 533f (0.812 g, 2.45 mmol) in MeOH and H$_2$O (3:1, 8 ml) was added NaOH (0.2 g, 5 mmol). The mixture was allowed to stir at room temperature for 4 hour before evaporated to remove the excess MeOH. The residue obtained was re-dissolved into water and ethyl acetate, adjusted pH=2 with 3N HCl. The organic layer was washed with water and brine, then dried over Na$_2$SO$_4$, filtrated and concentrated to provide 533g (0.59 g, 100%).

Step 7

533g (2.14 g) was separated by SFC by using the following conditions to provide compound 533h (1.1 g, 55%) and the other isomer (900 mg, 45%).

Column: Chiralpak AD-H 250×4.6 mm I.D., 5 um

Mobile phase: ethanol (0.05% DEA) in CO2 from 5% to 40%

Flow rate: 2.35 mL/min

Wavelength: 220 nm"

Step 8

The mixture of 533i (5.18 g, 10 mmol), Pd(dppf)Cl2 (0.732 g, 1 mmol) and TEA (5.6 mL, 40 mmol) in DMF/MeOH (75 mL, V/V=3:2) was allowed to stir under CO (1 MPa) at 80° C. for 48 hours. After filtration and concentration in vacuo, the resulting residue was purified using flash column chromatography on silica gel, eluting with petroleum ether:ethyl acetate (20/1) to provide compound 533j (3.4 g, 71%). LC/MS: Anal. Calcd. For [M+H]+ C25H20FN2O5S: 479.10. found 479.4.

Step 9

A solution of isopropylmagnesium chloride lithium chloride complex (52 mL, 67.4 mmol) was added dropwise to diisopropylamine (11 mL, 75 mmol), keeping the internal temperature under 30° C. The mixture was allowed to stir at 15° C. for 3 hours. Then this reaction mixture was added dropwise to a solution of 533j (3.4 g, 7.49 mmol) and chloroacetic acid (2.11 g, 22.5 mmol) in THF (100 mL) at 0° C., keeping the internal temperature under 9° C. After addition, the mixture was allowed to stir at 0° C. for 30 min, then at room temperature for 16 hours. 2.5M aq. HCl (50 mL) and brine (15 mL) were added, extracted with ethyl acetate. The organic layer was washed with brine, dried over sodium sulfate, filtered and concentrated to provide compound 533k (2.23 g, 55%).

Step 10

The mixture of 533k (0.775 g, 1.5 mmol), 533h (0.8 g, 3.32 mmol) and K2CO3 (0.827 g, 6 mmol) in DMF (20 mL) was allowed to stir at room temperature for 16h. The reaction mixture was quenched with water and extracted with ethyl acetate. The organic layer was washed with brine, dried over sodium sulfate, filtered and concentrated in vacuo The residue obtained was purified using flash column chromatography on silica gel, eluting with petroleum ether:ethyl acetate (5/1~2/1) to provide 533l (500 mg, 36%) as a yellow solid. LC/MS: Anal. Calcd. For [M+H]+C49H54FN4O11S: 925.34. found 925.6.

Step 10

A mixture of 533l (775 mg, 1.5 mmol) and NH$_4$OAc (0.8 g, 3.32 mmol) in 30 mL of xylenes was heated to 150° C. in a sealed tube for 20 hours. The solvent was removed in vacuo in vacuo and the resulting residue was purified using flash column chromatography on silica gel, eluting with petroleum ether:ethyl acetate (5/1~2/1) to provide 533m (200 mg, 41.84% yield) as a yellow solid. LC/MS: Anal. Calcd. For [M+H]+ C49H54FN8O5S: 885.38. found 885.6.

Step 12

To a solution of 533m (0.2 g, 0.226 mmol) in MeOH (2 ml) was added HCl— dioxane (5 mL). The mixture was allowed to stir at room temperature for 1 hour. Then the mixture was concentrated in vacuo to provide the crude product 533n (0.15 g, 97.4%) and used to the next step directly. LC/MS: Anal. Calcd. For [M+H]+ C39H38FN8OS: 685.28. found 685.4.

Step 13

To a solution of 533n (90 mg, 0.132 mmol) in DMF (5 mL) was added 2-((methoxycarbonyl)amino)-3-methylbutanoic acid (48 mg, 0.276 mmol) and stirred at 0° C. Then DMPEA (70 mg, 0.528 mmol) was added, followed by HATU (100 mg, 0.264 mmol). Then mixture was allowed to warm to room temperature for 0.5 hours. Then the mixture was filtered and purified using preparative HPLC to provide 533 (50 mg, 38.17%). 1H NMR (400 MHz, METHANOL-d4): 8.05 (s, 1 H, ArH), 7.95 (s, 1 H, ArH), 7.77 (s, 2 H, ArH), 7.57 (s, 2H, ArH), 7.42~7.39 (m, 2 H, ArH), 7.37 (s, 1H, ArH), 7.17 (s, 1 H, ArH), 7.11 (s, 1 H, ArH), 5.77~5.73 (m, 1 H, CH), 5.68~5.64 (m, 1 H, CH), 4.28~4.26 (m, 2 H, CH), 3.71 (s, 3 H, CH3), 3.69 (s, 3 H, CH3), 2.70~2.67 (m, 2 H, CH2), 2.41~2.35 (m, 1 H, CH), 2.19~2.13 (m, 3 H, CH), 2.12 (s, 6 H, CH3), 1.38~1.36 (m, 5H, CH), 1.11-1.07 (m, 16 H, CH), 0.97~0.88 (m, 2H, CH). LC/MS: Anal. Calcd. For [M+H]+ C53H60FN10O7S: 999.19. found 999.6.

Example 36

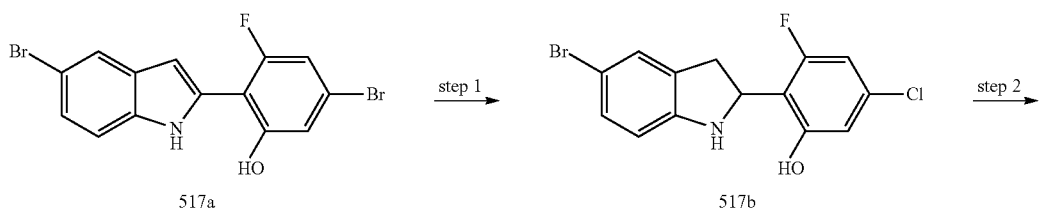

277
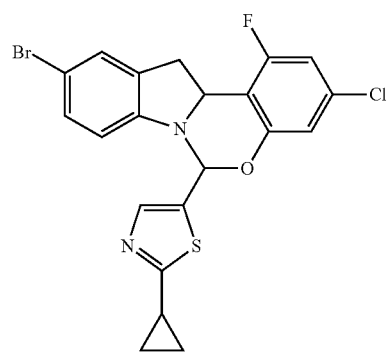
517c
step 3 →
278
-continued
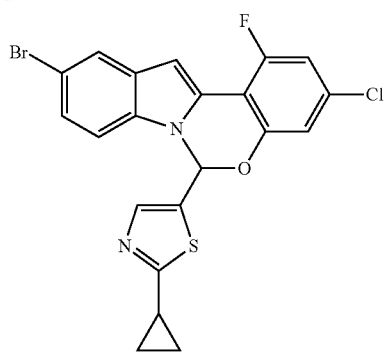
517d
step 4 →
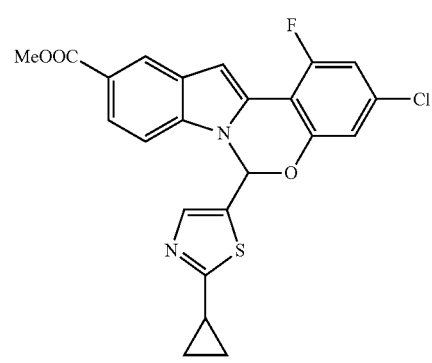
517e
step 5 →
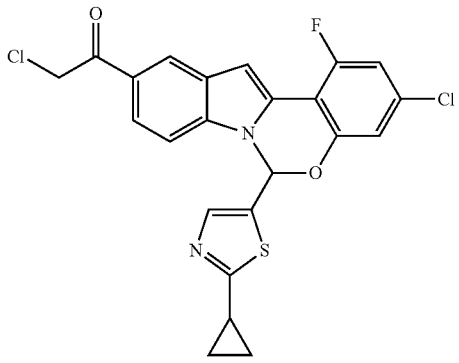
517f
+
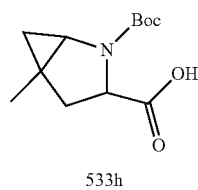
533h
step 6 →
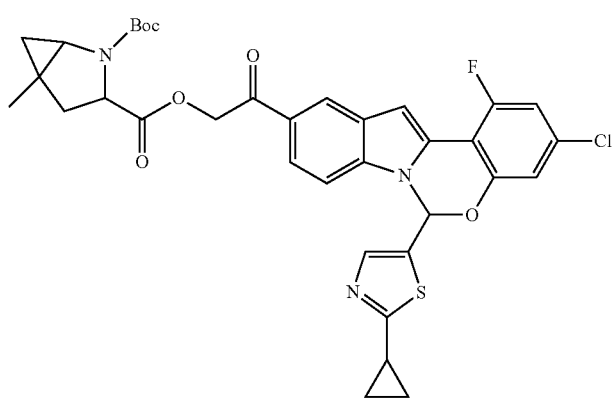
517h
step 7 →

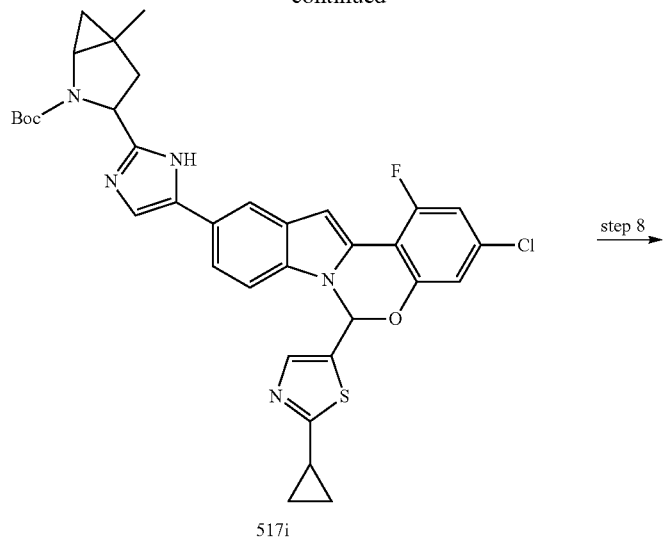
517i
→ step 8
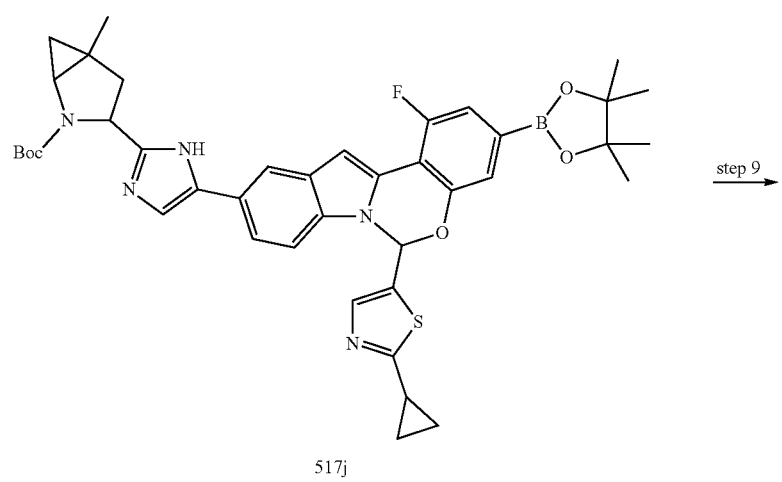
517j
→ step 9
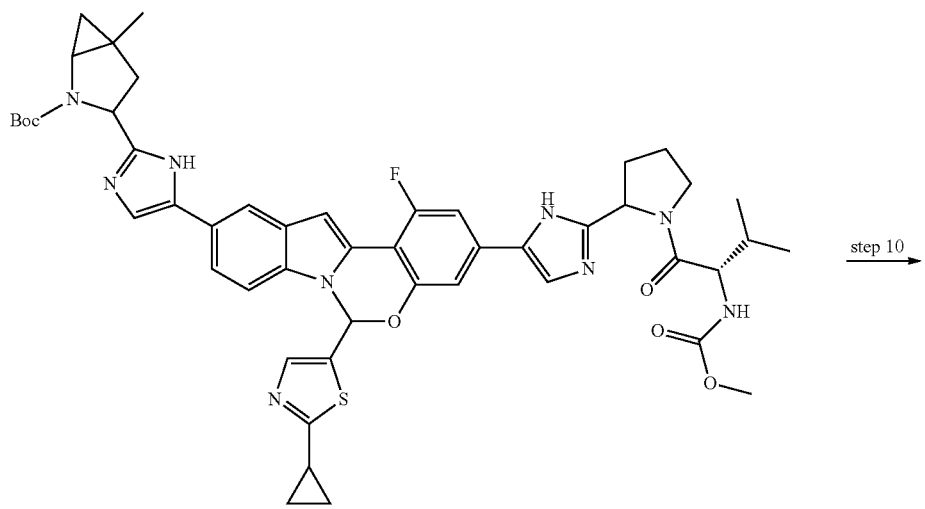
517k
→ step 10

-continued
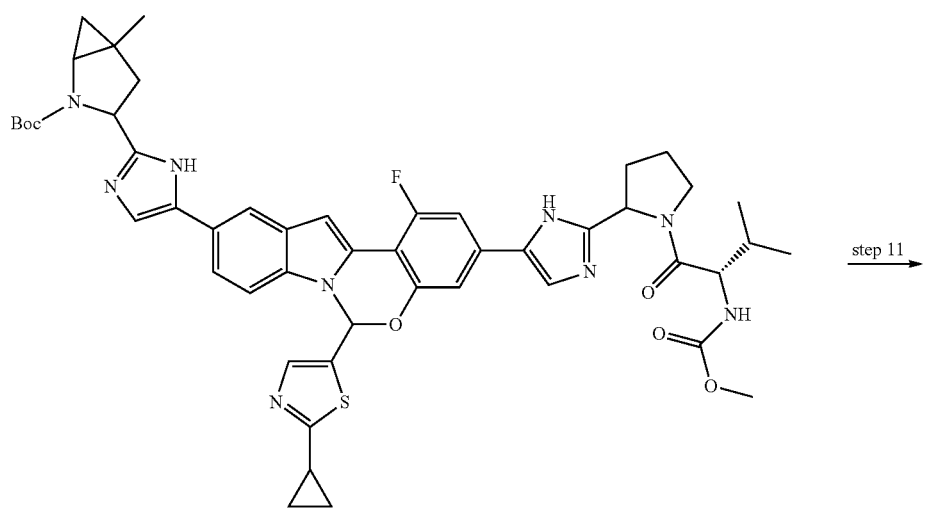
517l
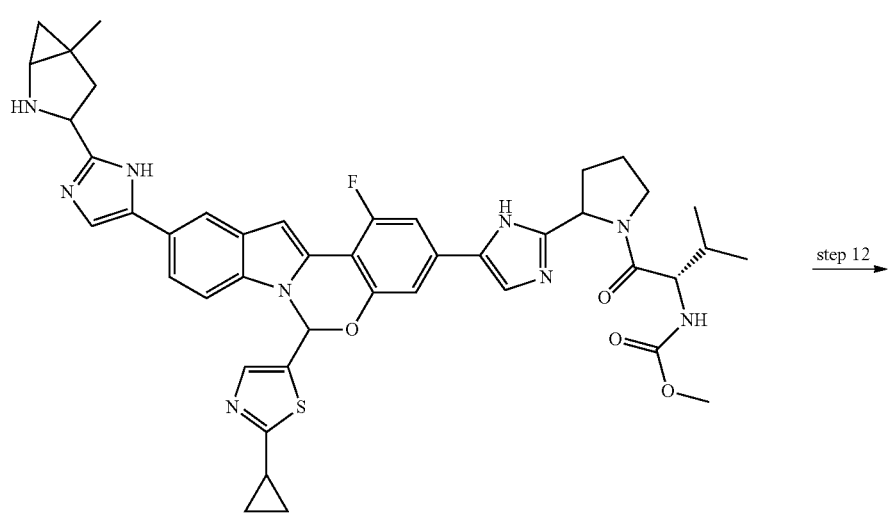
517m
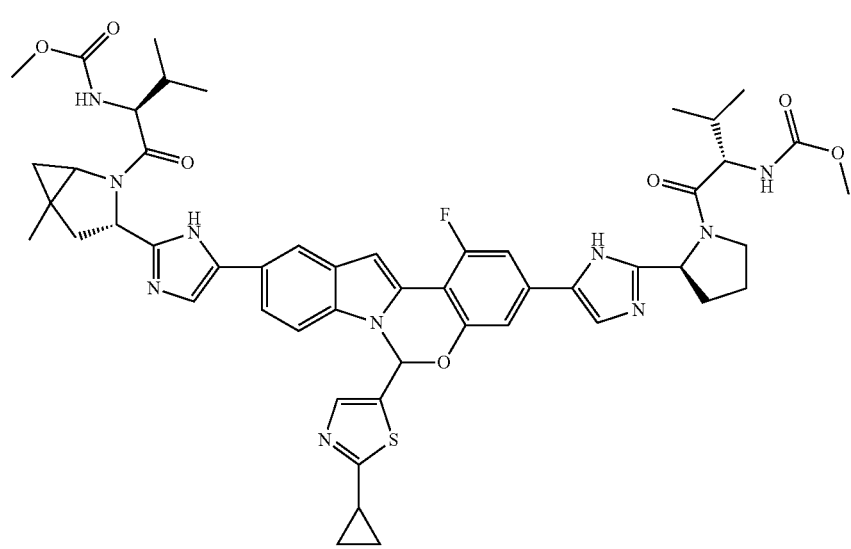
517

Step 1

Compound 517a was prepared in Example 19 of WO 2012/040923 A1.

To a 500 mL flask was added compound 517a (30 g, 88.06 mmol), Zinc (60 g, 923 mmol), and TFA (300 mL). The solution was allowed to stir at 75° C. for 24 hours. After cooling down, EtOAc (800 mL) and water (450 mL) were added. The organic layer was separated and washed with water two more time, Saturated NaHCO$_3$ twice, brine and dried over anhydrous Na$_2$SO$_4$. The solution was filtered and concentrated in vacuo Crude product was purified using flash column chromatography on silica gel (Hexane/EtOAc 0% to 30%) obtained compound 517b (16 g, 53.3% yield). LC/MS: Anal. Calcd. For [M+H]$^+$ C14H10BrClFNO: 343.59. found 343.9

Step 2

To a mixture of 517b (6 g, 18.5 mmol) and 2-cyclopropylthiazole-5-carbaldehyde (3.39 g, 22.2 mmol) in AcCN (60 mL) was added TFA (630 mg, 5.54 mmol) and stirred at room temperature for 16 hours. Then the reaction mixture was filtered to provide white solid and washed with AcCN (100 mL) to provide compound 517c (6.5 g, 78%).

Step 3

A mixture of 517c (6.7 g, 14.1 mmol) and DDQ (3.84 g, 16.9 mmol) in toluene (100 mL) was allowed to stir at 110° C. for 1.5 hour. Then the reaction mixture was filtered and concentrated and the resulting residue was purified using flash column chromatography on silica gel, eluting with petroleum ether:ethyl acetate (50/1~20/1) to provide compound 517d (6.1 g, 91%).

Step 4

The mixture of compound 517d (1 g, 2.1 mmol), TEA (0.6 mL, 4.2 mmol) and Pd(dppf)Cl$_2$ (0.154 g, 0.21 mmol) in DMF/MeOH (V/V=1:1, 60 mL) was allowed to stir under CO (50 psi) at 80° C. for 48 hours. After filtration and concentration in vacuo, the resulting residue was purified using flash column chromatography on silica gel, eluting with petroleum ether:ethyl acetate (50/1~20/1) to provide compound 517e (0.57 g, 60%) as a yellow solid.

Step 5

A solution of isopropylmagnesium chloride lithium chloride complex (52 mL, 67.4 mmol) was added dropwise to diisopropylamine (11 mL, 75 mmol), keeping the internal temperature below 30° C. The mixture was allowed to stir at 15° C. for 3 h before added dropwise to a solution of compound 517e (3.4 g, 7.49 mmol) and chloroacetic acid (2.11 g, 22.5 mmol) in THF (100 mL) at 0° C. After the addition, the mixture was allowed to stir at 0° C. for 30 min, then warmed to room temperature for 16 hours. The mixture was sequenced with 2.5M HCl solution (50 mL) and brine (15 mL), extracted with ethyl acetate. The organic layer was washed with brine, dried over sodium sulfate, filtered and concentrated to provide compound 517f (2.23 g, 55%) as a yellow solid.

Step 6

Compound 533h was prepared in Example 35.

A mixture of compound 517f (0.722 g, 1.53 mmol), 533h (0.442 g, 1.834 mmol) and K$_2$CO$_3$ (0.527 g, 3.82 mmol) in DMF (20 mL) was allowed to stir at room temperature for 16h, before water was added, extracted with ethyl acetate. The organic layer was washed with brine, dried over sodium sulfate, filtered and concentrated in vacuo The residue obtained was purified using flash column chromatography on silica gel, eluting with petroleum ether:ethyl acetate (5/1~2/1) to provide 517h (600 mg, 58%) as a yellow solid. LC/MS: Anal. Calcd. For [M+H]$^+$ C35H34C1FN3O6S: 678.18. found 678.4.

Step 7

A mixture of 517h (600 mg, 0.886 mmol) and NH$_4$OAc (1.3 g, 17.76 mmol) in 30 mL of xylenes was heated to 150° C. in a sealed tube for 20 hours. The solvent was removed in vacuo in vacuo and the resulting residue was purified using flash column chromatography on silica gel, eluting with petroleum ether:ethyl acetate (5/1~2/1) to provide 517i (282 mg, 48.45%) as a yellow solid. LC/MS: Anal. Calcd. For [M+H]$^+$ C35H34C1FN5O3S: 658.20. found 658.4.

Step 8

To a mixture of 517i (218 mg, 0.43 mmol), bis(pinacolato)diboron (218 mg, 0.858 mmol), KOAc (168 mg, 1.73 mmol), Pd$_2$(dba)$_3$ (40 mg, 0.043 mmol) and x-Phos (41 mg, 0.0858 mmol) degassed and sealed under N$_2$ was added dry dioxane (20 mL). Following further N$_2$ purging. The mixture was allowed to stir at 100° C. for 3 hours. The resulting reaction was then filtered, and the filtrate was washed with water (20 mL) and extracted with ethyl acetate (50 mL), washed with brine and dried over anhydrous sodium sulfate. After concentrated in vacuo, the resulting residue was purified using flash column chromatography on silica gel, eluting with petroleum ether:ethyl acetate (1/1~0/1) to provide 517j (310 mg, 96.27%). LC/MS: Anal. Calcd. For [M+H]$^+$ C41H46BFN5O5S: 750.32. found 750.6.

Step 9

A suspension of 517j (310 mg, 6.27 mmol), Cap 5 (170 mg, 0.445 mmol), Pd(dppf)$_2$Cl$_2$ (30 mg, 0.0414 mmol), Na$_2$CO$_3$ (87 mg, 0.818 mmol) and in THF/DMF/H$_2$O (5:1:1, 32 mL) was refluxed at 90° C. for about 15 hours under N$_2$ atmosphere. The resulting reaction was then filtered, and the filtrate was washed with water (150 mL) and extracted with ethyl acetate (50 mL), washed with brine and dried over anhydrous sodium sulfate. After concentrated in vacuo, was purified using flash column chromatography on silica gel, eluting with ethyl acetate:methanol (50/1~10/1) to provide 517k (250 mg, 66.14%). LC/MS: Anal. Calcd. For [M+H]$^+$ C49H55FN9O6S: 916.39. found 916.6.

Step 10

The compound 517k (400 mg) was separated by SFC by using the following conditions to provide compound 517l (140 mg, 41%) and the other isomer (200 mg, 59%).

Column: Chiralcel OJ-3 150×4.6 mm I.D., 3 um
Mobile phase: 40% of ethanol (0.05% DEA) in CO$_2$
Flow rate: 2.5 mL/min
Wavelength: 340n Step 10

To a solution of 517l (91 mg, 0.1 mmol) in MeOH (2 mL) was added HCl— dioxane (3 mL). The mixture was allowed to stir at room temperature for 1 hour. Then the mixture was concentrated in vacuo to provide the crude 517m (81 mg, 100% yield) and used to the next step directly.

Step 12

To a solution of 517m (62 mg, 0.076 mmol) in DMF (5 mL) was added 2-((methoxycarbonyl)amino)-3-methylbutanoic acid (20 mg, 0.112 mmol) and stirred at 0° C. Then DMPEA (30 mg, 0.228 mmol) was added, followed by HATU (29 mg, 0.076 mmol). Then mixture was allowed to warm to room temperature for 0.5 hours. Then the mixture was filtered and purified using pre-HPLC to provide 517 (25 mg, 33.7%). 1H NMR (CD3OD 400 MHz): δ 8.01 (s, 1 H, ArH), 7.94 (s, 1 H, ArH), 7.92 (s, 1 H, ArH), 7.75 (s, 1 H, ArH), 7.52 (s, 2 H, ArH), 7.49 (s, 1 H, ArH), 7.38 (s, 1 H, ArH), 7.32 (s, 1 H, ArH), 7.18 (s, 1 H, ArH), 7.10 (s, 1H, ArH), 5.21~5.23 (m, 1 H, CH), 5.04~4.99 (m, 1 H, CH), 4.51~4.50 (m, 1 H, CH), 4.22~4.20 (m, 1 H, CH), 3.86~3.84 (m, 1 H, CH), 3.66 (s, 6 H), 2.76~2.69 (m, 1 H, CH), 2.54 (m, 1 H), 2.2-22.18 (m, 2H), 2.17-2.15 (m, 6H), 1.06-1.02 (m, 2H), 1.01-0.97 (m, 2 H), 0.9-40.88 (m, 16 H). LC/MS: Anal. Calcd. For [M+H]+ C53H61FN10O8S: 973.15. found 973.6.

The following compounds of the present invention were made using the methods described in the Example above and substituting the appropriate reactants and/or reagents.

| ID | Structures | Isomer info | Observed [M + H]+ |
|---|---|---|---|
| 518 | | Isomer 2 | 973.2 |
| 519 | | Isomer 3 | 973.6 |
| 520 | | Isomer 4 | 973.6 |
Example 37
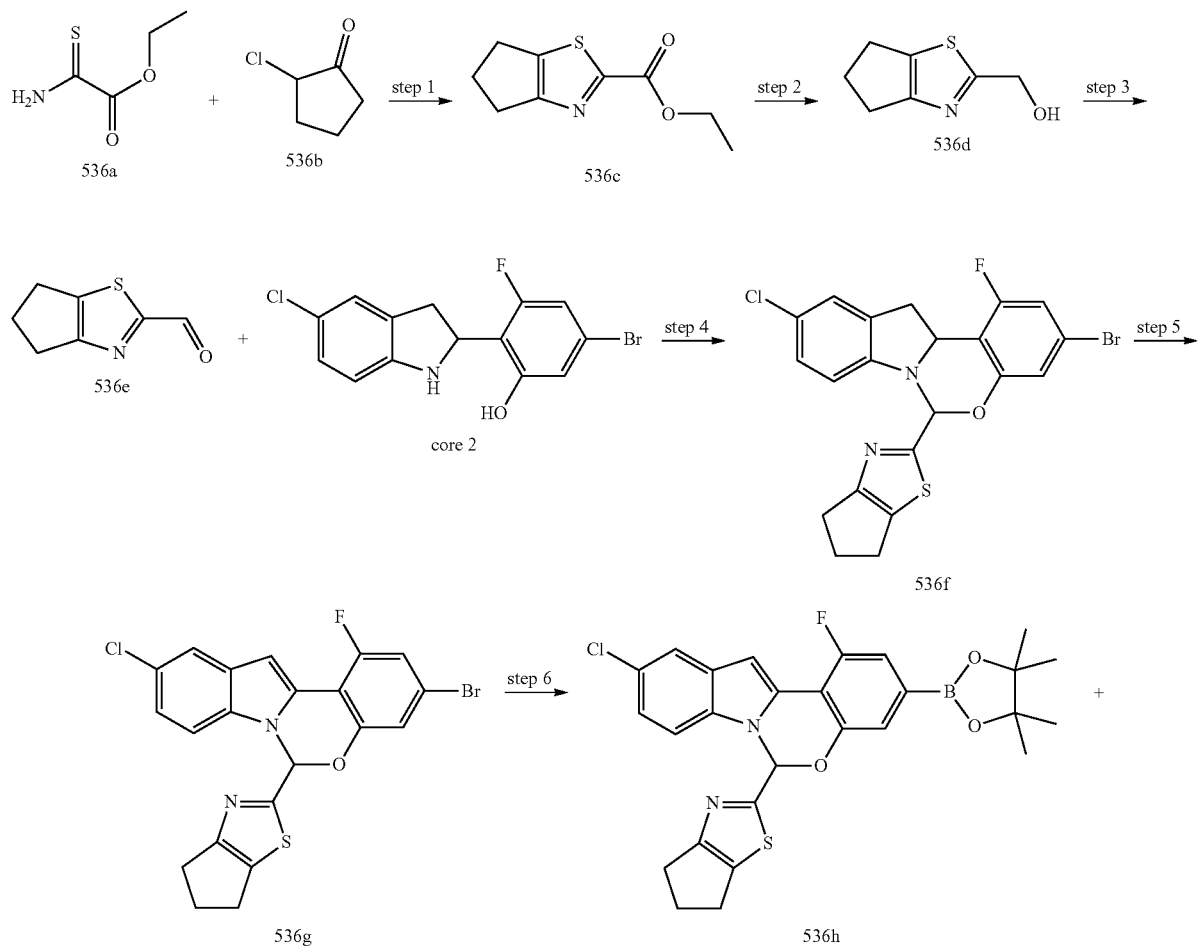

287 -continued 288
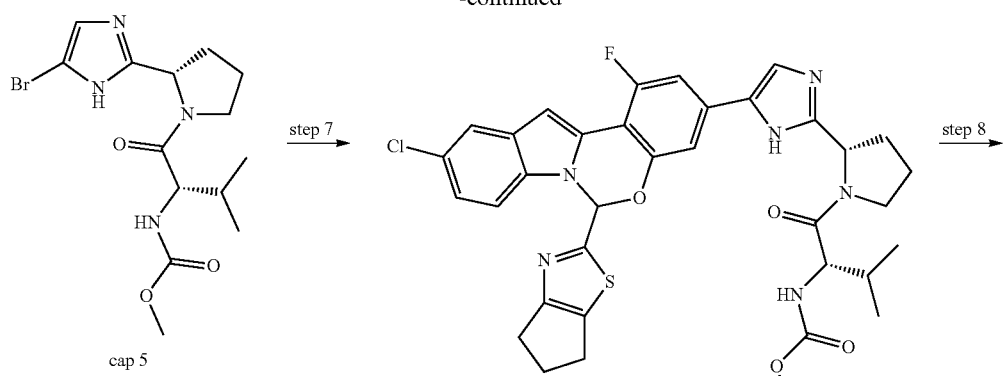
cap 5 → step 7 → 536i → step 8 →
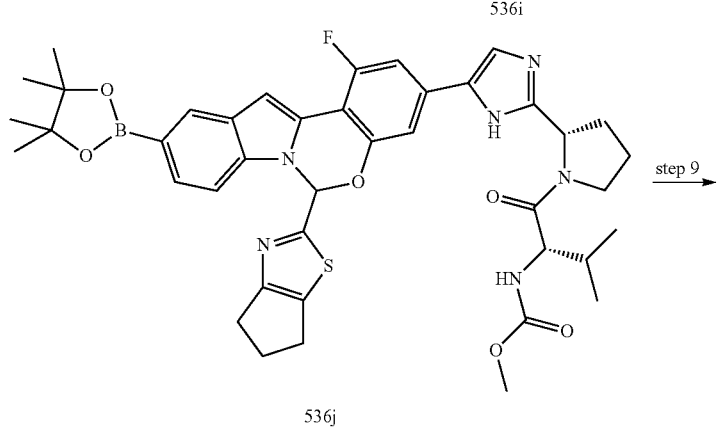
536j → step 9 →
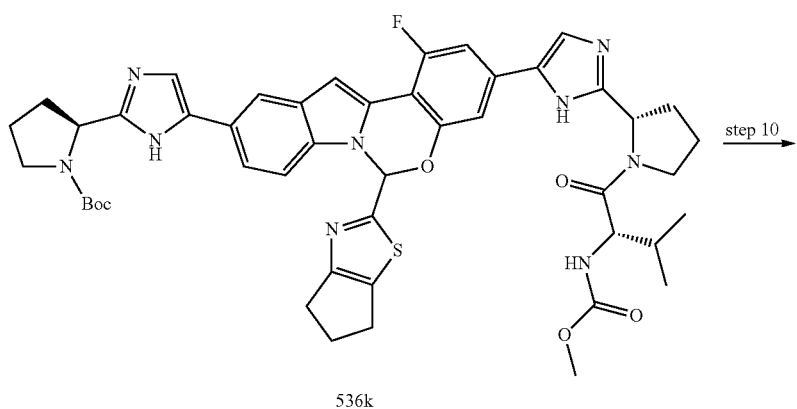
536k → step 10 →
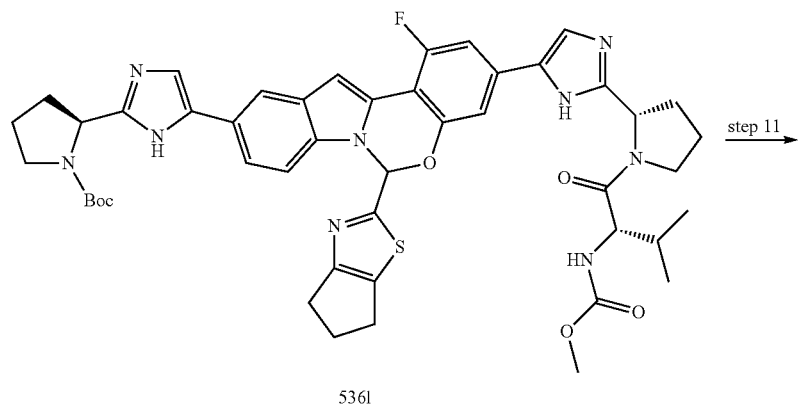
536l → step 11 →

-continued

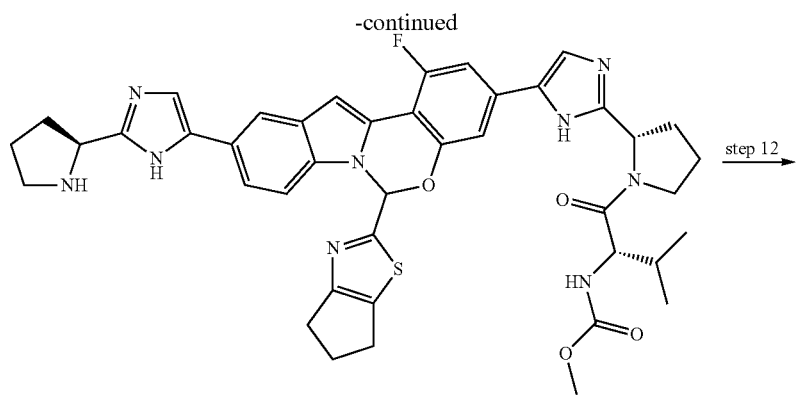

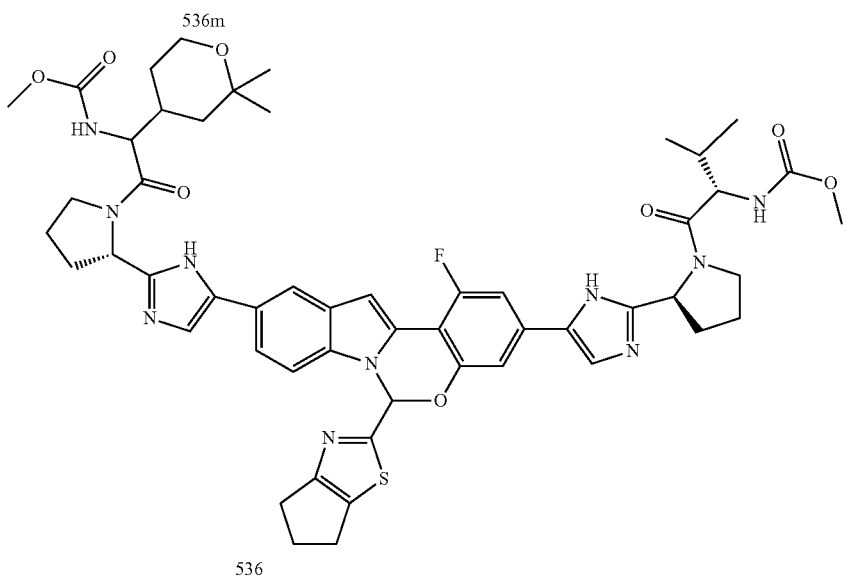

536

Step 1

A solution of compound 536a (19.3 g, 0.145 mol), compound 536b (19 g, 0.16 mol) in toluene (500 mL) was allowed to stir at 120° C. for 16 hours under $N_2$ atmosphere. The solution was washed with aqueous $NaHCO_3$ and brine, extracted with EtOAc. The organic layer was dried over $Na_2SO_4$. After filtrated, the filtrate was concentrated in vacuo, the resulting residue was purified using flash column chromatography on silica gel, eluting with ethyl acetate:methanol (50/1~10/1) to provide compound 536c (6.4 g, 23%).

Step 2

To the solution of compound 536c (6.4 g, 32.5 mmol) in THF (50 mL) was added LAH (1.85 g, 48.7 mmol) in portions at 0° C. in an ice-bath. The reaction mixture was allowed to stir at room temperature for 1 h, before quenched by water and extracted with EtOAc. The organic layer was washed with brine, dried over $Na_2SO_4$. After filtrated, the filtrate was concentrated in vacuo to provide compound 536d (3.0 g, 60%).

Step 3

To a suspension of compound 536d (0.8 g, 5.16 mmol) in DCM (10 mL) was added DMP (3.3 g, 7.74 mmol) in portions at 0° C. and then stirred at 30° C. for 2 hours. The organic phase was washed with saturated $Na_2S_2O_3$, saturated $NaHCO_3$, brine, dried over $Na_2SO_4$, and concentrated in vacuo to provide compound 536e (0.7 g, 88%).

Step 4

To a mixture of compound 536e (0.7 g, 4.58 mmol) and Core 2 (1.56 g, 4.57 mmol) in anhydrous $CH_3CN$ (15 ml) was added TFA (0.2 mL) at 25° C. The mixture was allowed to stir for 6 h at 25° C. The reaction mixture became a clear solution and then solid appeared. The solid was collected by filtration and washed with $CH_3CN$ to provide compound 536f (1.3 g, 62%).

Step 5

To a solution of 536f (1.35 g, 2.82 mmol) in dry toluene (15 mL) was added DDQ (0.96 g, 4.24 mmol). After refluxing for 2 hours, the solvent was removed in vacuo and diluted with EtOAc. The organic layer was washed with saturated $Na_2S_2O_3$ solution and brine, dried over $Na_2SO_4$, filtered and concentrated in vacuo The residue obtained was washed with MeOH (10 mL), filtered to provide compound 536g (1.2 g, 90% yield).

Step 6

A suspension of 536g (1.2 g, 2.52 mmol), bis(pinacolato)diboron (0.71 g, 2.77 mmol), KOAc (617 mg, 6.3 mmol) and $Pd(dppf)Cl_2$ (92 mg, 0.126 mmol) in dioxane (20 mL) was allowed to stir at 100° C. for 2 hours under $N_2$ atmosphere. The reaction mixture was cooled and concentrated in vacuo, the resulting residue was purified using column chromatography on silica gel, eluting with petroleum ether:ethyl acetate (20:1) to provide compound 536h (1.05 g, 79%).

Step 7

A mixture of compound 536h (1.05 g, 2.00 mmol), Cap 5 (0.9 g, 2.41 mmol), $Na_2CO_3$ (0.53 g, 5.0 mmol) and Pd(dppf)$Cl_2$ (73 mg, 0.1 mmol) in THF/$H_2O$ (v/v=5/1, 30 mL) was allowed to stir at 100° C. under $N_2$ atmosphere for about 15 hours. The resulting reaction was then washed with water and extracted with ethyl acetate, washed with brine and dried over anhydrous $Na_2SO_4$. After concentrated in vacuo, the resulting residue was purified using column chromatography on silica gel, eluting with petroleum ether:ethyl acetate (3:1 to 1:1) to provide compound 536i (1.1 g, 80%).

Step 8

The mixture of compound 536i (1.1 g, 1.60 mmol), bis(pinacolato)diboron (0.45 g, 1.76 mmol), KOAc (0.39 g, 4 mmol), $Pd_2(dba)_3$ (83 mg, 0.08 mmol), X-Phos (76 mg 0.16 mmol) in dry 1,4-dioxane (20 mL) was degassed and sealed under $N_2$. The mixture was allowed to stir at 120° C. for about 15 hours. After cooling to room temperature, the mixture was concentrated in vacuo and diluted with EtOAc. The organic layer was washed with water and brine, dried over $Na_2SO_4$, filtered and concentrated in vacuo The residue obtained was purified using chromatography on silica (petroleum ether:ethyl acetate 10%-60%) to provide product 536j (1.15 g, 92%).

Step 9

The mixture of compound 536j (0.75 g, 0.96 mmol), Cap 7a (334 mg, 1.06 mmol), $Na_2CO_3$ (255 mg, 2.4 mmol) and Pd(dppf)$Cl_2$ (35 mg, 0.048 mmol) in THF/$H_2O$ (v/v=5/1, 20 mL) was allowed to stir at 100° C. under $N_2$ atmosphere for about 15 hours. The resulting reaction was then washed with water and extracted with ethyl acetate, washed with brine and dried over anhydrous sodium sulfate. After concentrated in vacuo, the resulting residue was purified using column chromatography on silica gel, eluting with petroleum ether:ethyl acetate (3:1 to 1:3) to provide compound 536k (0.6 g, 71%).

Step 10

The compound of 536k (0.6 g) was separated by SFC by using the following conditions to provide 536l (0.2 g, 33%).

Column: Chiral pak OZ-H 250×4.6 mm I.D., 5 um

Mobile phase: Ethanol (0.05% DEA) in CO2 from 5% to 40%

Flow rate: 2.0 mL/min

Wavelength: 220 nm

Step 10

To a solution of compound 536l (0.2 g, 0.22 mmol) in 1,4-dioxane (10 mL) was added HCl/1,4-dioxane (5 mL, 4M). Then the mixture was allowed to stir at 25° C. for 1 hour. When the reaction completed, the mixture was concentrated in vacuo at 25° C. to provide compound 536m (178 mg, 100%).

Step 12

To a mixture of compound 536m (178 mg, 0.22 mmol), Cap 3 (54 mg, 0.22 mmol) and HATU (84 mg, 0.22 mmol) in DMF (4 mL) was added DIEA slowly to adjust pH to 8-9. The resulting mixture was allowed to stir at 25° C. for 30 minutes, and LC-MS judged the material was consumed up. The mixture was poured into ice-water, extracted with ethyl acetate, washed with brine and dried over anhydrous sodium sulfate. After concentrated in vacuo, the resulting residue was purified using preparative HPLC to provide 536 (137 mg, 60%). $^1$H NMR (MeOD 400 MHz): δ 8.06 (s, 1 H), 7.97 (s, 1 H), 7.89 (s, 1 H), 7.80 (s, 1 H), 7.61 (s, 2 H), 7.39-7.45 (m, 1 H), 7.31-7.37 (m, 1 H), 7.14-7.22 (m, 1 H), 5.19-5.29 (m, 2 H), 4.19-4.27 (m, 2 H), 4.06-4.14 (m, 2 H), 3.83-4.02 (m, 3 H), 3.65 (s, 7 H), 2.72-2.80 (m, 2 H), 2.64-2.71 (m, 2 H), 2.52-2.62 (m, 2 H), 1.98-2.47 (m, 11 H), 1.51-1.58 (m, 1 H), 1.20-1.32 (m, 4 H), 1.12 (d, J=8.6 Hz, 5 H), 0.84-1.01 (m, 6 H). LC/MS: Anal. Calcd. For [M+H]$^+$ C53H61FN10O8S: 1017.18. found 1017.8.

The following compounds of the present invention were made using the methods described in the Example above and substituting the appropriate reactants and/or reagents.

| ID | Structures | Isomer info | Observed [M + H]$^+$ |
|---|---|---|---|
| 537 | 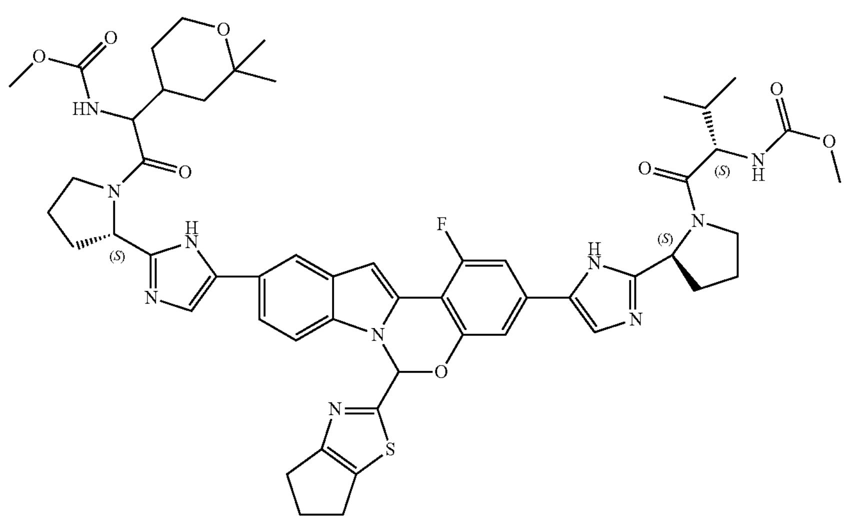 | Isomer 2 | 1017.8 |

-continued

| ID | Structures | Isomer info | Observed [M + H]+ |
|---|---|---|---|
| 486 | 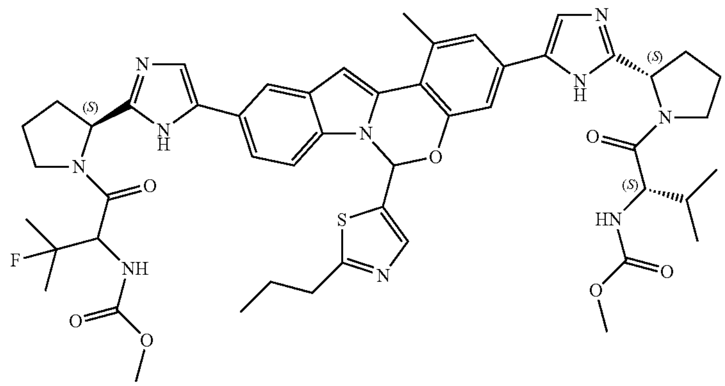 | Isomer 1 | 964.43 |
| 487 | 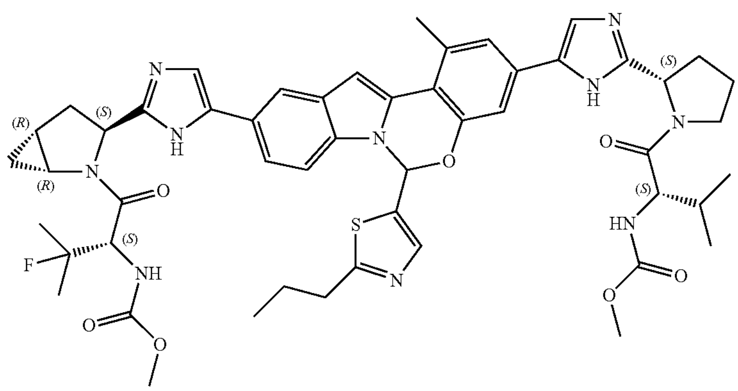 | Isomer 1 | 977.19 |
| 488 | 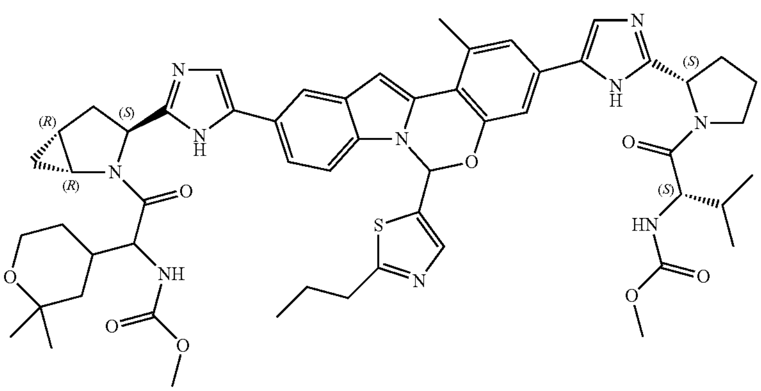 | Isomer 1 | 1029.29 |

Example 38
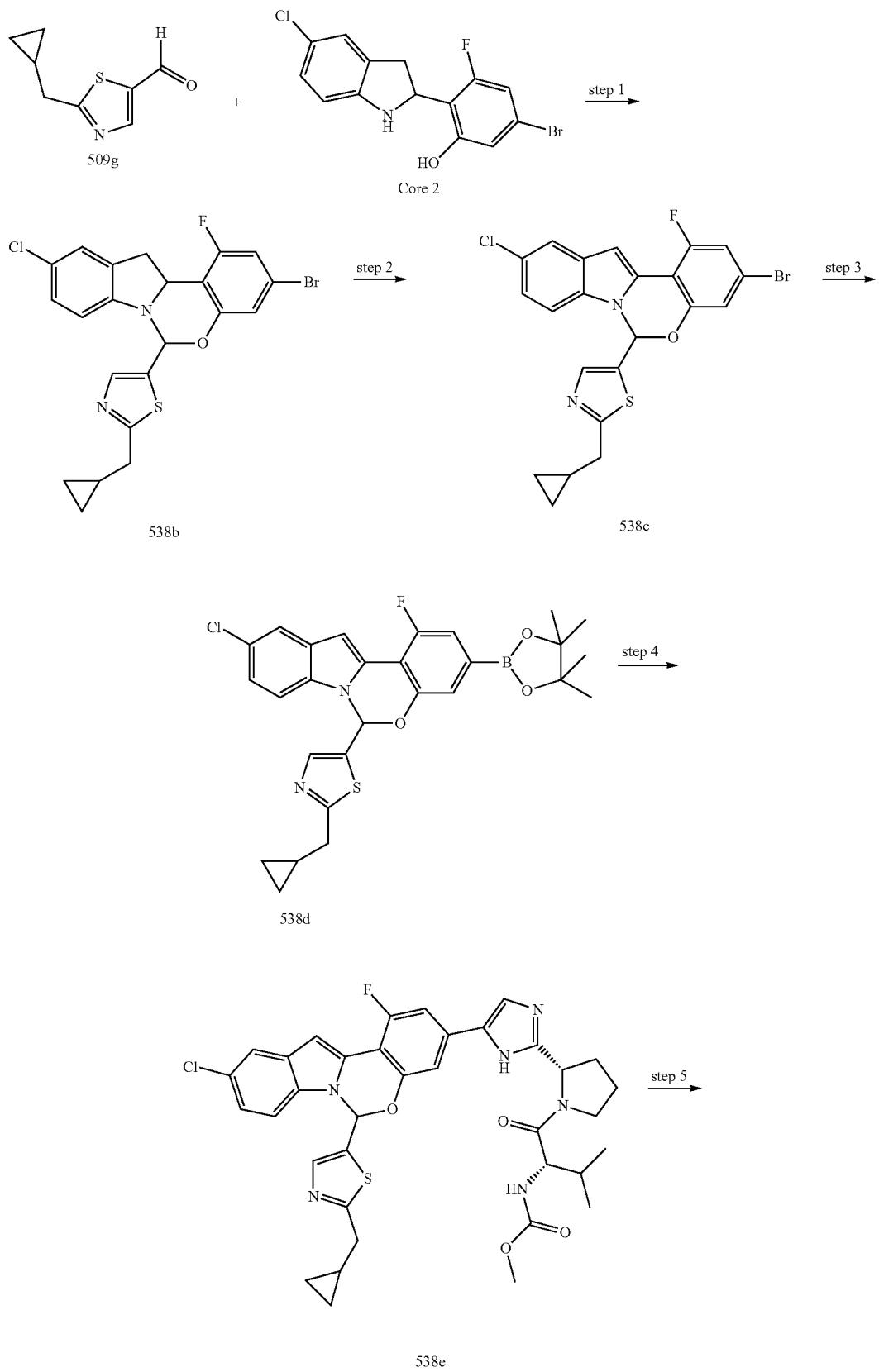

-continued
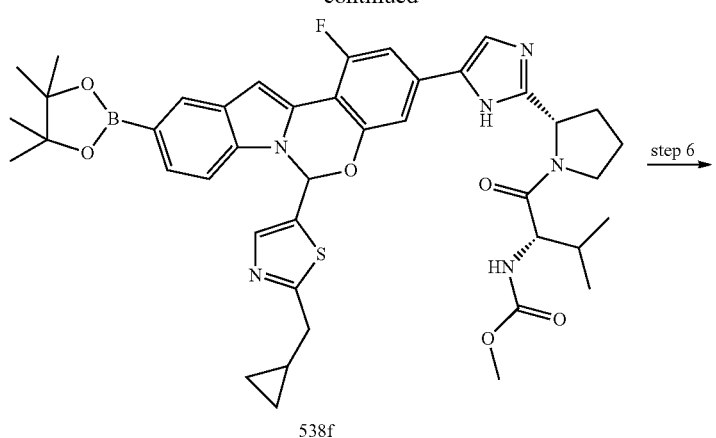
538f
step 6 →
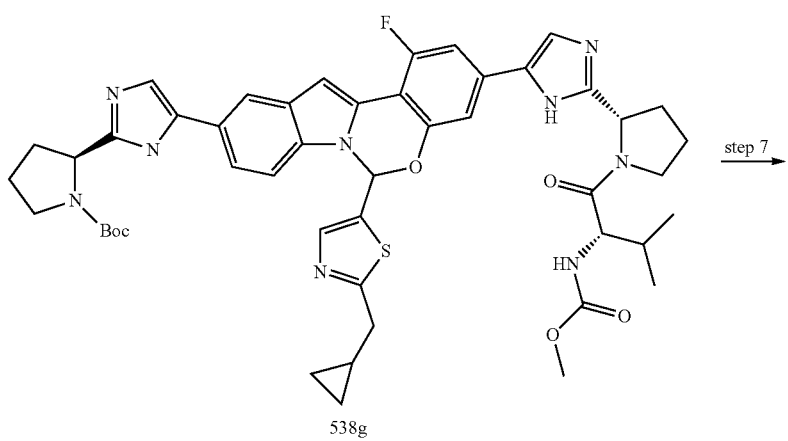
538g
step 7 →
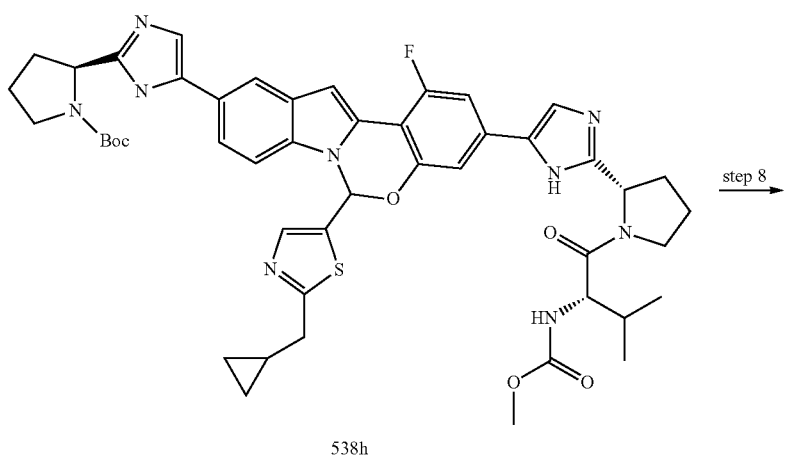
538h
step 8 →

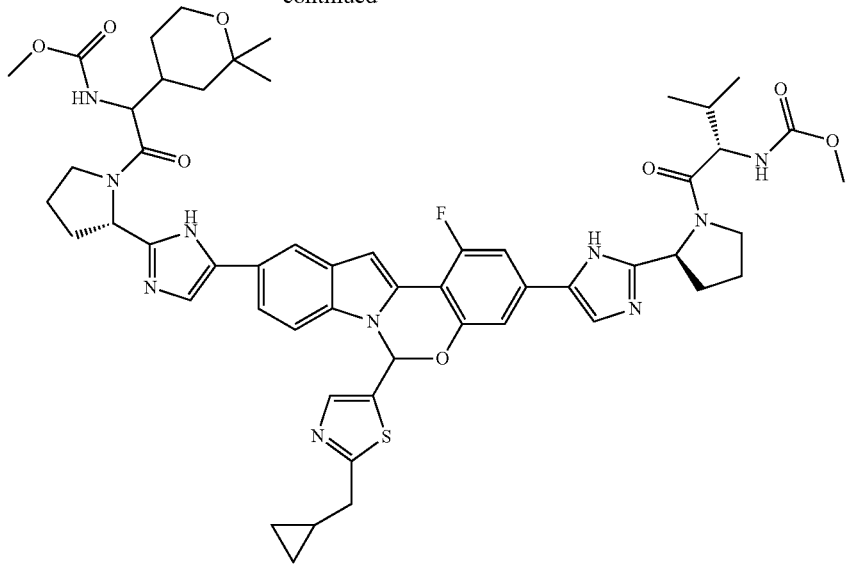

538

Step 1

Compound 509g was prepared in Example 29.

To a mixture of 509g (2 g, 12.2 mmol) and Core 2 (2 g, 6.1 mmol) in anhydrous $CH_3CN$ (20 mL) was added TFA (0.5 mL). The mixture was allowed to stir at room temperature for 12 hours. The reaction mixture became a clear solution and then solid appeared. The solid was collected by filtration and washed with MeOH to provide 538b (2 g, 65.37%).

Step 2

To a solution of 538b (2 g, 4.05 mmol) in dry toluene (20 mL) was added DDQ (1.38 g, 6.07 mmol). After refluxing for 2 hours, the solvent was removed in vacuo and re-dissolved with EtOAc. The organic layer was washed with saturated $Na_2S_2O_3$ solution and brine, dried over $Na_2SO_4$. After filtration and concentration in vacuo, the solid was washed with MeOH and collected to provide 538c (1.2 g, 60.3%).

Step 3

A suspension of 538c (1.2 g, 2.44 mmol), bis(pinacolato)diboron (0.9 g, 3.7 mmol), KOAc (808 mg, 8.2 mmol) and Pd(dppf)$Cl_2$ (121 mg, 0.16 mmol) in dioxane (50 mL) was allowed to stir at 100° C. for 2 hours under $N_2$ atmosphere. The reaction mixture was cooled and concentrated in vacuo, and the resulting residue was purified using flash column chromatography on silica gel, eluting with petroleum ether:ethyl acetate (20/1~5/1) to provide 538d (1.2 g, 91.6%).

Step 4

A suspension of 538d (1.2 g, 2.23 mmol), Cap5 (1.25 g, 3.35 mmol), (0.47 g, 4.46 mmol) and Pd(dppf)$Cl_2$ (327 mg, 0.45 mmol) in THF/DMF/$H_2O$ (v/v=5/1/1, 21 mL) was allowed to stir at 80° C. for about 15 hours under $N_2$ atmosphere. The resulting reaction was then washed with water and extracted with ethyl acetate, washed with brine and dried over anhydrous $Na_2SO_4$. After filtrated, the filtrate was concentrated in vacuo, the resulting residue was purified using flash column chromatography on silica gel, eluting with petroleum ether:ethyl acetate (5/1~1/1) to provide 538e (1.14 g, 74.03%).

Step 5

A suspension of 538e (1.14 g, 1.62 mmol), bis(pinacolato)diboron (0.618 g, 2.43 mmol), KOAc (0.317 g, 3.24 mmol), $Pd_2(dba)_3$ (302 mg, 0.32 mmol) and X-phos (298 mg, 0.65 mmol) in dioxane (15 mL) was allowed to stir at 120° C. for 3 hours under $N_2$ atmosphere. The reaction mixture was cooled and concentrated in vacuo, and the resulting residue was purified using flash column chromatography on silica gel, eluting with petroleum ether:ethyl acetate (1/1~0/1) to provide 538f (1.1 g, 85.27%).

Step 6

A suspension of 538f (1.1 g, 1.38 mmol), Cap 7a (0.664 g, 2.07 mmol), $Na_2CO_3$ (0.293 g, 2.76 mmol) and Pd(dppf)$Cl_2$ (202 mg, 0.276 mmol) in THF/DMF/$H_2O$ (v/v=5/1/1, 21 mL) was allowed to stir at 80° C. for about 15 hours under $N_2$ atmosphere. The resulting reaction was then washed with water and extracted with ethyl acetate, washed with brine and dried over anhydrous $Na_2SO_4$. After filtrated, the filtrate was concentrated in vacuo, the resulting residue was purified using flash column chromatography on silica gel, eluting with ethyl acetate:methanol (100/1~50/1) to provide 538g (0.9 g, 72%).

Step 7

The compound of 538g (900 mg) was separated by SFC by using the following conditions to provide 538h (250 mg, 56%).

Column: Chiralcel OZ-3 150×4.6 mm I.D., 3 um
Solvent: 50% ethanol (0.05% DEA) in $CO_2$
Flow rate: 2.5 mL/min
Wavelength: 270 nm Step 8

To a solution of 538h (250 mg, 0.276 mmol) in 5 mL of dioxane was added 2 mL of HCl-dioxane (2N). The resulting solution was allowed to stir at room temperature for 1 h, LC-MS showed the material was assumed. The solvent was concentrated in vacuo to provide crude 538i (200 mg, 90%).

Step 9

To a mixture of 538i (100 mg, 0.124 mmol), Cap 3 (30 mg, 0.124 mmol) and HATU (47 mg, 0.124 mmol)) in DMF (3 mL) was added DIPEA (80 mg, 0.62 mmol). The resulting mixture was allowed to stir at room temperature for 16 hours before the solution was subjected directly to HPLC to provide 538 (90 mg, 70%).

¹H NMR (MeOD) δ: 7.66 (m, 2 H), 7.33 (m, 1 H), 7.23 (m, 2 H), 7.18 (m, 2 H), 7.06 (m, 2 H), 6.80 (m, 1 H), 5.02 (m, 2 H), 4.44 (s, 3 H), 4.07 (m, 2 H), 3.79-3.72 (m, 8 H), 3.49-3.43 (m, 7 H), 2.54 (m, 3 H), 0.98 (s, 12 H), 0.32 (s, 3 H), 0.00 (s, 3 H). LC/MS: Anal. Calcd. For [M+H]⁺ C54H63FN10O8S: 1031.20. found 1031.8.

The following compounds of the present invention were made using the methods described in the Example above and substituting the appropriate reactants and/or reagents.

| ID | Structures | Isomer info | Observed [M + H]⁺ |
|---|---|---|---|
| 539 | | Isomer 2 | 1031.6 |
| 540 | | Isomer 3 | 1031.6 |
| 541 | | Isomer 4 | 1031.6 |

Example 39

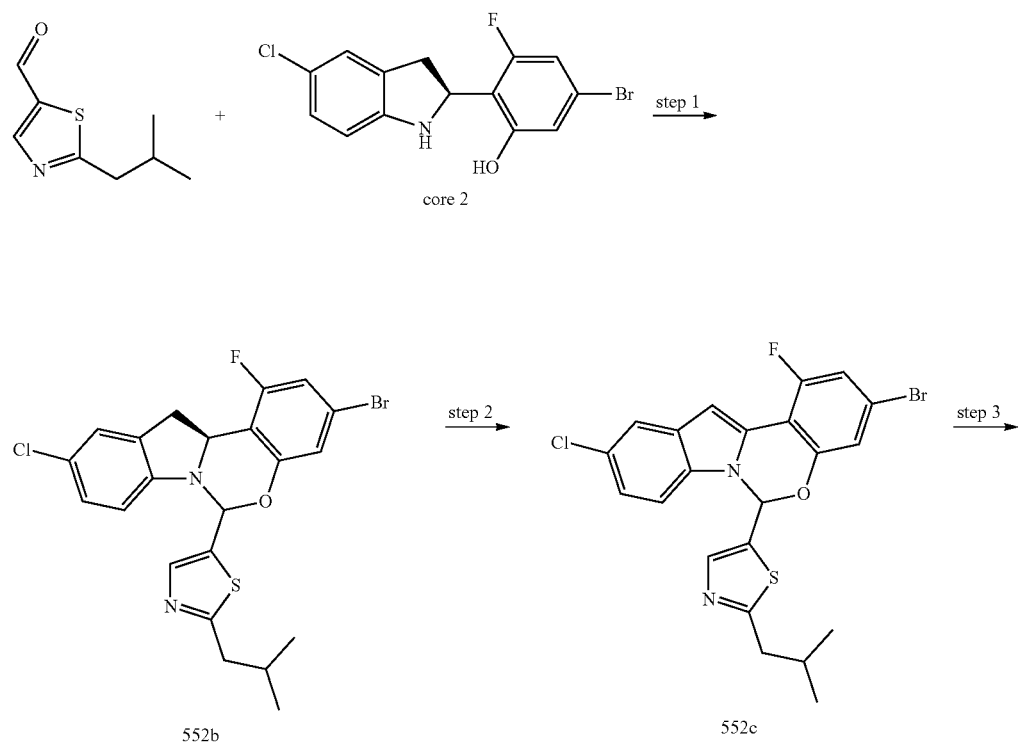

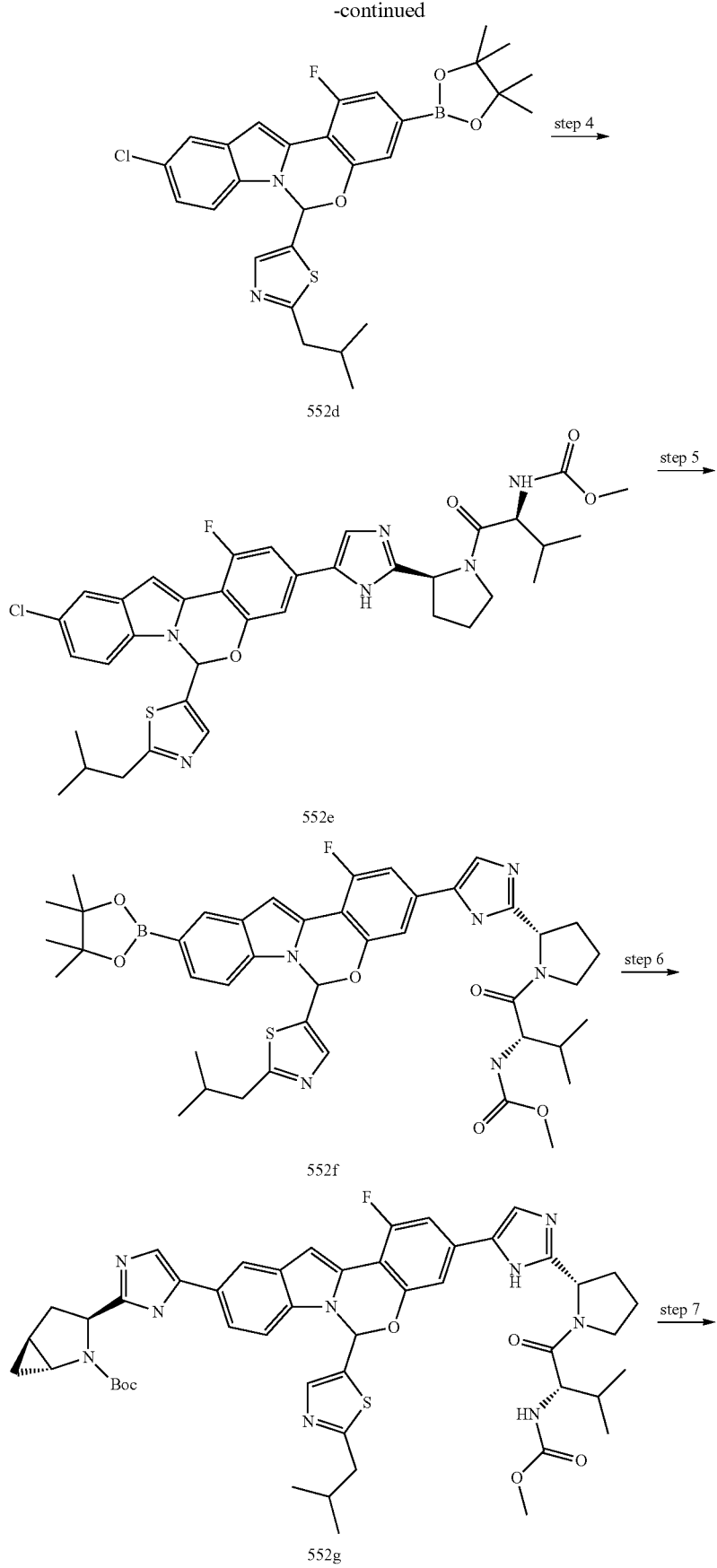

-continued
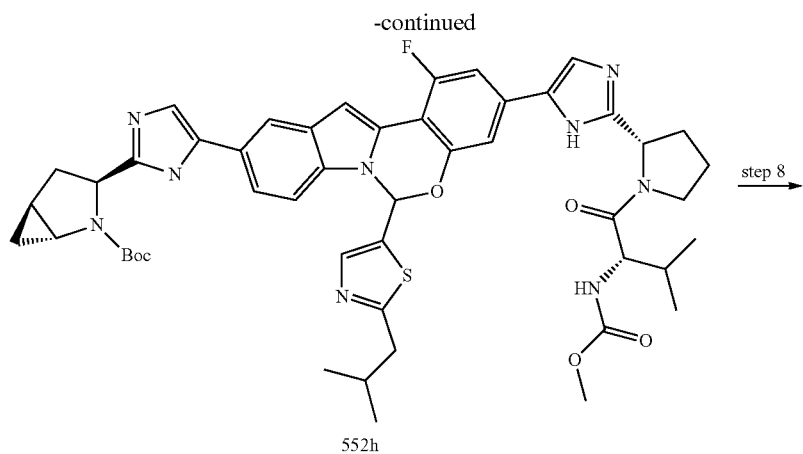
552h
step 8
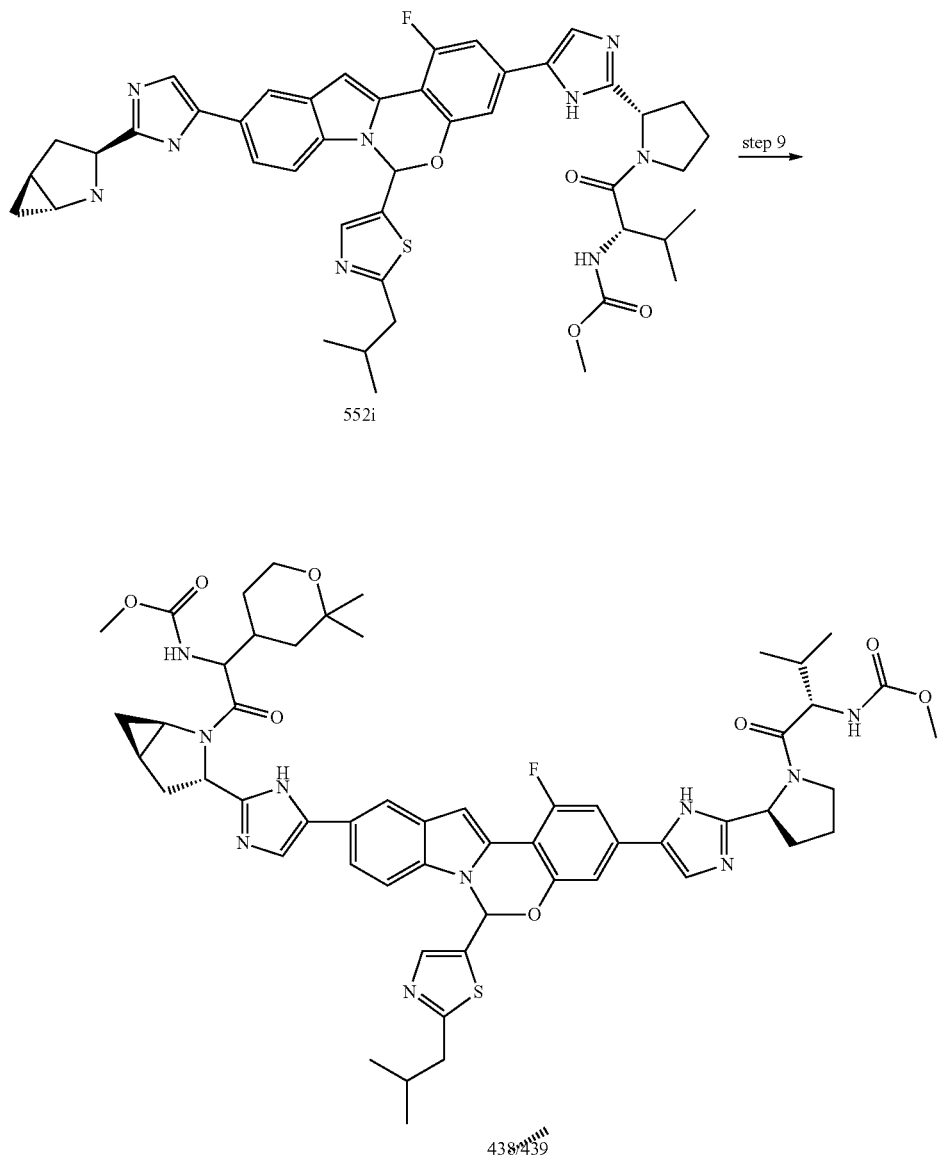
552i
step 9

Step 1

Compound 514b was prepared in Example 30.

To a mixture of 514b (3.4 g, 20.1 mmol) and Core 2 (4.47 g, 13.1 mmol) in anhydrous CH$_3$CN (50 mL) was added TFA (1 mL). The mixture was allowed to stir at room temperature for 12 hours. The reaction mixture became a clear solution and then solid appeared. The solid was collected by filtration and washed with MeOH to provide 552b (4.84 g, 49%).

Step 2

To a solution of 552b (4.84 g, 9.84 mmol) in dry toluene (20 mL) was added DDQ (3.32 g, 14.75 mmol). After refluxing for 2 hours, the solvent was removed in vacuo and re-dissolved with EtOAc. The organic layer was washed with saturated Na$_2$S$_2$O$_3$ solution and brine, dried over Na$_2$SO$_4$. After filtration and concentration in vacuo, the solid was washed with MeOH and collected to provide 552c (3.8 g, 79%).

Step 3

A suspension of 552c (3.8 g, 7.7 mmol), bis(pinacolato)diboron (2.55 g, 10 mmol), KOAc (2.26 g, 23.1 mmol) and Pd(dppf)Cl$_2$ (562 mg, 0.77 mmol) in dioxane (60 mL) was allowed to stir at 100° C. for 2 hours under N$_2$ atmosphere. The reaction mixture was cooled and concentrated in vacuo, and the resulting residue was purified using flash column chromatography on silica gel, eluting with petroleum ether:ethyl acetate (20/1~5/1) to provide 552d (3.3 g, 80%).

Step 4

A suspension of 552d (3.3 g, 6.1 mmol), Cap 5 (2.96 g, 7.97 mmol), Na$_2$CO$_3$ (1.94 g, 18.3 mmol) and Pd(dppf)Cl$_2$ (446 mg, 0.61 mmol) in THF/H$_2$O/DMF (v/v=5/2/1, 48 mL) was allowed to stir at 80° C. for about 15 hours under N$_2$ atmosphere. The resulting reaction was then washed with water and extracted with ethyl acetate, washed with brine and dried over anhydrous Na$_2$SO$_4$. After filtrated, the filtrate was concentrated in vacuo, the resulting residue was purified using flash column chromatography on silica gel, eluting with petroleum ether:ethyl acetate (5/1~1/1) to provide 552e (3.47 g, 81%).

Step 5

A suspension of 552e (3.47 g, 4.94 mmol), bis(pinacolato)diboron (1.63 g, 6.42 mmol), KOAc (1.45 g, 14.82 mmol), X-phos (705 mg, 1.48 mmol) and Pd$_2$dba$_3$ (458 mg, 0.5 mmol) in dioxane (60 mL) was allowed to stir at 120° C. for 3 hours under N$_2$ atmosphere. The reaction mixture was cooled and concentrated in vacuo, and the resulting residue was purified using flash column chromatography on silica gel, eluting with petroleum ether:ethyl acetate (1/1~0/1) to provide 552f (3.2 g, 82%).

Step 6

A suspension of 552f (3.2 g, 4.03 mmol), Cap 6 (1.68 g, 4.83 mmol), Na$_2$CO$_3$ (1.28 g, 12.09 mmol) and Pd(dppf)Cl$_2$ (292 mg, 0.4 mmol) in THF/H$_2$O/DMF (v/v=5/2/1, 64 mL) was allowed to stir at 80° C. for about 15 hours under N$_2$ atmosphere. The resulting reaction was then washed with water and extracted with ethyl acetate, washed with brine and dried over anhydrous Na$_2$SO$_4$. After filtrated, the filtrate was concentrated in vacuo, the resulting residue was purified using flash column chromatography on silica gel, eluting with ethyl acetate:methanol (100/1~50/1) to provide 552g (3.06 g, 83%).

Step 7

Compound 552h was got from compound 552g (3.06 g) by SFC separation by using the following conditions:

Injection Volume: 5;
Co-Solvent: 50% EtOH (0.05% DEA) in CO$_2$;
Column: OZ-H;
Flow rate: 2.0 mL/min
Wavelength: 220 nm Step 8

To a solution of 552h (800 mg, 0.87 mmol) in 5 mL of dioxane was added 2 mL of HCl-dioxane (2N). The resulting solution was allowed to stir at room temperature for 1 h, LC-MS showed the material was assumed. The solvent was concentrated in vacuo to provide crude 552i (709 mg, 100%).

Step 9

To a mixture of 552i (150 mg, 0.18 mmol), Cap 3 (48.5 mg, 0.2 mmol) and HATU (80 mg, 0.2 mmol) in DMF (10 mL) was added DIPEA (0.5 mL). The resulting mixture was allowed to stir at room temperature for 16 hours before the solution was subjected directly to preparative HPLC to provide 438 (56 mg, 30%).

$^1$H NMR (MeOD) δ: 7.99 (s, 2 H), 7.94 (s, 1 H), 7.73 (s, 1 H), 7.56 (s, 2 H), 7.40-7.38 (d, 1 H, J=8.0 Hz), 7.23 (s, 2 H), 7.16 (s, 1 H), 5.20-5.11 (m, 2 H), 4.49-4.47 (m, 1 H), 4.22-4.20 (m, 1 H), 4.07 (s, 1 H), 3.86-3.80 (m, 2 H), 3.65-3.64 (m, 8 H), 2.70-2.68 (m, 3 H), 2.66-2.65 (m, 2 H), 2.25-2.14 (m, 6 H), 2.07-2.05 (m, 1 H), 1.36-1.35 (m, 1 H), 1.27-1.20 (m, 4 H), 0.92-0.90 (m, 4 H), 0.87-0.86 (m, 7 H), 0.82-0.81 (m, 7 H). LC/MS: Anal. Calcd. For [M+H]$^+$ C55H65FN10O8S: 1045.23. found 1045.6.

To a mixture of 552i (150 mg, 0.18 mmol), Cap 4 (48.5 mg, 0.2 mmol) and HATU (80 mg, 0.2 mmol) in DMF (10 mL) was added DIPEA (0.5 mL). The resulting mixture was allowed to stir at room temperature for 16 hours before the solution was subjected directly to HPLC to provide 439 (50 mg, 27%).

$^1$H NMR (MeOD) δ: 7.99 (s, 2 H), 7.92 (s, 1 H), 7.73 (s, 1 H), 7.59 (s, 2 H), 7.56-7.54 (d, 1 H, J=8.0 Hz), 7.41 (s, 1 H), 7.31 (s, 1 H), 7.24 (s, 1 H), 5.21-5.11 (m, 2 H), 4.51-4.49 (m, 1 H), 4.21-4.19 (m, 1 H), 3.86 (s, 1 H), 3.83-3.81 (m, 2 H), 3.65-3.63 (m, 8 H), 2.71-2.69 (m, 3 H), 2.66-2.65 (m, 2 H), 2.25-2.14 (m, 6 H), 2.04-1.89 (m, 1 H), 1.39-1.35 (m, 1 H), 1.19-1.17 (m, 2 H), 0.92-0.90 (m, 8 H), 0.88-0.86 (m, 7 H), 0.83-0.81 (m, 7 H). LC/MS: Anal. Calcd. For [M+H]$^+$ C55H65FN10O8S: 1045.23. found 1045.8.

The following compounds of the present invention were made using the methods described in the Example above and substituting the appropriate reactants and/or reagents.

| ID | Structures | Isomer info | Observed [M + H]+ |
|---|---|---|---|
| 436 437 | | Isomer 3 Isomer 4 | 1045.8 1045.8 |
Example 40
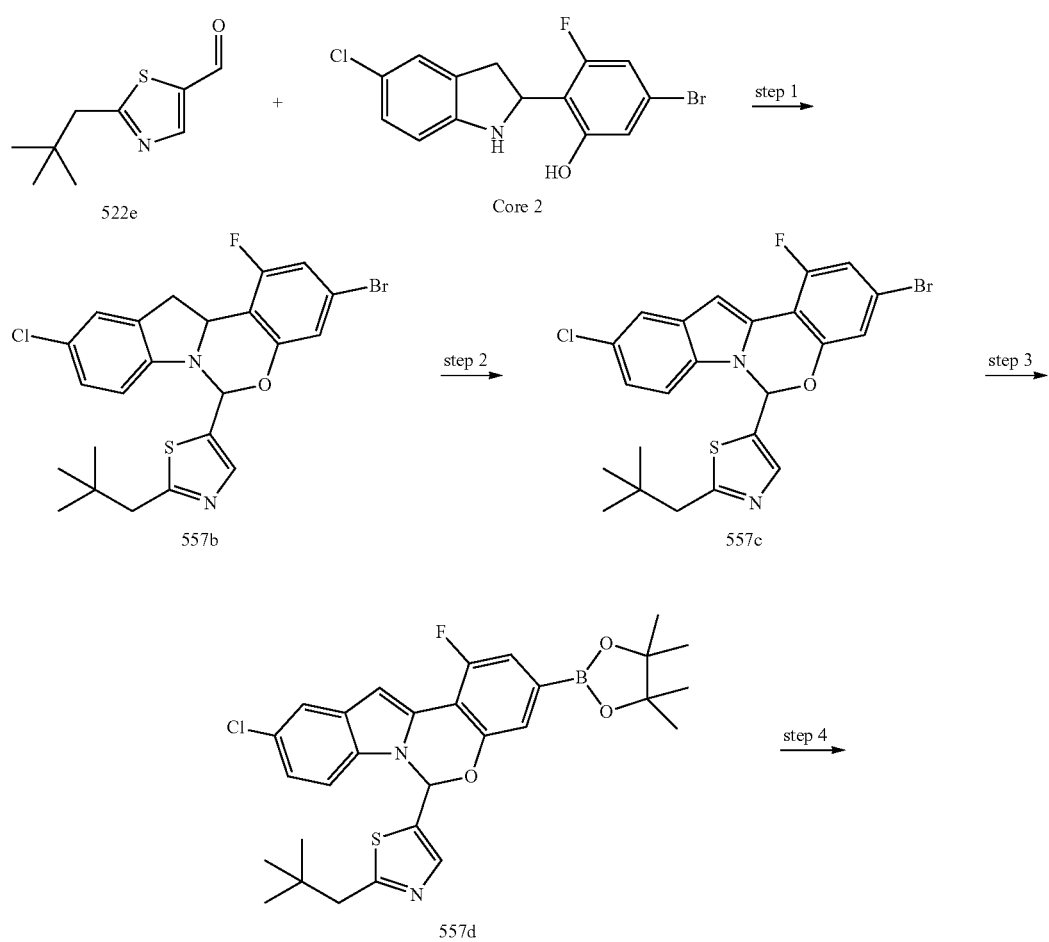

-continued
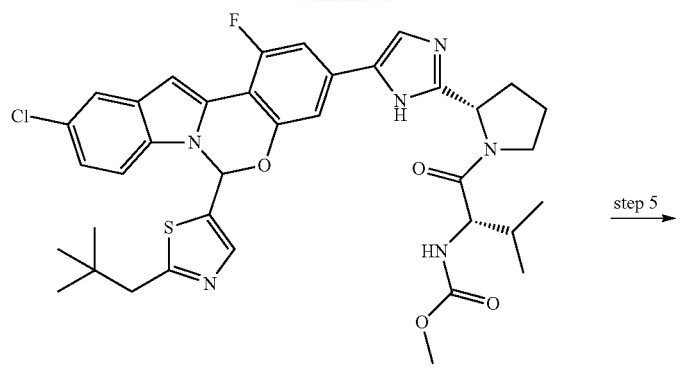
557e
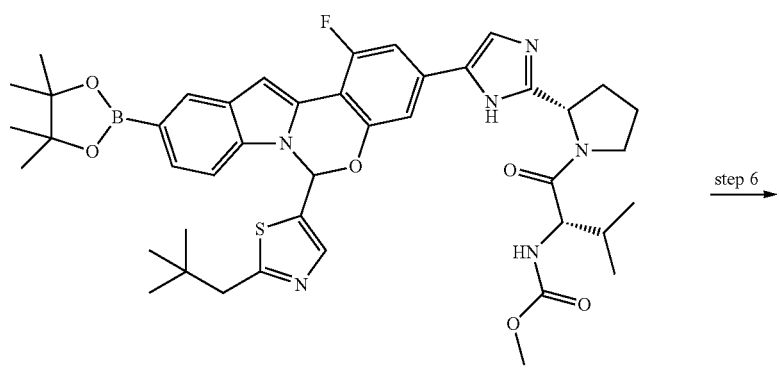
557f
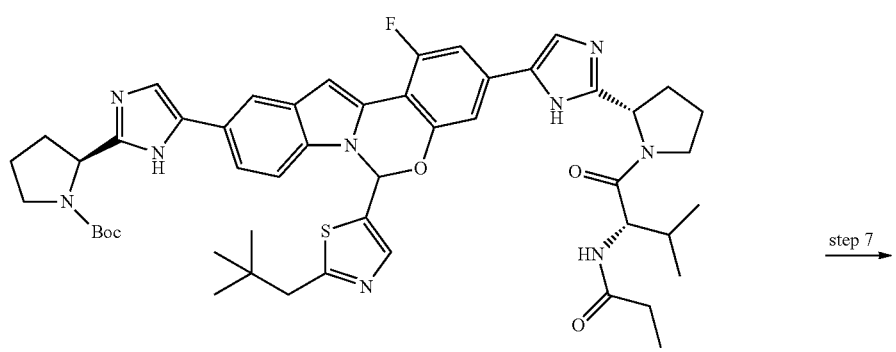
557g
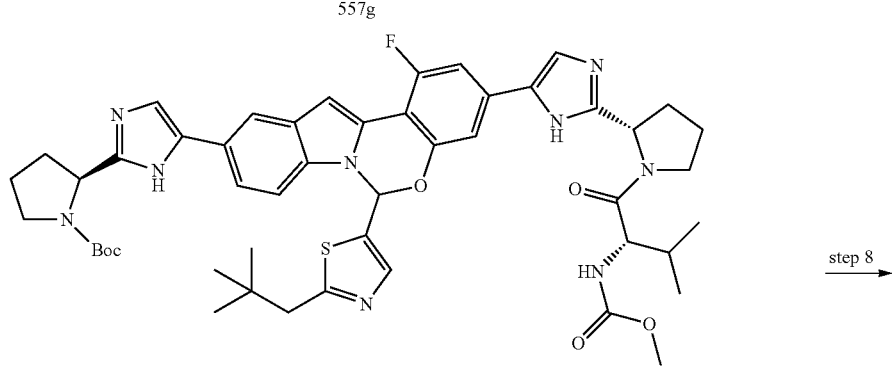
557h

-continued

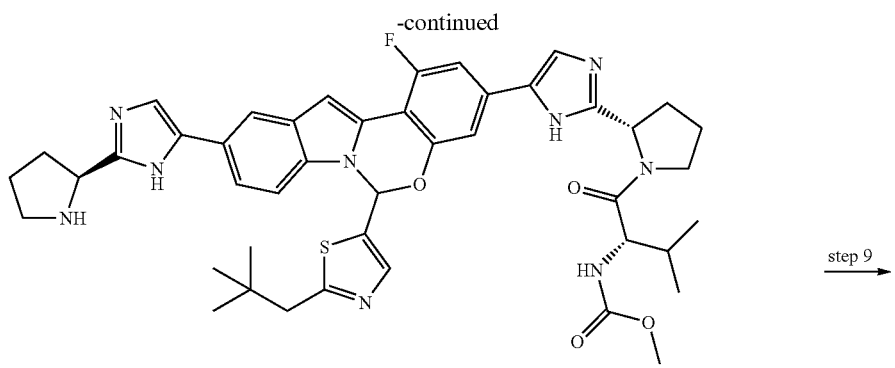

557i

→ step 9

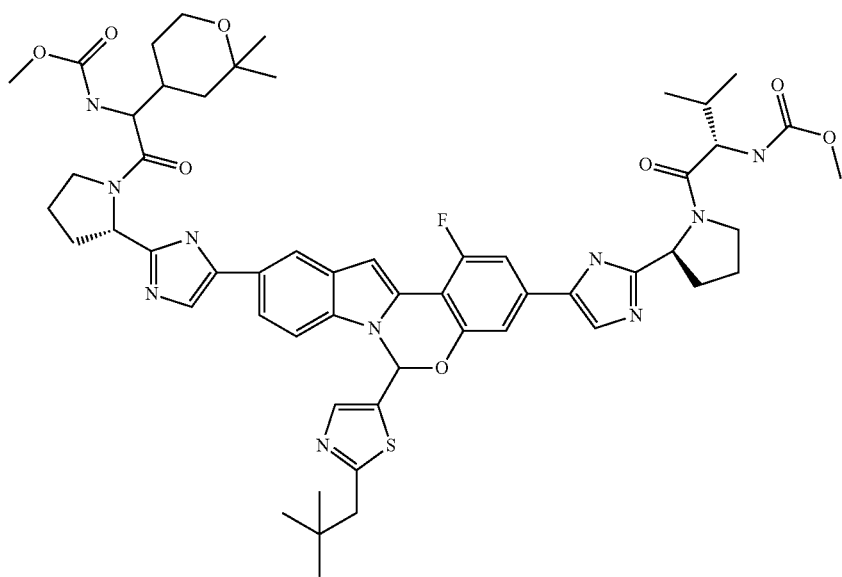

443

Step 1

Compound 522e was prepared in Example 32.

To a mixture of 522e (2.1 g, 11.4 mmol) and Core 2 (3.3 g, 10 mmol) in anhydrous $CH_3CN$ (50 mL) was added TFA (1 mL). The mixture was allowed to stir at room temperature for 12 hours. The reaction mixture became a clear solution and then solid appeared. The solid was collected by filtration and washed with MeOH to provide 557b (2.9 g, 58%).

Step 2

To a solution of 557b (2.9 g, 5.7 mmol) in dry toluene (30 mL) was added DDQ (1.9 g, 8.6 mmol). After refluxing for 2 hours, the solvent was removed in vacuo and re-dissolved with EtOAc. The organic layer was washed with saturated $Na_2S_2O_3$ solution and brine, dried over $Na_2SO_4$. After filtration and concentration in vacuo, the solid was washed with MeOH and collected to provide 557c (1.7 g, 61% yield).

Step 3

A suspension of 557c (1.7 g, 3.3 mmol), bis(pinacolato) diboron (0.9 g, 3.7 mmol), KOAc (808 mg, 8.2 mmol) and $Pd(dppf)Cl_2$ (121 mg, 0.16 mmol) in dioxane (50 mL) was allowed to stir at 100° C. for 2 hours under $N_2$ atmosphere. The reaction mixture was cooled and concentrated in vacuo, and the resulting residue was purified using flash column chromatography on silica gel, eluting with petroleum ether: ethyl acetate (20/1~5/1) to provide 557d (1.2 g, 67%).

Step 4

A suspension of 557d (1.2 g, 2.1 mmol), Cap 5 (892 mg, 2.4 mmol), $Na_2CO_3$ (557 mg, 5.3 mmol) and $Pd(dppf)Cl_2$ (77 mg, 0.105 mmol) in $THF/H_2O/DMF$ (v/v=5/2/1, 30 mL) was allowed to stir at 80° C. for about 15 hours under $N_2$ atmosphere. The resulting reaction was then washed with water and extracted with ethyl acetate, washed with brine and dried over anhydrous $Na_2SO_4$. After filtrated, the filtrate was concentrated in vacuo, the resulting residue was purified using flash column chromatography on silica gel, eluting with petroleum ether:ethyl acetate (5/1~1/1) to provide 557e (3.47 g, 81%).

Step 5

A suspension of 557e (800 mg, 1.1 mmol), bis(pinacolato)diboron (330 mg, 1.3 mmol), KOAc (270 mg, 2.7 mmol), X-phos (52 mg, 0.11 mmol) and $Pd_2dba_3$ (57 mg, 0.05 mmol) in dioxane (60 mL) was allowed to stir at 120° C. for 3 hours under $N_2$ atmosphere. The reaction mixture was cooled and concentrated in vacuo, and the resulting residue was purified using flash column chromatography on silica gel, eluting with petroleum ether:ethyl acetate (1/1~0/1) to provide 557f (0.68 g, 76%).

Step 6

A suspension of 557f (680 mg, 0.84 mmol), Cap 7a (291 mg, 0.92 mmol), $Na_2CO_3$ (218 mg, 2.1 mmol) and Pd(dppf)$Cl_2$ (31 mg, 0.04 mmol) in $THF/H_2O/DMF$ (v/v=5/2/1, 30 mL) was allowed to stir at 80° C. for about 15 hours under $N_2$ atmosphere. The resulting reaction was then washed with water and extracted with ethyl acetate, washed with brine and dried over anhydrous $Na_2SO_4$. After filtrated, the filtrate was concentrated in vacuo, the resulting residue was purified using flash column chromatography on silica gel, eluting with ethyl acetate:methanol (100/1~50/1) to provide 557g (460 mg, 60%).

Step 7

The compound of 557g (460 mg) was separated by SFC by using the following conditions to provide 557h (170 mg, 74%).

Column: Chiralcel OZ-3 150×4.6 mm I.D., 3 um
Mobile phase: 50% of methanol (0.05% DEA) in $CO_2$
Flow rate: 2.0 mL/min
Wavelength: 254 nm Step 8

To a solution of 557h (170 mg, 0.18 mmol) in 5 mL of dioxane was added 2 mL of HCl-dioxane (2N). The resulting solution was allowed to stir at room temperature for 1 h, LC-MS showed the material was assumed. The solvent was concentrated in vacuo to provide crude 557i (144 mg, 97%).

Step 9

To a mixture of 557i (144 mg, 0.17 mmol), Cap 3 (48.5 mg, 0.2 mmol) and HATU (80 mg, 0.2 mmol) in DMF (10 mL) was added DIPEA (0.5 mL). The resulting mixture was allowed to stir at room temperature for 16 hours before the solution was subjected directly to HPLC to provide 443 (90 mg, 51%).

$^1$H NMR (MeOD) δ: 8.13 (d, J=3.1 Hz, 2H), 8.02 (s, 1H), 7.84 (s, 1H), 7.65 (s, 2H), 7.50-7.41 (m, 3H), 7.27 (d, J=2.7 Hz, 1H), 5.28-5.18 (m, 2H), 4.22 (d, J=7.4 Hz, 2H), 4.11 (br. s., 2H), 4.01-3.84 (m, 3H), 3.73-3.60 (m, 7H), 2.84 (s, 2H), 2.56 (d, J=8.6 Hz, 2H), 2.27 (d, J=10.2 Hz, 2H), 2.23-2.12 (m, 4H), 2.06 (dd, J=6.8, 13.5 Hz, 2H), 1.23 (d, J=7.0 Hz, 4H), 1.10 (d, J=9.0 Hz, 6H), 0.95-0.85 (m, 15H)

LC/MS: Anal. Calcd. For [1/2M+H]$^+$ C55H67FN10O8S: 1047.25. found 1047.6.

The following compounds of the present invention were made using the methods described in the Example above and substituting the appropriate reactants and/or reagents.

| ID | Structures | Isomer info | Observed [M + H]$^+$ |
|---|---|---|---|
| 542 | 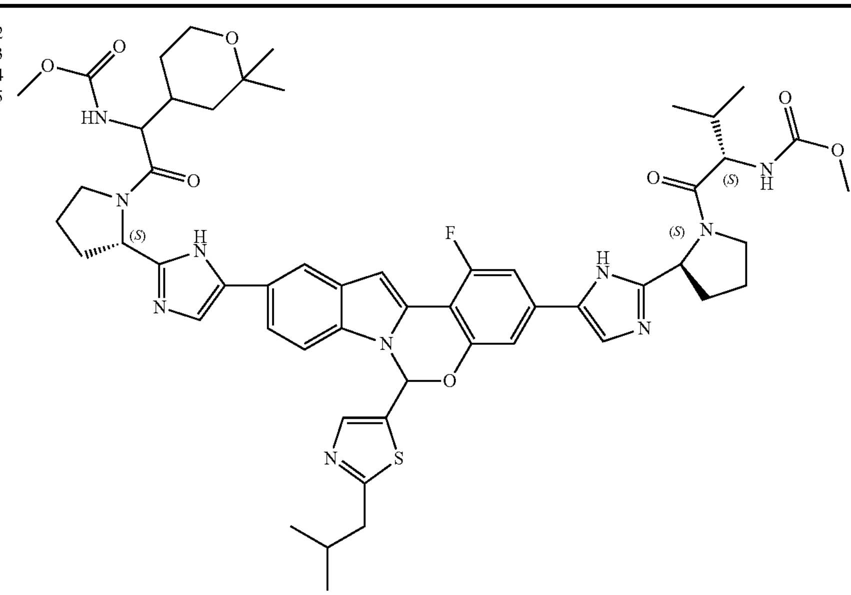 | Isomer 1 | 1033.8 |
| 543 | | Isomer 2 | 1033.6 |
| 544 | | Isomer 3 | 1033.4 |
| 545 | | Isomer 4 | 1033.6 |

-continued
| ID | Structures | Isomer info | Observed [M + H]+ |
|---|---|---|---|
| 546 547 | 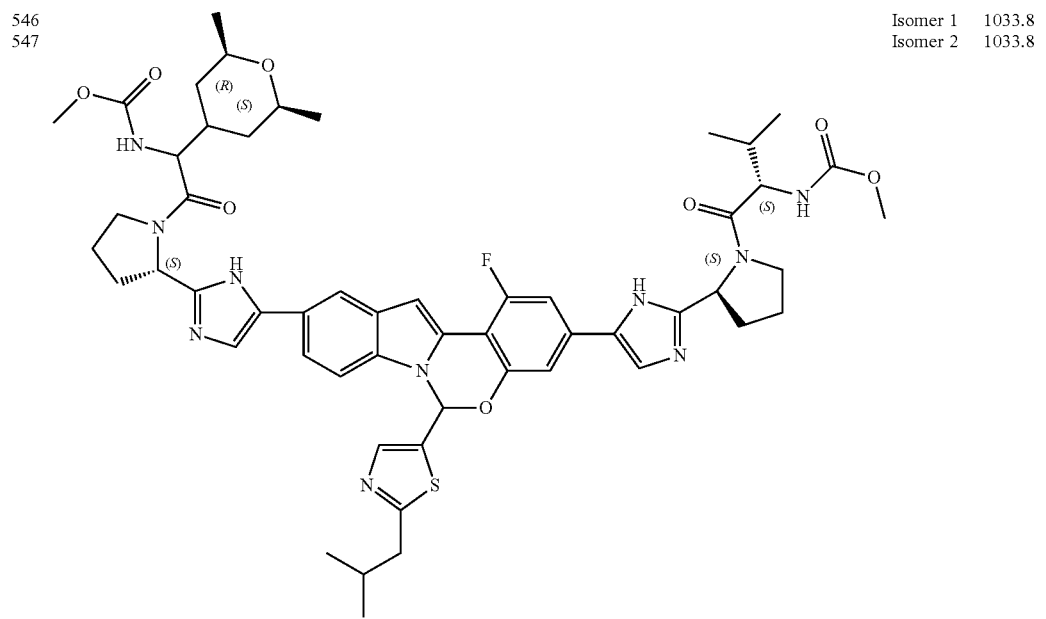 | Isomer 1 Isomer 2 | 1033.8 1033.8 |
| 434 435 | 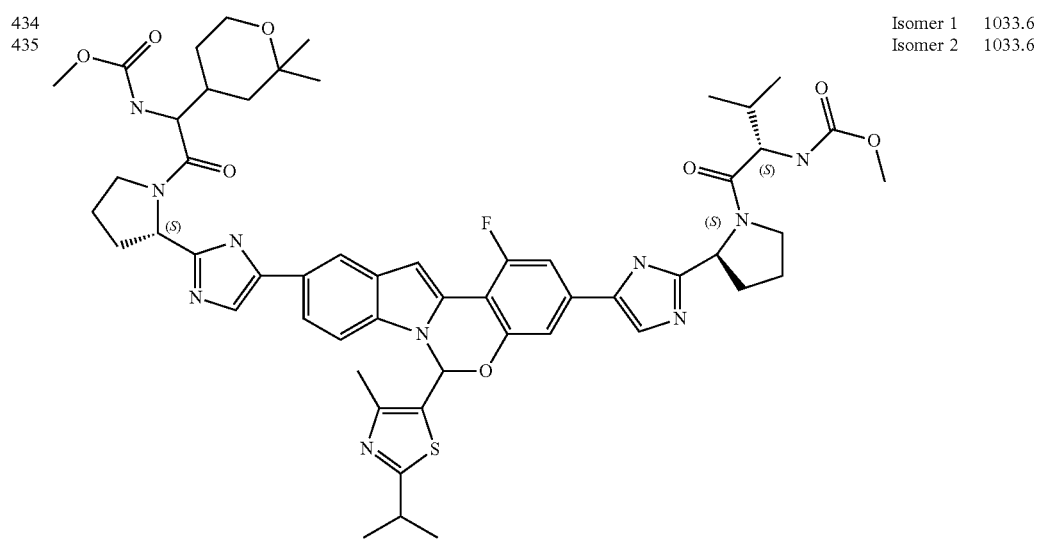 | Isomer 1 Isomer 2 | 1033.6 1033.6 |

| ID | Structures | Isomer info | Observed [M + H]+ |
|---|---|---|---|
| 440 441 | | Isomer 1 Isomer 2 | 1045.6 1045.8 |
| 442 443 | | Isomer 1 Isomer 2 | 1047.4 1047.6 |

| ID | Structures | Isomer info | Observed [M + H]+ |
|---|---|---|---|
| 444 445 | | Isomer 1 Isomer 2 | 1047.6 1047.6 |
| 446 447 | | Isomer 1 Isome 2 | 1059.8 1059.6 |

| ID | Structures | Isomer info | Observed [M + H]+ |
|---|---|---|---|
| 448 449 | | Isomer 1 Isomer 2 | 1061.8 1061.6 |
| 452 453 | | Isomer 1 Isomer 2 | 973.6 973.8 |

-continued

| ID | Structures | Isomer info | Observed [M + H]+ |
|---|---|---|---|
| 454 455 | | Isomer 1 Isomer 2 | 1001.6 1001.8 |
| 457 458 459 460 | | Isomer 1 Isomer 2 Isomer 3 Isomer 4 | 1031.8 1031.6 1031.8 1031.6 |

| ID | Structures | Isomer info | Observed [M + H]+ |
|---|---|---|---|
| 461 462 | | Isomer 1 Isomer 2 | 1031.6 1031.8 |
| 463 464 | | Isomer 1 Isomer 2 | 1043.8 1043.8 |

-continued

| ID | Structures | Isomer info | Observed [M + H]+ |
|---|---|---|---|
| 465 466 467 468 | | Isomer 1 Isomer 2 Isomer 3 Isomer 4 | 1043.6 1043.8 1043.6 1043.8 |
| 469 470 | | Isomer 1 Isomer 2 | 1059.6 1059.8 |

| ID | Structures | Isomer info | Observed [M + H]+ |
|---|---|---|---|
| 471
472 | | Isomer 1
Isomer 2 | 1059.8
1059.8 |
| 473
474 | | Isomer 1
Isomer 2 | 1071.8
1071.6 |

-continued

| ID | Structures | Isomer info | Observed [M + H]+ |
|---|---|---|---|
| 475 | | Isomer 1 | 1071.6 |
| 476 | | Isomer 3 | 1071.8 |
| 477 | | Isomer 2 | 1071.6 |

Example 41

Cell-Based HCV Replicon Assays

To measure cell-based anti-HCV activity of compounds of the present invention, two complimentary assays were employed using various replicons. In the first assay ("Replicon Assay A"), replicon cells were seeded at 2000 cells/well in 384-well 384-well flat bottom tissue culture treated clear bottom plate (Corning 3707) in the presence of the test compound. Various concentrations of test compound, typically in 10 serial dilutions, were added to the assay mixture, with the starting concentration ranging from 333.3 nM to 1.667 nM. The final concentration of DMSO was 0.5%. Fetal bovine serum was 5%, in the assay media. Cells were harvested on day 3 by removing media and washing the cells with a suitable wash buffer. The cells are lysed with the addition of 1× Qiagen lysis buffer (Cat #1062731). The replicon RNA level was measured using real time PCR (TaqMan® EZ RT-PCR, Applied Biosystems 403028) with the following primers and probes:

```
Neo Forward: CCG GCT ACC TGC CCA TTC

Neo Reverse: CCA GAT CAT CCT GAT CGA CAA G

Neo Probe: FAM-ACA TCG CAT CGA GCG AGC ACG TAC-
Tamra

Cyc probe: 5'-JOE-CGCGTCTCCTTTGAGCTGTTTGCA-
Tamra-3'

Cyc Forward Primer: ACGGCGAGCCCTTGG

Cyc Reverse Primer: TTTCTGCTGTCTTTGGGACCT
```

Cyclophilin RNA was used as endogenous control and was amplified in the same reaction as NS5B (multiplex PCR). The real-time RT-PCR reactions were run on ABI PRISM 7900HT Sequence Detection System using the following program: 50° C. for 2 minutes, 60° C. for 30 minutes, 95° C. for 5 minutes, 40 cycles of 94° C. for 20 sec, 55° C. for 1 minutes.

The amount of HCV replicon RNA per cell is quantified using a linear regression curve for a known nanogram (ng) amount of HCV replicon total RNA. This is established by plotting the Cycle Threshold values (Ct) from the Neo probe and primer set versus the log (ng) for each HCV replicon total RNA standard. The amount of HCV RNA for each replicon sample is calculated by taking the sample's Ct value, minus the line intercept, divided by the slope of the line. Similarly, the amount of Cyclophilin mRNA per cell is also quantified using a linear regression curve for a known nanogram (ng) amount of HCV replicon total RNA. Again, this is established by plotting the Cycle Threshold values (Ct) from the Cyclophilin probe and primer set versus the log (ng) for each HCV replicon total RNA standard.

In an alternate assay ("Replicon Assay B"), 1000 cells were seeded per well in a 384-well collagen coated black plate from Greiner bio-one (Cat #781946) in 5% FBS. Inhibitors of this invention were added at 24 h post-seeding, and the plates were incubated for 3 days. Cells were subsequently lysed with Qiagen lysis buffer (Cat #1062731) to extract the RNA. HCV replicon RNA level was measured by real-time PCR using the RNA-to-CT kit from Applied Biosystem (Cat #4392656) and genotype-specific primers and probes. The amplicon was located within NS5B. The sequence of the PCR primers are as follows: 5B.2F, ATGGACAGGCGCCCTGA (SEQ. ID NO. 1); 5B.2R, TTGATGGGCAGCTTGGTTTC (SEQ. ID NO. 2); the probe sequence was FAM-labeled CACGCCATGCGCT-GCGG (SEQ. ID NO. 3). To detect genotype 1A the primer 1A F, TGCGGAACCGGTGAGTACA and 1A R, GCGGGTTTATCCAAGAAAGGA were used; the probe sequence was FAM-CGGAATTGCCAGGACGACCGG.

The real-time RT-PCR reactions were run on ABI PRISM 7900HT or Viia7 Sequence Detection System using the following program: 48° C. for 30 minutes, 95° C. for 10 minutes, 40 cycles of 95° C. for 15 sec, 60° C. for 1 minutes. The 50% effective concentration ($EC_{50}$) was the drug concentration necessary to achieve an increase in the cycle threshold ($C_T$) of 1 over the projected baseline $C_T$. The $EC_{90}$ was the drug concentration necessary to achieve an increase in $C_T$ of 3.2 over the projected baseline $C_T$.

Data was obtained for various compounds of the present invention using the methods described in the Example above, and is presented in the table immediately below. Data for replicons 1A, 1AY93H and 2B were obtained using Replicon Assay A and data for replicons 1AQ30D and 1B were obtained using Replicon Assay B.

| ID | 1A IC50 (nM) | 1A Y93H IC50 (nM) | 1A Q30D IC50 (nM) | 1B IC50 (nM) | 2B IC50 (nM) |
|---|---|---|---|---|---|
| 1 | | | | | 0.88 |
| 2 | 0.0035 | 6.95 | 38.30 | 0.030 | 2.31 |
| 3 | 0.0015 | 0.048 | 1.052 | 0.002 | 0.14 |
| 4 | 0.0009 | 1.39 | | | 0.98 |
| 5 | | | | | 3.062 |
| 6 | | | | | 1.75 |
| 7 | 0.0014 | 4.23 | | | 2.14 |
| 8 | 0.0017 | 0.15 | | | 0.14 |
| 9 | 0.0016 | 0.86 | | | 1.56 |
| 10 | 0.0014 | 0.0035 | 0.097 | 0.002 | 0.011 |
| 11 | 0.0009 | 14.39 | | | 6.061 |
| 12 | 0.0009 | 0.18 | | | 2.210 |
| 13 | 0.0011 | 0.6211 | | | 0.446 |
| 14 | 0.0014 | 0.0034 | 0.115 | 0.002 | 0.015 |
| 15 | 0.0029 | 0.0059 | 0.118 | 0.003 | 0.025 |
| 16 | 0.0017 | 0.0830 | | 0.001 | 0.284 |
| 17 | 0.0012 | 1.0060 | | 0.002 | 0.528 |
| 18 | 0.0009 | 0.0069 | 0.072 | 0.001 | 0.016 |
| 19 | 0.0008 | 1.235 | | | 0.933 |
| 20 | 0.0015 | 0.0083 | 0.010 | 0.001 | 0.008 |
| 21 | 0.0008 | 0.0177 | 0.494 | 0.004 | 0.012 |
| 22 | 0.0009 | 0.8604 | | | 0.440 |
| 25 | 0.0025 | 0.0025 | 0.070 | 0.001 | 0.014 |
| 26 | 0.0009 | 0.1256 | | | 0.449 |
| 27 | 0.0016 | 0.0037 | 0.020 | 0.002 | 0.009 |
| 28 | 0.0012 | 0.1146 | 0.908 | 0.002 | 0.204 |
| 29 | 0.0020 | 1.094 | | | 0.192 |
| 30 | 0.0028 | 0.0118 | 0.112 | 0.003 | 0.014 |
| 31 | 0.0012 | 0.0063 | 0.046 | 0.001 | 0.004 |
| 32 | 0.0012 | 0.3444 | | | 0.231 |
| 33 | 0.0017 | 1.1790 | 1.667 | 0.001 | 0.746 |
| 34 | 0.0022 | 0.0331 | 0.144 | 0.001 | 0.022 |
| 35 | 0.0026 | 0.1608 | | | 0.125 |
| 36 | 0.0025 | 0.0040 | 0.038 | 0.003 | 0.005 |
| 37 | 0.0022 | 0.2566 | | | 0.226 |
| 38 | 0.0029 | 0.2042 | | | |
| 39 | 0.0037 | 0.0112 | | | 0.004 |
| 40 | 0.0035 | 0.0039 | 0.030 | 0.003 | 0.006 |
| 41 | 0.0017 | 0.1255 | 1.012 | 0.002 | 0.040 |
| 42 | 0.0016 | 0.0141 | 0.123 | 0.002 | 0.017 |
| 43 | 0.0023 | 0.0081 | 0.077 | 0.002 | 0.004 |
| 44 | 0.0008 | 0.1035 | 0.778 | 0.002 | 0.054 |
| 45 | 0.0018 | 0.0060 | 0.072 | 0.001 | 0.011 |
| 46 | 0.0018 | 0.5336 | | 0.001 | 0.252 |
| 47 | 0.0020 | 1.124 | 2.187 | 0.003 | 0.058 |
| 48 | 0.0015 | 0.0538 | 0.310 | 0.002 | 0.016 |
| 49 | 0.0010 | 0.0010 | 0.029 | 0.002 | 0.002 |
| 50 | 0.0007 | 0.1189 | 1.223 | 0.001 | 0.158 |
| 51 | 0.0022 | 0.0223 | 0.152 | 0.003 | 0.025 |
| 52 | 0.0023 | 0.7008 | | | 0.203 |
| 53 | 0.0016 | 0.0022 | 0.070 | 0.001 | 0.004 |
| 54 | 0.0013 | 0.4288 | | | 0.248 |
| 55 | 0.0012 | 0.0021 | | | 0.003 |
| 56 | 0.0011 | 0.2851 | | | 0.104 |
| 57 | 0.0016 | 0.0020 | 0.028 | 0.001 | 0.005 |
| 58 | 0.0026 | 0.0086 | | | 0.003 |
| 59 | 0.0026 | 0.1319 | 0.762 | 0.003 | 0.133 |
| 60 | 0.004 | 0.40 | | 0.004 | 0.184 |
| 61 | 0.0033 | 0.012 | 0.070 | 0.0017 | 0.006 |
| 62 | 0.0018 | 0.2124 | | | 0.427 |
| 63 | 0.0483 | 0.254 | | | 1.667 |
| 64 | 0.0012 | 0.1593 | | | 0.268 |
| 65 | 0.0021 | 0.0081 | 0.095 | 0.003 | 0.044 |
| 66 | 0.0023 | 0.0021 | 0.018 | 0.002 | 0.003 |
| 67 | 0.0020 | 0.2248 | 1.390 | 0.002 | 0.056 |
| 68 | 0.0014 | 0.0996 | | | 0.253 |
| 69 | 0.0424 | 2.8680 | | | |
| 70 | 0.0024 | 0.0038 | 0.034 | 0.002 | 0.005 |
| 71 | 0.0015 | 0.1241 | | 0.002 | 0.041 |
| 72 | 0.0029 | 0.006 | 0.099 | 0.0024 | 0.005 |
| 73 | 0.0057 | 0.5860 | | 0.005 | 0.146 |
| 74 | 0.0036 | 0.0053 | 0.021 | 0.004 | 0.005 |
| 75 | 0.0022 | 0.8748 | | | 0.491 |
| 76 | 0.0027 | 0.0322 | 0.422 | 0.003 | 0.141 |
| 77 | 0.0035 | 0.0056 | 0.053 | 0.001 | 0.005 |
| 78 | 0.0014 | 0.1653 | 1.859 | 0.001 | 0.193 |
| 79 | | 0.0041 | | | 0.002 |
| 80 | 0.0015 | 0.0504 | | | 0.047 |
| 81 | 0.0027 | 0.0190 | 0.384 | 0.002 | 0.027 |
| 82 | 0.0023 | 1.5830 | | | 1.099 |
| 83 | 0.0030 | 0.0067 | 0.120 | 0.003 | 0.048 |
| 84 | 0.0037 | 0.0708 | | | 0.425 |
| 85 | 0.0014 | | | | 1.079 |
| 86 | 0.0008 | 0.0063 | 0.187 | 0.002 | 0.028 |
| 87 | 0.0025 | 0.0714 | 0.068 | 0.864 | 0.003 |
| 88 | 0.0028 | | 0.415 | | |
| 89 | 0.0017 | 0.0028 | 0.081 | 0.003 | 0.029 |
| 90 | 0.0025 | 0.0038 | 0.090 | 0.003 | 0.018 |
| 91 | 0.0021 | 0.0537 | | | 0.170 |
| 92 | 0.0037 | 0.0045 | 0.064 | 0.006 | 0.005 |
| 93 | 0.0036 | 0.0426 | 0.631 | 0.003 | 0.069 |
| 94 | 0.0030 | 0.0035 | 0.045 | 0.003 | 0.004 |
| 95 | 0.0029 | 0.0369 | 0.328 | 0.005 | 0.085 |
| 96 | 0.0024 | 0.0037 | 0.020 | 0.003 | 0.006 |
| 97 | 0.0025 | 0.0278 | 0.287 | 0.003 | 0.098 |
| 98 | 0.0027 | 0.010 | | 0.0012 | 0.003 |
| 99 | 0.0016 | 0.26 | | | 0.10 |
| 102 | 0.0021 | 0.0069 | 0.040 | | |
| 103 | 0.0025 | 0.1937 | 0.260 | | |
| 104 | 0.0028 | 0.0041 | 0.028 | 0.003 | 0.004 |
| 105 | 0.0022 | 0.0029 | 0.017 | 0.004 | 0.004 |
| 106 | 0.0032 | 0.0336 | 0.284 | 0.005 | 0.067 |
| 107 | 0.0026 | 0.0292 | 0.233 | 0.004 | 0.017 |
| 108 | 0.0028 | 0.0033 | 0.016 | 0.004 | 0.007 |
| 109 | 0.0034 | 0.0303 | 0.176 | 0.004 | 0.069 |
| 110 | 0.0033 | 0.003 | 0.027 | 0.004 | 0.007 |
| 111 | 0.0022 | 0.005 | | 0.002 | 0.003 |
| 112 | 0.0019 | 0.0044 | 0.036 | 0.003 | 0.004 |
| 113 | 0.0020 | 0.6782 | | | 0.176 |
| 114 | 0.0027 | | | 0.003 | |
| 115 | 0.008 | 0.79 | | | |
| 200 | 0.0049 | 0.0796 | 0.961 | 0.003 | 0.014 |
| 201 | 0.0057 | | | | 0.54 |
| 202 | 0.0078 | 0.189 | 2.3 | 0.006 | 0.026 |
| 203 | 0.00447 | 0.0166 | 0.654 | 0.003 | 0.007 |
| 204 | 0.0040 | 0.0579 | 0.772 | 0.002 | 0.013 |
| 205 | 0.006 | 2.46 | | | 0.57 |
| 206 | 0.007 | 0.023 | 0.83 | 0.004 | 0.03 |
| 207 | 0.003 | 0.26 | | 0.005 | 0.25 |
| 208 | 0.0028 | 0.0243 | 0.268 | 0.003 | 0.011 |
| 209 | 0.0030 | 0.197 | | | 0.155 |
| 210 | 0.0049 | 0.0163 | 0.216 | 0.002 | 0.006 |
| 212 | 0.0068 | 0.0354 | 0.499 | 0.008 | 0.007 |
| 213 | 0.0078 | 0.0252 | 0.126 | 0.007 | 0.005 |
| 214 | 0.0027 | 0.02 | 0.44 | 0.008 | 0.004 |
| 215 | 0.0024 | 0.828 | | | 0.090 |
| 216 | 0.0024 | 0.2919 | | 0.004 | 0.086 |
| 217 | 0.0032 | 0.0085 | 0.241 | 0.005 | 0.011 |
| 218 | 0.0020 | 0.1198 | | | 0.035 |
| 219 | 0.0027 | 0.0130 | 0.096 | 0.004 | 0.003 |
| 220 | 0.004 | 0.01 | 0.046 | 0.005 | 0.004 |
| 221 | 0.007 | 0.06 | 0.39 | 0.008 | 0.006 |

| ID | 1A IC50 (nM) | 1A Y93H IC50 (nM) | 1A Q30D IC50 (nM) | 1B IC50 (nM) | 2B IC50 (nM) |
| --- | --- | --- | --- | --- | --- |
| 222 | 0.0027 | 0.0059 | 0.044 | 0.006 | 0.007 |
| 223 | 0.006 | 0.30 | 2.98 | 0.008 | 0.115 |
| 224 | 0.0027 | 0.4615 | | | 0.204 |
| 225 | | | | | |
| 226 | | | | | 0.005 |
| 227 | | | | | 0.016 |
| 228 | | | | | |
| 229 | | | | | |
| 300 | 0.0030 | 0.0041 | 0.066 | 0.003 | 0.011 |
| 301 | 0.0014 | 0.2197 | 2.12 | 0.004 | 0.335 |
| 302 | 0.0029 | 0.0071 | 0.168 | 0.001 | 0.077 |
| 303 | 0.0026 | 0.0475 | | 0.003 | 0.942 |
| 304 | 0.0020 | 0.1227 | 0.954 | 0.003 | 0.048 |
| 305 | 0.0030 | 0.0031 | 0.015 | 0.004 | 0.004 |
| 306 | 0.0030 | 0.2442 | | | 0.145 |
| 307 | 0.0042 | 0.0083 | 0.047 | 0.005 | 0.006 |
| 308 | 0.0041 | 0.0757 | 0.496 | 0.003 | 0.047 |
| 309 | 0.0018 | 0.0218 | 0.047 | 0.006 | 0.003 |
| 310 | 0.0026 | 0.0954 | 0.806 | 0.003 | 0.120 |
| 311 | 0.0020 | 0.0019 | 0.011 | 0.002 | 0.003 |
| 312 | 0.0031 | 0.0380 | 0.873 | 0.002 | 0.061 |
| 312 | 0.0025 | 0.0044 | 0.009 | 0.003 | 0.007 |
| 313 | 0.0032 | 0.2306 | | 0.045 | 0.122 |
| 314 | 0.0026 | | | | 0.002 |
| 315 | 0.0027 | 0.0028 | | 0.002 | 0.004 |
| 316 | 0.0011 | 0.0162 | | 0.004 | 0.012 |
| 319 | 0.0025 | 0.0029 | 0.051 | 0.003 | 0.017 |
| 320 | 0.0017 | 0.036 | 0.590 | 0.003 | 0.203 |
| 321 | 0.0029 | 0.0019 | 0.007 | 0.003 | 0.004 |
| 322 | 0.0027 | 0.0512 | 0.324 | 0.004 | 0.058 |
| 323 | 0.0032 | 0.0051 | | | 0.078 |
| 324 | 0.0020 | 0.2629 | | | 1.667 |
| 325 | 0.0034 | 0.0402 | | | 0.040 |
| 326 | 0.0021 | 0.3414 | | | 0.808 |
| 327 | 0.0012 | 0.0020 | | | 0.011 |
| 328 | 0.0015 | 0.0463 | | | 0.163 |
| 329 | | | | | 0.16 |
| 330 | | | | | 0.016 |
| 400 | | | | | >1.67 |
| 401 | 0.0085 | 0.3465 | | | 0.634 |
| 402 | | | | | |
| 403 | 0.0064 | 0.0160 | | | 0.142 |
| 404 | 0.0120 | 0.0386 | | | 0.206 |
| 405 | 0.0012 | 0.0504 | | | 0.027 |
| 406 | 0.0030 | 0.0034 | | | 0.005 |
| 407 | 0.0027 | 0.143 | 0.482 | 0.004 | 0.192 |
| 408 | | | | | |
| 409 | 0.0108 | 0.5765 | 5.096 | 0.007 | 1.28 |
| 410 | | | | | 1.50 |
| 411 | 0.0512 | | | | |
| 412 | | | | | 0.12 |
| 413 | 0.0036 | 0.0196 | | | 0.173 |
| 414 | | | | | |
| 415 | 0.0016 | 2.875 | | 0.002 | 1.434 |
| 416 | 0.0022 | 0.085 | 1.769 | 0.003 | 0.119 |
| 417 | 0.0031 | 0.9958 | | | 0.453 |
| 418 | 0.0023 | 0.0083 | 0.255 | 0.003 | 0.095 |
| 419 | 0.0041 | 17.91 | | | 6.468 |
| 420 | 0.0101 | 1.871 | | | 5.561 |
| 421 | 0.0037 | 0.0140 | | | 0.103 |
| 422 | 0.0210 | | 1.667 | 0.015 | 35.22 |
| 423 | 0.0053 | 0.0526 | 0.444 | 0.007 | 0.041 |
| 424 | 0.0019 | 0.0554 | 0.058 | 0.694 | 0.003 |
| 425 | 0.0069 | 0.5336 | | | 1.782 |
| 426 | 0.0022 | | | | |
| 427 | 0.0024 | | | | |
| 428 | | | | | |
| 429 | 0.0012 | | | | |
| 430 | 0.006 | 19.5 | | | 7.1 |
| 431 | 0.033 | 0.56 | | | 3.1 |
| 432 | 0.001 | 2.6 | | 0.001 | 4.0 |
| 433 | 0.0001 | 0.06 | 1.6 | 0.001 | 0.3 |
| 434 | 0.0023 | 0.729 | | 0.0035 | 0.293 |
| 435 | 0.0028 | 0.618 | | 0.0038 | 0.181 |
| 436 | 0.0011 | 0.126 | | | 0.318 |
| 437 | 0.0022 | 0.176 | 0.283 | 0.0031 | 0.210 |
| 438 | 0.0036 | 0.004 | 0.030 | 0.0037 | 0.006 |
| 439 | 0.0027 | 0.004 | 0.018 | 0.0021 | 0.006 |
| 440 | 0.0023 | 0.146 | 0.967 | 0.0036 | 0.320 |
| 441 | 0.0025 | 0.003 | 0.011 | 0.0034 | 0.006 |
| 442 | 0.0015 | 0.653 | | 0.0023 | 0.119 |
| 443 | 0.0031 | 0.008 | 0.028 | 0.0031 | 0.006 |
| 444 | 0.0022 | 0.005 | 0.038 | 0.0038 | 0.007 |
| 445 | 0.0028 | 0.107 | 0.949 | 0.0046 | 0.096 |
| 446 | 0.0018 | 0.004 | 0.034 | 0.0034 | 0.005 |
| 447 | 0.0028 | 0.259 | 0.607 | 0.0033 | 0.059 |
| 448 | 0.0047 | 0.013 | 0.113 | 0.0060 | 0.011 |
| 449 | 0.0043 | 0.064 | 0.737 | 0.0034 | 0.044 |
| 451 | 0.0025 | | | 0.0027 | |
| 452 | 0.0027 | 0.004 | 0.093 | 0.0025 | 0.040 |
| 453 | 0.0023 | 0.210 | 2.14 | 0.002 | 0.65 |
| 454 | 0.0023 | 0.002 | 0.047 | 0.0031 | 0.052 |
| 455 | 0.0017 | 0.981 | | 0.0034 | |
| 456 | 0.0009 | 0.021 | 0.559 | 0.0027 | 0.316 |
| 457 | 0.0033 | 0.007 | 0.070 | 0.0036 | 0.005 |
| 458 | 0.0030 | 0.007 | 0.024 | 0.0035 | 0.007 |
| 459 | 0.0023 | 0.296 | | 0.0030 | 0.083 |
| 460 | 0.0027 | 0.288 | | 0.0039 | 0.138 |
| 461 | 0.0022 | 0.320 | | 0.0038 | 0.132 |
| 462 | 0.0035 | 0.007 | 0.038 | 0.0031 | 0.007 |
| 463 | 0.0026 | 0.002 | 0.012 | 0.0028 | 0.007 |
| 464 | 0.0028 | 0.197 | 1.229 | 0.0034 | 0.282 |
| 465 | 0.0027 | 0.002 | 0.022 | 0.0039 | 0.005 |
| 466 | 0.0027 | 0.002 | 0.015 | 0.003 | 0.005 |
| 467 | 0.0030 | 0.209 | 1.401 | 0.0034 | 0.158 |
| 468 | 0.0033 | 0.155 | 1.231 | 0.0029 | 0.234 |
| 469 | 0.0030 | 0.002 | 0.019 | 0.0034 | 0.005 |
| 470 | 0.0026 | 0.514 | | 0.0035 | 0.106 |
| 471 | 0.0028 | 0.003 | 0.013 | 0.0035 | 0.004 |
| 472 | 0.0021 | 0.555 | 2.696 | 0.0036 | 0.150 |
| 473 | 0.0026 | 0.002 | 0.011 | 0.0028 | 0.010 |
| 474 | 0.0015 | 0.269 | | 0.0036 | 0.263 |
| 475 | 0.0024 | 0.001 | 0.016 | 0.0039 | 0.008 |
| 476 | 0.0011 | 0.316 | | 0.0035 | 0.190 |
| 477 | 0.0032 | 0.003 | 0.009 | 0.0037 | 0.008 |
| 486 | 0.0041 | 0.342 | | | 0.031 |
| 487 | 0.0039 | 0.050 | 0.311 | 0.0042 | 0.017 |
| 488 | 0.0069 | 0.035 | 0.214 | 0.0080 | 0.012 |
| 491 | 0.0029 | 0.010 | 0.300 | 0.0026 | 0.013 |
| 492 | 0.0028 | 0.030 | 0.535 | 0.0029 | 0.146 |
| 493 | 0.0042 | 0.025 | 0.346 | 0.0028 | 0.012 |
| 495 | 0.0016 | 0.270 | | 0.0025 | 0.184 |
| 496 | 0.0069 | | | 0.0035 | |
| 497 | 0.0064 | 0.084 | 0.568 | 0.0066 | 0.073 |
| 498 | 0.0096 | 0.877 | 1.667 | 0.0053 | 0.646 |
| 499 | 0.0069 | 0.223 | 1.088 | 0.0088 | 0.622 |
| 500 | 0.0225 | 7.786 | 16.67 | 0.0184 | 1.667 |
| 501 | 0.0039 | 0.857 | | 0.0036 | 1.316 |
| 502 | 0.0016 | | | 0.0025 | 2.306 |
| 503 | 0.0022 | 0.149 | | | 0.362 |
| 504 | 0.0026 | 1.667 | | 0.0024 | 1.667 |
| 505 | 0.0015 | 0.152 | | | 0.220 |
| 509 | 0.0020 | 0.014 | | 0.0028 | 0.018 |
| 510 | 0.0010 | 0.629 | | | 0.624 |
| 511 | 0.0097 | 0.049 | 0.847 | 0.0087 | 0.095 |
| 512 | 0.0085 | 0.347 | | 0.0039 | 0.783 |
| 513 | | | | | 1.207 |

339
-continued
| ID | 1A IC50 (nM) | 1A Y93H IC50 (nM) | 1A Q30D IC50 (nM) | 1B IC50 (nM) | 2B IC50 (nM) |
|---|---|---|---|---|---|
| 514 | 0.0022 | 0.012 | 0.174 | 0.0030 | 0.035 |
| 515 | 0.0013 | 4.449 |  | 0.0029 | 1.844 |
| 516 | 0.0017 | 3.221 |  | 0.0026 |  |
| 517 | 0.0017 | 0.392 |  | 0.0033 | 0.874 |
| 518 | 0.0025 | 0.016 | 0.099 | 0.0024 | 0.015 |
| 519 | 0.0031 | 0.669 | 0.951 | 0.0021 | 0.598 |
| 520 | 0.0033 | 2.714 |  | 0.0037 |  |
| 521 | 0.0038 | 1.826 |  | 0.0018 | 0.887 |
| 522 | 0.0014 | 0.011 | 0.163 | 0.0010 | 0.015 |
| 523 | 0.0012 | 0.130 |  |  |  |
| 524 | 0.0030 | 0.008 | 0.183 | 0.0020 | 0.105 |
| 525 | 0.0045 |  |  | 0.0022 |  |
| 526 | 0.0024 |  |  | 0.0011 | 0.537 |
| 527 | 0.0024 | 0.005 | 0.065 | 0.0029 | 0.014 |
| 528 | 0.0014 | 1.149 |  |  | 0.727 |
| 529 | 0.0026 | 0.006 | 0.126 | 0.0033 | 0.051 |
| 530 | 0.0016 | 0.152 |  | 0.0029 | 0.607 |
| 531 | 0.0025 | 0.022 | 0.328 | 0.0038 | 0.056 |
| 532 | 0.0013 | 1.759 |  | 0.0036 | 1.183 |
| 533 | 0.0262 |  | 2.516 | 0.0196 |  |
| 534 | 0.0024 | 0.094 | 0.267 | 0.0030 | 0.030 |
| 535 | 0.0031 | 0.084 | 0.172 | 0.0032 | 0.012 |
| 536 | 0.0023 | 0.029 |  | 0.0027 | 0.029 |
| 537 | 0.0019 | 3.328 |  |  | 0.198 |
| 538 | 0.0012 | 0.579 |  |  | 0.117 |
| 539 | 0.0023 | 0.013 |  | 0.0029 | 0.006 |
| 540 | 0.0025 | 0.006 | 0.022 | 0.0030 | 0.005 |
| 541 | 0.0021 | 0.401 | 1.469 | 0.0031 | 0.119 |
| 542 | 0.0014 | 0.495 |  |  | 0.124 |
| 543 | 0.0021 | 0.167 |  |  | 0.153 |
340
-continued
| ID | 1A IC50 (nM) | 1A Y93H IC50 (nM) | 1A Q30D IC50 (nM) | 1B IC50 (nM) | 2B IC50 (nM) |
|---|---|---|---|---|---|
| 544 | 0.0031 | 0.005 | 0.051 | 0.0036 | 0.006 |
| 545 | 0.0026 | 0.004 | 0.015 | 0.0028 | 0.006 |
| 546 | 0.0014 | 0.315 |  |  | 0.165 |
| 547 | 0.0028 | 0.005 | 0.028 | 0.0018 | 0.006 |
NOTE:
Blank entries denote that data was not available.
The invention claimed is:
1. A compound having the structure:
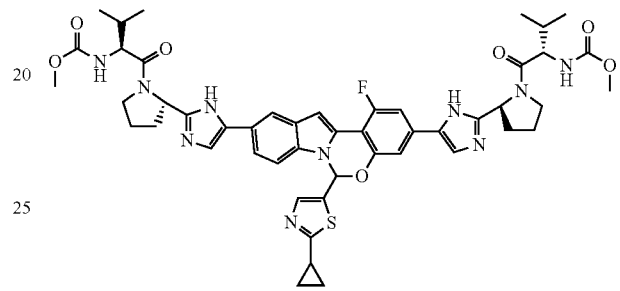
or a pharmaceutically acceptable salt thereof.
2. A compound having the structure:
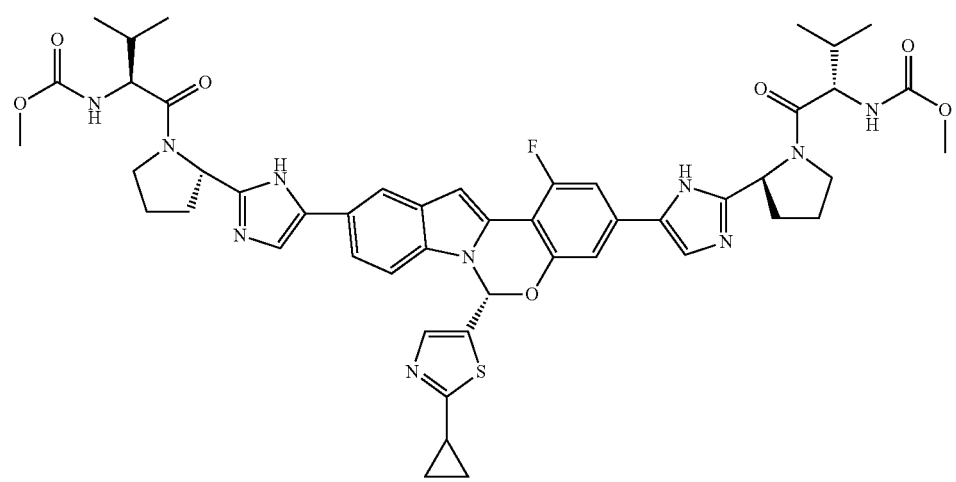 [SMILES: COC(=O)N[C@H](C(=O)N1CCC[C@H]1c1ncc(-c2cc(F)c3c(c2)O[C@H](c2cnc(C4CC4)s2)n2c-3cc3cc(-c4cnc([C@@H]5CCCN5C(=O)[C@@H](NC(=O)OC)C(C)C)[nH]4)ccc32)[nH]1)C(C)C]
or a pharmaceutically acceptable salt thereof.

3. A compound having the structure:

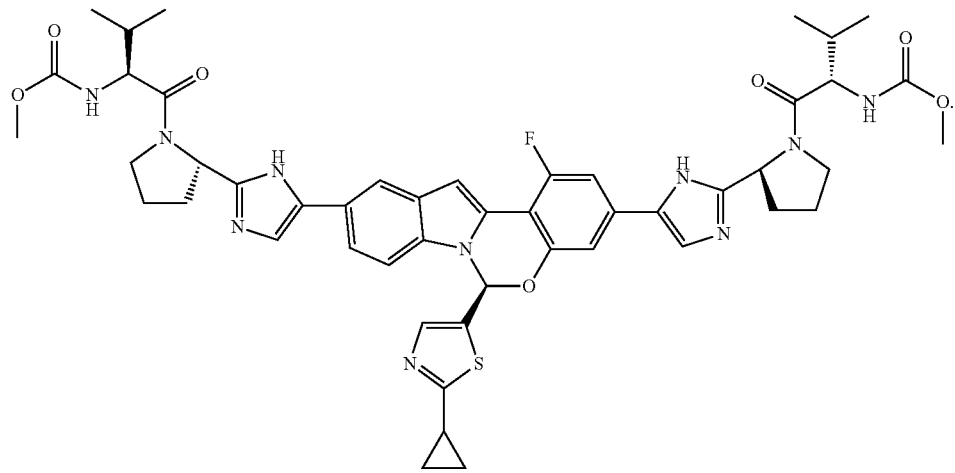 [SMILES: COC(=O)N[C@H](C(=O)N1CCC[C@H]1c1ncc(-c2cc(F)c3c(c2)O[C@@H](c2cnc(C4CC4)s2)n2c-3cc3cc(-c4cnc([C@@H]5CCCN5C(=O)[C@@H](NC(=O)OC)C(C)C)[nH]4)ccc32)[nH]1)C(C)C]

4. A pharmaceutically acceptable salt of the compound having the structure:

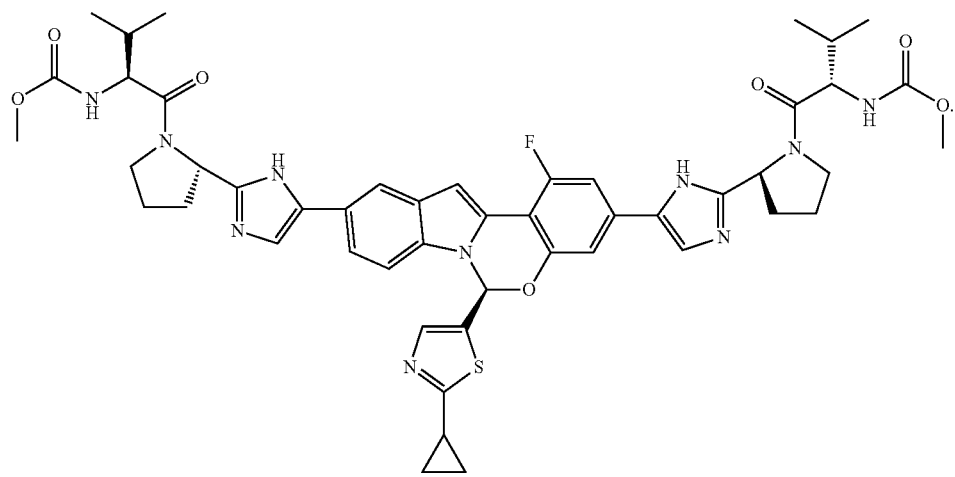 [SMILES: COC(=O)N[C@H](C(=O)N1CCC[C@H]1c1ncc(-c2cc(F)c3c(c2)O[C@@H](c2cnc(C4CC4)s2)n2c-3cc3cc(-c4cnc([C@@H]5CCCN5C(=O)[C@@H](NC(=O)OC)C(C)C)[nH]4)ccc32)[nH]1)C(C)C]

5. A pharmaceutical composition comprising an effective amount of the compound of claim 1, or a pharmaceutically acceptable salt thereof, and a pharmaceutically acceptable carrier.

6. The pharmaceutical composition of claim 5, further comprising one or more additional therapeutic agents, wherein the additional therapeutic agents are each independently selected from HCV protease inhibitors, HCV NS5A inhibitors and HCV NS5B polymerase inhibitors.

7. A pharmaceutical composition consisting essentially of the compound of claim 1, or a pharmaceutically acceptable salt thereof, a HCV protease inhibitor, a HCV NS5B polymerase inhibitor and a pharmaceutically acceptable carrier, wherein the amounts of the compound of claim 1, or a pharmaceutically acceptable salt thereof, the HCV protease inhibitor and the HCV NS5B polymerase inhibitor are together effective to treat HCV infection in a human patient.

8. The pharmaceutical composition of claim 7, wherein the HCV protease inhibitor is the compound having the structure:

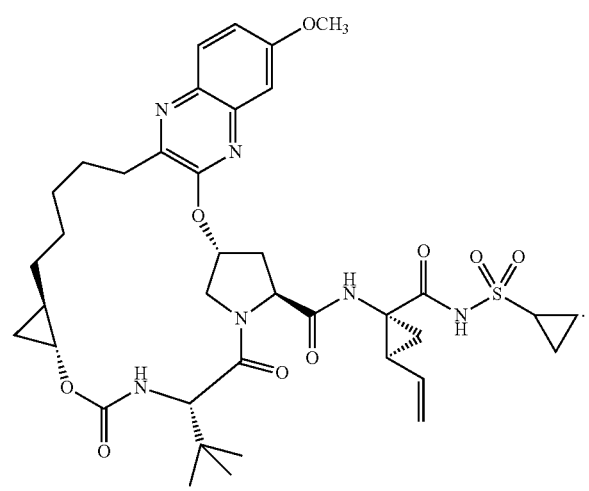 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1]

9. The pharmaceutical composition of claim 8, wherein the HCV NS5B polymerase inhibitor is a nucleoside.

10. A method of treating a human patient infected with HCV, comprising the step of administering an amount of the compound of claim 1, or a pharmaceutically acceptable salt thereof, effective to treat infection by HCV in said human patient.

11. The method of claim 10, further comprising administering one or more additional therapeutic agents to said human patient, wherein the additional therapeutic agents are each independently selected from HCV protease inhibitors, HCV NS5A inhibitors and HCV NS5B polymerase inhibitors.

12. The method of claim 11, wherein the one or more additional therapeutic agents comprise a HCV protease inhibitor and a HCV NS5B polymerase inhibitor.

13. The method of claim 12, wherein the HCV protease inhibitor is the compound having the structure:

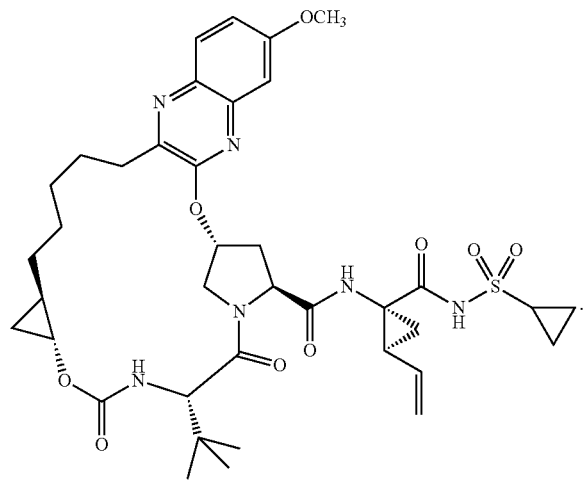 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1]

14. The method of claim 13, wherein the HCV NS5B polymerase inhibitor is a nucleoside.

15. A pharmaceutical composition comprising an effective amount of the compound of claim 3 and a pharmaceutically acceptable carrier.

16. The pharmaceutical composition of claim 15, further comprising one or more additional therapeutic agents, wherein the additional therapeutic agents are each independently selected from HCV protease inhibitors, HCV NS5A inhibitors and HCV NS5B polymerase inhibitors.

17. A pharmaceutical composition consisting essentially of the compound of claim 3, a HCV protease inhibitor, a HCV NS5B polymerase inhibitor and a pharmaceutically acceptable carrier, wherein the amounts of the compound of claim 3, the HCV protease inhibitor and the HCV NS5B polymerase inhibitor are together effective to treat HCV infection in a human patient.

18. The pharmaceutical composition of claim 17, wherein the HCV protease inhibitor is the compound having the structure:

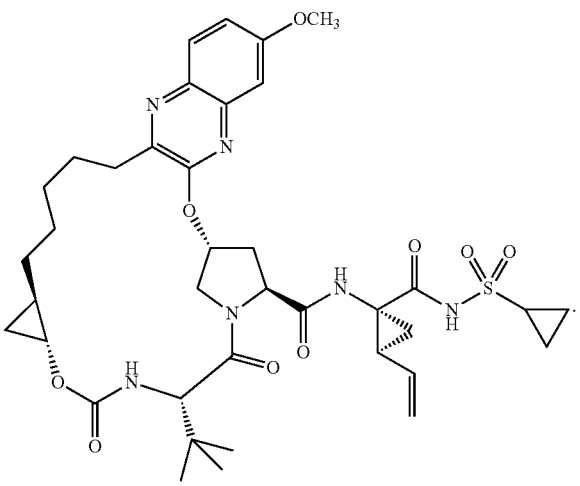 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1]

19. The pharmaceutical composition of claim 18, wherein the HCV NS5B polymerase inhibitor is a nucleoside.

20. A method of treating a human patient infected with HCV, comprising the step of administering an amount of the compound of claim 3 effective to treat infection by HCV in said human patient.

21. The method of claim 20, further comprising administering one or more additional therapeutic agents to said human patient, wherein the additional therapeutic agents are each independently selected from HCV protease inhibitors, HCV NS5A inhibitors and HCV NS5B polymerase inhibitors.

22. The method of claim 21, wherein the one or more additional therapeutic agents comprise a HCV protease inhibitor and a HCV NS5B polymerase inhibitor.

23. The method of claim 22, wherein the HCV protease inhibitor is the compound having the structure:

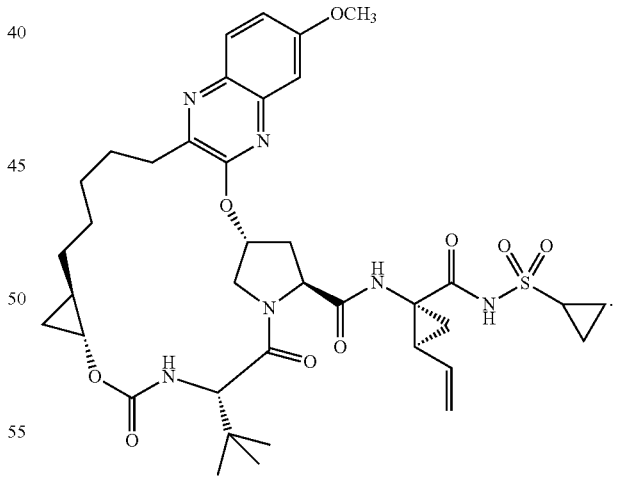

24. The method of claim 23, wherein the HCV NS5B polymerase inhibitor is a nucleoside.

* * * * *